United States Patent
Gan

(10) Patent No.: US 9,040,521 B2
(45) Date of Patent: May 26, 2015

(54) METHODS AND COMPOSITIONS FOR MODULATING TAU LEVELS

(75) Inventor: Li Gan, Burlingame, CA (US)

(73) Assignee: THE J. DAVID GLADSTONE INSTITUTES, San Francisco, CA (US)

(*) Notice: Subject to any disclaimer, the term of this patent is extended or adjusted under 35 U.S.C. 154(b) by 524 days.

(21) Appl. No.: 13/502,659

(22) PCT Filed: Sep. 15, 2010

(86) PCT No.: PCT/US2010/048989
§ 371 (c)(1),
(2), (4) Date: May 15, 2012

(87) PCT Pub. No.: WO2011/056300
PCT Pub. Date: May 12, 2011

(65) Prior Publication Data
US 2012/0225864 A1    Sep. 6, 2012

Related U.S. Application Data

(60) Provisional application No. 61/258,822, filed on Nov. 6, 2009.

(51) Int. Cl.
| | | |
|---|---|---|
| *A61K 31/551* | (2006.01) | |
| *G01N 33/556* | (2006.01) | |
| *A61K 38/50* | (2006.01) | |
| *G01N 33/68* | (2006.01) | |

(52) U.S. Cl.
CPC ............... *A61K 38/50* (2013.01); *A61K 31/551* (2013.01); *G01N 33/556* (2013.01); *G01N 33/6896* (2013.01); *G01N 2800/2814* (2013.01)

(58) Field of Classification Search
CPC .... A61K 31/551; G01N 33/556; A61P 25/18; A61P 25/28; C12N 5/07; C12N 5/0793
USPC .................................... 514/218; 435/7.9, 375
See application file for complete search history.

(56) References Cited

U.S. PATENT DOCUMENTS

| | | |
|---|---|---|
| 2006/0025337 A1 | 2/2006 | Sinclair |
| 2006/0223812 A1 | 10/2006 | Mandelkow et al. |
| 2008/0194803 A1 | 8/2008 | Sinclair |
| 2008/0220449 A1 | 9/2008 | Vasan |
| 2009/0117543 A1 | 5/2009 | Sinclair |

FOREIGN PATENT DOCUMENTS

| | | |
|---|---|---|
| JP | 2008/533024 | 8/2008 |
| WO | WO 2006/096780 | 9/2006 |
| WO | WO 2007/008548 | 1/2007 |
| WO | WO 2007/019344 | 2/2007 |
| WO | WO 2008/156866 | 12/2008 |

OTHER PUBLICATIONS

Manzo et al., "Histone Acetyltransferase Inhibitors and Preclinical Studies", Expert Opinion Therapeutic Patents (2009), 19(6):761-774.
Balasubramanyam, et al., Curcumin, a Novel p300/CREB-Binding Protein-Specific Inhibitor of Acetyltransferase, Represses the Acetylation of Histone/Nonhistone Proteins and Histone Acetyltransferase-dependent Chromatin Transcription., J Biol Chem. 2004, 279(49):51163-71.
Biernat, et al., "The Switch of Tau Protein to an Alzheimer-like State Includes the Phosphorylation of Two Serine-Proline Motifs Upstream of the Microtubule Binding Region", EMBO J. 1992, 11(4):1593-1597.
Bowers, et al., "Virtual Ligand Screening of the p300/CBP Histone Acetyltransferase: Identification of a Selective Small Molecule Inhibitor", Chemistry & Biology, 2010, vol. 17,pp. 471-482.
Ghosh, et al., "Comparison of Pathways Controlling Toxicity in the Eye and Brain in *Drosophila* Models of Human Neurodegenerative Diseases", Hum Mol Genet. 2004, 13(18):2011-2018.
Mai, et al., "Identification of 4-Hydroxyquinolines Inhibitors of p300/CBP Histone Acetyltransferases", Bioorganic & Medicinal Chemistry Letters, 2009, vol. 19, pp. 1132-1135.
Min, et al., "Acetylation of Tau Inhibits its Degradation and Contributes to Taupathy", Neuron. Sep. 23, 2010, 67(6):953-66.
Morimoto et al., "The Dietary Compound Curcumin Inhibits p300 Histone Acetyltransferase Activity and Prevents Heart Failure in Rats", J Clin Invest, 2008, 118(3):868-78.
Stimson, et al., "Isothiazolones as Inhibitors of PCAF and p300 Histone Acetyltransferase Activity", 2005, Mol Cancer Ther, 4(1), 1521-1532.
Anonymous, "DNA-RNA Transcription Regulators", [Published online] Nov. 5, 2008, [Retrieved from] http://www.sigmaaldrich.com/life-science/cell-biology/, [Retrieved on] Sep. 3, 2013.
Cole, Philip A., "Chemical Probes for Histone-Modifying Enzymes", Nature Chemical Biology, Oct. 2008, 4(10):590-597.
Kim, Dohoon et al., "SIRT1 Deacetylase Protects Against Neurodegeneration in Models for Alzheimer's Disease and Amyotrophic Later Sclerosis", EMBO Journal, Jun. 21, 2007, 26(13):3169-3179.
Rouaux, Caroline et al., "Critical Loss of CBP/p300 Histone Acetylase Activity by Caspase-6 During Neurodegeneration", EMBO Journal, Dec. 15, 2003, 22(24):6537-6549.
Rouaux, Caroline et al., "Sodium Valproate Exerts Neuroprotective Effects in vivo through CREB-Binding Protein-Dependent Mechanisms but Does Not Improve Survival in an Amyotrophic Lateral Sclerosis Mouse Model", Journal of Neuroscience, May 23, 2007, 27(21):5535-5545.

*Primary Examiner* — Raymond Henley, III
(74) *Attorney, Agent, or Firm* — Bozicevic, Field & Francis LLP; Paula A. Borden

(57) ABSTRACT

Methods and agents for reducing a level of an acetylated Tau polypeptide in a cell are provided. Methods for treating a tauopathy in an individual are also provided. Also provided is a method for diagnosing a cognitive impairment disorder in an individual. Methods for identifying an agent suitable for treating a tauopathy are also provided.

18 Claims, 19 Drawing Sheets

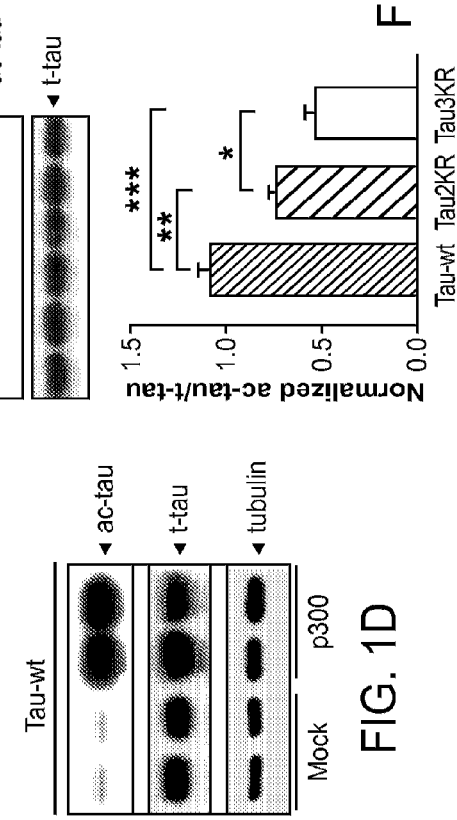
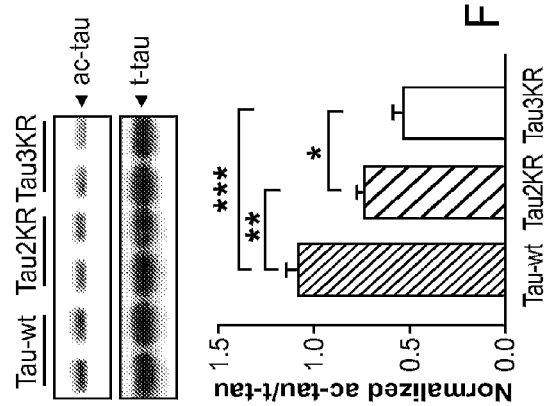
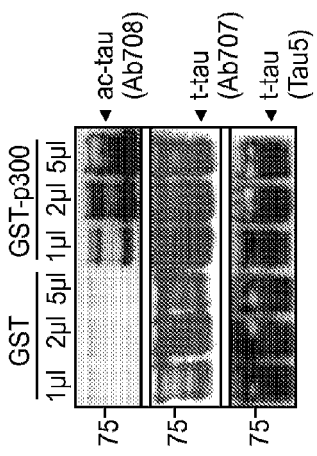
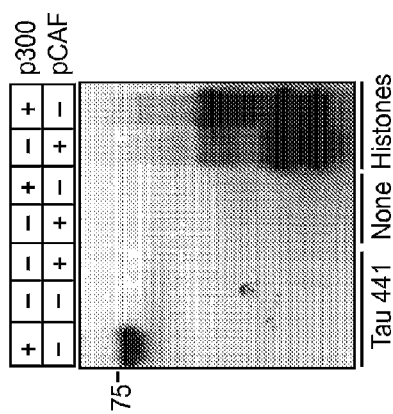
FIG. 1A  FIG. 1B  FIG. 1C  FIG. 1D  FIG. 1E

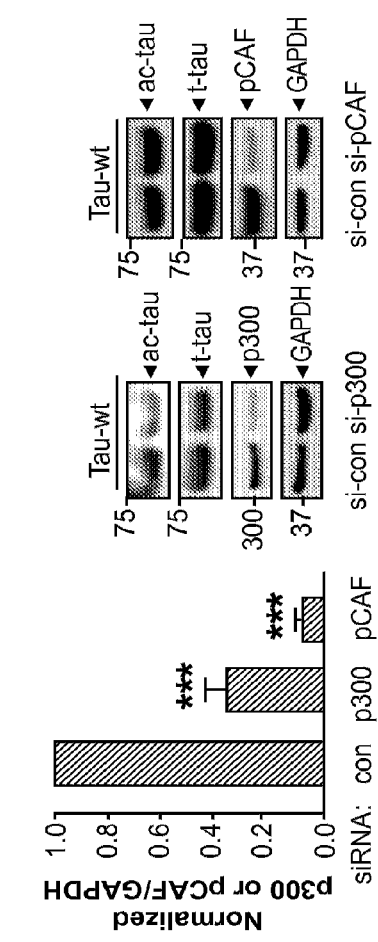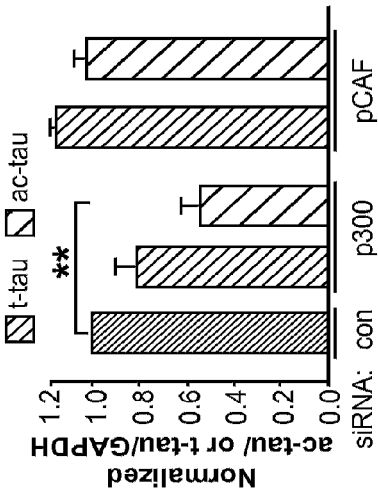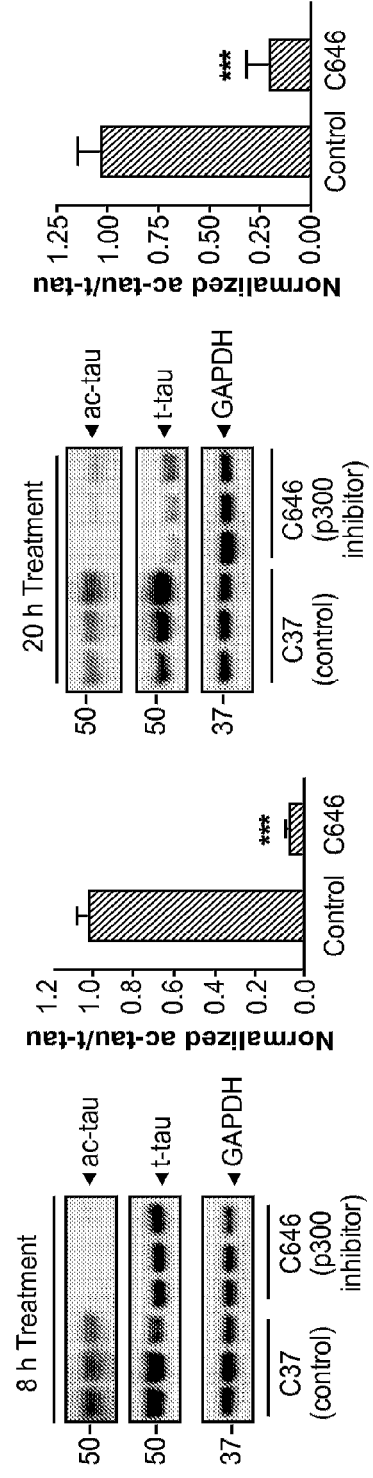

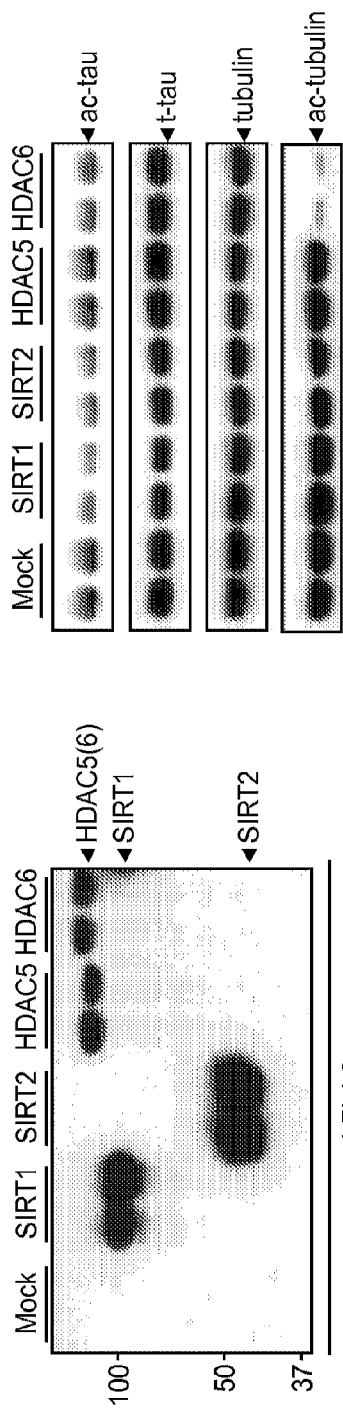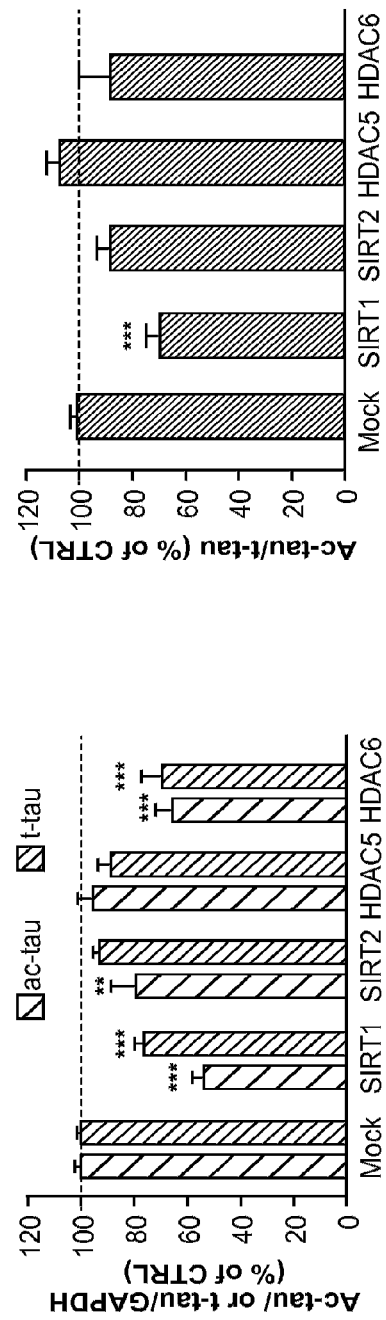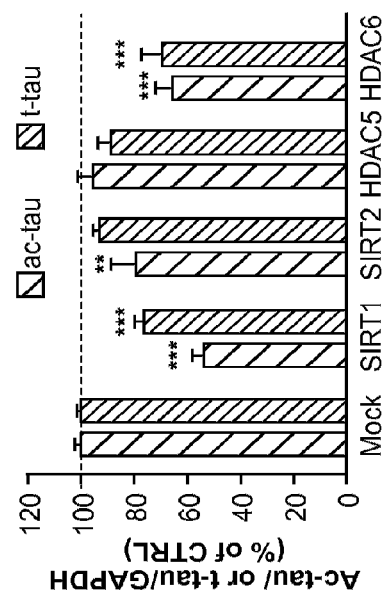
FIG. 3A
FIG. 3B
FIG. 3C
FIG. 3D

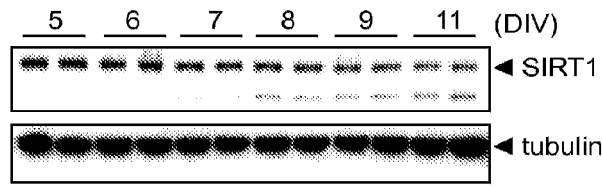
FIG. 4A
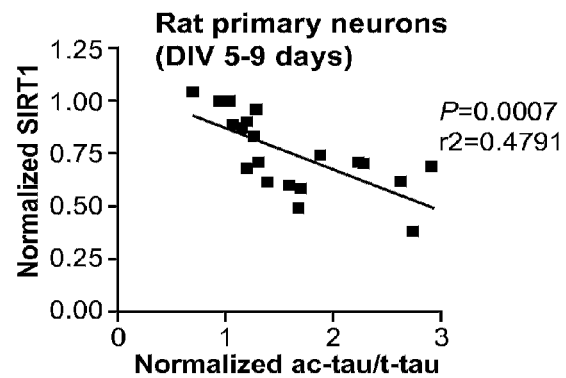
FIG. 4B
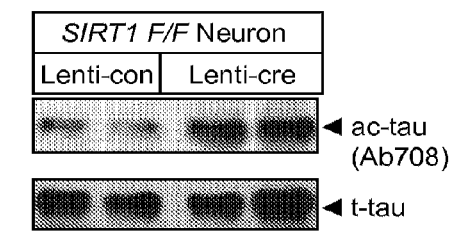
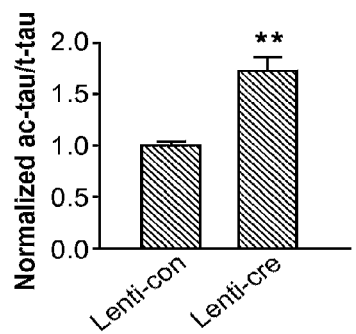
FIG. 4C

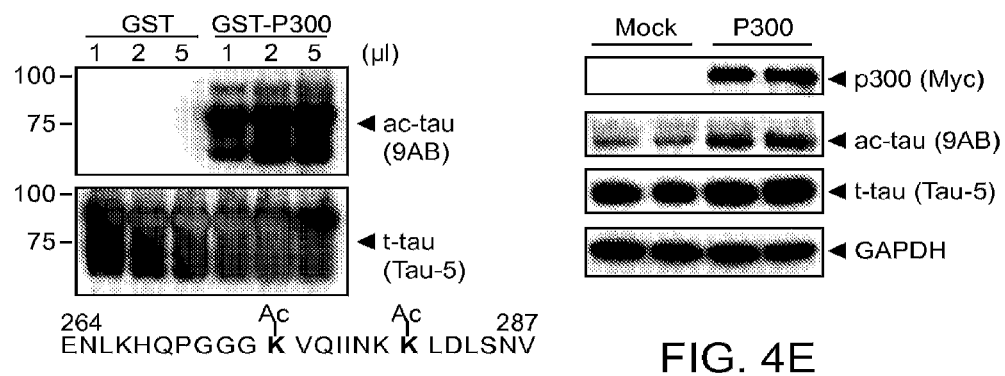
FIG. 4D
FIG. 4E
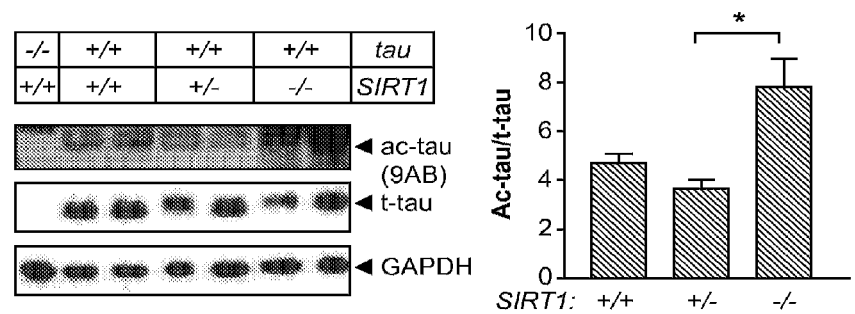
FIG. 4F

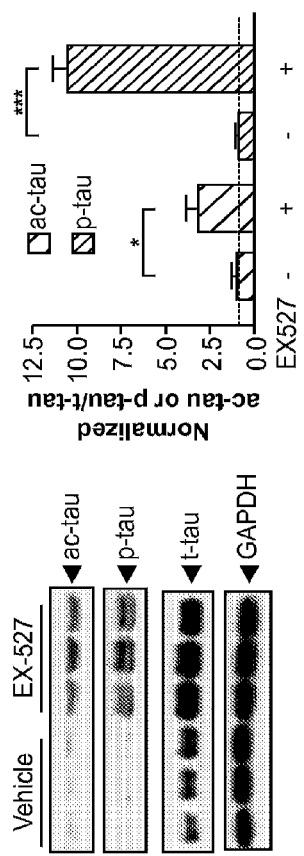
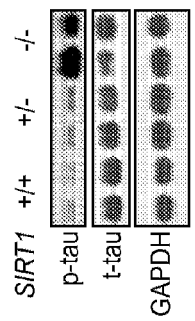
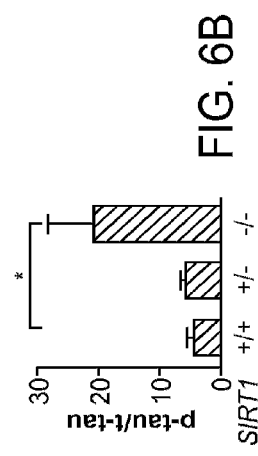
FIG. 6A
FIG. 6B

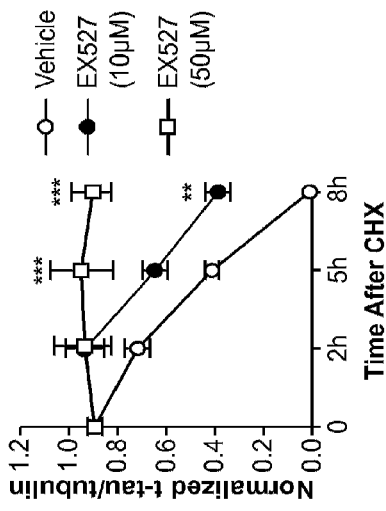
FIG. 6F
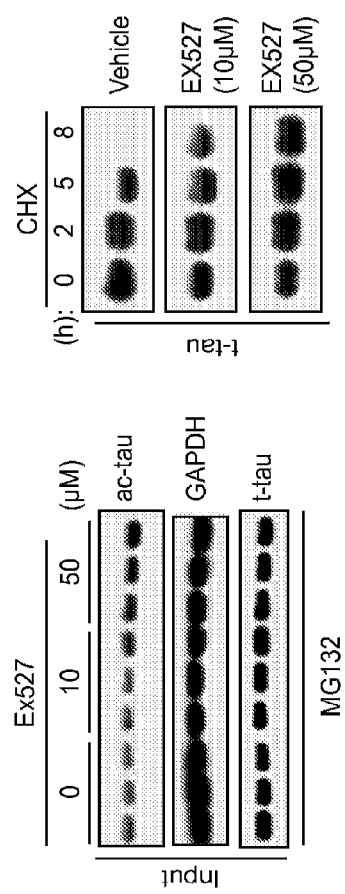
FIG. 6G
FIG. 6H
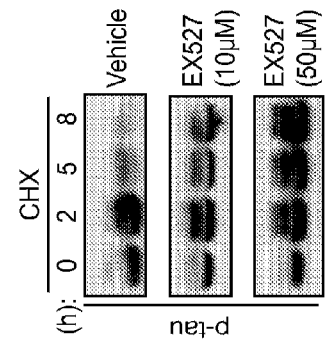
FIG. 6I
FIG. 6J
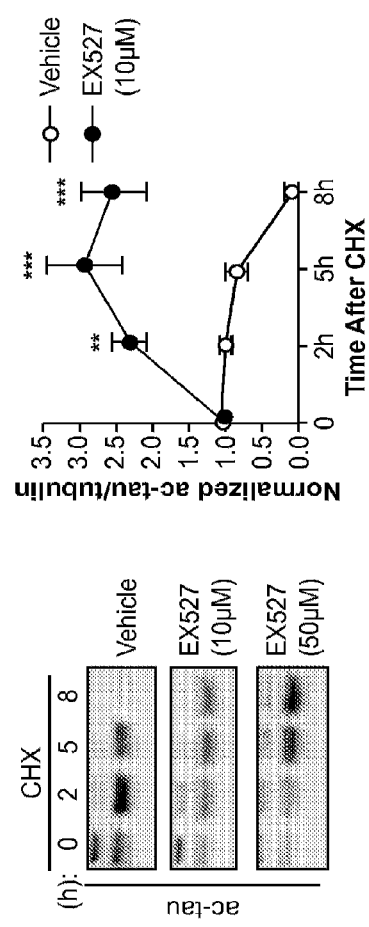
FIG. 6K

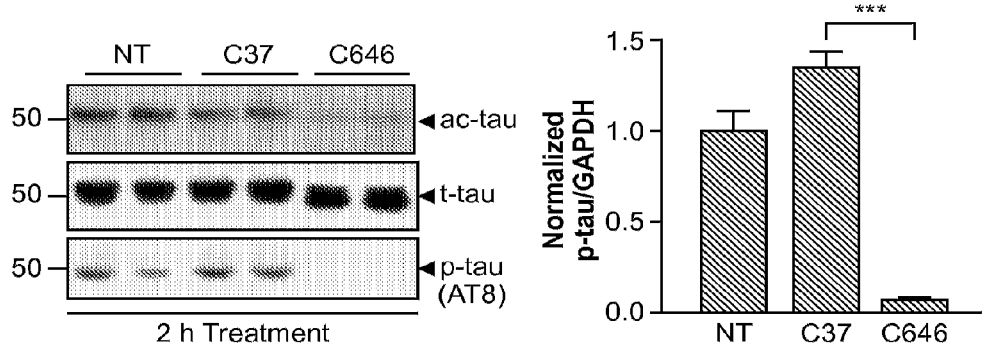
FIG. 8A
FIG. 8B
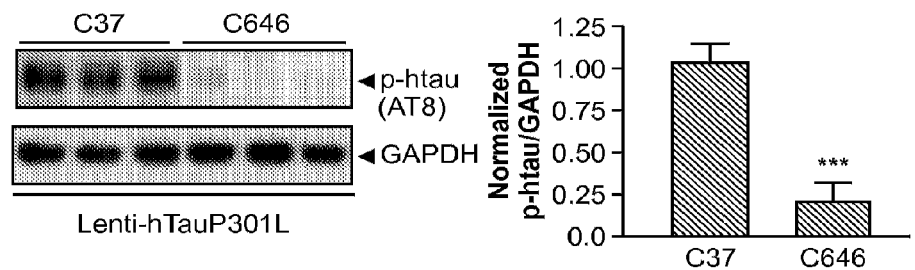
FIG. 8C
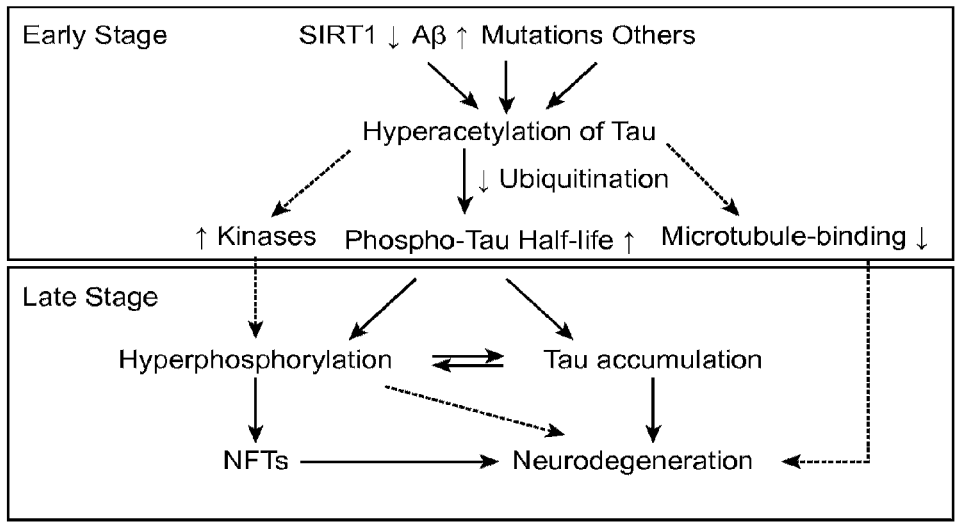
FIG. 8D

| | | |
|---|---|---|
| seq_id_1 | MAEPRQEFEVMEDHAGTYGLGDRKDQGGYTMHQDQEGDTDAGLKESPLQTPTEDGSEEPG | 60 |
| seq_id_2 | MAEPRQEFEVMEDHAGTYGLGDRKDQGGYTMHQDQEGDTDAGLK---------------- | 44 |
| seq_id_3 | MAEPRQEFEVMEDHAGTYGLGDRKDQGGYTMHQDQEGDTDAGLK---------------- | 44 |
| seq_id_4 | MAEPRQEFEVMEDHAGTYGLGDRKDQGGYTMHQDQEGDTDAGLKESPLQTPTEDGSEEPG | 60 |
| seq_id_6 | MAEPRQEFEVMEDHAGTYGLGDRKDQGGYTMHQDQEGDTDAGLKESPLQTPTEDGSEEPG | 60 |
| seq_id_5 | MAEPRQEFEVMEDHAGTYGLGDRKDQGGYTMHQDQEGDTDAGLKESPLQTPTEDGSEEPG | 60 |
| | ******************************************  | |
| seq_id_1 | SETSDAKSTPTAEDVTAPLVDEGAPGKQAAAQPHTEIPEGTTAEEAGIGDTPSLEDEAAG | 120 |
| seq_id_2 | ------------------------------------AEEAGIGDTPSLEDEAAG | 62 |
| seq_id_3 | ------------------------------------AEEAGIGDTPSLEDEAAG | 62 |
| seq_id_4 | SETSDAKSTP-------------------------------TAEAEEAGIGDTPSLEDEAAG | 91 |
| seq_id_6 | SETSDAKSTPTAEDVTAPLVDEGAPGKQAAAQPHTEIPEGTTAEEAGIGDTPSLEDEAAG | 120 |
| seq_id_5 | SETSDAKSTPTAEDVTAPLVDEGAPGKQAAAQPHTEIPEGTTAEEAGIGDTPSLEDEAAG | 120 |
| | ********************** | |
| seq_id_1 | HVTQ---------------------------------------------------- | 124 |
| seq_id_2 | HVTQ---------------------------------------------------- | 66 |
| seq_id_3 | HVTQ---------------------------------------------------- | 66 |
| seq_id_4 | HVTQ---------------------------------------------------- | 95 |
| seq_id_6 | HVTQEPESGKVVQEGFLREPGPPGLSHQLMSGMPGAPLLPEGPREATRQPSGTGPEDTEG | 180 |
| seq_id_5 | HVTQEPESGKVVQEGFLREPGPPGLSHQLMSGMPGAPLLPEGPREATRQPSGTGPEDTEG | 180 |
| | **** | |
| seq_id_1 | -------------------------------------------------------- | |
| seq_id_2 | -------------------------------------------------------- | |
| seq_id_3 | -------------------------------------------------------- | |
| seq_id_4 | -------------------------------------------------------- | |
| seq_id_6 | GRHAPELLKHQLLGDLHQEGPPLKGAGGKERPGSKEEVDEDRDVDESSPQDSPPSKASPA | 240 |
| seq_id_5 | GRHAPELLKHQLLGDLHQEGPPLKGAGGKERPGSKEEVDEDRDVDESSPQDSPPSKASPA | 240 |

FIG. 9A

```
seq_id_1    ------------------------------------------------------------
seq_id_2    ------------------------------------------------------------
seq_id_3    ------------------------------------------------------------
seq_id_4    ------------------------------------------------------------
seq_id_6    QDGRPPQTAAREATSIPGFPAEGAIPLPVDFLSKVSTEIPASEPDGPSVGRAKGQDAPLE  300
seq_id_5    QDGRPPQTAAREATSIPGFPAEGAIPLPVDFLSKVSTEIPASEPDGPSVGRAKGQDAPLE  300 seq_id_1    ------------------------------------------------------------
seq_id_2    ------------------------------------------------------------
seq_id_3    ------------------------------------------------------------
seq_id_4    ------------------------------------------------------------
seq_id_6    FTFHVEITPNVQKEQAHSEEHLGRAAFPGAPGEGPEARGPSLGEDTKEADLPEPSEKQPA  360
seq_id_5    FTFHVEITPNVQKEQAHSEEHLGRAAFPGAPGEGPEARGPSLGEDTKEADLPEPSEKQPA  360 seq_id_1    ----------------ARMVSKSKDGTGSDDKKAK-------------------------  143
seq_id_2    ----------------ARMVSKSKDGTGSDDKKAK-------------------------   85
seq_id_3    ----------------ARMVSKSKDGTGSDDKKAK-------------------------   85
seq_id_4    ----------------ARMVSKSKDGTGSDDKKAK-------------------------  114
seq_id_6    AAPRGKPVSRVPQLKARMVSKSKDGTGSDDKKAKTSTRSSAKTLKNRPCLSPKHPTPGSS  420
seq_id_5    AAPRGKPVSRVPQLKARMVSKSKDGTGSDDKKAKTSTRSSAKTLKNRPCLSPKHPTPGSS  420
                           ****************** seq_id_1    ----------------------------------------GADGKTKIATPRGAAPPGQK  163
seq_id_2    ----------------------------------------GADGKTKIATPRGAAPPGQK  105
seq_id_3    ----------------------------------------GADGKTKIATPRGAAPPGQK  105
seq_id_4    ----------------------------------------GADGKTKIATPRGAAPPGQK  134
seq_id_6    DPLIQPSSPAVCPEPPSSPKHVSSVTSRTGSSGAKEMKLKGADGKTKIATPRGAAPPGQK  480
seq_id_5    DPLIQPSSPAVCPEPPSSPKHVSSVTSRTGSSGAKEMKLKGADGKTKIATPRGAAPPGQK  480
                                                    ********************
```

FIG. 9B

```
seq_id_1      ----------------------------------------GEPPKSGDRSGYSSPGSPGT  205
seq_id_2      ----------------------------------------GEPPKSGDRSGYSSPGSPGT  147
seq_id_3      ----------------------------------------GEPPKSGDRSGYSSPGSPGT  147
seq_id_4      ----------------------------------------GEPPKSGDRSGYSSPGSPGT  176
seq_id_6      GQANATRIPAKTPPAPKTPPSSATKQVQRRPPAGPRSFRGEPPKSGDRSGYSSPGSPGT  540
seq_id_5      GQANATRIPAKTPPAPKTPPSS------------------GEPPKSGDRSGYSSPGSPGT  522
                                                      ******************** seq_id_1      PGSRSRTPSLPTPTREPKKVAVVRTPPKSPSSAKSRLQTAPVPMPDLKNVKSKIGSTEN  265
seq_id_2      PGSRSRTPSLPTPTREPKKVAVVRTPPKSPSSAKSRLQTAPVPMPDLKNVKSKIGSTEN  207
seq_id_3      PGSRSRTPSLPTPTREPKKVAVVRTPPKSPSSAKSRLQTAPVPMPDLKNVKSKIGSTEN  207
seq_id_4      PGSRSRTPSLPTPTREPKKVAVVRTPPKSPSSAKSRLQTAPVPMPDLKNVKSKIGSTEN  236
seq_id_6      PGSRSRTPSLPTPTREPKKVAVVRTPPKSPSSAKSRLQTAPVPMPDLKNVKSKIGSTEN  600
seq_id_5      PGSRSRTPSLPTPTREPKKVAVVRTPPKSPSSAKSRLQTAPVPMPDLKNVKSKIGSTEN  582
              ************************************************************ seq_id_1      LKHQPGGGKVQIINKKLDLSNVQSKCGSKDNIKHVPGGGSVQIVYKPVDLSKVTSKCGSL  325
seq_id_2      LKHQPGGGKVQIINKKLDLSNVQSKCGSKDNIKHVPGGGSVQIVYKPVDLSKVTSKCGSL  267
seq_id_3      LKHQPGGGK---------------------------------------------------  236
seq_id_4      LKHQPGGGKVQIINKKLDLSNVQSKCGSKDNIKHVPGGGSVQIVYKPVDLSKVTSKCGSL  296
seq_id_6      LKHQPGGGKVQIINKKLDLSNVQSKCGSKDNIKHVPGGGSVQIVYKPVDLSKVTSKCGSL  660
seq_id_5      ---------VQIVYKPVDLSKVTSKCGSL  642
                                                               ************ seq_id_1      GNIHHKPGGGQVEVKSEKLDFKDRVQSKIGSLDNITHVPGGNKKIETHKLTFRENAKAK  385
seq_id_2      GNIHHKPGGGQVEVKSEKLDFKDRVQSKIGSLDNITHVPGGNKKIETHKLTFRENAKAK  327
seq_id_3      GNIHHKPGGGQVEVKSEKLDFKDRVQSKIGSLDNITHVPGGNKKIETHKLTFRENAKAK  296
seq_id_4      GNIHHKPGGGQVEVKSEKLDFKDRVQSKIGSLDNITHVPGGNKKIETHKLTFRENAKAK  356
seq_id_6      GNIHHKPGGGQVEVKSEKLDFKDRVQSKIGSLDNITHVPGGNKKIETHKLTFRENAKAK  720
seq_id_5      GNIHHKPGGGQVEVKSEKLDFKDRVQSKIGSLDNITHVPGGNKKIETHKLTFRENAKAK  702
              ************************************************************
```

FIG. 9C

```
seq_id_1   TDHGAEIVYKSPVVSGDTSPRHLSNVSSTGSIDMVDSPQLATLADEVSASLAKQGL  441
seq_id_2   TDHGAEIVYKSPVVSGDTSPRHLSNVSSTGSIDMVDSPQLATLADEVSASLAKQGL  383
seq_id_3   TDHGAEIVYKSPVVSGDTSPRHLSNVSSTGSIDMVDSPQLATLADEVSASLAKQGL  352
seq_id_4   TDHGAEIVYKSPVVSGDTSPRHLSNVSSTGSIDMVDSPQLATLADEVSASLAKQGL  412
seq_id_6   TDHGAEIVYKSPVVSGDTSPRHLSNVSSTGSIDMVDSPQLATLADEVSASLAKQGL  776
seq_id_5   TDHGAEIVYKSPVVSGDTSPRHLSNVSSTGSIDMVDSPQLATLADEVSASLAKQGL  758
           *******************************************************
```

FIG. 9D

```
mouse  MADPRQEFDTMEDHAG--------DYTLLQDQEGDMDHGLKESPPQPPADDGAEEPG   49
rat    MAEPRQEFDTMEDQAG--------DYTMLQDQEGDMDHGLKESPPQPPADDGSEEPG   49
human  MAEPRQEFEVMEDHAGTVGLGDRKDQGGYTMHQDQEGDTDAGLKESPLQTPTEDGSEEPG  60
       *.********* ***.**        **:***************** ***:****:****

mouse  SETSDAKSTPTAEDVTAPLVDERAPDKQAAAQPHTEIPEGITAEEAGIGDTPNQEDQAAG  109
rat    SETSDAKSTPTAEDVTAPLVEERAPDKQATAQSHTEIPEGTTAEEAGIGDTPNMEDQAAG  109
human  SETSDAKSTPTAEDVTAPLVDEGAPGKQAAAQPHTEIPEGTTAEEAGIGDTPSLEDEAAG  120
       ********************:*  *:.:*** ******. :*** mouse  HVTQARVA--SKDRTGNDEKKAKGADGKTGAKIATPRGAASPAQKGTSNATRIPAKTTPS  167
rat    HVTQARVAGVSKDRTGNDEKKAKGADGKTGAKIATPRGAATPGQKGTSNATRIPAKTTPS  169
human  HVTQARMVSKSKDGTGSDDKKAKGADGKT--KIATPRGAAPPGQKGQANATRIPAKTPPA  178
       ******:.. *** **.*:*********   ********.* .***  :********.

mouse  PKTPPGSGEPPKSGERSGYSSPGSPGTPGSRSRTPSLPTPPTREPKKVAVVRTPPKSPSA  227
rat    PKTPPGSGEPPKSGERSGYSSPGSPGTPGSRSRTPSLPTPPTREPKKVAVVRTPPKSPSA  229
human  PKTPPSSGEPPKSGDRSGYSSPGSPGTPGSRSRTPSLPTPPTREPKKVAVVRTPPKSPSS  238
       *****.*******.:*********************************************:

mouse  SKSRLQTAPVPMPDLKNVRSKIGSTENLKHQPGGGKVQIINKKLD_SNVQSKCGSKDNIK  287
rat    SKSRLQTAPVPMPDLKNVRSKIGSTENLKHQPGGGKVQIINKKLD_SNVQSKCGSKDNIK  289
human  AKSRLQTAPVPMPDLKNVKSKIGSTENLKHQPGGGKVQIVNKKLD_SNVQSKCGSKDNIK  298
       :***************:***************::*************** mouse  HVPGGGSVQIVYKPVDLSKVTSKCGSLGNIHHKPGGGQVEVKSEK_DFKDRVQSKIGSLD  347
rat    HVPGGGSVQIVYKPVDLSKVTSKCGSLGNIHHKPGGGQVEVKSEK_DFKDRVQSKIGSLD  349
human  HVPGGGSVQIVYKPVDLSKVTSKCGSLGNIHHKPGGGQVEVKSEK_DFKDRVQSKIGSLD  358
       ************************************************************ mouse  NITHVPGGGNKKIETHKLTFRENAKAKTDHGAEIVYKSPVVSGDTSPRHLSNVSSTGSID  407
rat    NITHVPGGGNKKIETHKLTFRENAKAKIDHGAEIVYKSPVVSGDTSPRHLSNVSSTGSID  409
human  NITHVPGGGNKKIETHKLTFRENAKAKTDHGAEIVYKSPVVSGDTSPRHLSNVSSTGSID  418
       ************************:***************************** mouse  MVDSPQLATLADEVSASLAKQGL 430  (SEQ ID NO:8)
rat    MVDSPQLATLADEVSASLAKQGL 432  (SEQ ID NO:7)
human  MVDSPQLATLADEVSASLAKQGL 441  (SEQ ID NO:1)
       ***********************
```

FIG. 10

METHODS AND COMPOSITIONS FOR MODULATING TAU LEVELS

CROSS-REFERENCE

This application claims the benefit of U.S. Provisional Patent Application No. 61/258,822, filed Nov. 6, 2009, which application is incorporated herein by reference in its entirety.

BACKGROUND

Neurodegenerative diseases represent a heterogeneous group of genetic and acquired neurological disorders that result in severe and progressive cognitive and motor impairment with on-set during mid- to late-life. The most common cause of dementia is Alzheimer's disease. In less than 5% of the cases Alzheimer's disease genetic factors are involved, the rest of the cases are sporadic.

Tau protein is expressed in central nervous system and plays a critical role in the neuronal architecture by stabilizing intracellular microtubule network. Impairment of the physiological role of the tau protein either by truncation, hyperphosphorylation or by disturbing the balance between the six naturally occurring tau isoforms leads to the formation of neurofibrillary tangles (NFT), dystrophic neurites and neuropil threads. These structures represent ultrastructural hallmarks of Alzheimer's Disease (AD). The major protein subunit of these structures is microtubule associated protein Tau. The amount of NFT found in autopsies of AD patients correlates with clinical symptoms including intellectual decline. Therefore, Tau protein plays a critical role in AD pathology. The recent discovery of co-segregation of specific mutations in the Tau gene with the disease frontotemporal dementia with Parkinsonism linked to chromosome 17 (FTDP-17) has confirmed that certain abnormalities in the Tau protein can be a primary cause of neurodegeneration and dementia in affected individuals.

There is a need in the art for methods of treating tauopathies.

Literature

U.S. Patent Publication No. 2009/0117543; U.S. Patent Publication No. 2008/0194803; U.S. Patent Publication No. 2006/0025337.

SUMMARY OF THE INVENTION

Methods and agents for reducing a level of an acetylated Tau polypeptide in a cell are provided. Methods for treating a tauopathy in an individual are also provided. Also provided is a method for diagnosing a cognitive impairment disorder in an individual. Methods for identifying an agent suitable for treating a tauopathy are also provided.

BRIEF DESCRIPTION OF THE DRAWINGS

FIGS. 1A-G depicts in vitro and in vivo acetylation of Tau. FIG. 1B depicts SEQ ID NO:1.

FIGS. 2A-E depict acetylation of Tau by p300 acetyltransferase.

FIGS. 3A-I depict deacetylation of Tau by SIRT1, SIRT2, and HDAC6 in in vitro cell culture.

FIGS. 4A-F depict SIRT1-mediated reduction of Tau acetylation in in vitro neurons and in vivo. FIG. 4D depicts SEQ ID NO: 52.

FIGS. 6A-K depict the effect of acetylation on Tau turnover and Tau ubiquitination.

FIGS. 8A-D depict the effect of reduction of Tau acetylation on p-Tau.

FIGS. 9A-D depict an amino acid sequence alignment of human Tau isoform amino acid sequences.

FIG. 10 presents an amino acid sequence alignment of rat, mouse, and human Tau (isoform 2) amino acid sequences.

DEFINITIONS

Figures 1F, 1G:
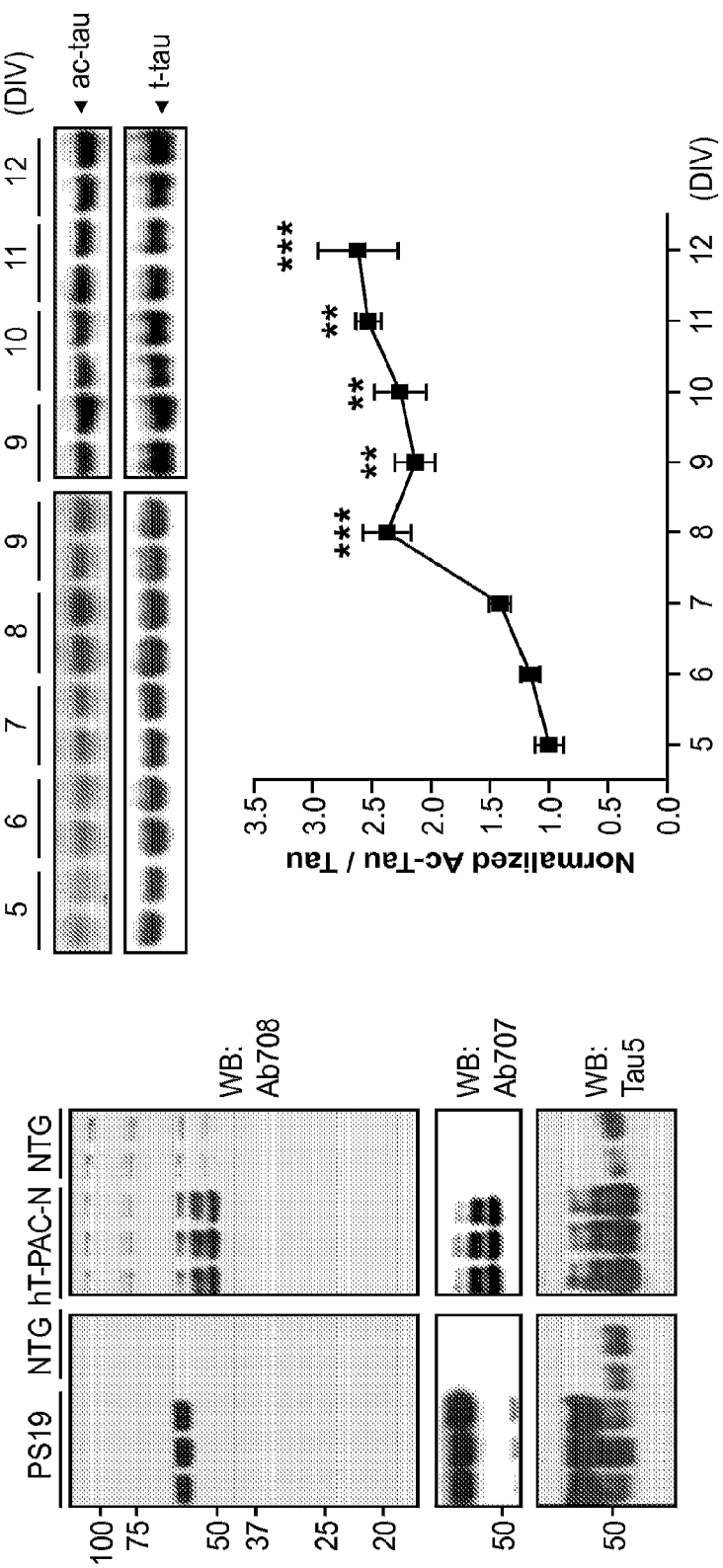

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment", as used herein, covers any treatment of a disease in a mammal, e.g., in a human, and includes: (a) preventing the disease from occurring in a subject which may be predisposed to the disease but has not yet been diagnosed as having it; (b) inhibiting the disease, i.e., arresting its development; and (c) relieving the disease, e.g., causing regression of the disease, e.g., to completely or partially remove symptoms of the disease.

The term "effective amount" or "therapeutically effective amount" means a dosage sufficient to provide for treatment for the disease state being treated or to otherwise provide the desired effect (e.g., induction of an effective immune response, reduction of chronic immune hyperactivity, etc.). The precise dosage will vary according to a variety of factors such as subject-dependent variables (e.g., weight, age, etc.), the disease, and the treatment being effected.

The terms "individual," "host," "subject," and "patient," used interchangeably herein, refer to a mammal, including, but not limited to, murines, lagomorphs, non-human primates, humans, etc. In some embodiments, an individual is a human. In some embodiments, an individual is a rodent (e.g., a mouse, a rat, etc.) or a lagomorph.

A "pharmaceutically acceptable excipient," "pharmaceutically acceptable diluent," "pharmaceutically acceptable carrier," and "pharmaceutically acceptable adjuvant" means an excipient, diluent, carrier, and adjuvant that are useful in preparing a pharmaceutical composition that are generally safe, non-toxic and neither biologically nor otherwise undesirable, and include an excipient, diluent, carrier, and adjuvant that are acceptable for veterinary use as well as human pharmaceutical use. "A pharmaceutically acceptable excipient, diluent, carrier and adjuvant" as used in the specification and claims includes one and more than one such excipient, diluent, carrier, and adjuvant.

As used herein, a "pharmaceutical composition" is meant to encompass a composition suitable for administration to a subject, such as a mammal, e.g., a human. In general a "pharmaceutical composition" is sterile, and is free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intratracheal and the like. In some embodiments the composition is suitable for administration by a transdermal route, using a penetration enhancer other than dimethylsulfoxide (DMSO). In other embodiments, the pharmaceutical compositions are suitable for administration by a route other than transdermal administration. A pharmaceutical composition will in some embodiments include a compound and a pharmaceutically acceptable excipient. In some embodiments, a pharmaceutically acceptable excipient is other than DMSO.

As used herein, "pharmaceutically acceptable derivatives" of a compound of the invention include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and are either pharmaceutically active or are prodrugs.

A "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a Tau polypeptide" includes a plurality of Tau polypeptides and reference to "the agent" includes reference to one or more agents and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

Methods and agents for reducing a level of an acetylated Tau polypeptide in a cell are provided. Methods for treating a tauopathy in an individual are also provided. Also provided is a method for diagnosing a cognitive impairment disorder in an individual. Methods for identifying an agent suitable for treating a tauopathy are also provided.

The following observations were made: 1) Tau is acetylated; 2) acetylation of Tau is increased in early-stage Alzheimer's Disease (e.g., mild cognitive impairment) patients; 3) acetylation of Tau precedes phosphorylation of Tau in disease; 4) Tau is deacetylated by a histone deacetylase (e.g., SIRT1, SIRT2, HDAC6); and 5) Tau is acetylated by a histone acetyltransferase (e.g., p300). Agents that inhibit acetylation of Tau, and agents that deacetylated acetylated Tau, are suitable for reducing the level of acetylated Tau in a cell that produces Tau, e.g., in a neuron or a glial cell. Such agents are useful for treating a tauopathy in an individual.

The level of acetylated Tau can provide a diagnostic measure for a cognitive impairment disorder, and can serve as a marker for response to treatment for a tauopathy. Antibodies specific for acetylated Tau are thus useful in various diagnostic assays, which are provided.

Identification of candidate agents for use in the treatment of a tauopathy can be carried out by identifying an agent that increases deacetylation of acetylated Tau, or by identifying an agent that inhibits acetylation of Tau. The present disclosure thus provides methods for identifying an agent suitable for treating a tauopathy.

Methods of Reducing the Level of Acetylated Tau Polypeptide in a Neuronal Cell

The present disclosure provides a method for reducing the level of an acetylated Tau (Ac-Tau) polypeptide in a cell (e.g., a cell that normally produces Tau, e.g., a neuron or a glial cell). The method generally involves contacting a cell (e.g., a neuronal cell or a glial cell) with an agent that reduces the level of Ac-Tau polypeptide in the cell, e.g., an agent that increases the activity of a polypeptide that deacetylates an Ac-Tau polypeptide in the cell; an agent that decreases the activity of a polypeptide that acetylates a Tau polypeptide in the cell; etc. The present disclosure provides a method for treating a tauopathy in an individual. The method comprising administering to an individual in need thereof an effective amount of an agent that reduces the level of Ac-Tau in a cell (e.g., a neuronal cell or a glial cell) in the individual.

Tau amino acid sequences are known in the art. See, e.g., the amino acid sequences found under the GenBank accession numbers in parentheses in the following: Human Tau transcript variant 1 mRNA (NM_016835.3) and isoform 1 protein (NP_058519.2); human Tau transcript variant 2 mRNA (NM_005910.4) and isoform 2 protein (NP_005901.2); human Tau transcript variant 3 mRNA (NM_016834.3) and isoform 3 protein (NP_058518.1); human Tau transcript variant 4 mRNA (NM_016841.3) and isoform 4 protein (NP_058525.1); human Tau transcript variant 5 mRNA (NM_001123067.2) and isoform 5 protein (NP_001116539.1); and human Tau transcript variant 6 mRNA (NM_001123066.2) and isoform 6 protein (NP_001116538.1).

Exemplary Tau amino acid sequences are depicted in FIGS. 9A-D (SEQ ID NOs:1-6, respectively), where the sequences in FIGS. 9A-D are: *Homo sapiens* Tau isoform 2 (GenBank Accession No. NP_005901; SEQ ID NO:1); *Homo sapiens* Tau isoform 3 (GenBank Accession No. NP_058518; SEQ ID NO:2); *Homo sapiens* Tau isoform 4 (GenBank Accession No. NP_058525; SEQ ID NO:3); *Homo sapiens* Tau isoform 5 (GenBank Accession No. NP_001116539; SEQ ID NO:4); *Homo sapiens* Tau isoform 1 (GenBank Accession No. NP_058519; SEQ ID NO:5); and *Homo sapiens* Tau isoform 6 (GenBank Accession No. NP_001116538; SEQ ID NO:6). The amino acid sequences set forth in SEQ ID NOs:1-6 are aligned in FIGS. 9A-D.

FIG. 10 depicts an amino acid sequence alignment of human Tau isoform 1 (SEQ ID NO:1), rat Tau (SEQ ID NO:7), and mouse Tau (SEQ ID NO:8).

A Tau polypeptide can comprise an amino acid sequence having at least about 75%, at least about 80%, at least about 85%, at least about 90%, at least about 95%, at least about 98%, at least about 99%, or 100%, amino acid sequence identity to a contiguous stretch of about 350 amino acids of any one of the amino acid sequences set forth in SEQ ID NOs:1-6. A Tau polypeptide can comprise an amino acid sequence having at least about 75%, at least about 80%, at least about 85%, at least about 90%, at least about 95%, at least about 98%, at least about 99%, or 100%, amino acid sequence identity to a contiguous stretch of from about 350 amino acids to 383 amino acids of the amino acid sequence set forth in SEQ ID NO:2 (*Homo sapiens* Tau isoform 3). A Tau polypeptide can comprise an amino acid sequence having at least about 75%, at least about 80%, at least about 85%, at least about 90%, at least about 95%, at least about 98%, at least about 99%, or 100%, amino acid sequence identity to a contiguous stretch of from about 350 amino acids to about 412 amino acids of the amino acid sequence set forth in SEQ ID NO:4 (*Homo sapiens* Tau isoform 5). A Tau polypeptide can comprise an amino acid sequence having at least about 75%, at least about 80%, at least about 85%, at least about 90%, at least about 95%, at least about 98%, at least about 99%, or 100%, amino acid sequence identity to a contiguous stretch of from about 350 amino acids to about 400 amino acids, or from about 400 amino acids to about 441 amino acids, of the amino acid sequence set forth in SEQ ID NO:1 (*Homo sapiens* Tau isoform 2). A Tau polypeptide can comprise an amino acid sequence having at least about 75%, at least about 80%, at least about 85%, at least about 90%, at least about 95%, at least about 98%, at least about 99%, or 100%, amino acid sequence identity to a contiguous stretch of from about 350 amino acids to about 400 amino acids, from about 400 amino acids to about 500 amino acids, from about 500 amino acids to about 600 amino acids, from about 600 amino acids to about 700 amino acids, or from about 700 amino acids to about 758 amino acids, of the amino acid sequence set forth in SEQ ID NO:5 (*Homo sapiens* Tau isoform 1). A Tau polypeptide can comprise an amino acid sequence having at least about 75%, at least about 80%, at least about 85%, at least about 90%, at least about 95%, at least about 98%, at least about 99%, or 100%, amino acid sequence identity to a contiguous stretch of from about 350 amino acids to about 400 amino acids, from about 400 amino acids to about 500 amino acids, from about 500 amino acids to about 600 amino acids, from about 600 amino acids to about 700 amino acids, or from about 700 amino acids to about 776 amino acids, of the amino acid sequence set forth in SEQ ID NO:6 (*Homo sapiens* Tau isoform 6).

FIG. 1B provides an amino acid sequence of a Tau isoform 2 polypeptide (SEQ ID NO:1). Tubulin binding regions of the amino acid sequence set forth in SEQ ID NO:1 and shown in FIG. 1B include amino acids 243-274, amino acids 275-305, and amino acids 337-368. Corresponding tubulin binding regions in other Tau polypeptides can be readily determined experimentally, or by examining the amino acid sequence alignment presented in FIGS. 12A-D.

Possible phosphorylation sites of a Tau isoform 2 polypeptide (e.g., as depicted in FIG. 1B and as set forth in SEQ ID NO:1) include the following amino acids: 46, 50, 69, 111, 123, 153, 175, 181, 195, 198, 199, 202, 205, 208, 210, 212, 214, 217, 231, 235, 237, 238, 258, 262, 293, 305, 320, 324, 352, 356, 373, 394, 396, 400, 404, 409, 412, 413, 416, and 422. For example, one or more of serine residues 46, 199, 202, 235, 262, 396, 404, and 422 and/or one or more of threonine residues 50, 69, 111, 153, 175, 181, 205, 212, 217, and 231 of a Tau polypeptide can be phosphorylated. Corresponding phosphorylation sites in other Tau polypeptides can be readily determined experimentally, or by examining the amino acid sequence alignment presented in FIGS. 9A-D and FIG. 10.

A Tau polypeptide can have a length of from about 350 amino acids to about 780 amino acids, e.g., from about 350 amino acids to about 385 amino acids, from about 385 amino acids to about 415 amino acids, from about 415 amino acids to about 445 amino acids, from about 445 amino acids to about 760 amino acids, or from about 760 amino acids to about 780 amino acids. In some embodiments, a Tau polypeptide has a length of 352 amino acids, 383 amino acids, 412 amino acids, 441 amino acids, 758 amino acids, or 776 amino acids.

A number of Lysine (Lys) residues on a Tau polypeptide can be acetylated. For example, a Tau isoform 2 can be acetylated at one or more amino acids, including but not limited to, Lys-163, Lys-174, Lys-180, Lys-190, Lys-267, Lys-274, Lys-281, Lys-369, and Lys-385 (e.g., of the amino acid sequence depicted in FIG. 1B and as set forth in SEQ ID NO:1). Corresponding acetylation sites in other Tau polypeptides can be readily determined experimentally (e.g., as described in the Examples), or by examining the amino acid sequence alignment presented in FIGS. 9A-D. For example, as shown in FIGS. 9A-D, Lys-163 of Tau isoform 2 corresponds to amino acid 105 of Tau isoform 3, amino acid 105 of Tau isoform 4, amino acid 134 of Tau isoform 5, amino acid 480 of Tau isoform 6, and amino acid 580 of Tau isoform 1.

In some embodiments, an acetylated Tau polypeptide is acetylated at two, three, four, five, six, seven, eight, or nine of Lys-163, Lys-174, Lys-180, Lys-190, Lys-267, Lys-274, Lys-281, Lys-369, and Lys-385 of a Tau isoform 2 polypeptide or corresponding lysine residues in a different Tau isoform. In some embodiments, an acetylated Tau polypeptide comprises acetylated Lys-163, acetylated Lys-174, and acetylated Lys-190 of a Tau isoform 2 polypeptide or corresponding lysine residues in a different Tau isoform. In some embodiments, an acetylated Tau polypeptide comprises acetylated Lys-163, acetylated Lys-174, acetylated Lys-180, acetylated Lys-190, acetylated Lys-267, acetylated Lys 274, acetylated Lys-281, acetylated Lys-369, and acetylated Lys-385 of a Tau isoform 2 polypeptide or corresponding lysine residues in a different Tau isoform.

An agent that decreases the level of acetylated Tau polypeptide in a cell that normally produces Tau (e.g., a neuronal cell; a glial cell) includes an agent that reduces the level of acetylated Tau polypeptide in the cell by at least about 10%, at least about 15%, at least about 20%, at least about 25%, at least about 30%, at least about 35%, at least about 40%, at least about 45%, at least about 50%, at least about 60%, at least about 70%, at least about 80%, or more than 80%, compared to the level of acetylated Tau polypeptide in the cell in the absence of the agent.

A decrease in the level of acetylated Tau polypeptide in a cell (e.g., in a cell that normally produces Tau, such as a neuron or a glial cell) can result in a decrease in the level of phosphorylated Tau and/or a decrease in the level of total Tau. Thus, in some embodiments, an agent that decreases the level of acetylated Tau polypeptide in a cell (e.g., in a cell that normally produces Tau, such as a neuron or a glial cell) also decreases the level of phosphorylated Tau polypeptide in the cell. An agent that decreases the level of acetylated Tau polypeptide in a cell that normally produces Tau (e.g., a neuronal cell; a glial cell) in some embodiments reduces the level of phosphorylated Tau in the cell by at least about 10%, at least about 15%, at least about 20%, at least about 25%, at least about 30%, at least about 35%, at least about 40%, at least about 45%, at least about 50%, at least about 60%, at least about 70%, at least about 80%, or more than 80%, compared to the level of phosphorylated Tau in the cell in the absence of the agent.

A decrease in the level of acetylated Tau polypeptide in a cell (e.g., in a cell that normally produces Tau, such as a neuron or a glial cell) can result in a decrease in total Tau levels. Thus, in some embodiments, an agent that decreases the level of acetylated Tau polypeptide in a cell (e.g., in a cell that normally produces Tau, such as a neuron or a glial cell) also decreases the level of total Tau polypeptide in the cell. An agent that decreases the level of acetylated Tau polypeptide in a cell that normally produces Tau (e.g., a neuronal cell; a glial cell) in some embodiments reduces the level of total Tau in the cell by at least about 10%, at least about 15%, at least about 20%, at least about 25%, at least about 30%, at least about 35%, at least about 40%, at least about 45%, at least about 50%, at least about 60%, at least about 70%, at least about 80%, or more than 80%, compared to the level of total Tau in the cell in the absence of the agent.

A decrease in the level of acetylated Tau polypeptide in a cell (e.g., in a cell that normally produces Tau, such as a neuron or a glial cell) can result in an increase in a biological activity of a Tau polypeptide. Thus, in some embodiments, an agent that decreases the level of acetylated Tau polypeptide in a cell (e.g., in a cell that normally produces Tau, such as a neuron or a glial cell) also increases a biological activity of Tau polypeptide in the cell. An agent that decreases the level of acetylated Tau polypeptide in a cell that normally produces Tau (e.g., a neuronal cell; a glial cell) in some embodiments increases the level of active Tau polypeptide in the cell by at least about 10%, at least about 15%, at least about 20%, at least about 25%, at least about 30%, at least about 35%, at least about 40%, at least about 45%, at least about 50%, at least about 60%, at least about 70%, at least about 80%, at least about 2-fold, at least about 2.5-fold, at least about 3-fold, at least about 5-fold, at least about 7-fold, at least about 10-fold, or more than 10-fold, compared to the level of active Tau polypeptide in the cell in the absence of the agent. Tau biological activity includes, e.g., stabilization of microtubules.

Agents that increase Tau Deacetylation

Agents that increase Tau deacetylation include agents that increase the activity of a polypeptide that deacetylates an acetylated Tau polypeptide. Polypeptides that deacetylate an acetylated Tau polypeptide include, e.g., a histone deacetylase, SIRT1, SIRT2, HDAC6, etc. Agents that increase the activity of a polypeptide that deacetylates an acetylated Tau polypeptide include, e.g., agents that increase the activity of one or more of SIRT1, SIRT2, and HDAC6. Agents that increase the activity of a polypeptide that deacetylates an acetylated Tau polypeptide also include agents that increase the protein levels of such a polypeptide, e.g., a nucleic acid comprising a nucleotide sequence encoding SIRT1, SIRT2, HDAC6, etc.

SIRT1

SIRT1 (also known as (silent mating type information regulation 2 homolog) 1 (S. cerevisiae)) gene encodes a member of the sirtuin family of proteins, homologs to the yeast Sir2 protein. Members of the sirtuin family are characterized by a sirtuin core domain and are grouped into four classes. The protein encoded by this gene is included in class I of the sirtuin family. Alternative splicing results in multiple transcript variants. Transcript variant 1 (NM_012238.4) represents the longer transcript and encodes the longer isoform a (NP_036370.2). Transcript variant 2 (NM_001142498.1) encodes isoform b (NP_001135970.1).

A SIRT1 polypeptide includes a polypeptide that deacetylates an acetylated Tau polypeptide in a cell that produces Tau (e.g., a neuronal cell and/or a glial cell), and that comprises an amino acid sequence having at least about 75%, at least about 80%, at least about 85%, at least about 90%, at least about 95%, at least about 98%, at least about 99%, or 100%, amino acid sequence identity to a contiguous stretch of from about 400 amino acids to about 450 amino acids, or from about 450 amino acids to about 555 amino acids, of the amino acid sequence set forth in SEQ ID NO:9 (GenBank AAH12499; *Homo sapiens* SIRT1). A SIRT1 polypeptide includes a polypeptide that deacetylates an acetylated Tau polypeptide in a cell that produces Tau (e.g., a neuronal cell and/or a glial cell), and that comprises an amino acid sequence having at least about 75%, at least about 80%, at least about 85%, at least about 90%, at least about 95%, at least about 98%, at least about 99%, or 100%, amino acid sequence identity to a contiguous stretch of from about 500 amino acids to about 600 amino acids, from about 600 amino acids to about 700 amino acids, or from about 700 amino acids to about 747 amino acids, of the amino acid sequence set forth in SEQ ID NO:10 (GenBank NP_036370; *Homo sapiens* SIRT1 isoform a). A SIRT1 polypeptide includes a polypeptide that deacetylates an acetylated Tau polypeptide in a cell that produces Tau (e.g., a neuronal cell and/or a glial cell), and that comprises an amino acid sequence having at least about 75%, at least about 80%, at least about 85%, at least about 90%, at least about 95%, at least about 98%, at least about 99%, or 100%, amino acid sequence identity to a contiguous stretch of from about 300 amino acids to about 400 amino acids, or from about 400 amino acids to about 452 amino acids, of the amino acid sequence set forth in SEQ ID NO:11 (GenBank NP_001135970; *Homo sapiens* SIRT1 isoform b).

SIRT1 Activators

A number of SIRT1 activators are known in the art. A suitable SIRT1 activator can increase the enzymatic activity of a SIRT1 polypeptide (e.g., the enzymatic activity of a SIRT1 polypeptide in deacetylating an acetylated Tau polypeptide in a neuron or a glial cell) by at least about 25%, at least about 50%, at least about 75%, at least about 2-fold, at least about 2.5-fold, at least about 5-fold, at least about 10-fold, at least about 20-fold, or more than 20-fold. In some embodiments, the SIRT1 activator is a SIRT1-selective activator.

A suitable SIRT1 activator can increase SIRT1 enzymatic activity at an $EC_{50}$ (half maximal effective concentration) of from about 1 nM to about 1 mM, e.g., from about 1 nM to about 10 nM, from about 10 nM to about 15 nM, from about 15 nM to about 25 nM, from about 25 nM to about 50 nM, from about 50 nM to about 75 nM, from about 75 nM to about 100 nM, from about 100 nM to about 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 450 nM, from about 450 nM to about 500 nM, from about 500 nM to about 750 nM, from about 750 nM to about 1 µM, from about 1 µM to about 10 µM, from about 10 µM to about 25 µM, from about 25 µM to about 50 µM, from about 50 µM to about 75 µM, from about 75 µM to about 100 µM, from about 100 µM to about 250 µM from about 250 µM to about 500 µM, or from about 500 µM to about 1 mM.

Examples of SIRT1 activators that are suitable for use in a subject method include, but are not limited to, resveratrol ((E)-5-(p-Hydroxystyryl)resorcinol (E)-5-(4-hydroxystyryl) benzene-1,3-diol); or 3,5,4'-trihydroxy-trans-stilbene); butein (3,4,2',4'-tetrahydroxychalcone); piceatannol (3,5,3', 4'-tetrahydroxy-trans-stilbene); isoliquiritigenin (4,2',4'-trihydroxychalcone); fisetin (3,7,3',4'-tetrahydroxyflavone); quercetin (3,5,7,3',4'-pentahydroxyflavone); a SIRT1 activator as described in U.S. Pat. No. 7,345,178; a SIRT1 activator as described in U.S. Patent Publication No. 2008/02555382; and a SIRT1 activator as described in U.S. Patent Publication No. 2009/0012080. Pharmaceutically acceptable salts of any of the foregoing SIRT1 activators are also suitable for use in a subject method.

For example, a suitable SIRT1 activator is a compound of any one of Formulas I-XXVIII as described in U.S. Pat. No. 7,345,178, where substituents are as described in U.S. Pat. No. 7,345,178, or a pharmaceutically acceptable salt of a compound of any one of Formulas I-XXVIII as described in U.S. Pat. No. 7,345,178, provided that the compound activates SIRT1 activity. For example, a suitable SIRT1 activator includes a compound shown in Table 4 of U.S. Pat. No. 7,345,178.

For example, suitable SIRT1 activators are shown in Table 1, below.

TABLE 1

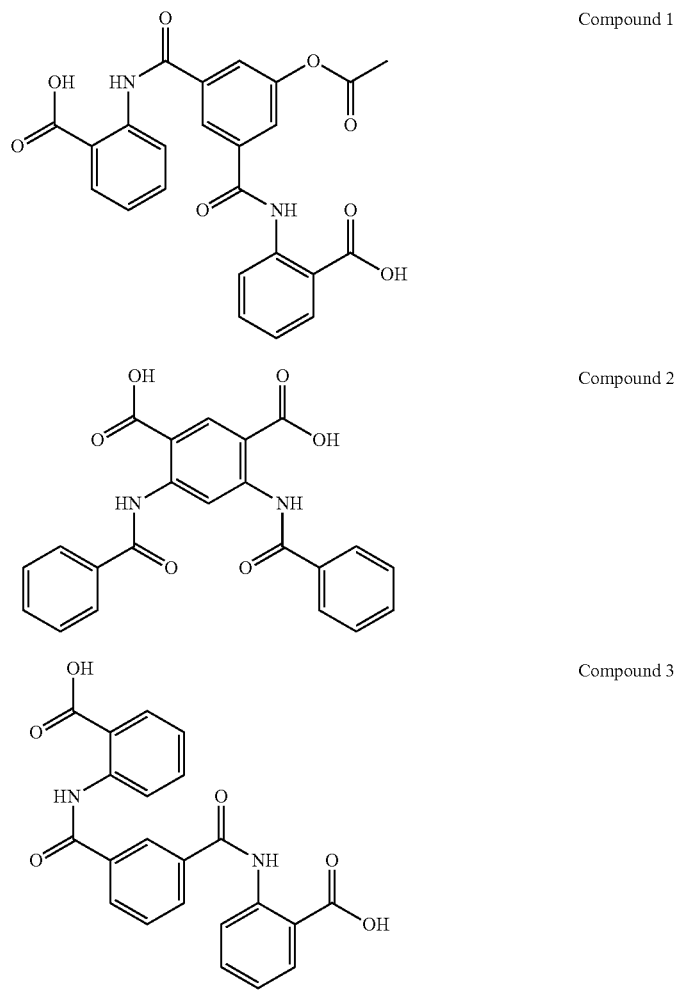

Compound 1

Compound 2

Compound 3

TABLE 1-continued
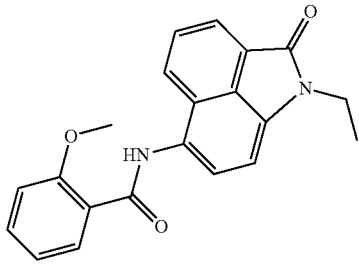 [SMILES: CCN1C(=O)c2cccc3c(NC(=O)c4ccccc4OC)ccc1c23]
Compound 4
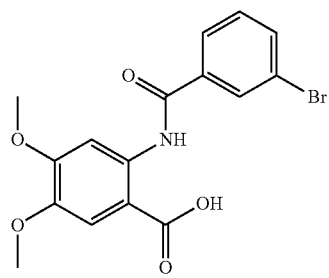 [SMILES: COc1cc(NC(=O)c2cccc(Br)c2)c(C(=O)O)cc1OC]
Compound 5
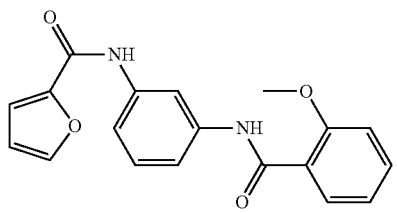 [SMILES: COc1ccccc1C(=O)Nc1cccc(NC(=O)c2ccco2)c1]
Compound 6
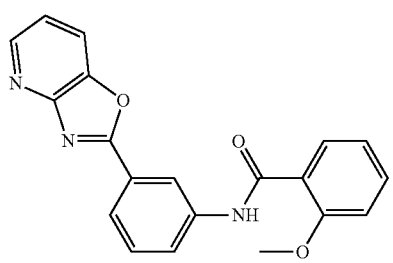 [SMILES: COc1ccccc1C(=O)Nc1cccc(-c2nc3ncccc3o2)c1]
Compound 7
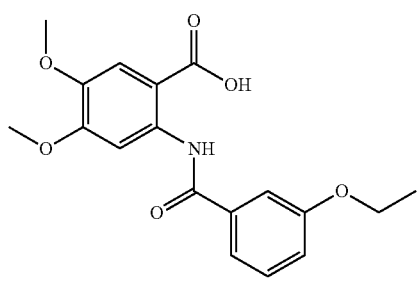 [SMILES: CCOc1cccc(C(=O)Nc2cc(OC)c(OC)cc2C(=O)O)c1]
Compound 8

TABLE 1-continued
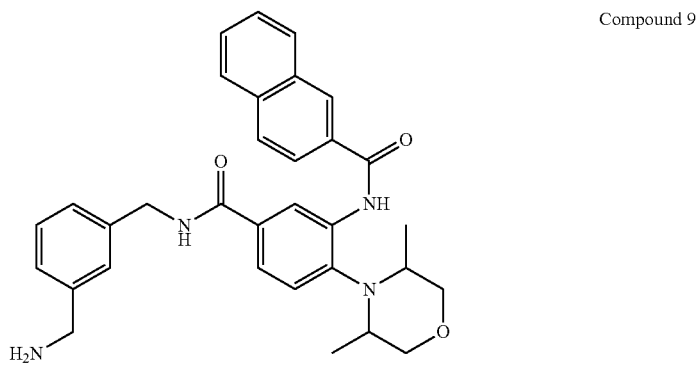
Compound 9
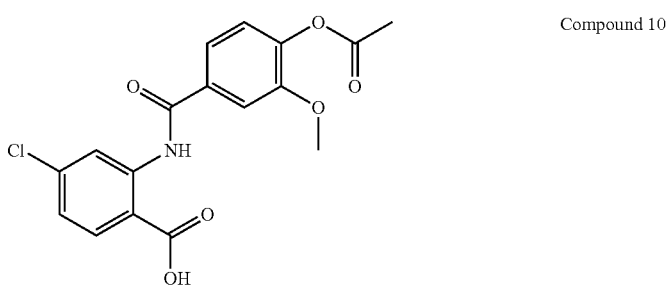
Compound 10
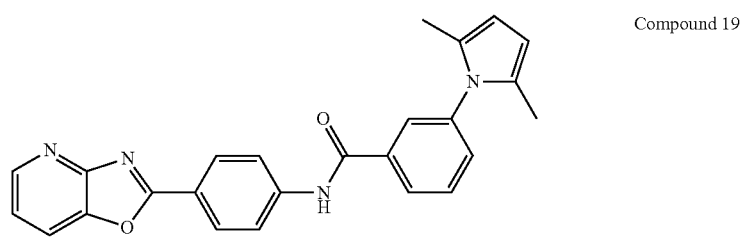
Compound 19
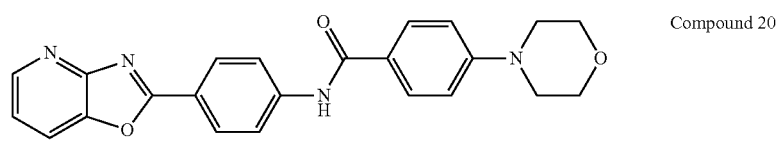
Compound 20
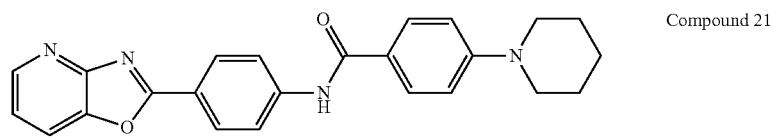
Compound 21
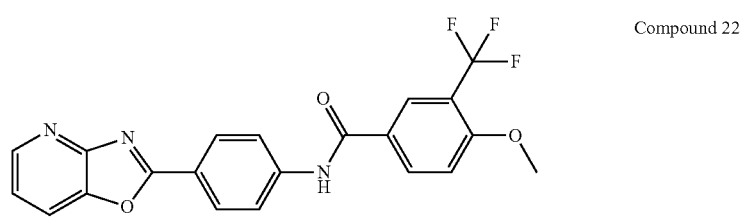
Compound 22
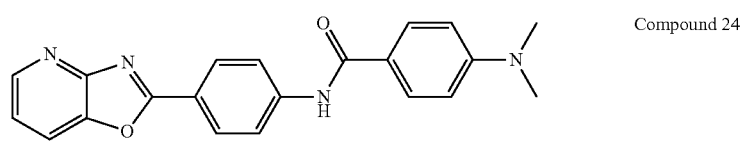
Compound 24

TABLE 1-continued
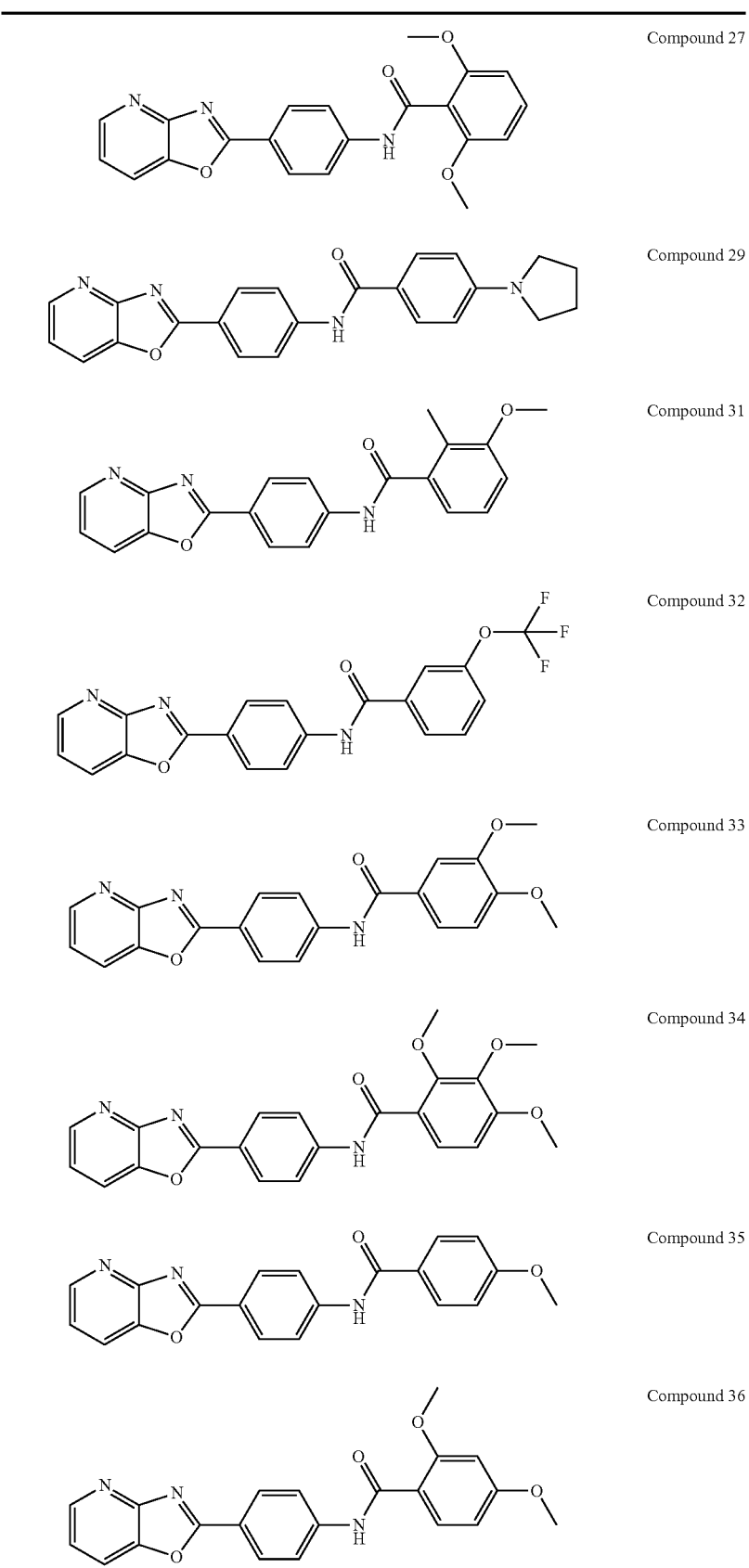

TABLE 1-continued
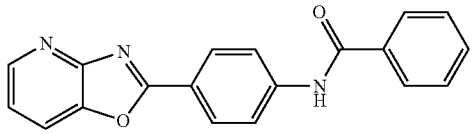 [SMILES: O=C(Nc1ccc(-c2nc3ncccc3o2)cc1)c1ccccc1] Compound 37
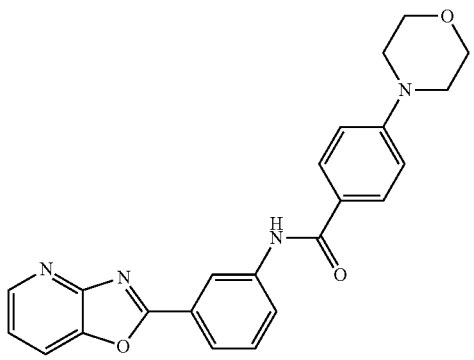 [SMILES: O=C(Nc1cccc(-c2nc3ncccc3o2)c1)c1ccc(N2CCOCC2)cc1] Compound 38
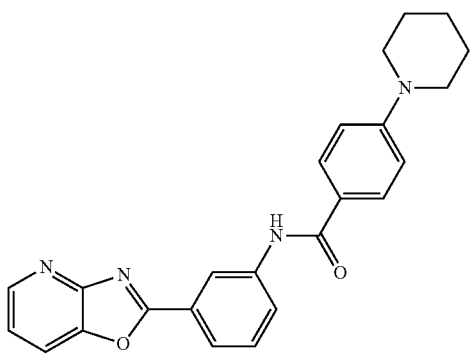 [SMILES: O=C(Nc1cccc(-c2nc3ncccc3o2)c1)c1ccc(N2CCCCC2)cc1] Compound 39
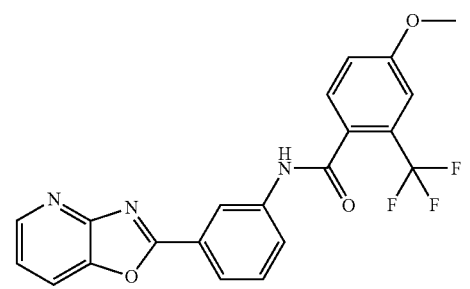 [SMILES: COc1ccc(C(=O)Nc2cccc(-c3nc4ncccc4o3)c2)c(C(F)(F)F)c1] Compound 40
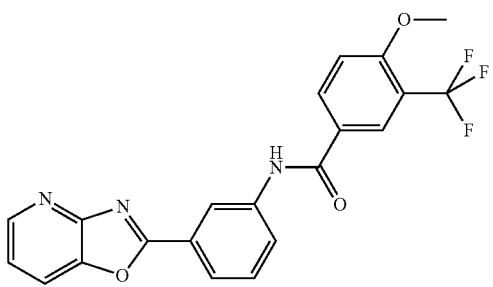 [SMILES: COc1ccc(C(=O)Nc2cccc(-c3nc4ncccc4o3)c2)cc1C(F)(F)F] Compound 41

TABLE 1-continued
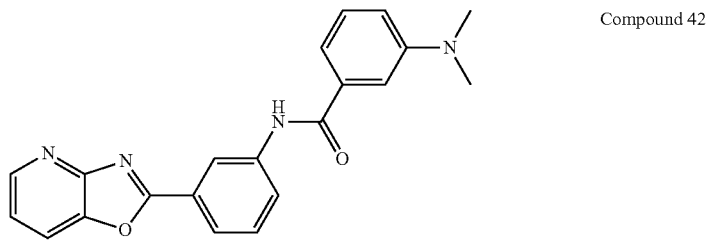
Compound 42
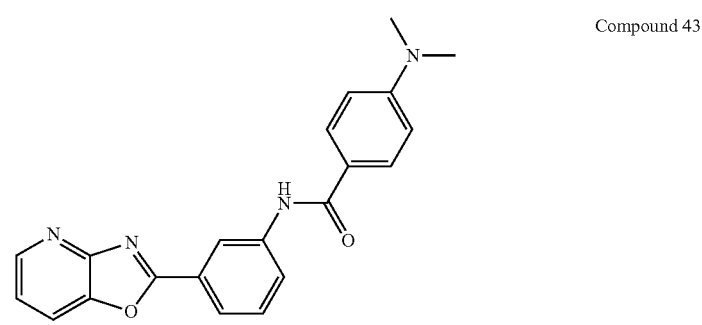
Compound 43
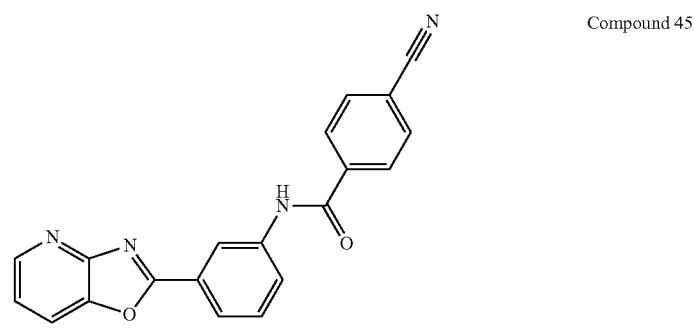
Compound 45
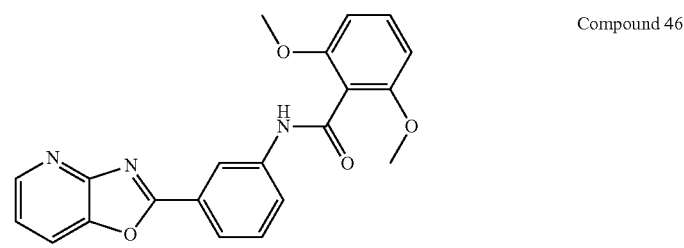
Compound 46
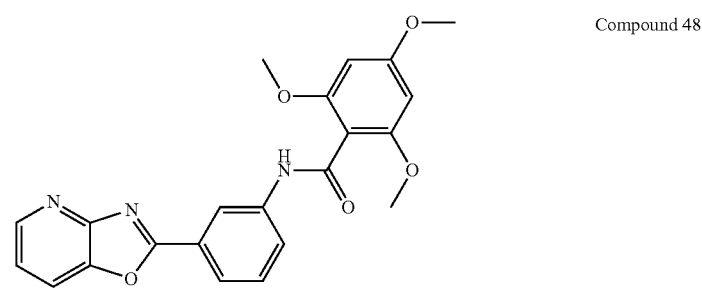
Compound 48

TABLE 1-continued
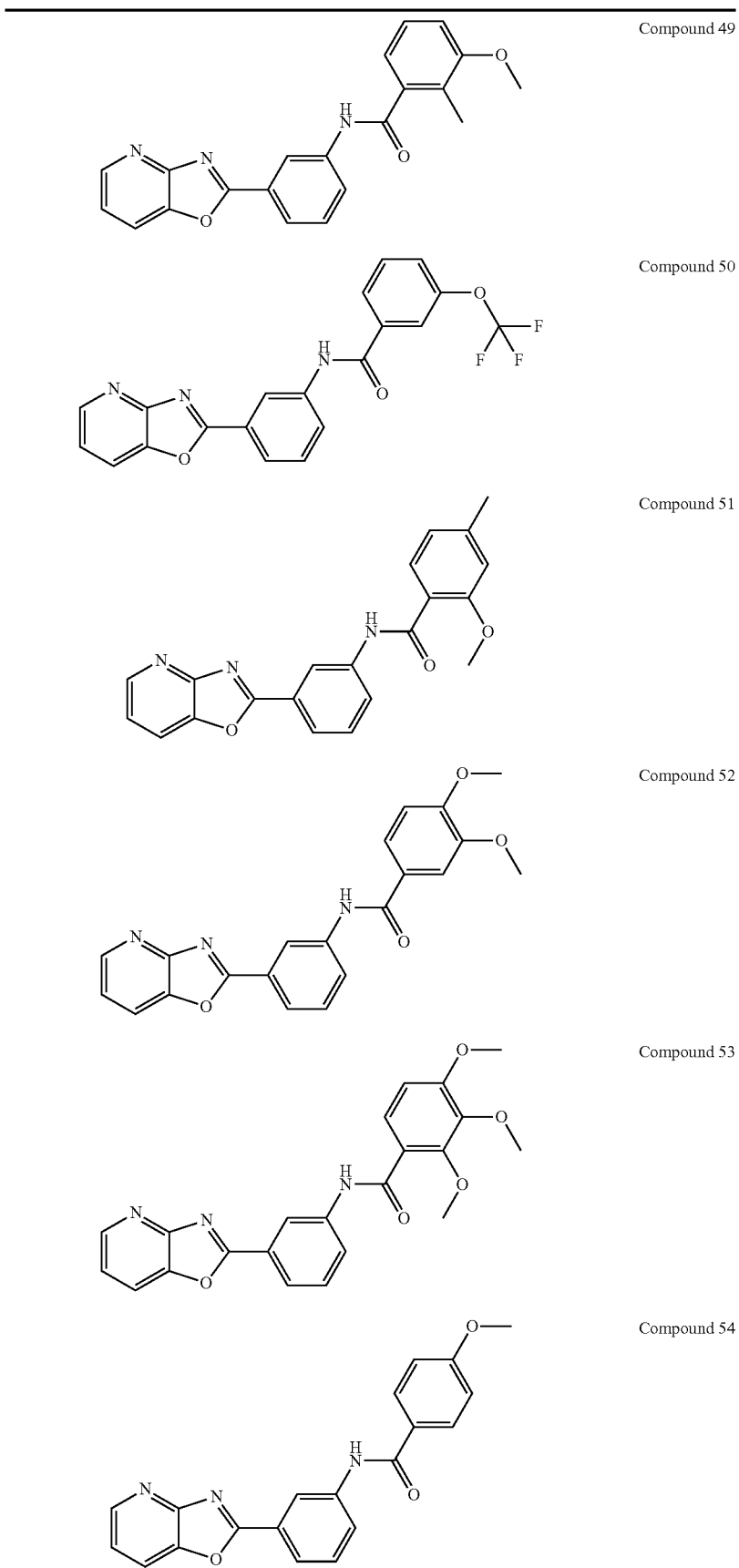
Compound 49
Compound 50
Compound 51
Compound 52
Compound 53
Compound 54

TABLE 1-continued
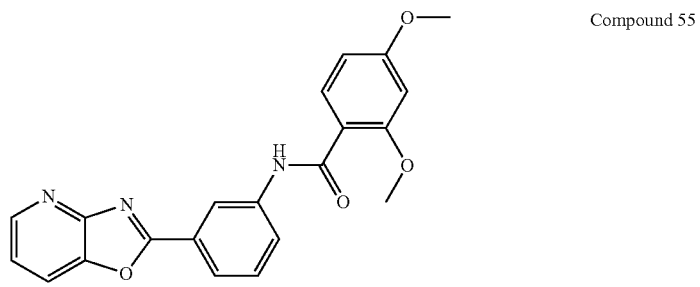
Compound 55
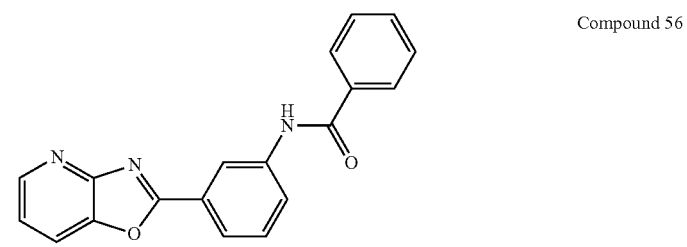
Compound 56
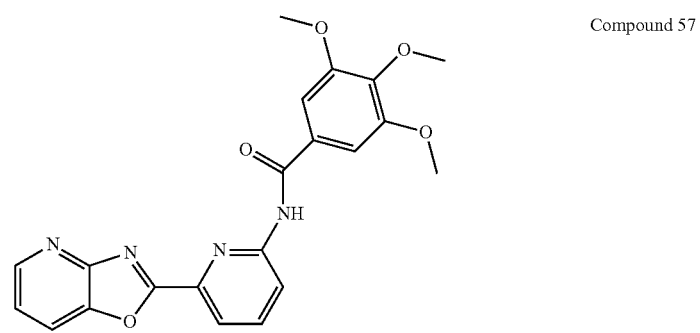
Compound 57
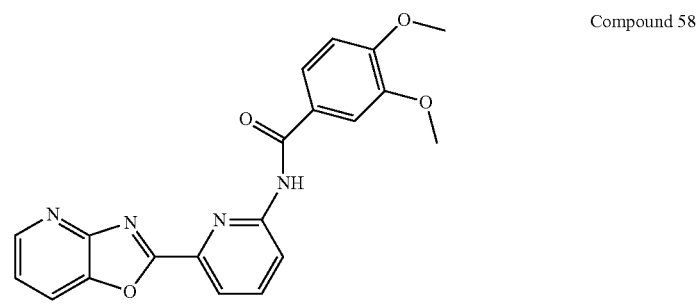
Compound 58
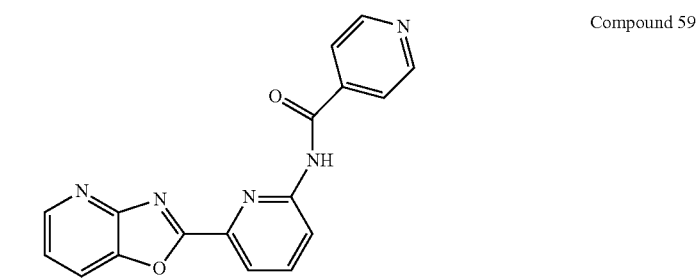
Compound 59

TABLE 1-continued
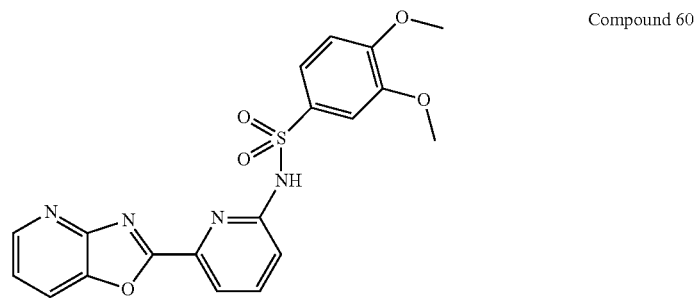
Compound 60
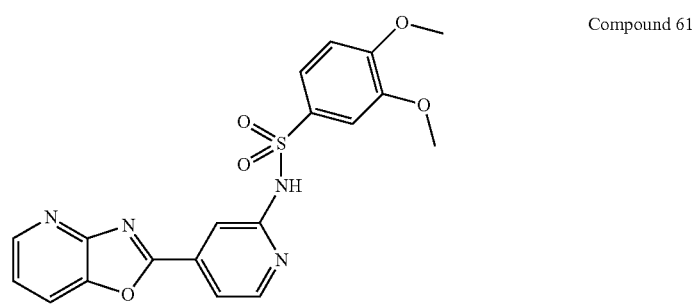
Compound 61
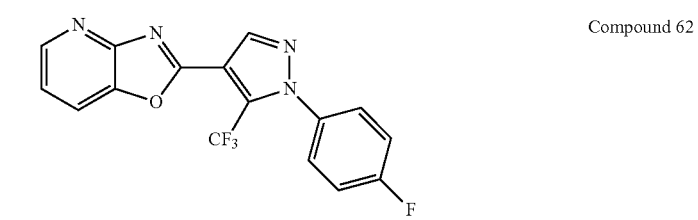
Compound 62
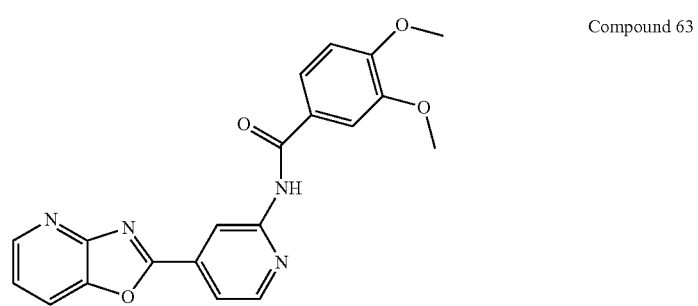
Compound 63
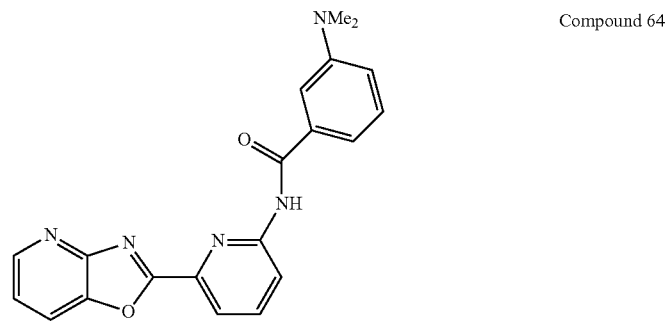
Compound 64

TABLE 1-continued
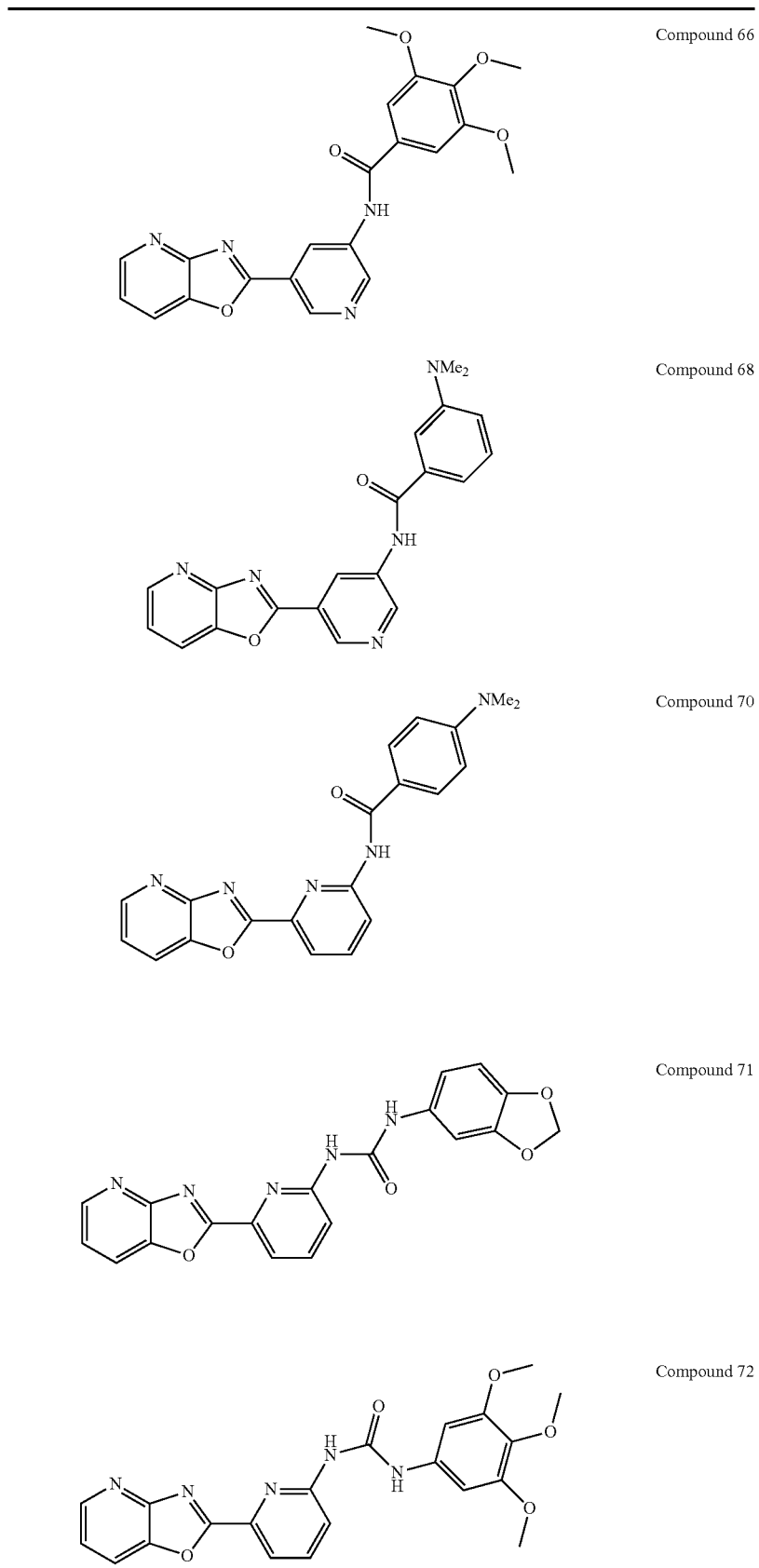

TABLE 1-continued
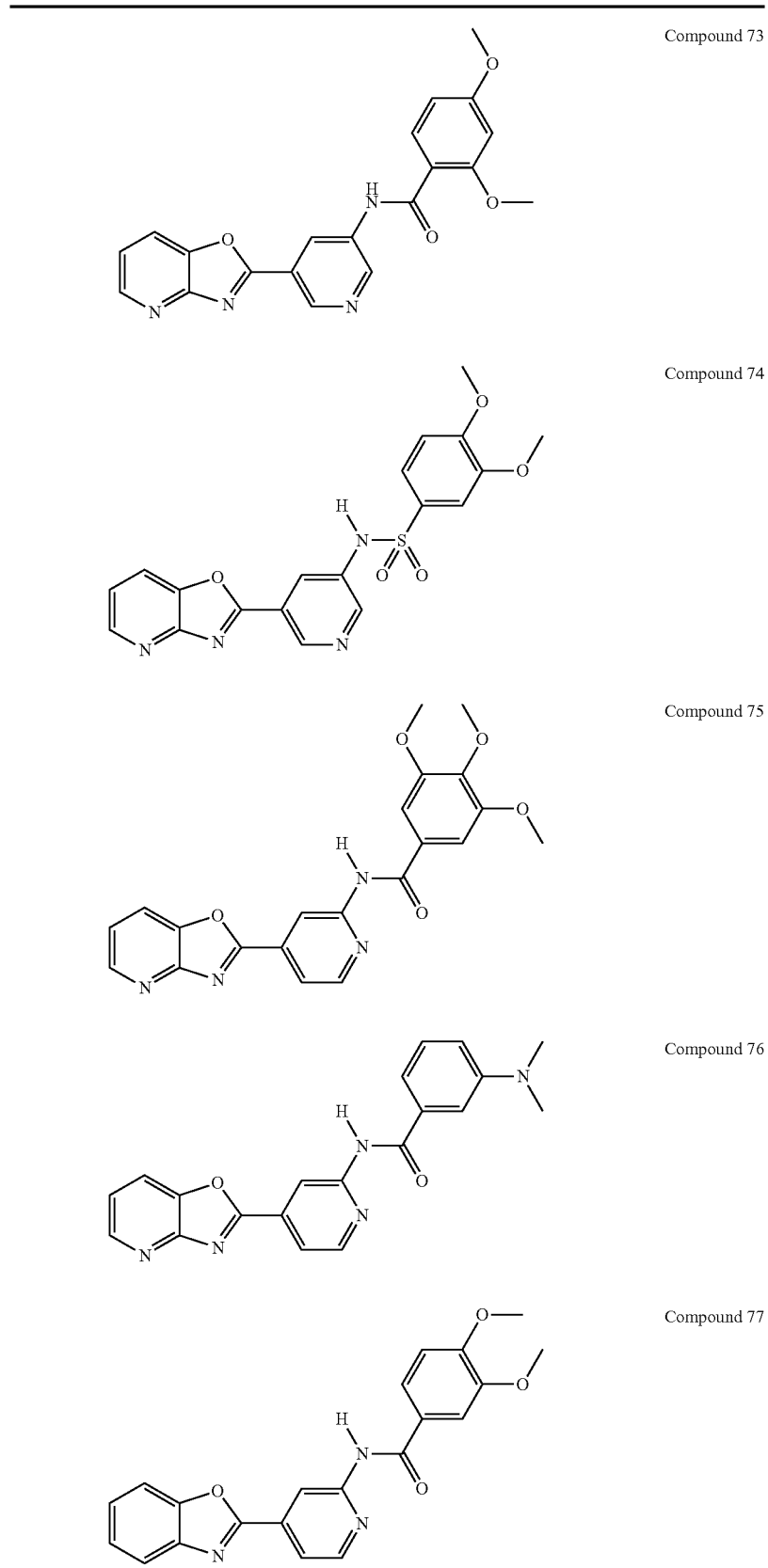
Compound 73
Compound 74
Compound 75
Compound 76
Compound 77

TABLE 1-continued
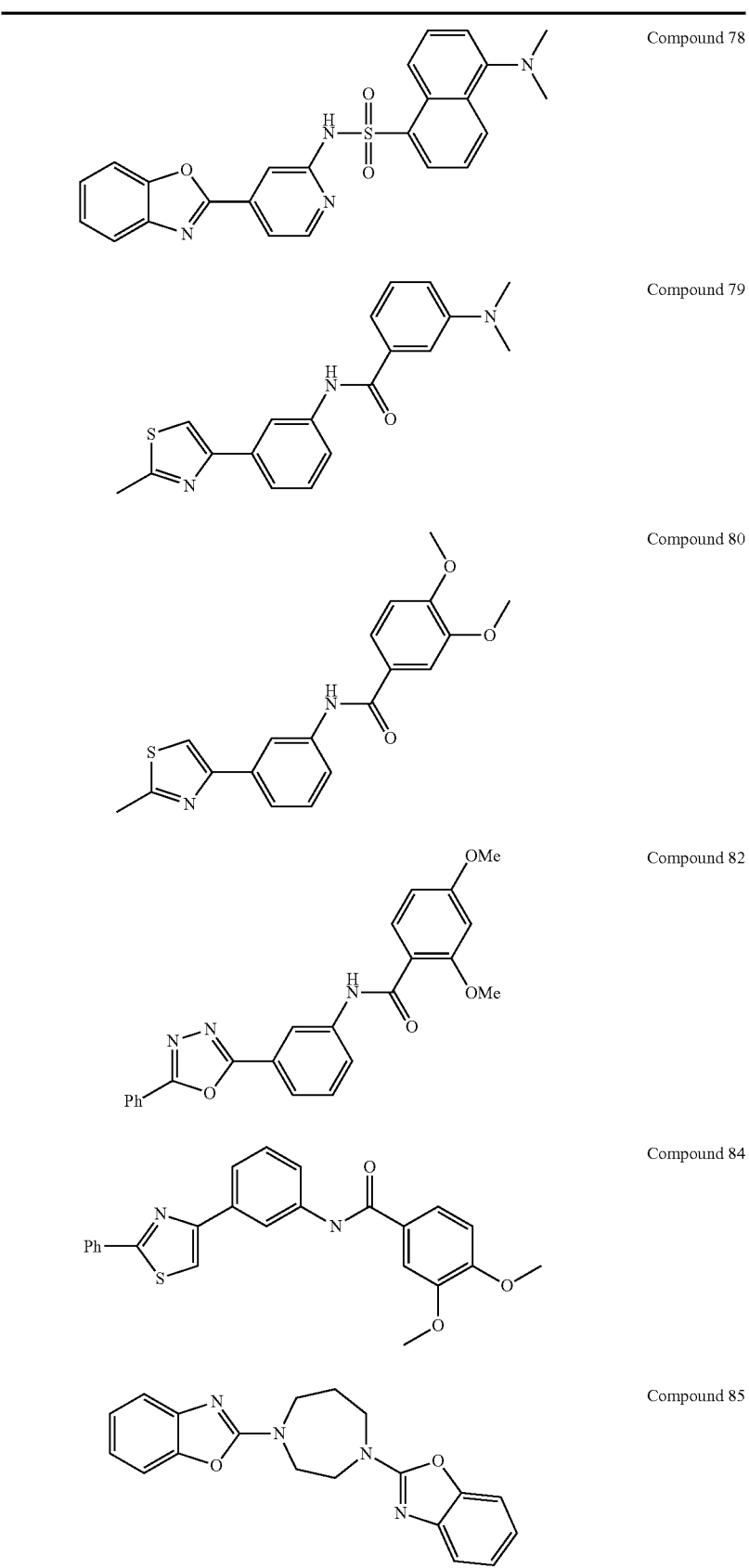
Compound 78
Compound 79
Compound 80
Compound 82
Compound 84
Compound 85

TABLE 1-continued
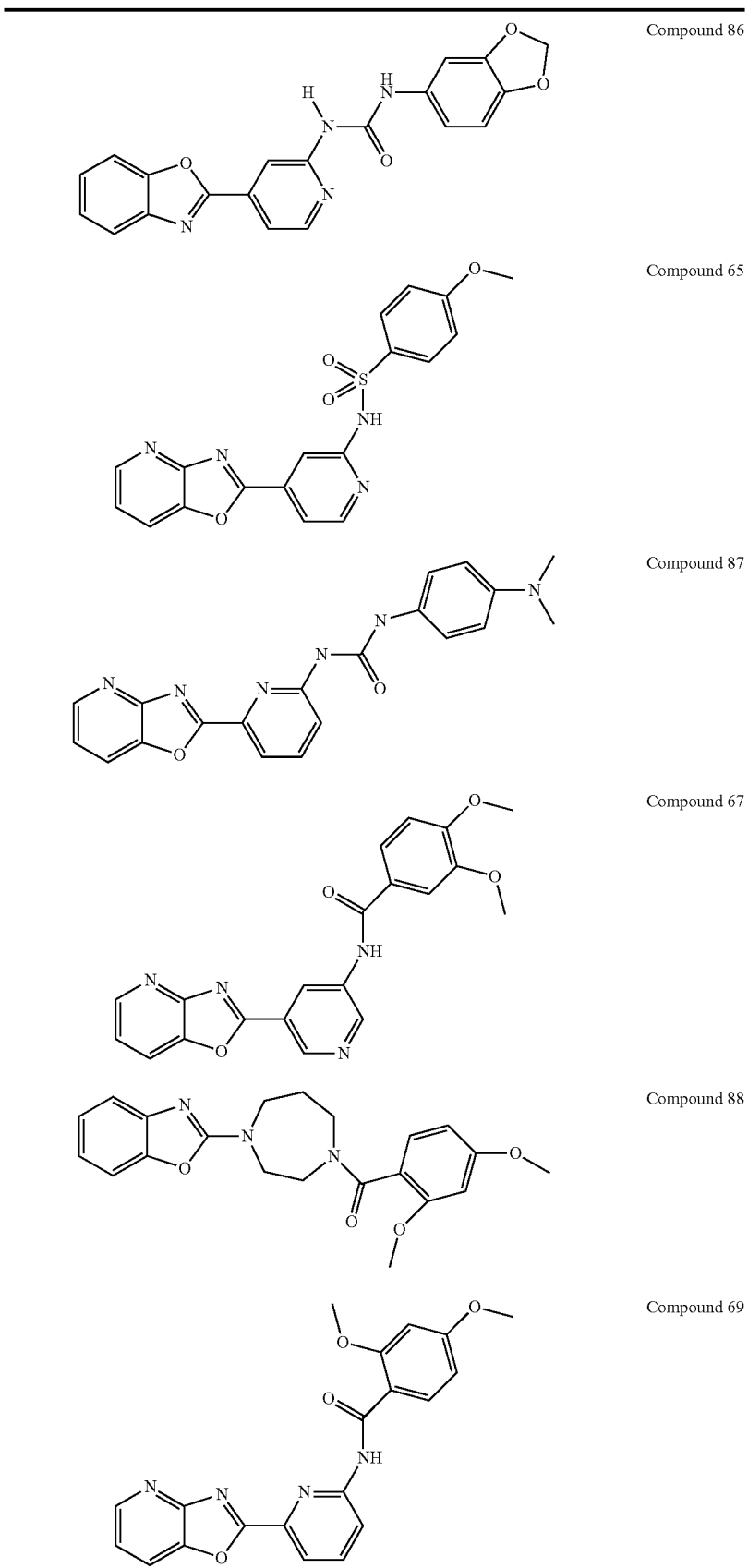
Compound 86
Compound 65
Compound 87
Compound 67
Compound 88
Compound 69

TABLE 1-continued
| | |
|---|---|
| 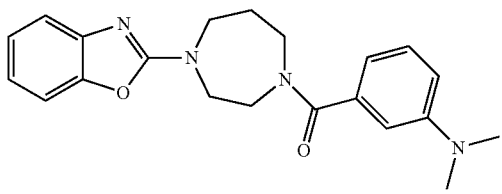 [SMILES: CN(C)c1cccc(C(=O)N2CCCN(c3nc4ccccc4o3)CC2)c1] | Compound 89 |
| 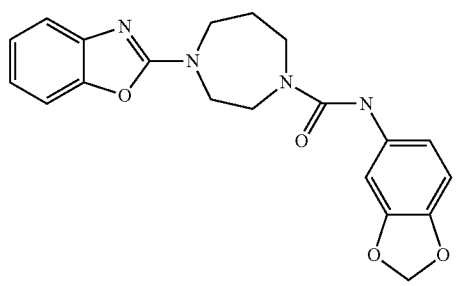 [SMILES: O=C(Nc1ccc2c(c1)OCO2)N1CCCN(c2nc3ccccc3o2)CC1] | Compound 90 |
| 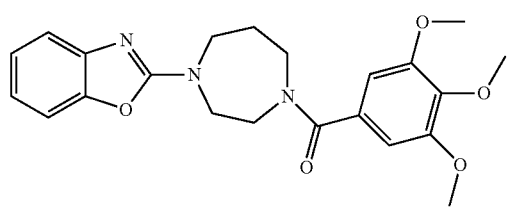 [SMILES: COc1cc(C(=O)N2CCCN(c3nc4ccccc4o3)CC2)cc(OC)c1OC] | Compound 91 |
| 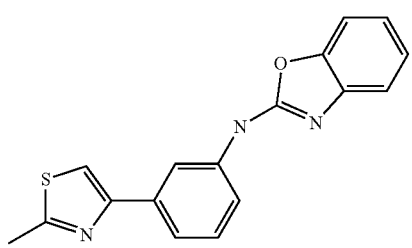 [SMILES: Cc1nc(-c2cccc(Nc3nc4ccccc4o3)c2)cs1] | Compound 92 |
| 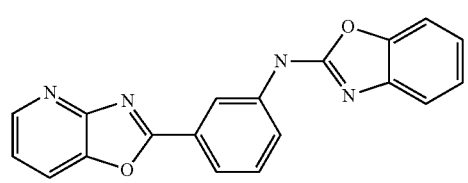 [SMILES: c1cc(Nc2nc3ccccc3o2)cc(-c2nc3ncccc3o2)c1] | Compound 93 |
| 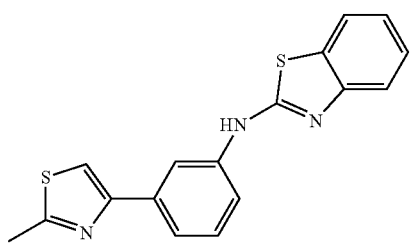 | Compound 94 |
| 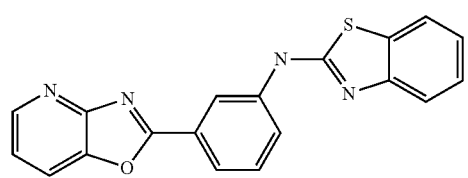 [SMILES: c1cc(Nc2nc3ccccc3s2)cc(-c2nc3ncccc3o2)c1] | Compound 95 |

TABLE 1-continued
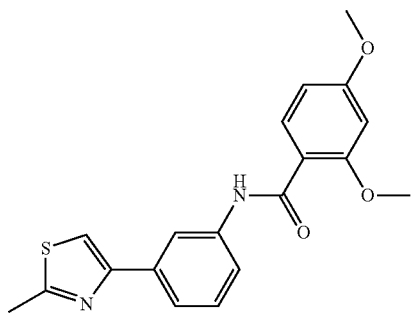
Compound 81
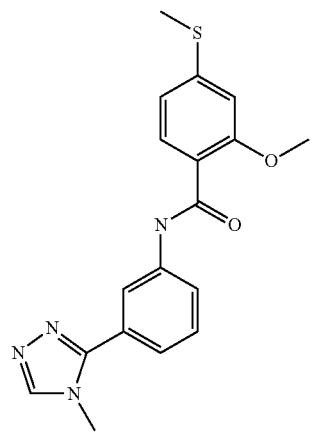 [SMILES: COc1cc(SC)ccc1C(=O)Nc1cccc(-c2nncn2C)c1]
Compound 83
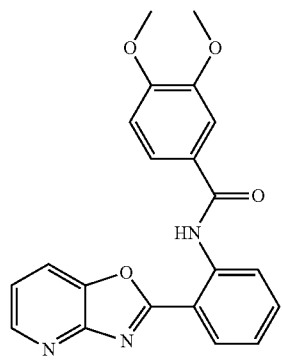 [SMILES: COc1ccc(C(=O)Nc2ccccc2-c2nc3ncccc3o2)cc1OC]
Compound 96
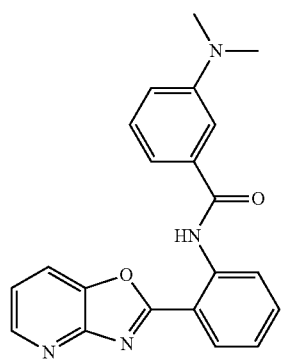 [SMILES: CN(C)c1cccc(C(=O)Nc2ccccc2-c2nc3ncccc3o2)c1]
Compound 97

TABLE 1-continued
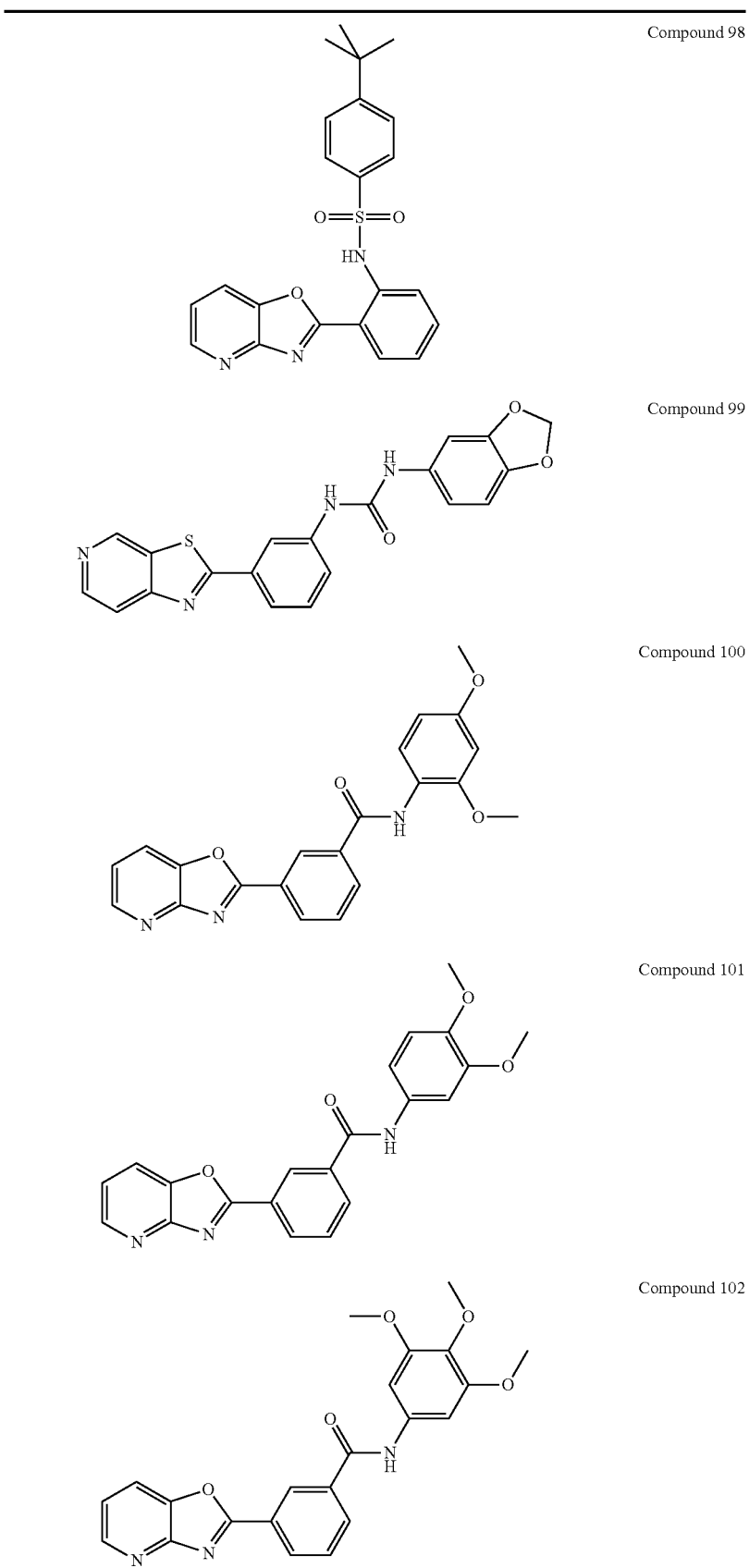
Compound 98
Compound 99
Compound 100
Compound 101
Compound 102

TABLE 1-continued
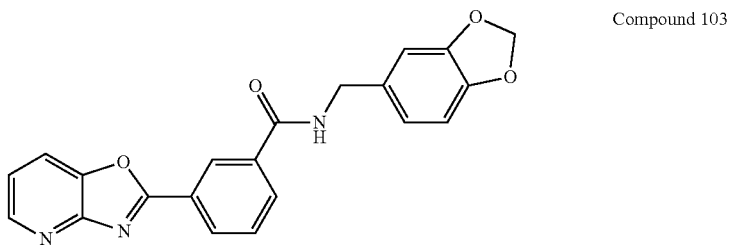
Compound 103
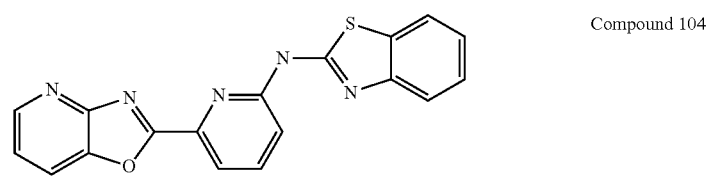
Compound 104
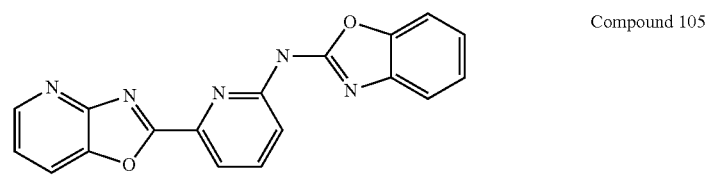
Compound 105
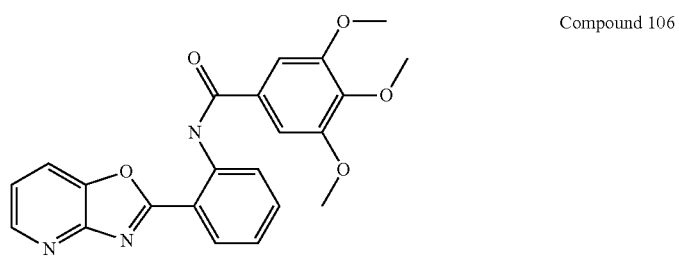
Compound 106
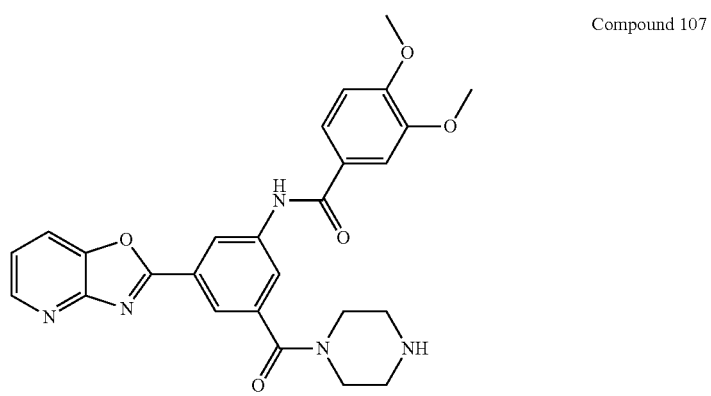
Compound 107
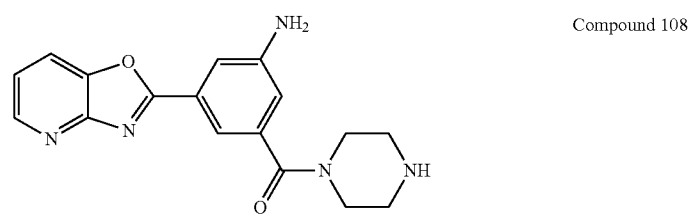
Compound 108

TABLE 1-continued
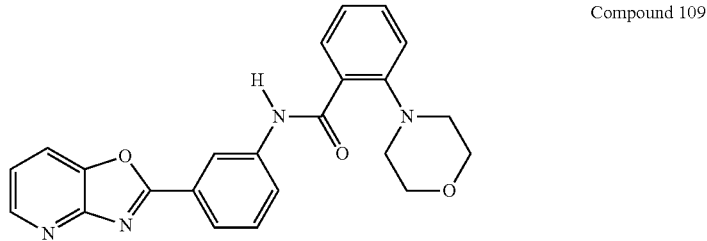
Compound 109
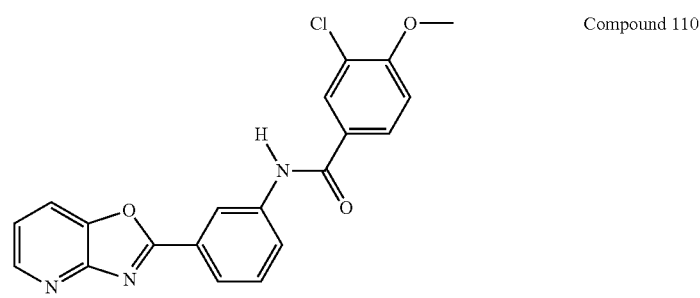
Compound 110
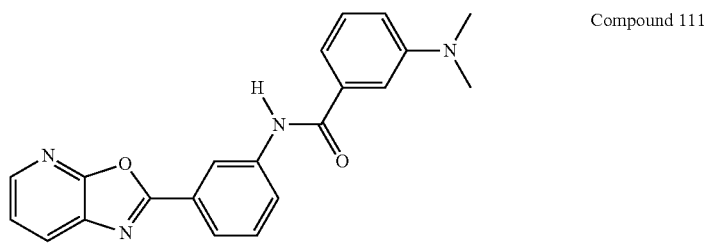
Compound 111
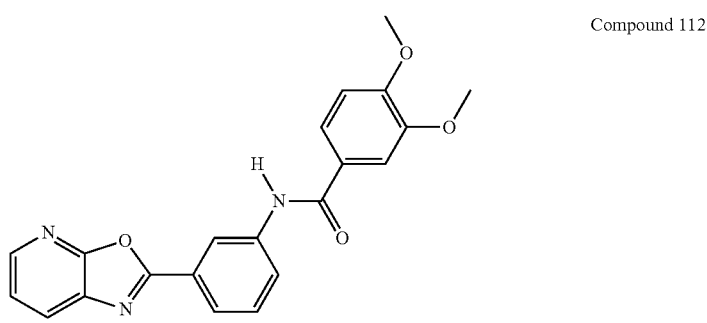
Compound 112
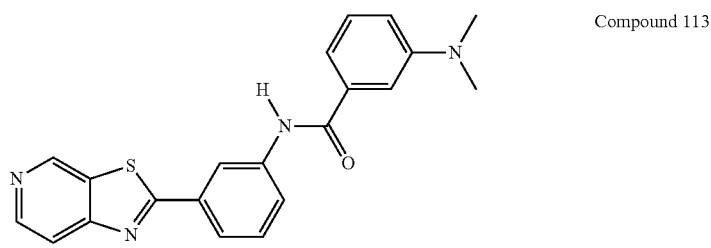
Compound 113

TABLE 1-continued
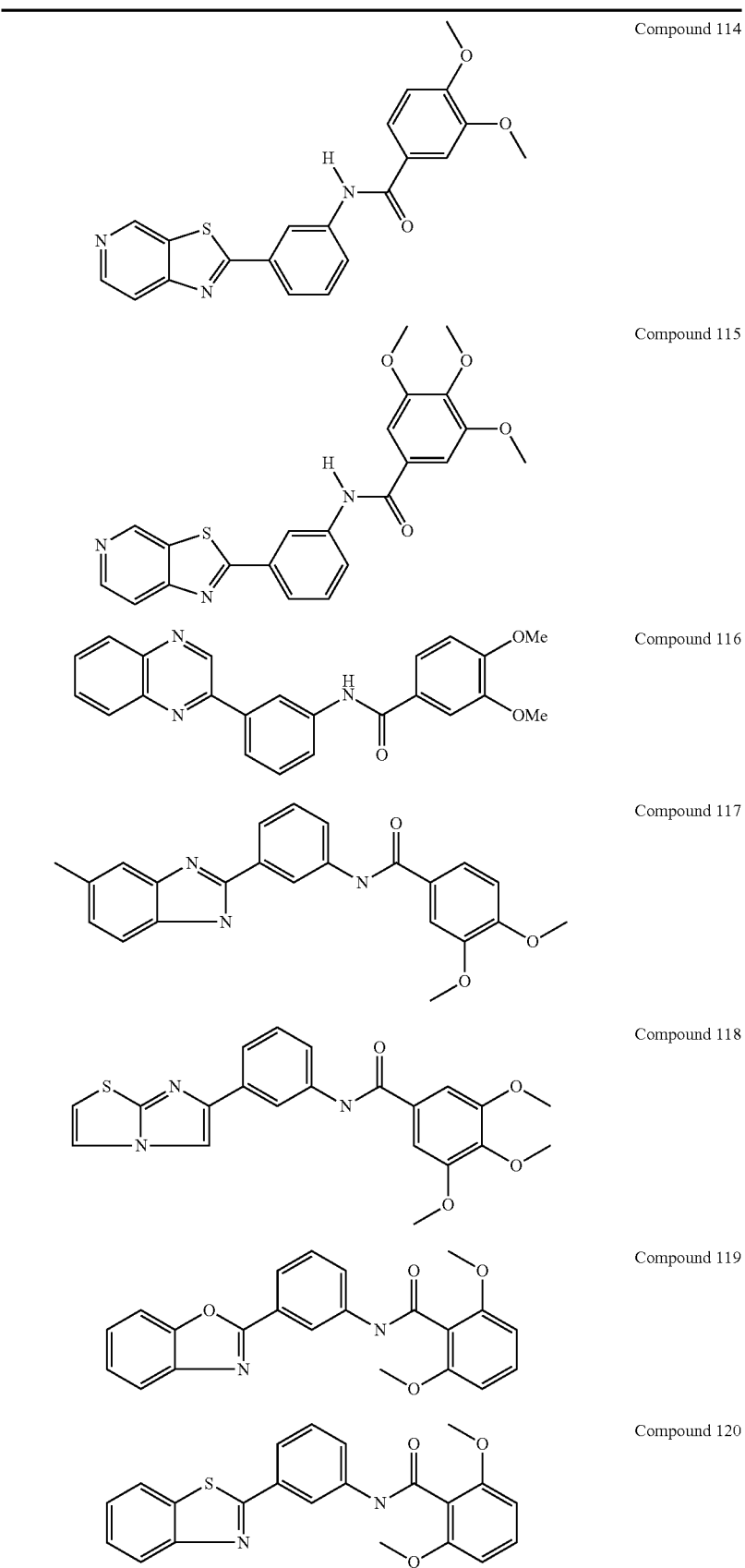
Compound 114
Compound 115
Compound 116
Compound 117
Compound 118
Compound 119
Compound 120

TABLE 1-continued
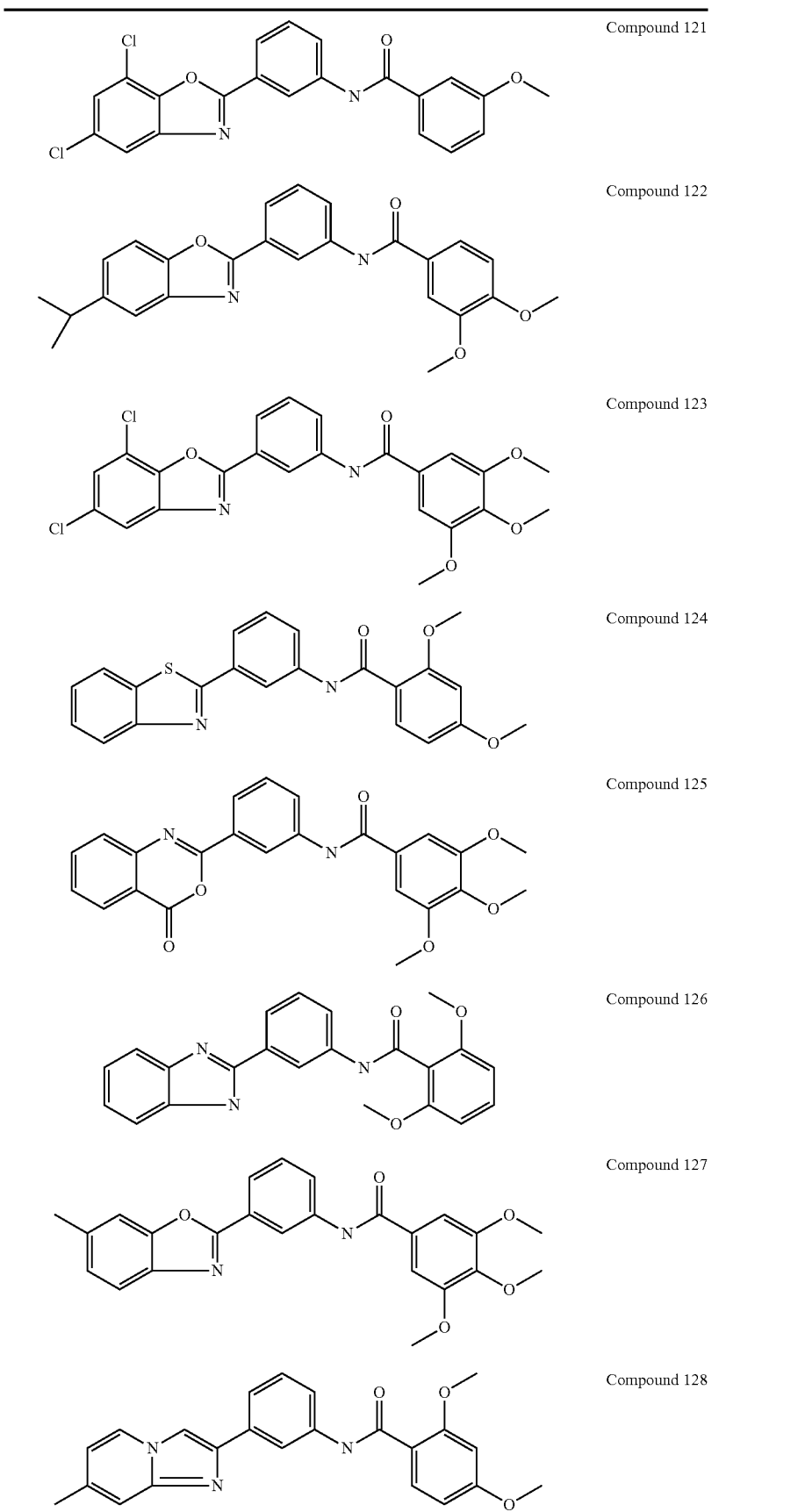
Compound 121
Compound 122
Compound 123
Compound 124
Compound 125
Compound 126
Compound 127
Compound 128

TABLE 1-continued
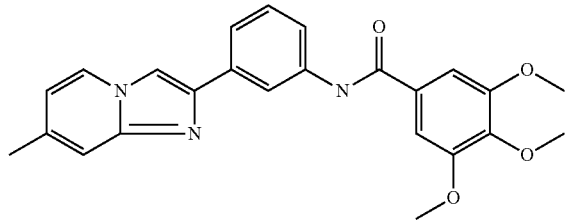
Compound 129
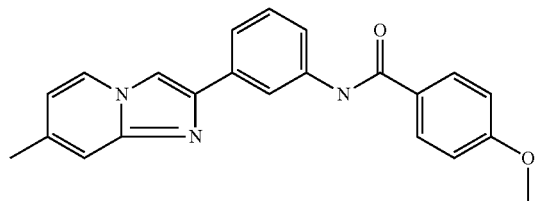
Compound 130
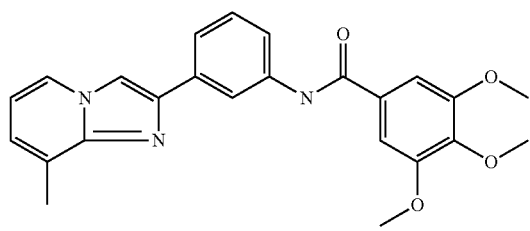 [SMILES: COc1cc(C(=O)Nc2cccc(-c3cn4cccc(C)c4n3)c2)cc(OC)c1OC]
Compound 131
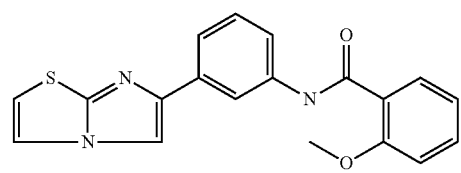 [SMILES: COc1ccccc1C(=O)Nc1cccc(-c2cn3ccsc3n2)c1]
Compound 132
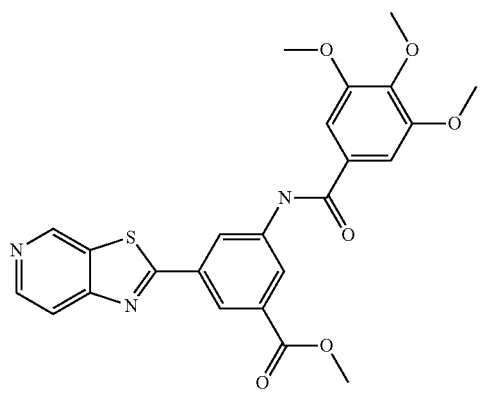 [SMILES: COC(=O)c1cc(NC(=O)c2cc(OC)c(OC)c(OC)c2)cc(-c2nc3ccncc3s2)c1]
Compound 133
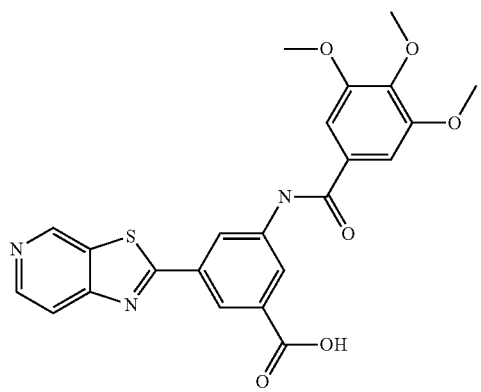 [SMILES: COc1cc(C(=O)Nc2cc(C(=O)O)cc(-c3nc4ccncc4s3)c2)cc(OC)c1OC]
Compound 134

TABLE 1-continued
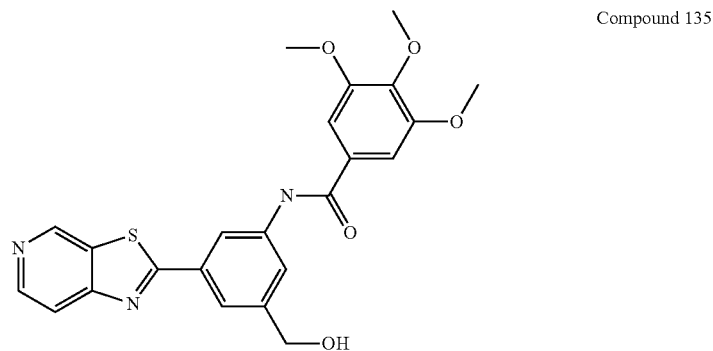
Compound 135
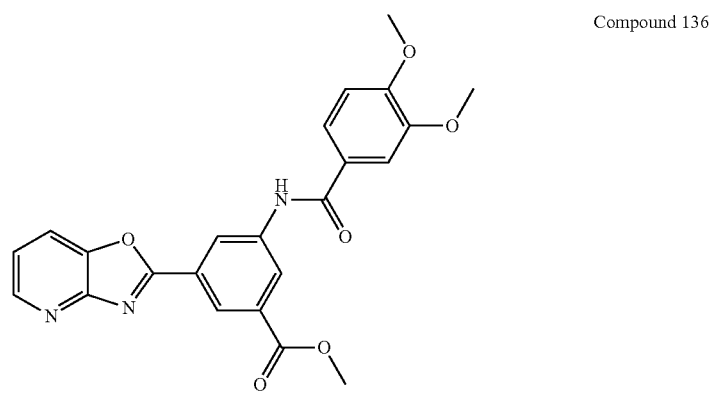
Compound 136
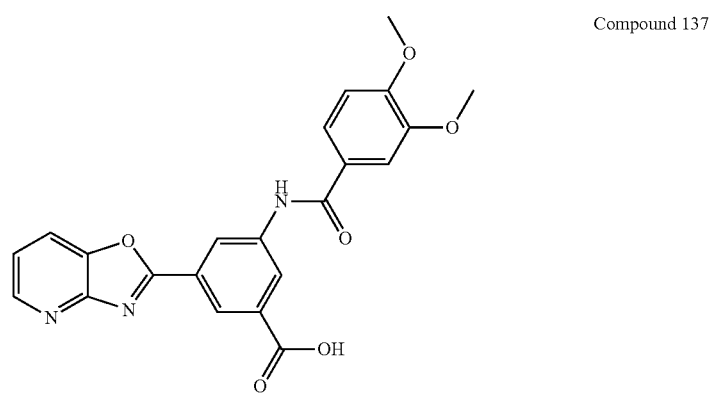
Compound 137
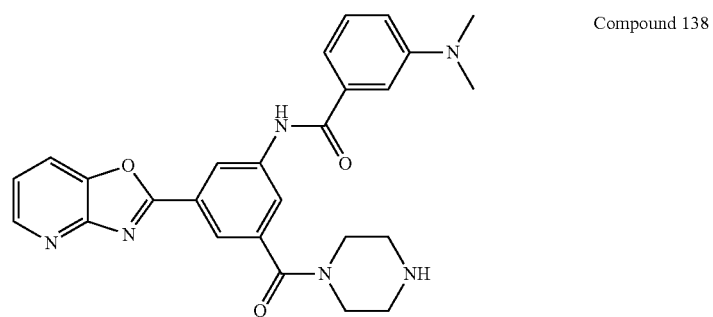
Compound 138

TABLE 1-continued
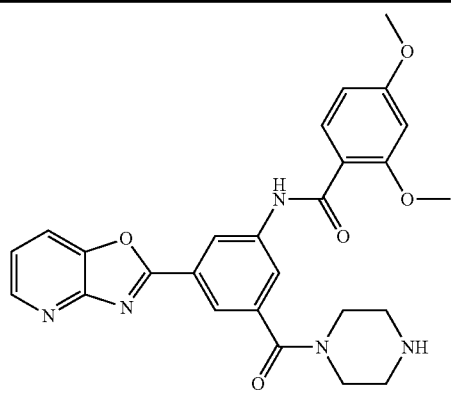
Compound 139
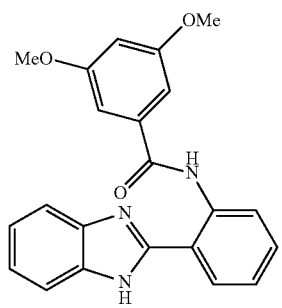 [SMILES: COc1cc(OC)cc(C(=O)Nc2ccccc2-c2nc3ccccc3[nH]2)c1]
Compound 141
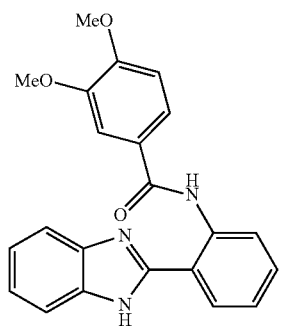 [SMILES: COc1ccc(C(=O)Nc2ccccc2-c2nc3ccccc3[nH]2)cc1OC]
Compound 142
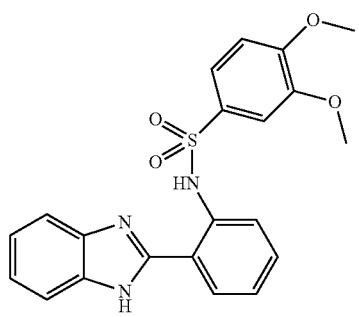 [SMILES: COc1ccc(S(=O)(=O)Nc2ccccc2-c2nc3ccccc3[nH]2)cc1OC]
Compound 143
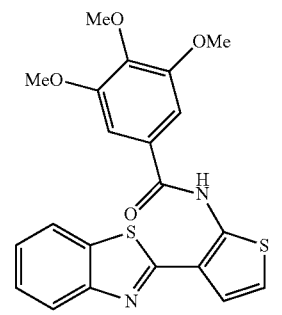 [SMILES: COc1cc(C(=O)Nc2sccc2-c2nc3ccccc3s2)cc(OC)c1OC]
Compound 144

TABLE 1-continued
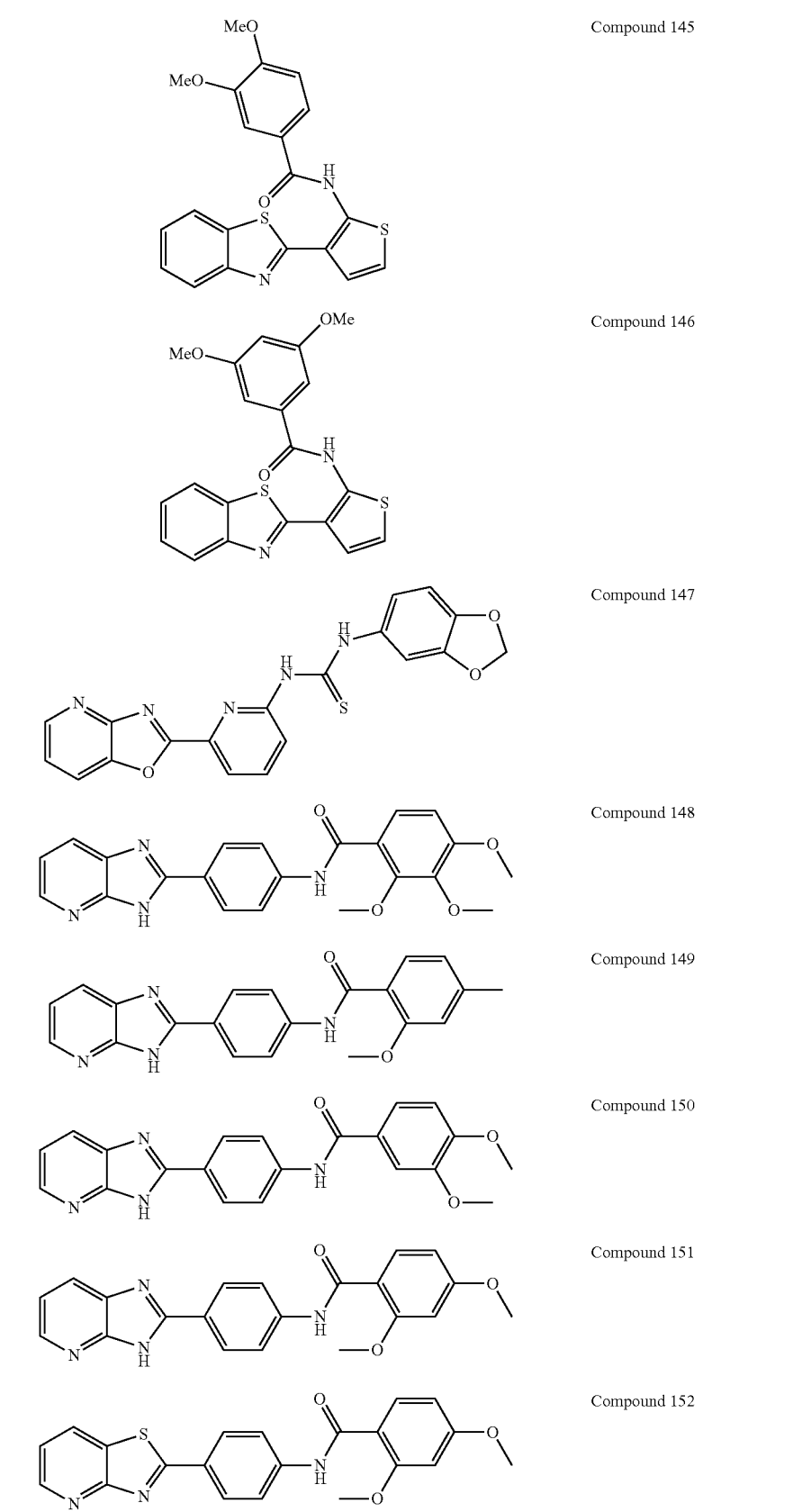
Compound 145
Compound 146
Compound 147
Compound 148
Compound 149
Compound 150
Compound 151
Compound 152

TABLE 1-continued
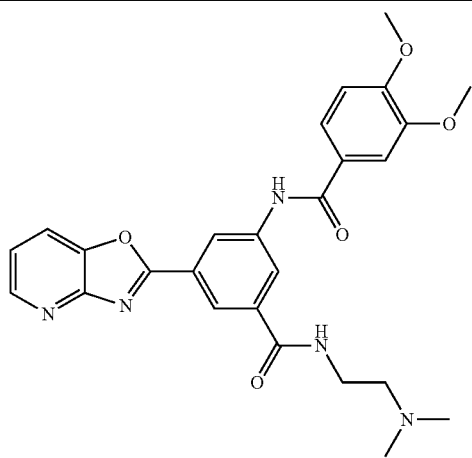
Compound 153
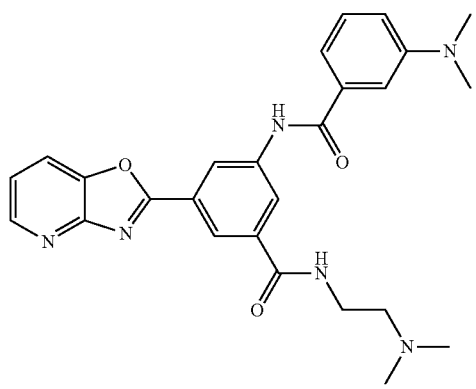 [SMILES: CN(C)CCNC(=O)c1cc(NC(=O)c2cccc(N(C)C)c2)cc(-c2nc3ncccc3o2)c1]
Compound 154
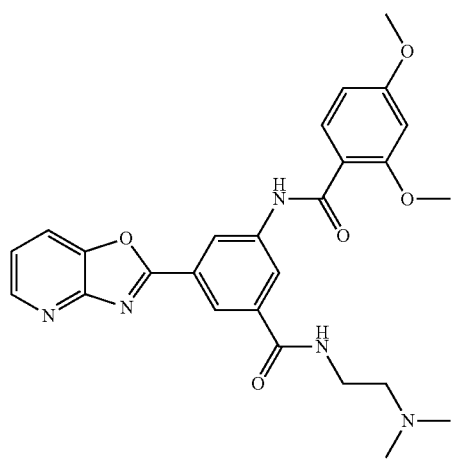 [SMILES: COc1ccc(C(=O)Nc2cc(C(=O)NCCN(C)C)cc(-c3nc4ncccc4o3)c2)c(OC)c1]
Compound 155

TABLE 1-continued
| | |
|---|---|
| 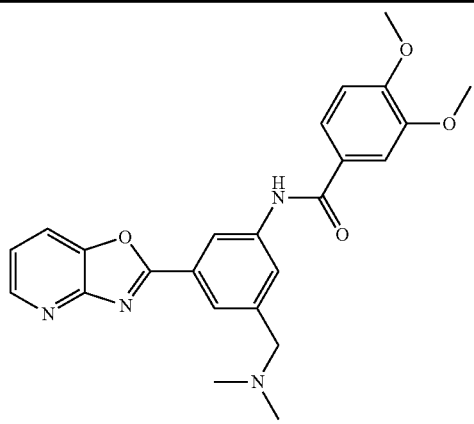 | Compound 156 |
| 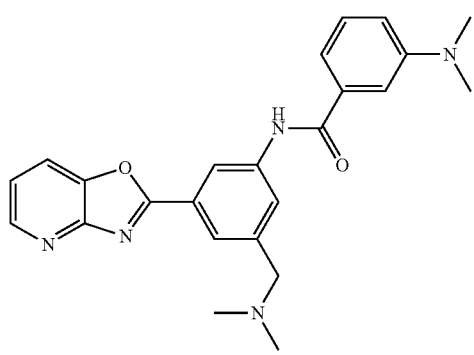 [SMILES: CN(C)Cc1cc(NC(=O)c2cccc(N(C)C)c2)cc(-c2nc3ncccc3o2)c1] | Compound 157 |
| 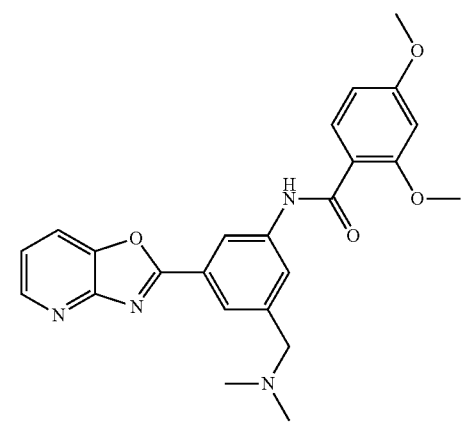 [SMILES: COc1ccc(C(=O)Nc2cc(CN(C)C)cc(-c3nc4ncccc4o3)c2)c(OC)c1] | Compound 158 |
| 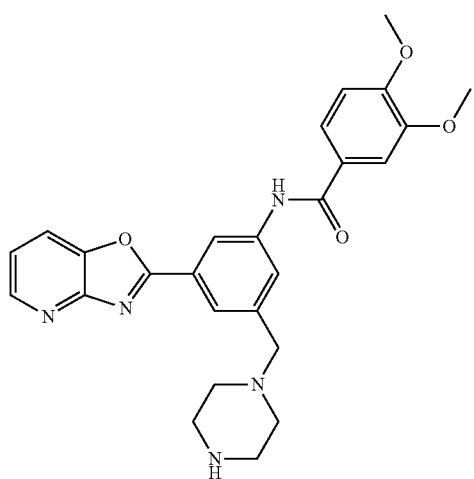 [SMILES: COc1ccc(C(=O)Nc2cc(CN3CCNCC3)cc(-c3nc4ncccc4o3)c2)cc1OC] | Compound 159 |

TABLE 1-continued
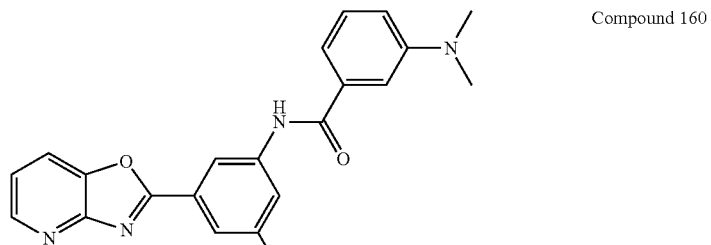
Compound 160
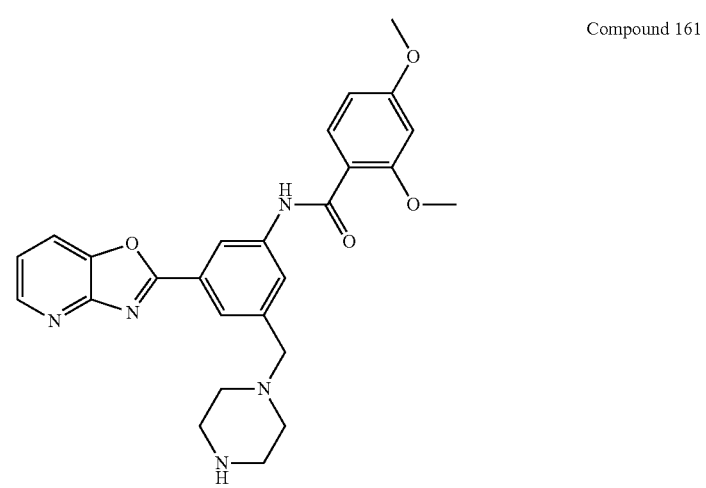
Compound 161
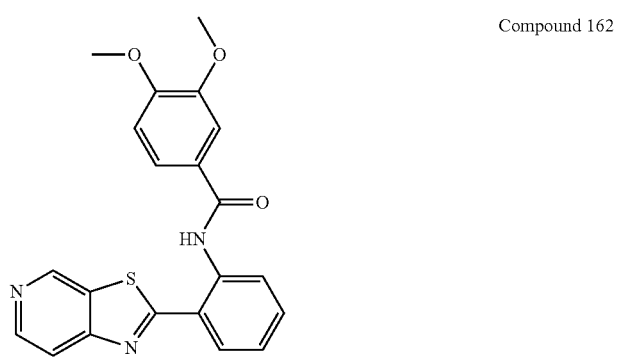
Compound 162
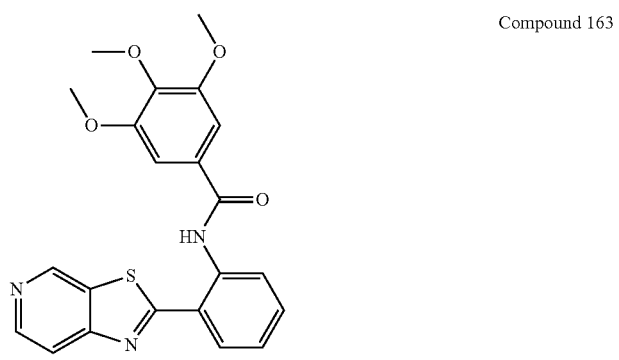
Compound 163

TABLE 1-continued
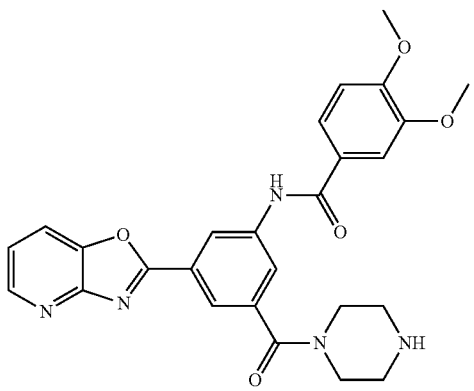 [SMILES: COc1ccc(C(=O)Nc2cc(C(=O)N3CCNCC3)cc(-c3nc4ncccc4o3)c2)cc1OC]
Compound 164
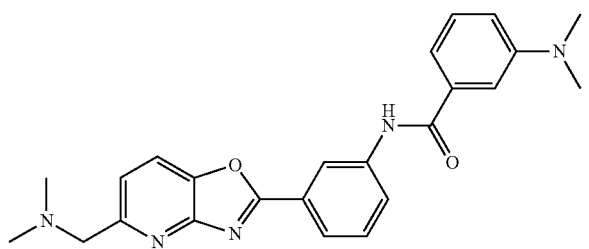
Compound 165
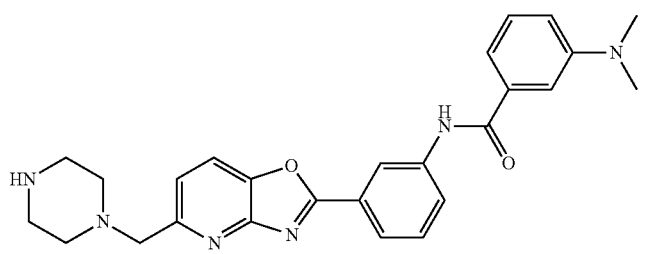 [SMILES: CN(C)c1cccc(C(=O)Nc2cccc(-c3nc4nc(CN5CCNCC5)ccc4o3)c2)c1]
Compound 166
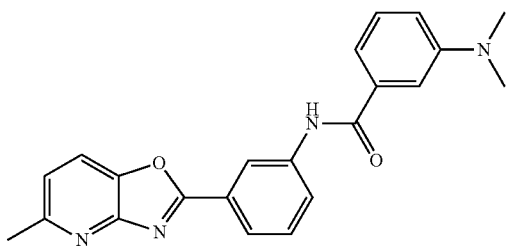
Compound 167
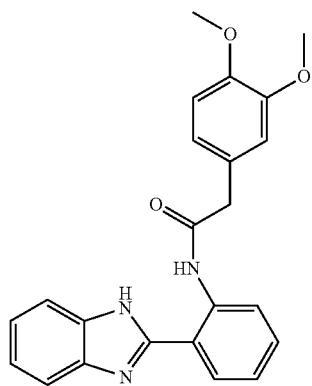 [SMILES: COc1ccc(CC(=O)Nc2ccccc2-c2nc3ccccc3[nH]2)cc1OC]
Compound 168

TABLE 1-continued
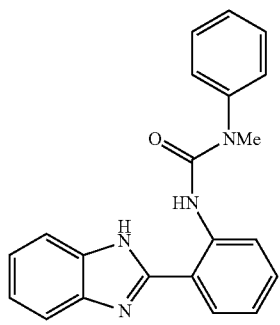 [SMILES: CN(C(=O)Nc1ccccc1-c1nc2ccccc2[nH]1)c1ccccc1]
Compound 169
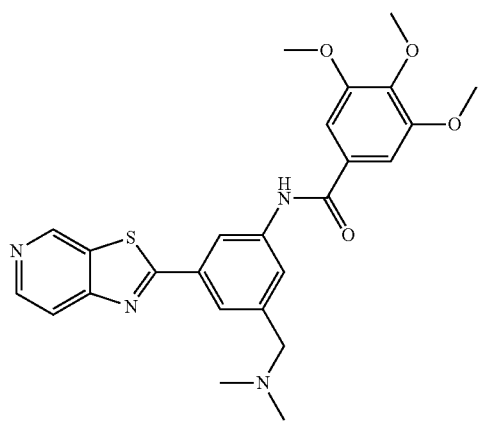 [SMILES: COc1cc(C(=O)Nc2cc(CN(C)C)cc(-c3nc4ccncc4s3)c2)cc(OC)c1OC]
Compound 174
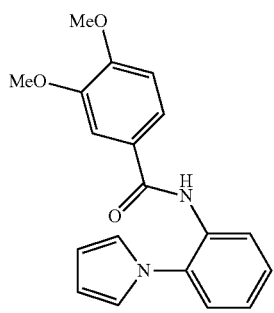 [SMILES: COc1ccc(C(=O)Nc2ccccc2-n2cccc2)cc1OC]
Compound 175
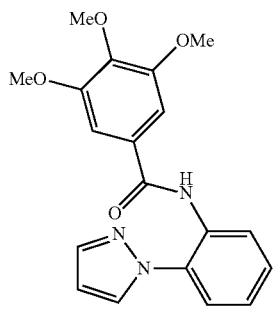 [SMILES: COc1cc(C(=O)Nc2ccccc2-n2cccn2)cc(OC)c1OC]
Compound 176

TABLE 1-continued
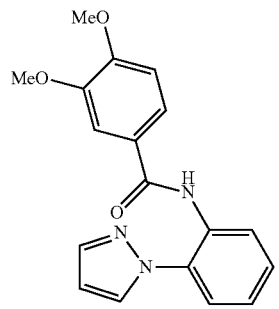 [SMILES: COc1ccc(C(=O)Nc2ccccc2-n2cccn2)cc1OC]
Compound 177
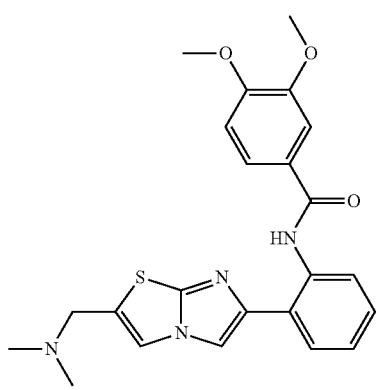 [SMILES: COc1ccc(C(=O)Nc2ccccc2-c2cn3cc(CN(C)C)sc3n2)cc1OC]
Compound 178
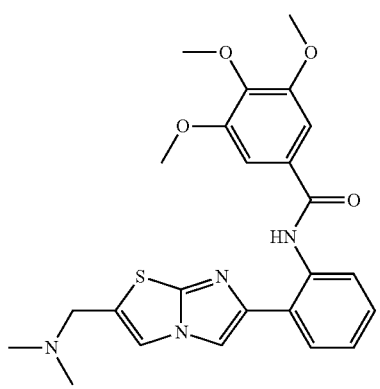 [SMILES: COc1cc(C(=O)Nc2ccccc2-c2cn3cc(CN(C)C)sc3n2)cc(OC)c1OC]
Compound 179
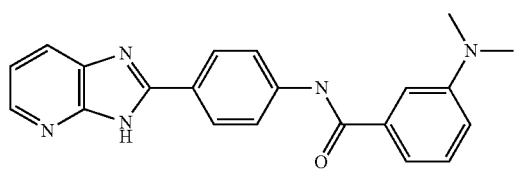 [SMILES: CN(C)c1cccc(C(=O)Nc2ccc(-c3nc4cccnc4[nH]3)cc2)c1]
Compound 180
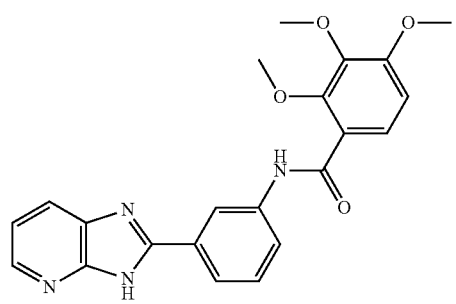 [SMILES: COc1ccc(C(=O)Nc2cccc(-c3nc4cccnc4[nH]3)c2)c(OC)c1OC]
Compound 181

TABLE 1-continued
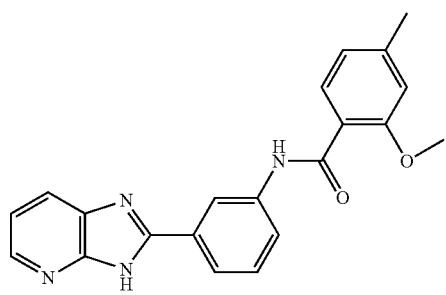 [SMILES: COc1cc(C)ccc1C(=O)Nc1cccc(-c2nc3cccnc3[nH]2)c1]
Compound 182
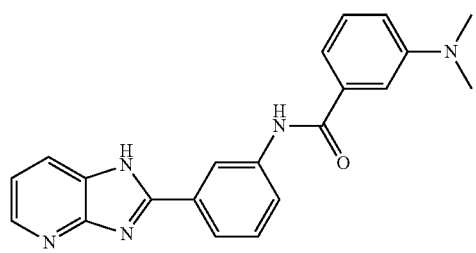 [SMILES: CN(C)c1cccc(C(=O)Nc2cccc(-c3nc4ncccc4[nH]3)c2)c1]
Compound 183
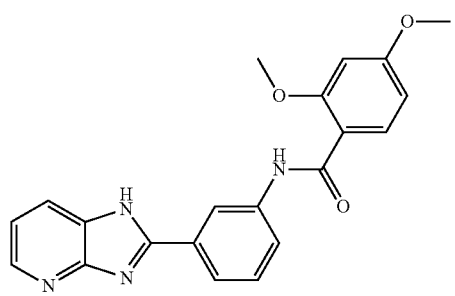 [SMILES: COc1ccc(C(=O)Nc2cccc(-c3nc4ncccc4[nH]3)c2)c(OC)c1]
Compound 184
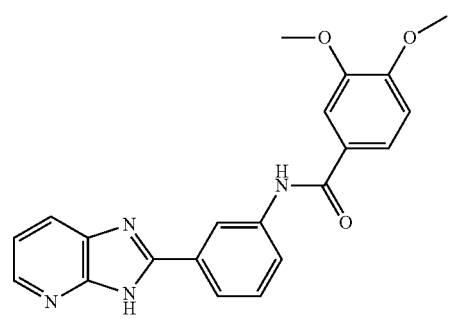 [SMILES: COc1ccc(C(=O)Nc2cccc(-c3nc4cccnc4[nH]3)c2)cc1OC]
Compound 185
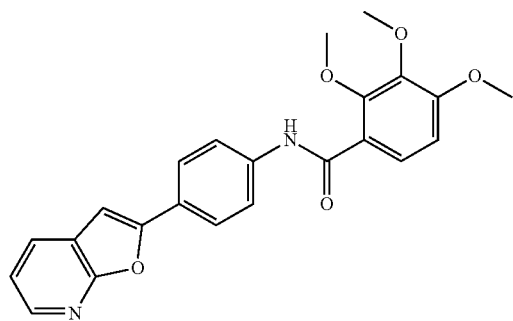 [SMILES: COc1ccc(C(=O)Nc2ccc(-c3cc4cccnc4o3)cc2)c(OC)c1OC]
Compound 186

TABLE 1-continued
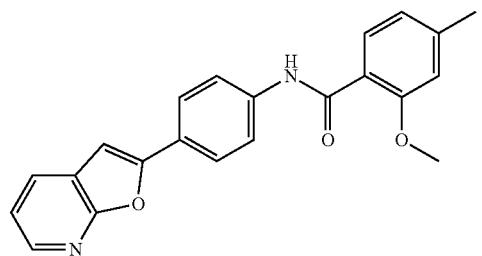 [SMILES: COc1cc(C)ccc1C(=O)Nc1ccc(-c2cc3cccnc3o2)cc1]
Compound 187
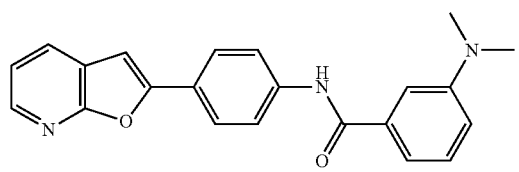 [SMILES: CN(C)c1cccc(C(=O)Nc2ccc(-c3cc4cccnc4o3)cc2)c1]
Compound 188
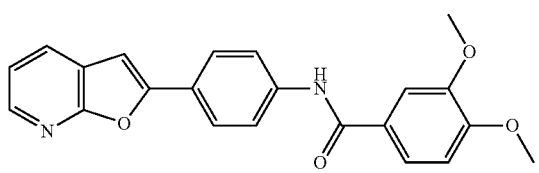 [SMILES: COc1ccc(C(=O)Nc2ccc(-c3cc4cccnc4o3)cc2)cc1OC]
Compound 189
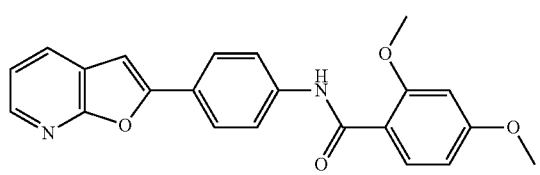 [SMILES: COc1ccc(C(=O)Nc2ccc(-c3cc4cccnc4o3)cc2)c(OC)c1]
Compound 190
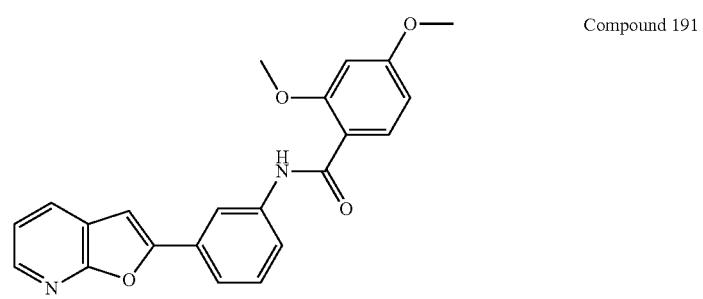
Compound 191
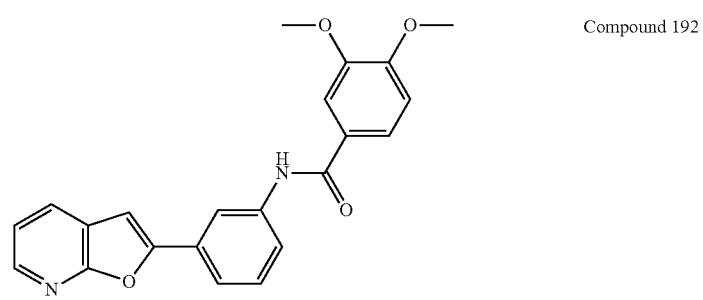
Compound 192

TABLE 1-continued
| | |
|---|---|
| 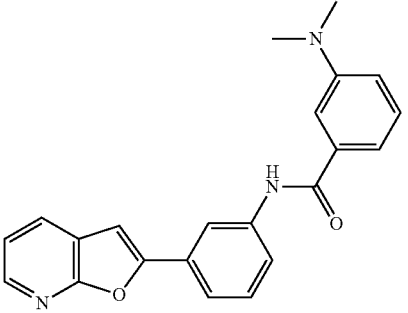 [SMILES: CN(C)c1cccc(C(=O)Nc2cccc(-c3cc4cccnc4o3)c2)c1] | Compound 193 |
| 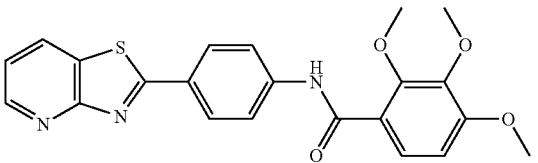 [SMILES: COc1ccc(C(=O)Nc2ccc(-c3nc4ncccc4s3)cc2)c(OC)c1OC] | Compound 194 |
| 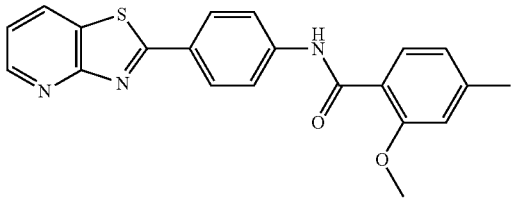 [SMILES: COc1cc(C)ccc1C(=O)Nc1ccc(-c2nc3ncccc3s2)cc1] | Compound 195 |
| 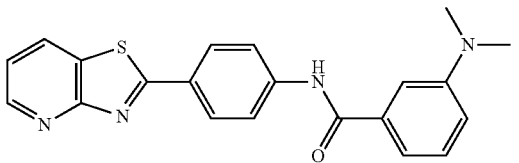 [SMILES: CN(C)c1cccc(C(=O)Nc2ccc(-c3nc4ncccc4s3)cc2)c1] | Compound 196 |
| 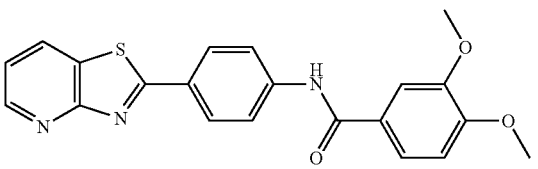 [SMILES: COc1ccc(C(=O)Nc2ccc(-c3nc4ncccc4s3)cc2)cc1OC] | Compound 197 |
| 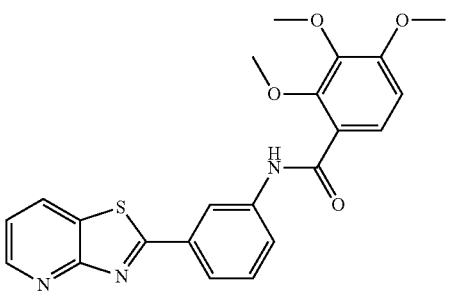 [SMILES: COc1ccc(C(=O)Nc2cccc(-c3nc4ncccc4s3)c2)c(OC)c1OC] | Compound 198 |
| 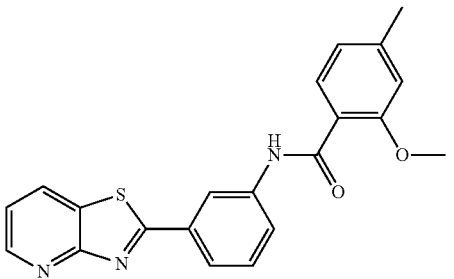 [SMILES: COc1cc(C)ccc1C(=O)Nc1cccc(-c2nc3ncccc3s2)c1] | Compound 199 |

TABLE 1-continued
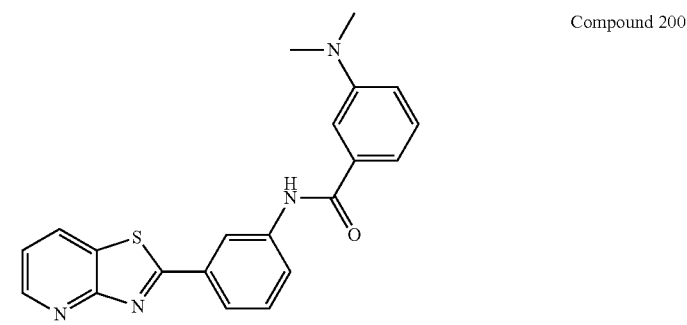
Compound 200
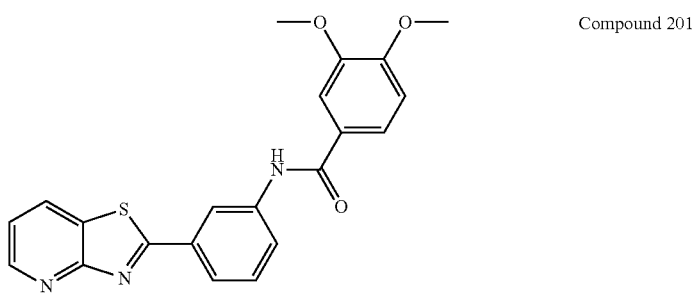
Compound 201
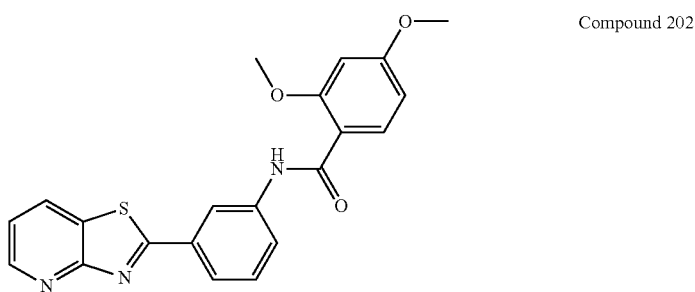
Compound 202
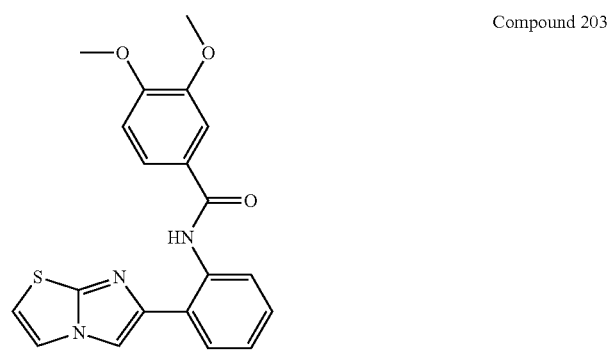
Compound 203
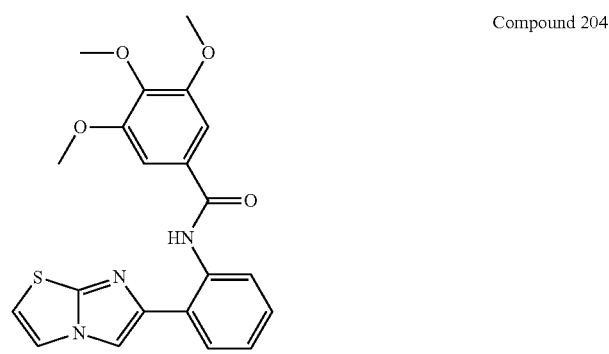
Compound 204

TABLE 1-continued
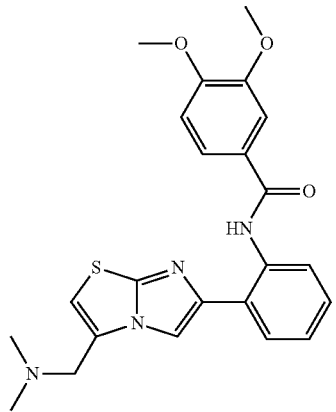 [SMILES: COc1ccc(C(=O)Nc2ccccc2-c2cn3c(CN(C)C)csc3n2)cc1OC]
Compound 205
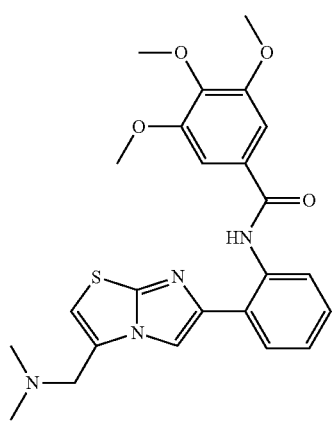 [SMILES: COc1cc(C(=O)Nc2ccccc2-c2cn3c(CN(C)C)csc3n2)cc(OC)c1OC]
Compound 206
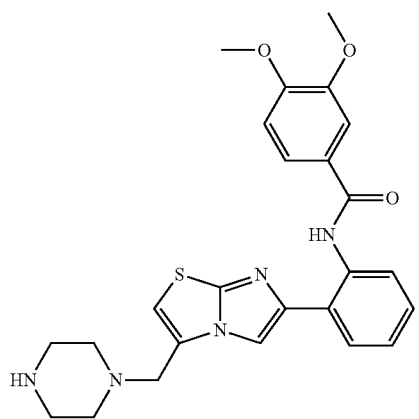 [SMILES: COc1ccc(C(=O)Nc2ccccc2-c2cn3c(CN4CCNCC4)csc3n2)cc1OC]
Compound 207

TABLE 1-continued
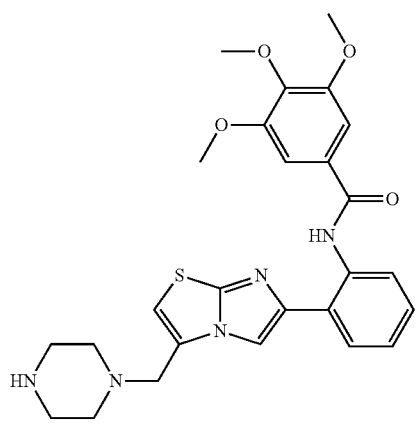 [SMILES: COc1cc(C(=O)Nc2ccccc2-c2cn3c(CN4CCNCC4)csc3n2)cc(OC)c1OC]
Compound 208
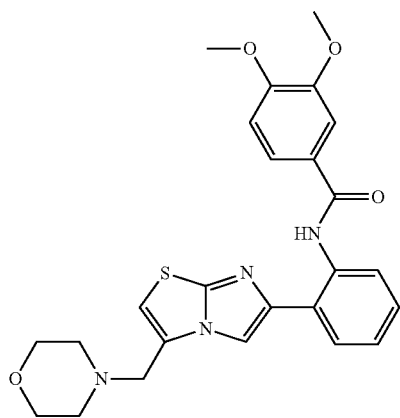 [SMILES: COc1ccc(C(=O)Nc2ccccc2-c2cn3c(CN4CCOCC4)csc3n2)cc1OC]
Compound 209
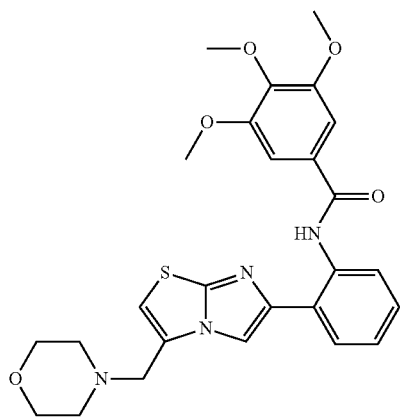 [SMILES: COc1cc(C(=O)Nc2ccccc2-c2cn3c(CN4CCOCC4)csc3n2)cc(OC)c1OC]
Compound 210
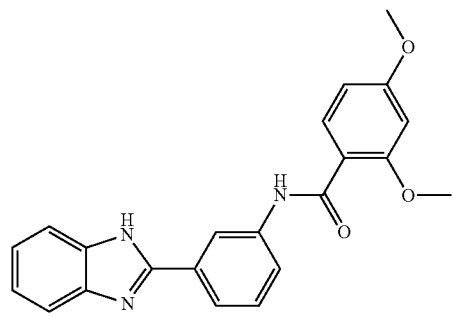 [SMILES: COc1ccc(C(=O)Nc2cccc(-c3nc4cccnc4s3)c2)c(OC)c1]
Compound 211

TABLE 1-continued
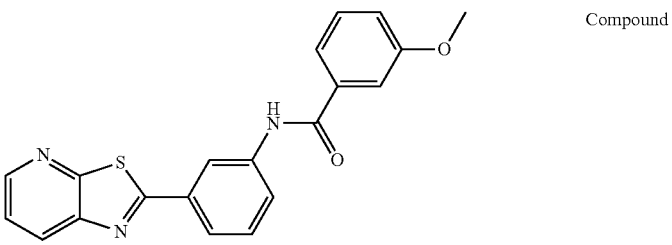
Compound 212
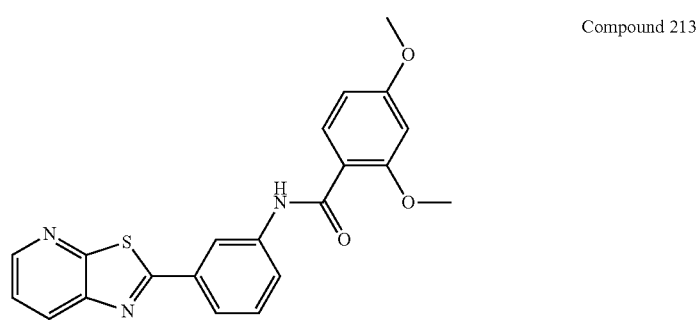
Compound 213
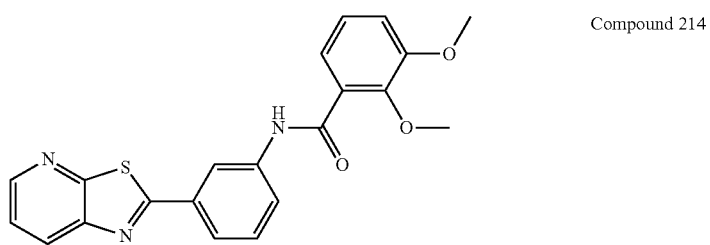
Compound 214
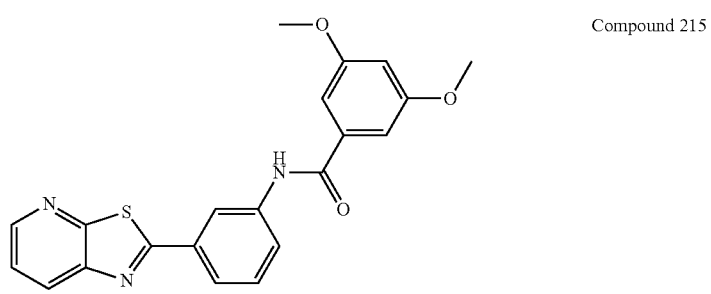
Compound 215
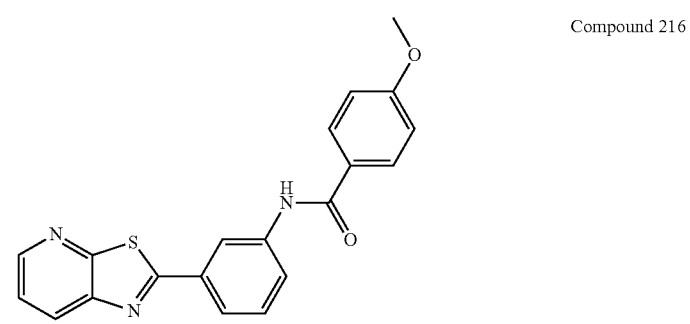
Compound 216

TABLE 1-continued
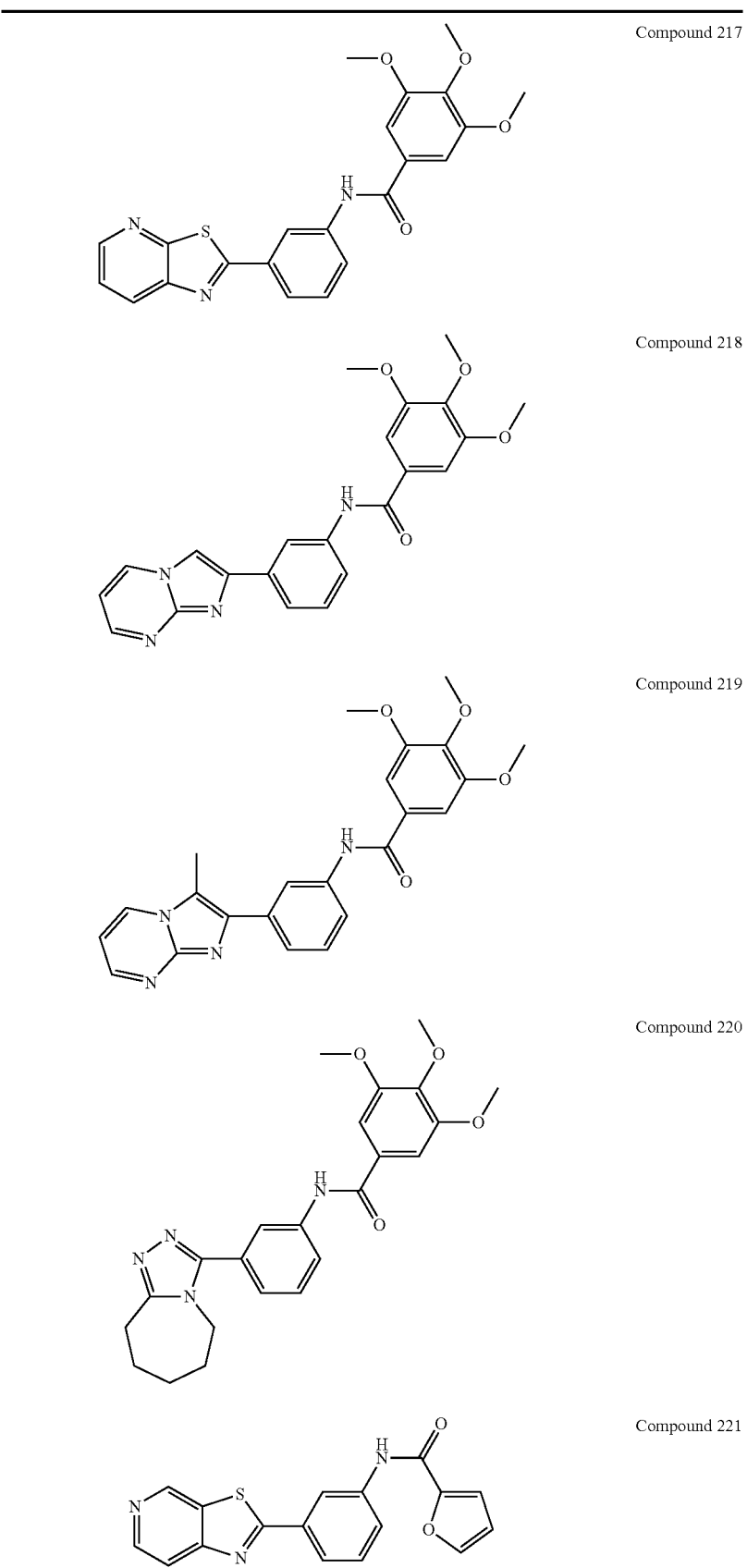
Compound 217
Compound 218
Compound 219
Compound 220
Compound 221

TABLE 1-continued
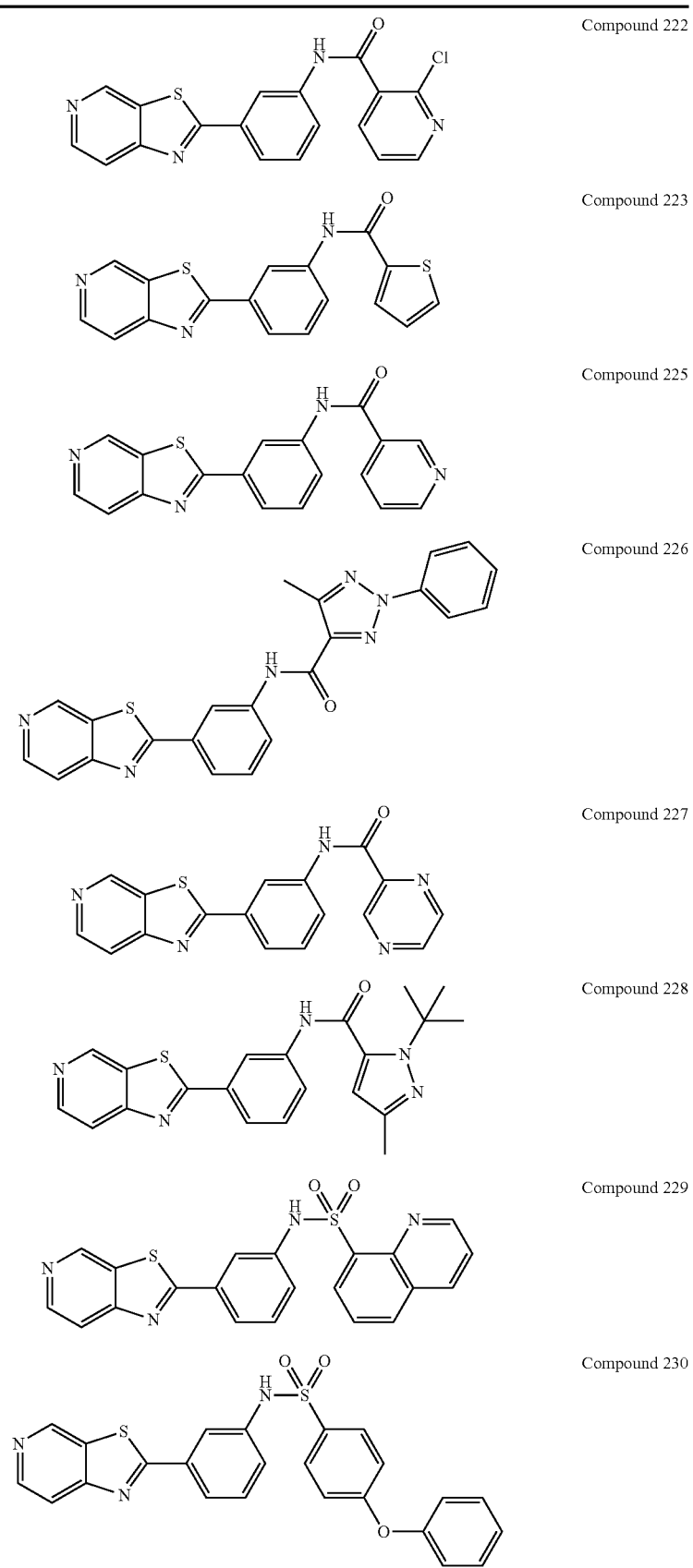
Compound 222
Compound 223
Compound 225
Compound 226
Compound 227
Compound 228
Compound 229
Compound 230

TABLE 1-continued
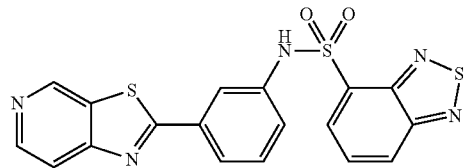 [SMILES: O=S(=O)(Nc1cccc(-c2nc3ccncc3s2)c1)c1cccc2nsnc12] Compound 231
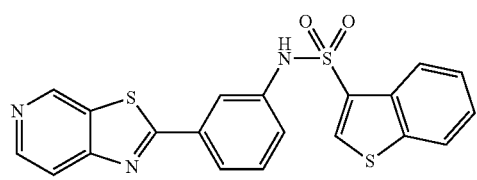 [SMILES: O=S(=O)(Nc1cccc(-c2nc3ccncc3s2)c1)c1csc2ccccc12] Compound 232
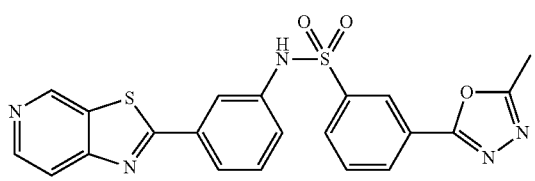 [SMILES: Cc1nnc(-c2cccc(S(=O)(=O)Nc3cccc(-c4nc5ccncc5s4)c3)c2)o1] Compound 234
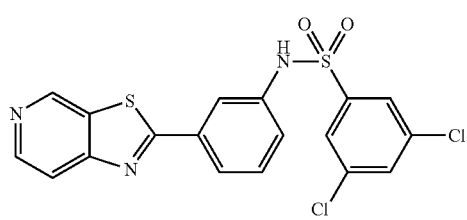 [SMILES: O=S(=O)(Nc1cccc(-c2nc3ccncc3s2)c1)c1cc(Cl)cc(Cl)c1] Compound 235
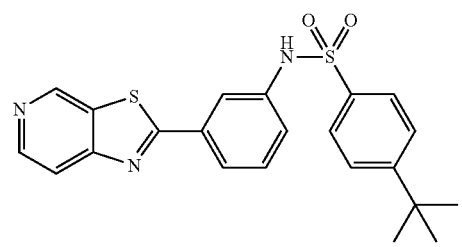 [SMILES: CC(C)(C)c1ccc(S(=O)(=O)Nc2cccc(-c3nc4ccncc4s3)c2)cc1] Compound 236
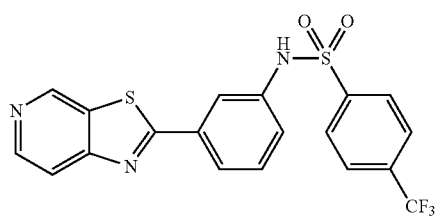 [SMILES: O=S(=O)(Nc1cccc(-c2nc3ccncc3s2)c1)c1ccc(C(F)(F)F)cc1] Compound 237
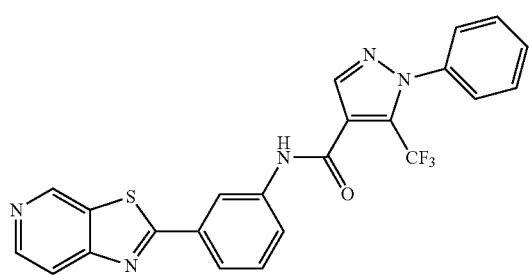 [SMILES: O=C(Nc1cccc(-c2nc3ccncc3s2)c1)c1cnn(-c2ccccc2)c1C(F)(F)F] Compound 238

TABLE 1-continued
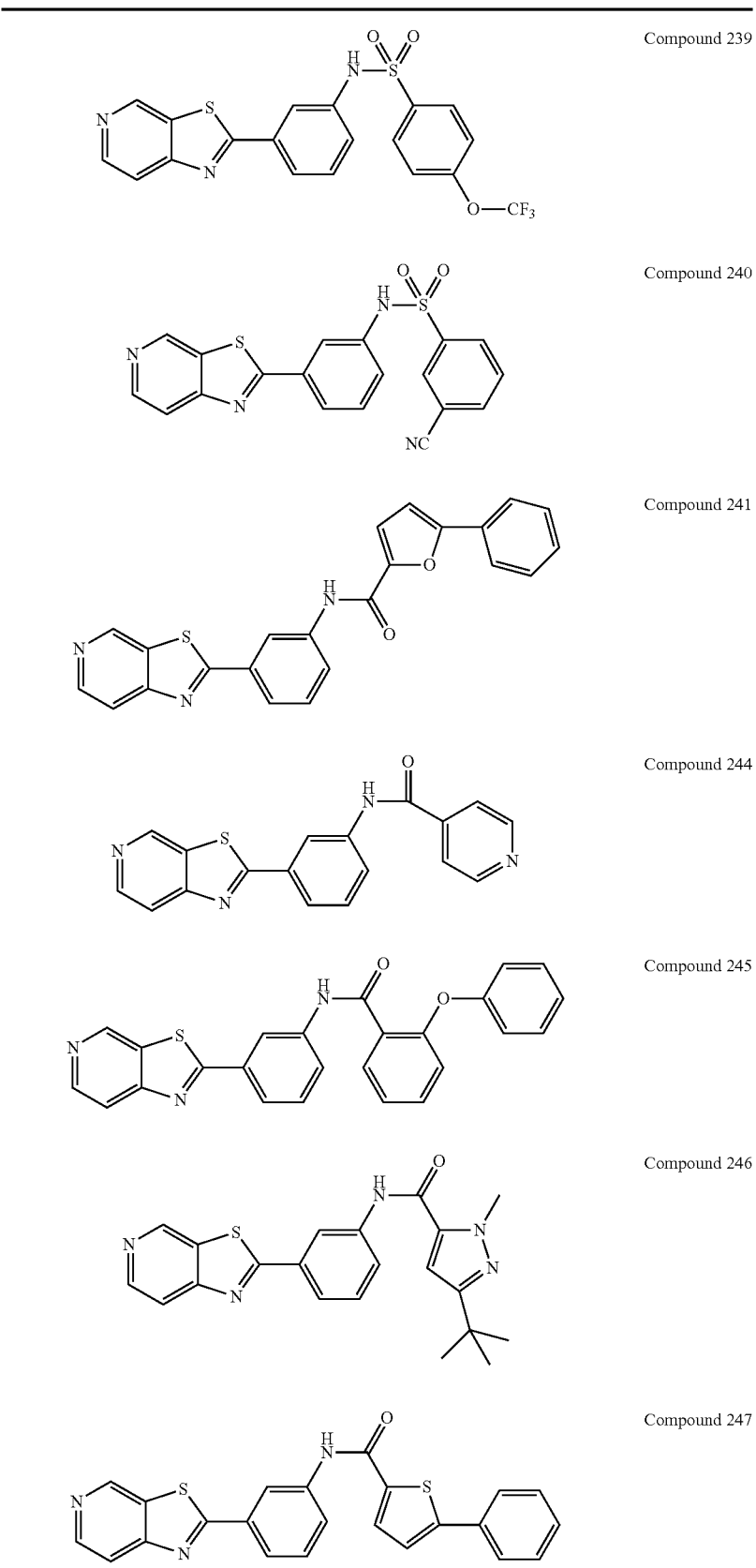
Compound 239
Compound 240
Compound 241
Compound 244
Compound 245
Compound 246
Compound 247

TABLE 1-continued
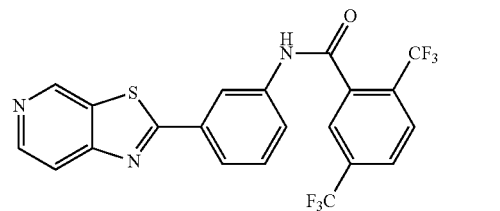 [SMILES: O=C(Nc1cccc(-c2nc3ccncc3s2)c1)c1cc(C(F)(F)F)ccc1C(F)(F)F]
Compound 248
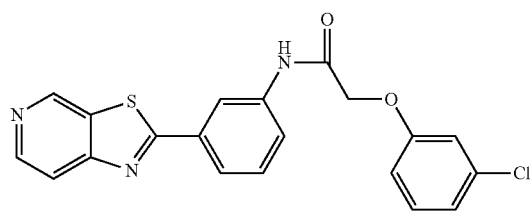 [SMILES: O=C(COc1cccc(Cl)c1)Nc1cccc(-c2nc3ccncc3s2)c1]
Compound 249
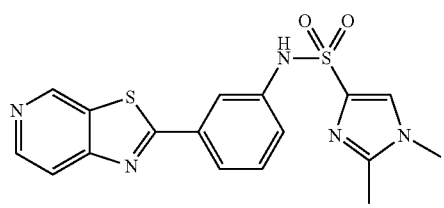 [SMILES: Cc1nc(S(=O)(=O)Nc2cccc(-c3nc4ccncc4s3)c2)cn1C]
Compound 250
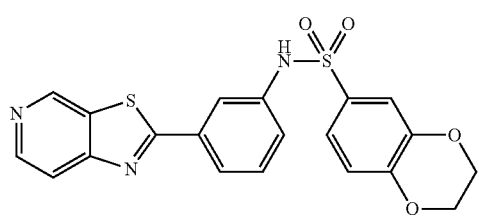 [SMILES: O=S(=O)(Nc1cccc(-c2nc3ccncc3s2)c1)c1ccc2c(c1)OCCO2]
Compound 251
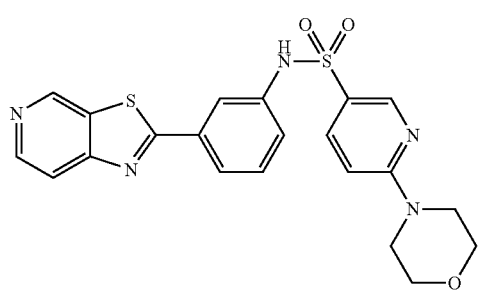 [SMILES: O=S(=O)(Nc1cccc(-c2nc3ccncc3s2)c1)c1ccc(N2CCOCC2)nc1]
Compound 252
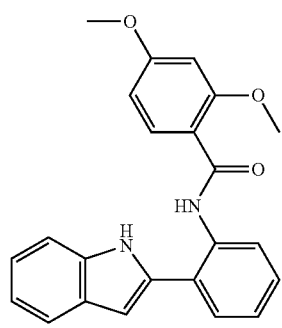 [SMILES: COc1ccc(C(=O)Nc2ccccc2-c2cc3ccccc3[nH]2)c(OC)c1]
Compound 253

TABLE 1-continued
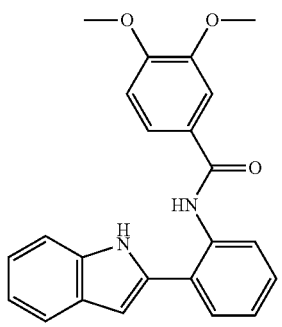 [SMILES: COc1ccc(C(=O)Nc2ccccc2-c2cc3ccccc3[nH]2)cc1OC]
Compound 254
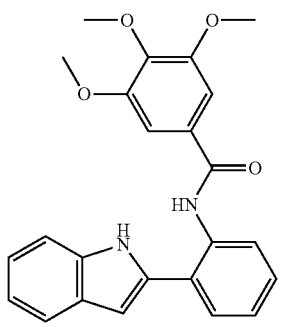 [SMILES: COc1cc(C(=O)Nc2ccccc2-c2cc3ccccc3[nH]2)cc(OC)c1OC]
Compound 255
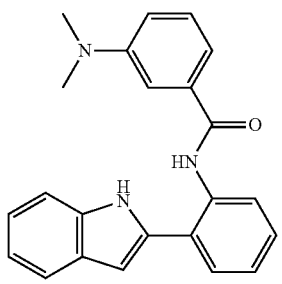 [SMILES: CN(C)c1cccc(C(=O)Nc2ccccc2-c2cc3ccccc3[nH]2)c1]
Compound 256
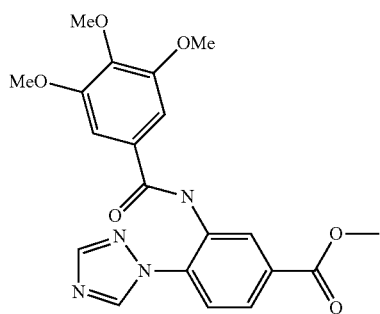 [SMILES: COC(=O)c1ccc(-n2cncn2)c(NC(=O)c2cc(OC)c(OC)c(OC)c2)c1]
Compound 257
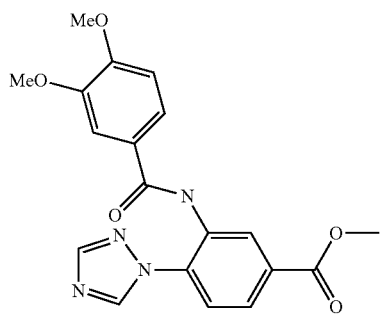 [SMILES: COC(=O)c1ccc(-n2cncn2)c(NC(=O)c2ccc(OC)c(OC)c2)c1]
Compound 258

TABLE 1-continued
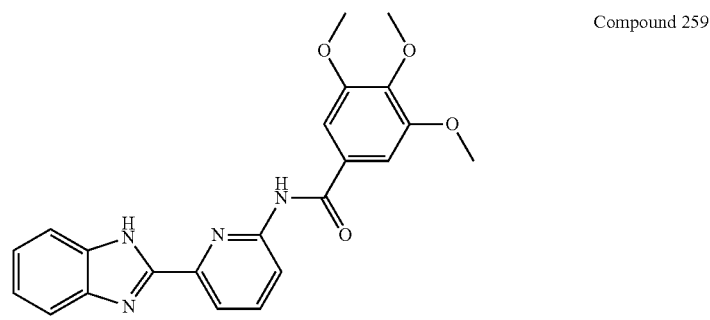
Compound 259
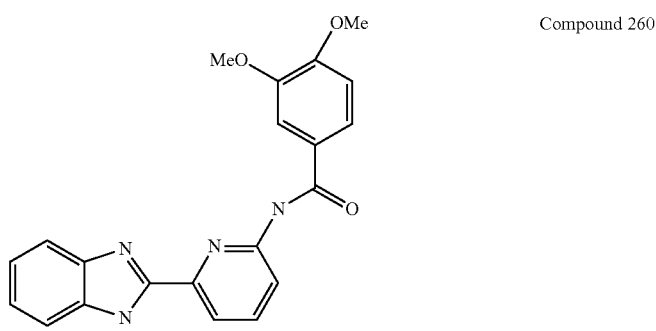
Compound 260
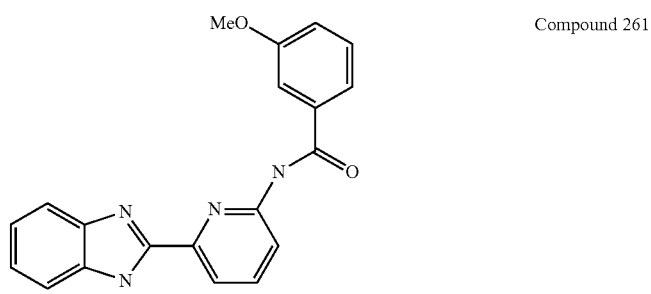
Compound 261
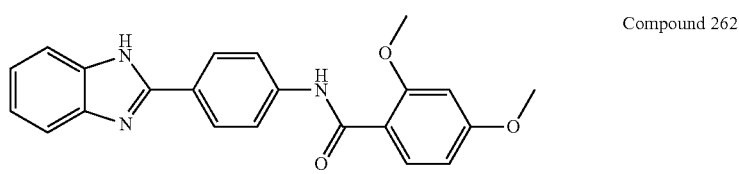
Compound 262
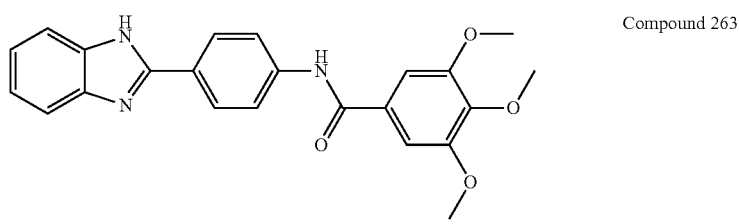
Compound 263
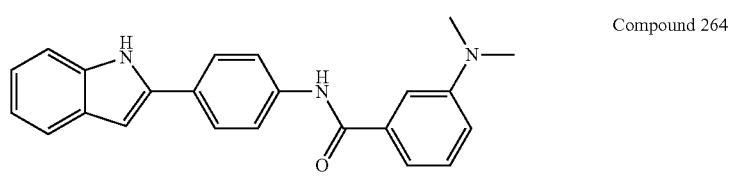
Compound 264

TABLE 1-continued
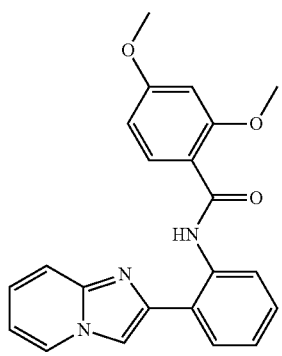 [SMILES: COc1ccc(C(=O)Nc2ccccc2-c2cn3ccccc3n2)c(OC)c1]
Compound 265
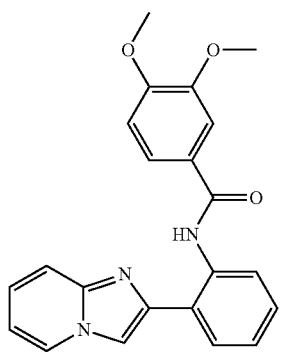 [SMILES: COc1ccc(C(=O)Nc2ccccc2-c2cn3ccccc3n2)cc1OC]
Compound 266
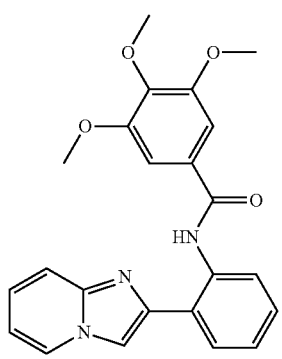 [SMILES: COc1cc(C(=O)Nc2ccccc2-c2cn3ccccc3n2)cc(OC)c1OC]
Compound 267
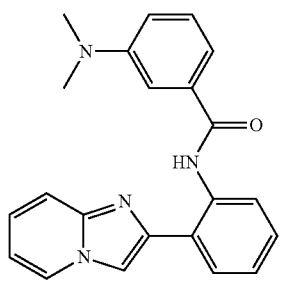 [SMILES: CN(C)c1cccc(C(=O)Nc2ccccc2-c2cn3ccccc3n2)c1]
Compound 268

TABLE 1-continued
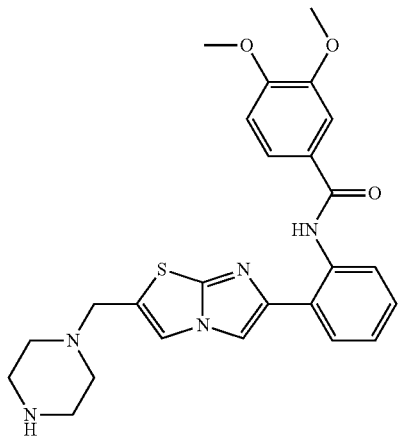 [SMILES: COc1ccc(C(=O)Nc2ccccc2-c2cn3cc(CN4CCNCC4)sc3n2)cc1OC]
Compound 270
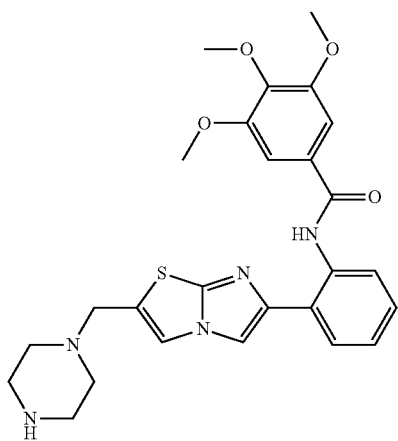 [SMILES: COc1cc(C(=O)Nc2ccccc2-c2cn3cc(CN4CCNCC4)sc3n2)cc(OC)c1OC]
Compound 271
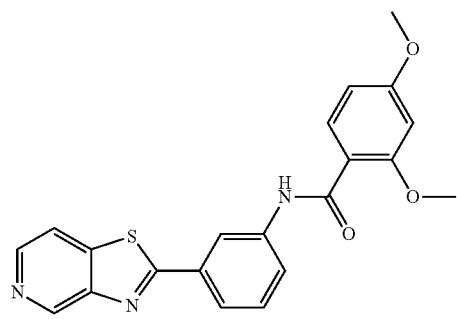 [SMILES: COc1ccc(C(=O)Nc2cccc(-c3nc4cnccc4s3)c2)c(OC)c1]
Compound 272
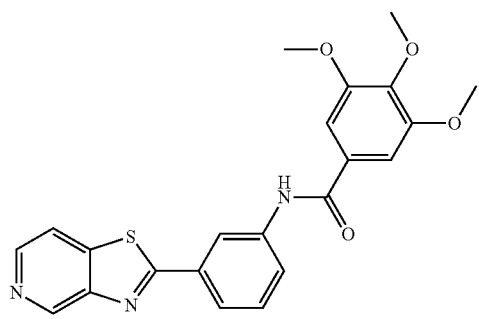 [SMILES: COc1cc(C(=O)Nc2cccc(-c3nc4cnccc4s3)c2)cc(OC)c1OC]
Compound 273

TABLE 1-continued
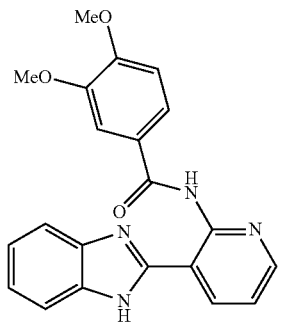
Compound 276
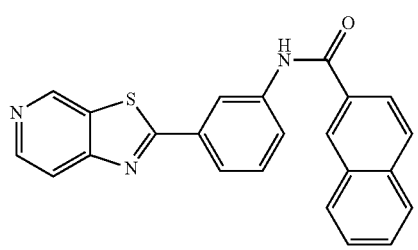 [SMILES: O=C(Nc1cccc(-c2nc3ccncc3s2)c1)c1ccc2ccccc2c1]
Compound 280
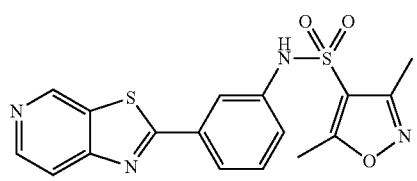 [SMILES: Cc1noc(C)c1S(=O)(=O)Nc1cccc(-c2nc3ccncc3s2)c1]
Compound 282
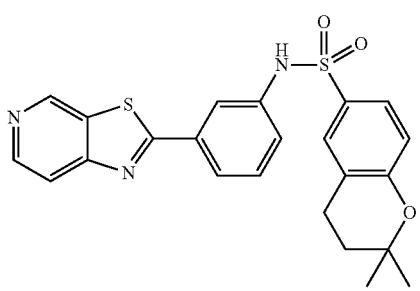 [SMILES: CC1(C)CCc2cc(S(=O)(=O)Nc3cccc(-c4nc5ccncc5s4)c3)ccc2O1]
Compound 283
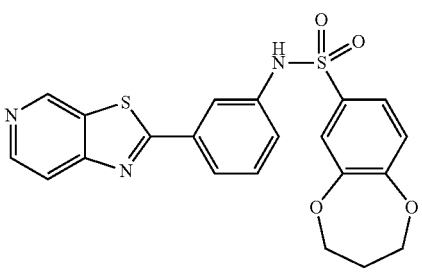 [SMILES: O=S(=O)(Nc1cccc(-c2nc3ccncc3s2)c1)c1ccc2c(c1)OCCCO2]
Compound 284
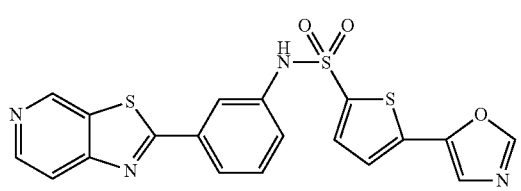 [SMILES: O=S(=O)(Nc1cccc(-c2nc3ccncc3s2)c1)c1ccc(-c2cnco2)s1]
Compound 285

TABLE 1-continued
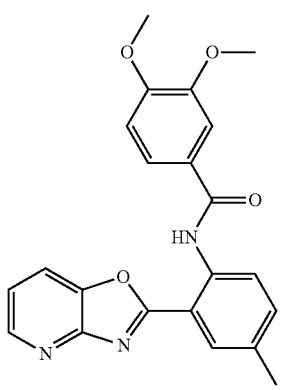 [SMILES: COc1ccc(C(=O)Nc2ccc(C)cc2-c2nc3ncccc3o2)cc1OC]
Compound 286
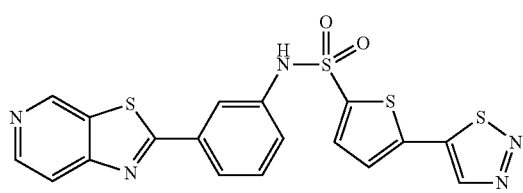 [SMILES: O=S(=O)(Nc1cccc(-c2nc3ccncc3s2)c1)c1ccc(-c2cnns2)s1]
Compound 287
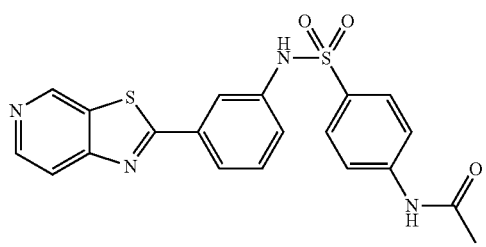 [SMILES: CC(=O)Nc1ccc(S(=O)(=O)Nc2cccc(-c3nc4ccncc4s3)c2)cc1]
Compound 288
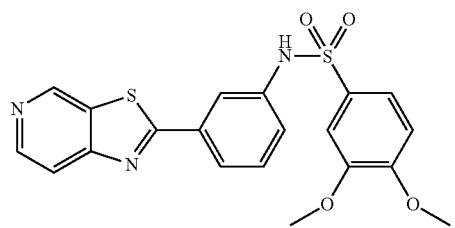 [SMILES: COc1ccc(S(=O)(=O)Nc2cccc(-c3nc4ccncc4s3)c2)cc1OC]
Compound 289
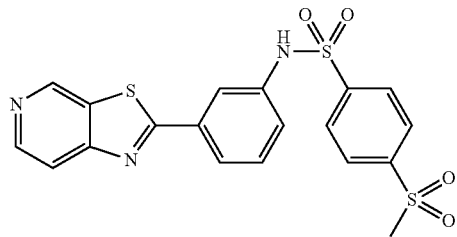 [SMILES: CS(=O)(=O)c1ccc(S(=O)(=O)Nc2cccc(-c3nc4ccncc4s3)c2)cc1]
Compound 290
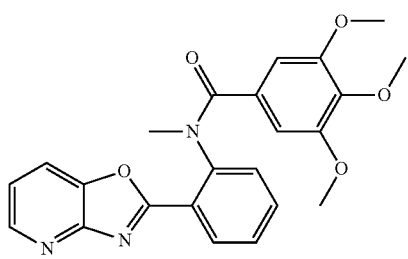 [SMILES: COc1cc(C(=O)N(C)c2ccccc2-c2nc3ncccc3o2)cc(OC)c1OC]
Compound 292

TABLE 1-continued
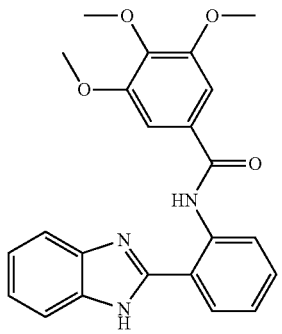 [SMILES: COc1cc(C(=O)Nc2ccccc2-c2nc3ccccc3[nH]2)cc(OC)c1OC]
Compound 293
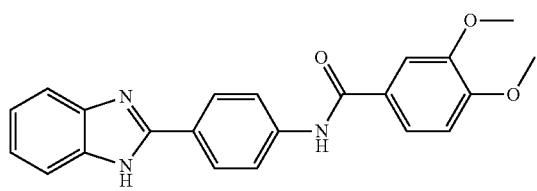 [SMILES: COc1ccc(C(=O)Nc2ccc(-c3nc4ccccc4[nH]3)cc2)cc1OC]
Compound 294
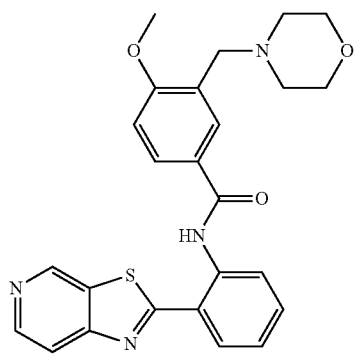 [SMILES: COc1ccc(C(=O)Nc2ccccc2-c2nc3ccncc3s2)cc1CN1CCOCC1]
Compound 295
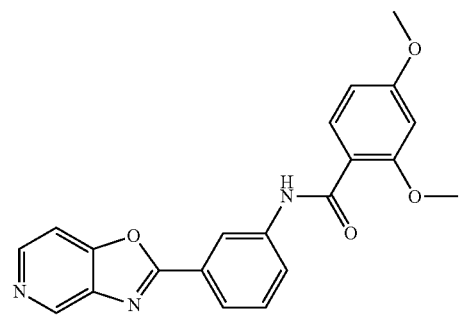 [SMILES: COc1ccc(C(=O)Nc2cccc(-c3nc4cnccc4o3)c2)c(OC)c1]
Compound 296
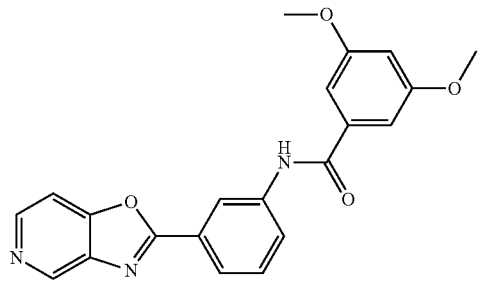 [SMILES: COc1cc(OC)cc(C(=O)Nc2cccc(-c3nc4cnccc4o3)c2)c1]
Compound 297

TABLE 1-continued
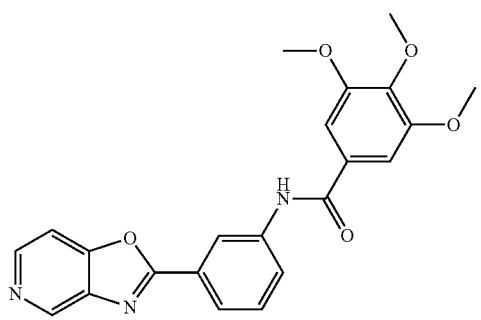 [SMILES: COc1cc(C(=O)Nc2cccc(-c3nc4cnccc4o3)c2)cc(OC)c1OC]
Compound 298
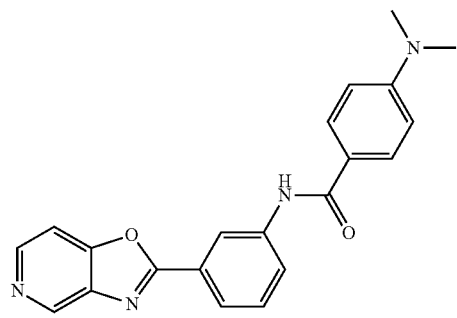 [SMILES: CN(C)c1ccc(C(=O)Nc2cccc(-c3nc4cnccc4o3)c2)cc1]
Compound 299
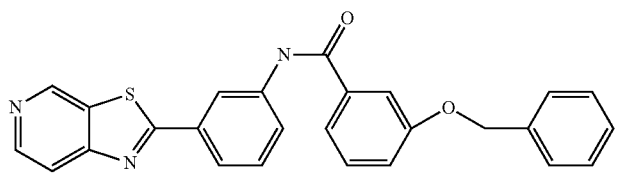 [SMILES: O=C(Nc1cccc(-c2nc3ccncc3s2)c1)c1cccc(OCc2ccccc2)c1]
Compound 303
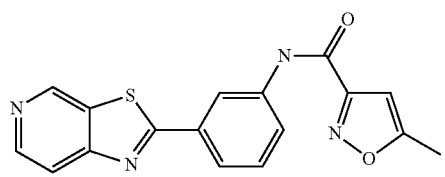 [SMILES: Cc1cc(C(=O)Nc2cccc(-c3nc4ccncc4s3)c2)no1]
Compound 304
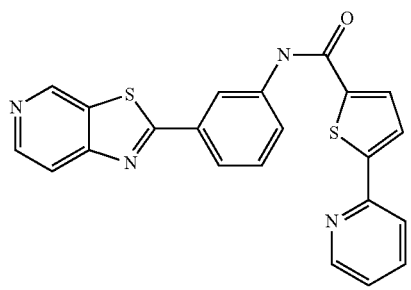 [SMILES: O=C(Nc1cccc(-c2nc3ccncc3s2)c1)c1ccc(-c2ccccn2)s1]
Compound 305
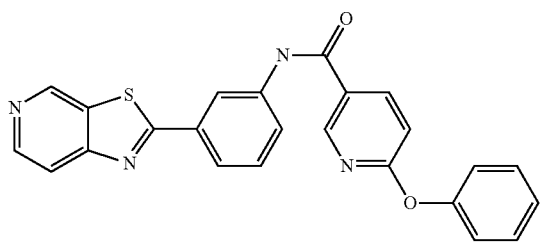 [SMILES: O=C(Nc1cccc(-c2nc3ccncc3s2)c1)c1ccc(Oc2ccccc2)nc1]
Compound 306

TABLE 1-continued
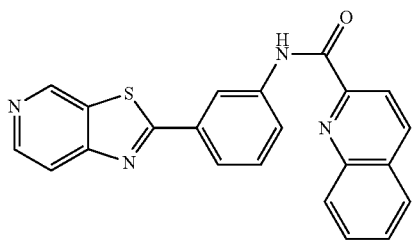 [SMILES: O=C(Nc1cccc(-c2nc3ccncc3s2)c1)c1ccc2ccccc2n1]
Compound 307
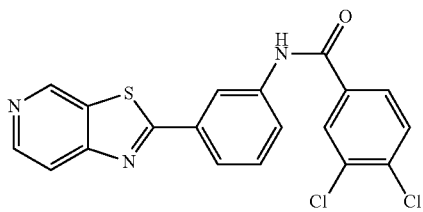 [SMILES: O=C(Nc1cccc(-c2nc3ccncc3s2)c1)c1ccc(Cl)c(Cl)c1]
Compound 308
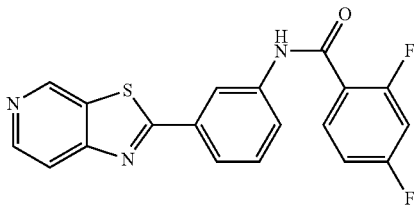 [SMILES: O=C(Nc1cccc(-c2nc3ccncc3s2)c1)c1ccc(F)cc1F]
Compound 309
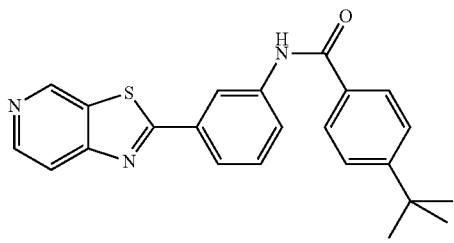 [SMILES: CC(C)(C)c1ccc(C(=O)Nc2cccc(-c3nc4ccncc4s3)c2)cc1]
Compound 310
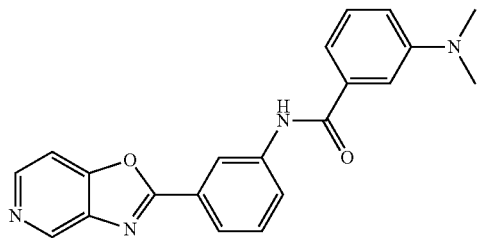 [SMILES: CN(C)c1cccc(C(=O)Nc2cccc(-c3nc4cnccc4o3)c2)c1]
Compound 311
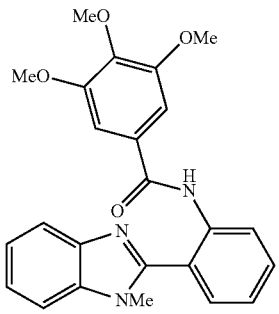 [SMILES: COc1cc(C(=O)Nc2ccccc2-c2nc3ccccc3n2C)cc(OC)c1OC]
Compound 313

TABLE 1-continued
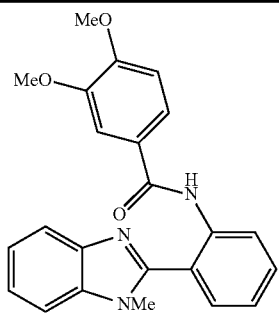
Compound 314
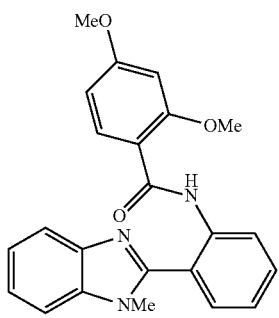 [SMILES: COc1ccc(C(=O)Nc2ccccc2-c2nc3ccccc3n2C)c(OC)c1]
Compound 315
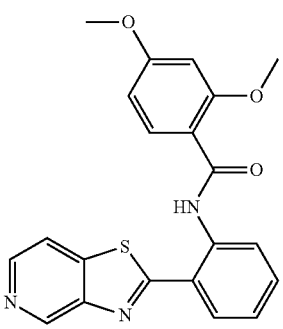
Compound 317
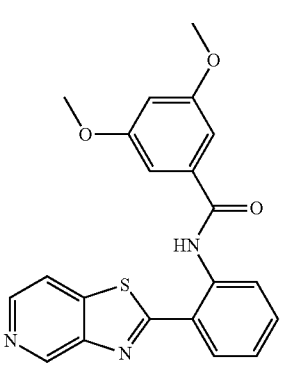
Compound 318
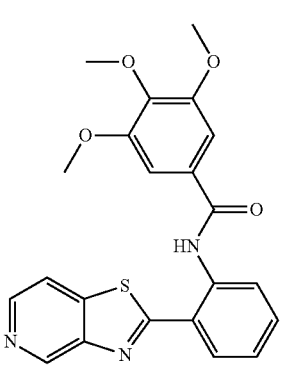 [SMILES: COc1cc(C(=O)Nc2ccccc2-c2nc3cnccc3s2)cc(OC)c1OC]
Compound 319

TABLE 1-continued
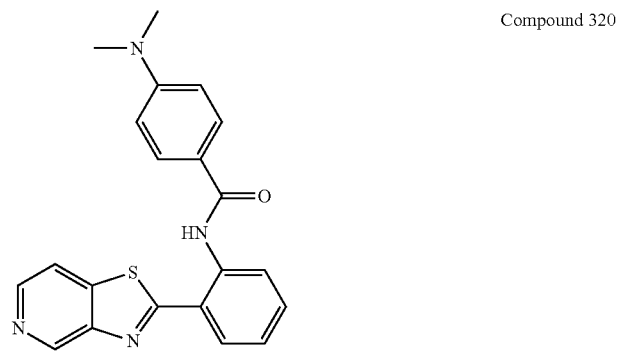
Compound 320
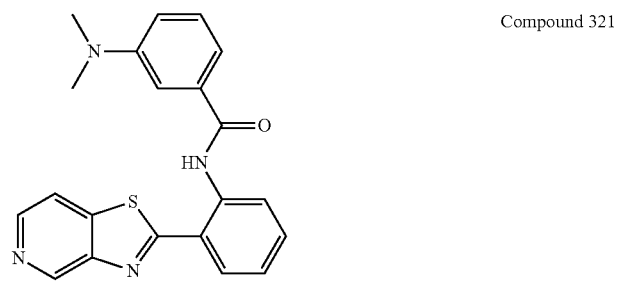
Compound 321
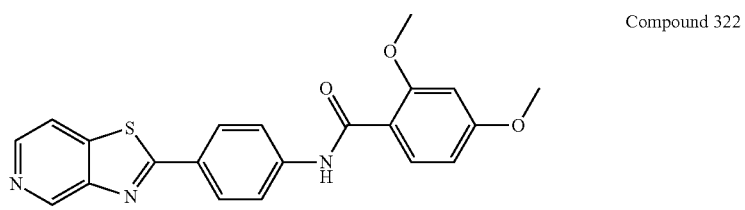
Compound 322
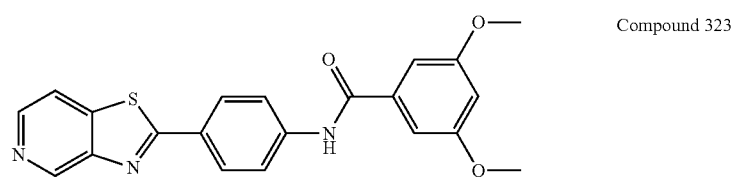
Compound 323
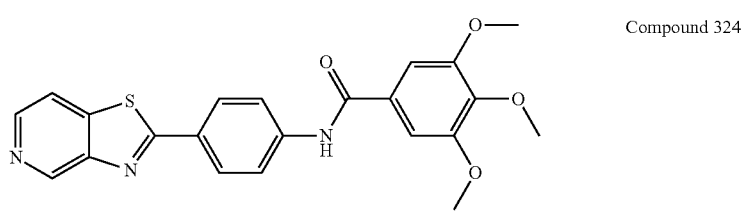
Compound 324
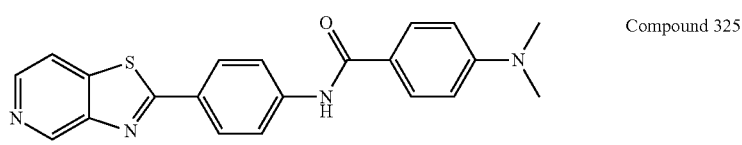
Compound 325

TABLE 1-continued
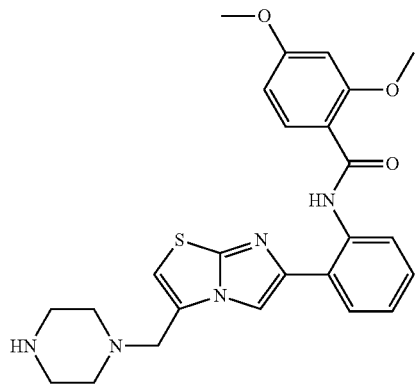 [SMILES: COc1ccc(C(=O)Nc2ccccc2-c2cn3c(CN4CCNCC4)csc3n2)c(OC)c1]
Compound 326
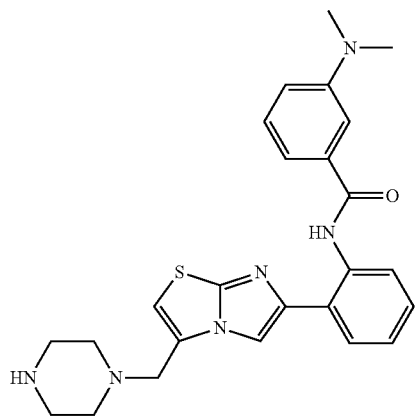 [SMILES: CN(C)c1cccc(C(=O)Nc2ccccc2-c2cn3c(CN4CCNCC4)csc3n2)c1]
Compound 327
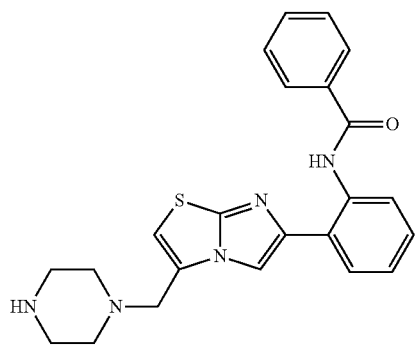 [SMILES: O=C(Nc1ccccc1-c1cn2c(CN3CCNCC3)csc2n1)c1ccccc1]
Compound 328
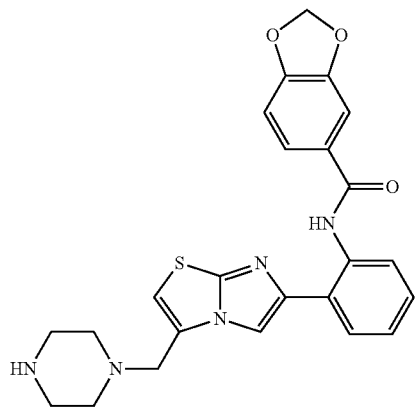 [SMILES: O=C(Nc1ccccc1-c1cn2c(CN3CCNCC3)csc2n1)c1ccc2c(c1)OCO2]
Compound 329

TABLE 1-continued
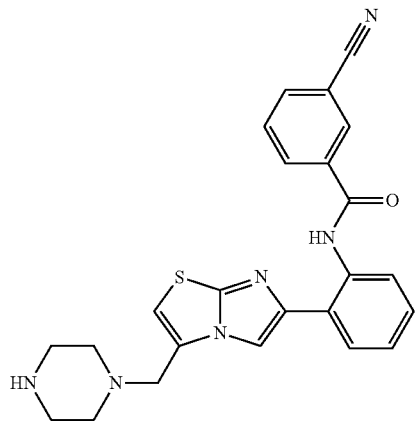 [SMILES: N#Cc1cccc(C(=O)Nc2ccccc2-c2cn3c(CN4CCNCC4)csc3n2)c1]
Compound 330
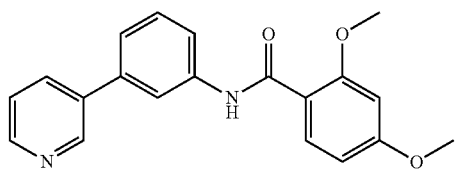 [SMILES: COc1ccc(C(=O)Nc2cccc(-c3cccnc3)c2)c(OC)c1]
Compound 331
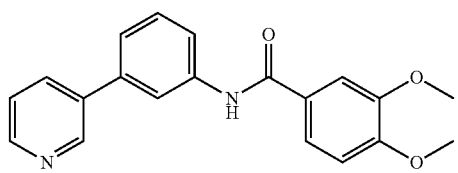 [SMILES: COc1ccc(C(=O)Nc2cccc(-c3cccnc3)c2)cc1OC]
Compound 332
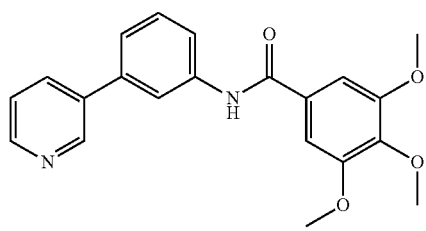 [SMILES: COc1cc(C(=O)Nc2cccc(-c3cccnc3)c2)cc(OC)c1OC]
Compound 333
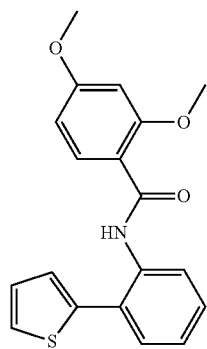 [SMILES: COc1ccc(C(=O)Nc2ccccc2-c2cccs2)c(OC)c1]
Compound 334

TABLE 1-continued
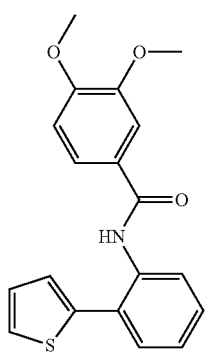 [SMILES: COc1ccc(C(=O)Nc2ccccc2-c2cccs2)cc1OC]
Compound 335
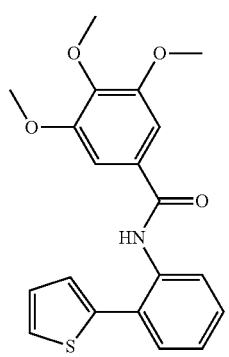 [SMILES: COc1cc(C(=O)Nc2ccccc2-c2cccs2)cc(OC)c1OC]
Compound 336
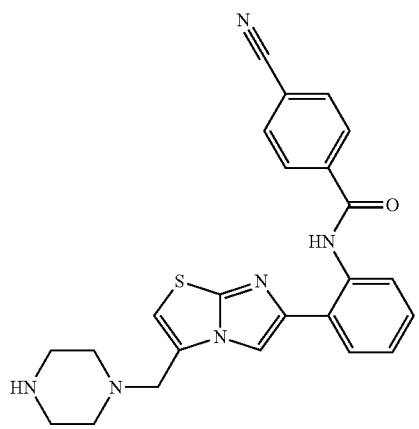 [SMILES: N#Cc1ccc(C(=O)Nc2ccccc2-c2cn3c(CN4CCNCC4)csc3n2)cc1]
Compound 337
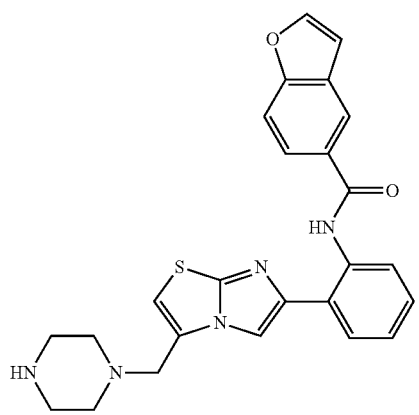 [SMILES: O=C(Nc1ccccc1-c1cn2c(CN3CCNCC3)csc2n1)c1ccc2occc2c1]
Compound 338

TABLE 1-continued
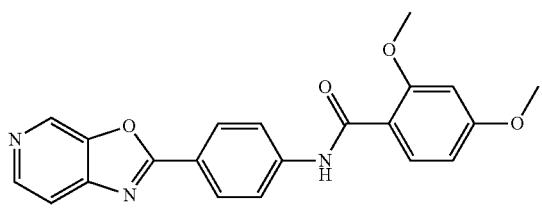 [SMILES: COc1ccc(C(=O)Nc2ccc(-c3nc4ccncc4o3)cc2)c(OC)c1] Compound 339
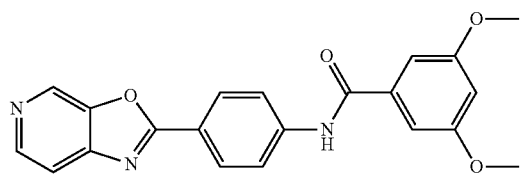 [SMILES: COc1cc(OC)cc(C(=O)Nc2ccc(-c3nc4ccncc4o3)cc2)c1] Compound 340
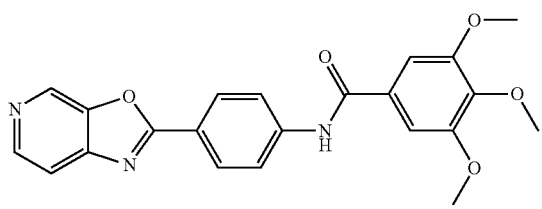 [SMILES: COc1cc(C(=O)Nc2ccc(-c3nc4ccncc4o3)cc2)cc(OC)c1OC] Compound 341
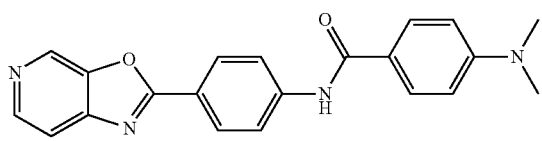 Compound 342
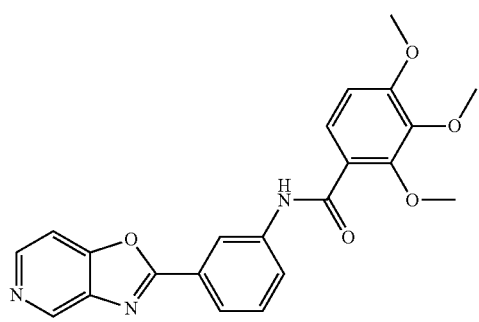 Compound 343
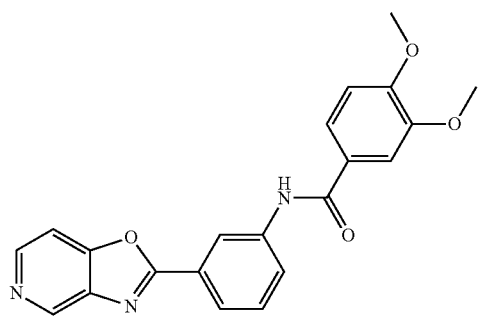 Compound 344
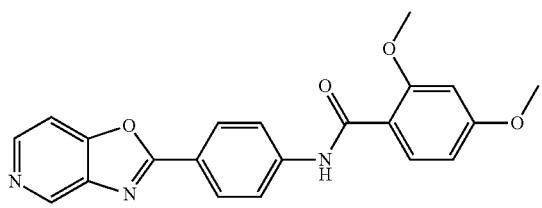 [SMILES: COc1ccc(C(=O)Nc2ccc(-c3nc4cnccc4o3)cc2)c(OC)c1] Compound 345

TABLE 1-continued
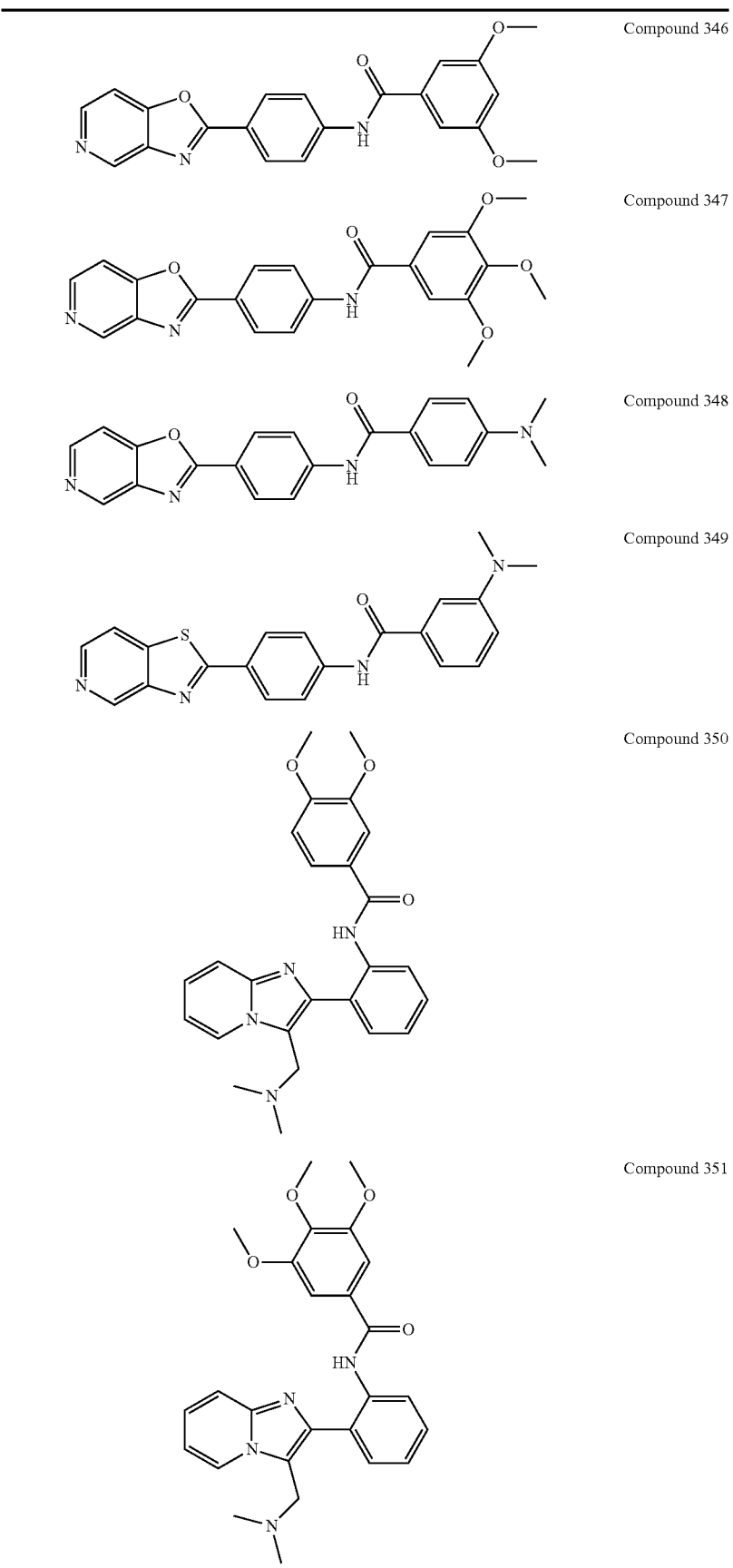
Compound 346
Compound 347
Compound 348
Compound 349
Compound 350
Compound 351

TABLE 1-continued
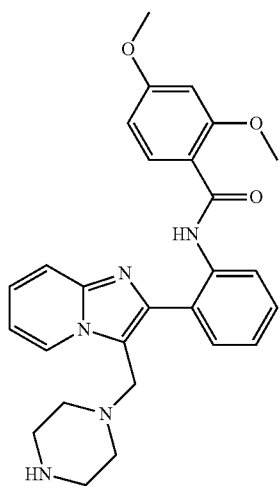 [SMILES: COc1ccc(C(=O)Nc2ccccc2-c2nc3ccccn3c2CN2CCNCC2)c(OC)c1]
Compound 359
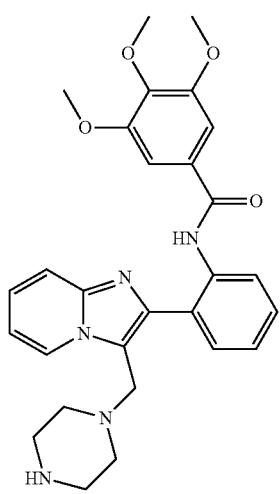 [SMILES: COc1cc(C(=O)Nc2ccccc2-c2nc3ccccn3c2CN2CCNCC2)cc(OC)c1OC]
Compound 362
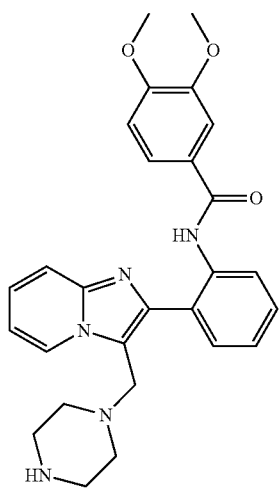 [SMILES: COc1ccc(C(=O)Nc2ccccc2-c2nc3ccccn3c2CN2CCNCC2)cc1OC]
Compound 364

TABLE 1-continued
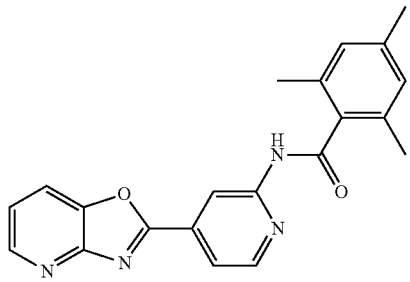 [SMILES: Cc1cc(C)c(C(=O)Nc2cc(-c3nc4ncccc4o3)ccn2)c(C)c1]
Compound 367
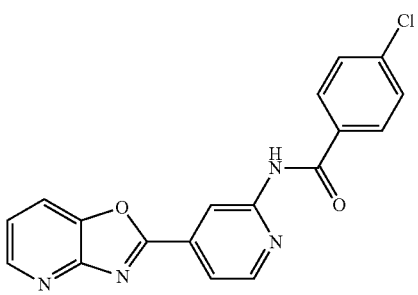 [SMILES: O=C(Nc1cc(-c2nc3ncccc3o2)ccn1)c1ccc(Cl)cc1]
Compound 369
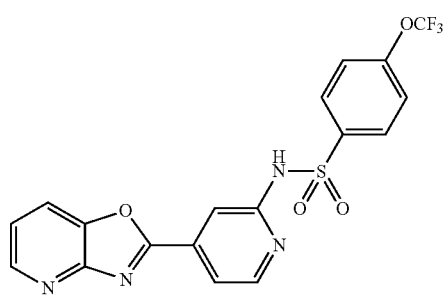 [SMILES: O=S(=O)(Nc1cc(-c2nc3ncccc3o2)ccn1)c1ccc(OC(F)(F)F)cc1]
Compound 370
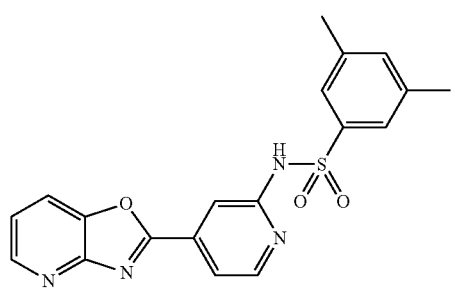 [SMILES: Cc1cc(C)cc(S(=O)(=O)Nc2cc(-c3nc4ncccc4o3)ccn2)c1]
Compound 371
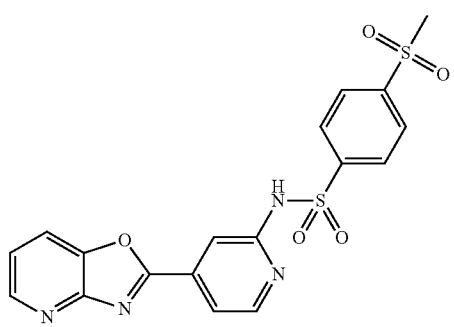 [SMILES: CS(=O)(=O)c1ccc(S(=O)(=O)Nc2cc(-c3nc4ncccc4o3)ccn2)cc1]
Compound 372

TABLE 1-continued
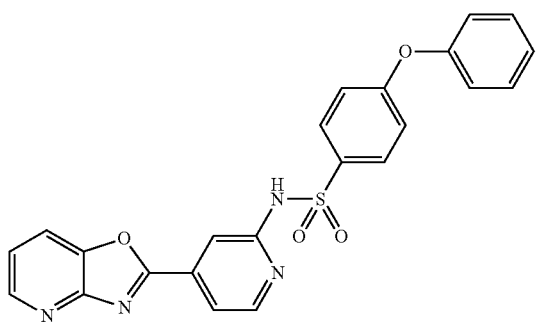 [SMILES: O=S(=O)(Nc1cc(-c2nc3ncccc3o2)ccn1)c1ccc(Oc2ccccc2)cc1]
Compound 373
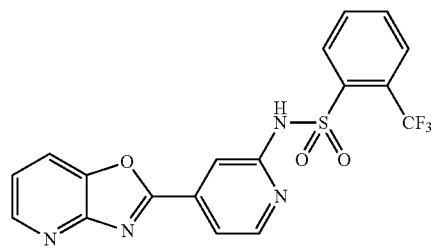 [SMILES: O=S(=O)(Nc1cc(-c2nc3ncccc3o2)ccn1)c1ccccc1C(F)(F)F]
Compound 374
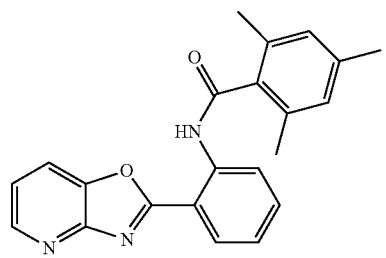 [SMILES: Cc1cc(C)c(C(=O)Nc2ccccc2-c2nc3ncccc3o2)c(C)c1]
Compound 375
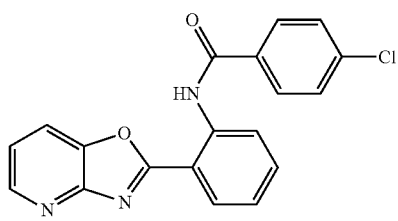 [SMILES: O=C(Nc1ccccc1-c1nc2ncccc2o1)c1ccc(Cl)cc1]
Compound 376
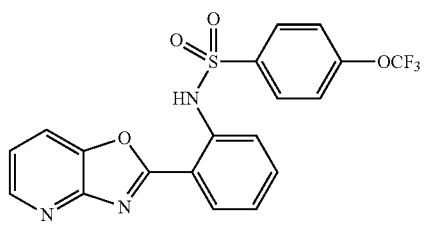 [SMILES: O=S(=O)(Nc1ccccc1-c1nc2ncccc2o1)c1ccc(OC(F)(F)F)cc1]
Compound 377
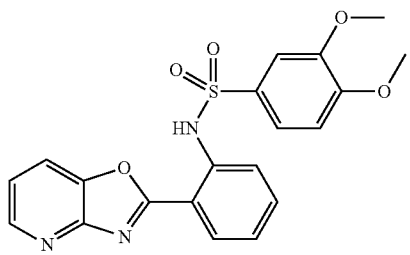 [SMILES: COc1ccc(S(=O)(=O)Nc2ccccc2-c2nc3ncccc3o2)cc1OC]
Compound 378

TABLE 1-continued
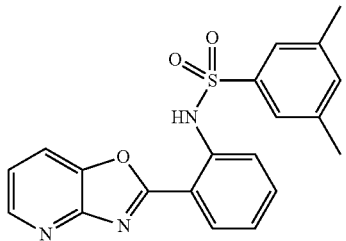 [SMILES: Cc1cc(C)cc(S(=O)(=O)Nc2ccccc2-c2nc3ncccc3o2)c1]
Compound 379
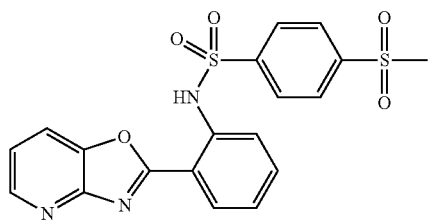 [SMILES: CS(=O)(=O)c1ccc(S(=O)(=O)Nc2ccccc2-c2nc3ncccc3o2)cc1]
Compound 380
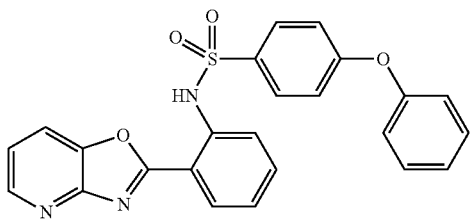 [SMILES: O=S(=O)(Nc1ccccc1-c1nc2ncccc2o1)c1ccc(Oc2ccccc2)cc1]
Compound 381
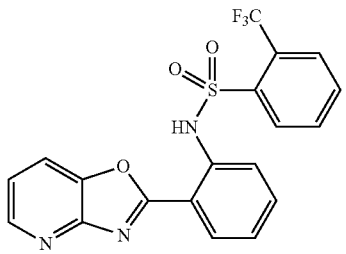 [SMILES: O=S(=O)(Nc1ccccc1-c1nc2ncccc2o1)c1ccccc1C(F)(F)F]
Compound 382
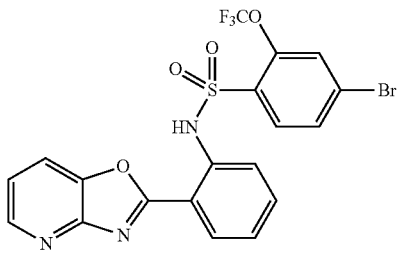 [SMILES: O=S(=O)(Nc1ccccc1-c1nc2ncccc2o1)c1ccc(Br)cc1OC(F)(F)F]
Compound 383
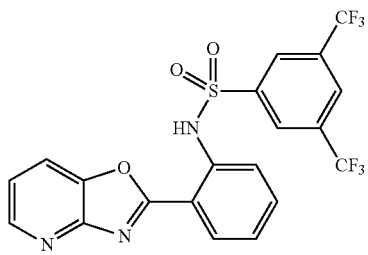 [SMILES: O=S(=O)(Nc1ccccc1-c1nc2ncccc2o1)c1cc(C(F)(F)F)cc(C(F)(F)F)c1]
Compound 384

TABLE 1-continued
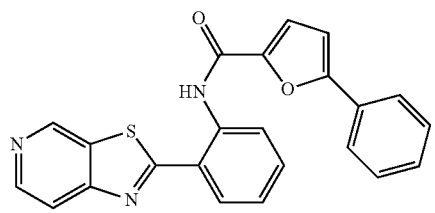 [SMILES: O=C(Nc1ccccc1-c1nc2ccncc2s1)c1ccc(-c2ccccc2)o1]
Compound 385
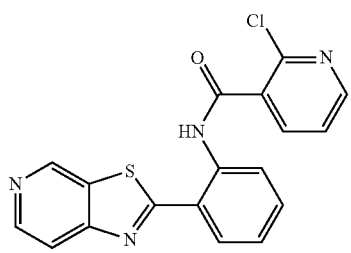 [SMILES: O=C(Nc1ccccc1-c1nc2ccncc2s1)c1cccnc1Cl]
Compound 387
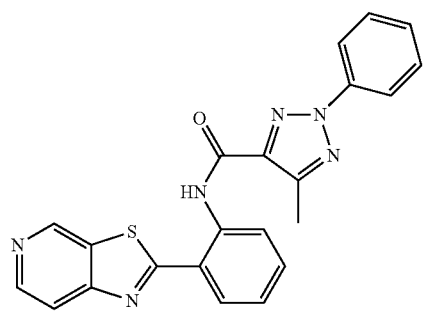 [SMILES: Cc1nn(-c2ccccc2)nc1C(=O)Nc1ccccc1-c1nc2ccncc2s1]
Compound 390
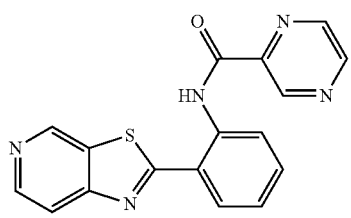 [SMILES: O=C(Nc1ccccc1-c1nc2ccncc2s1)c1cnccn1]
Compound 391
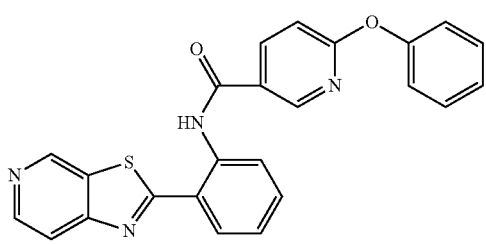 [SMILES: O=C(Nc1ccccc1-c1nc2ccncc2s1)c1ccc(Oc2ccccc2)nc1]
Compound 392
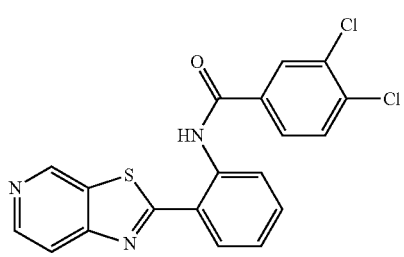 [SMILES: O=C(Nc1ccccc1-c1nc2ccncc2s1)c1ccc(Cl)c(Cl)c1]
Compound 393

TABLE 1-continued
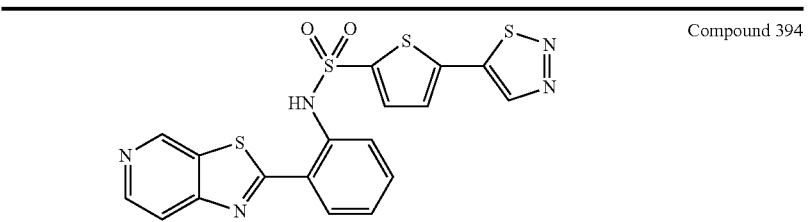 Compound 394
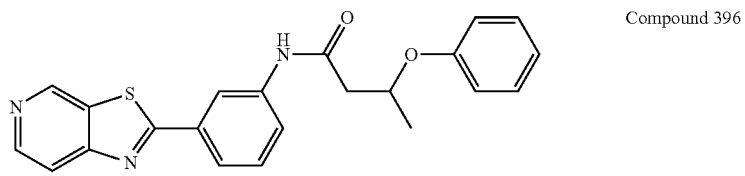 Compound 396
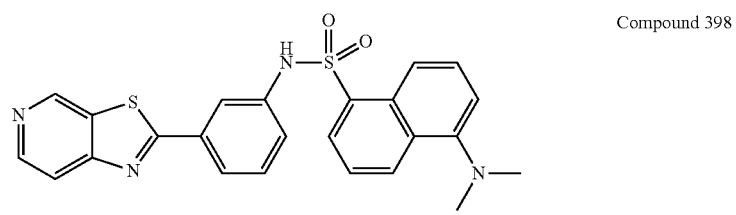 Compound 398
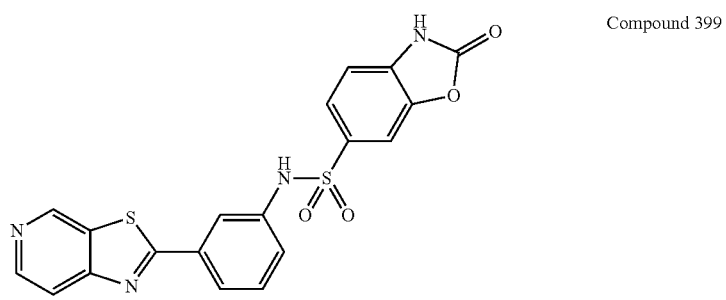 Compound 399
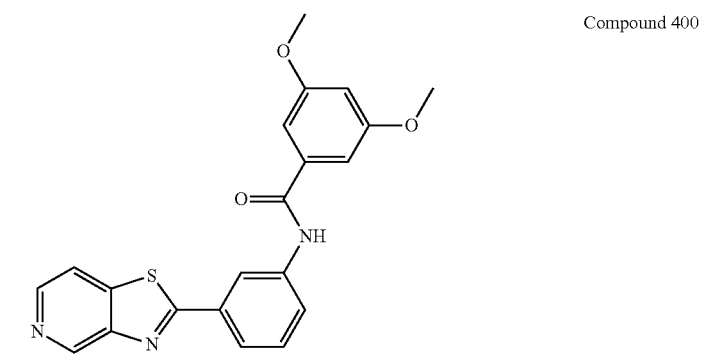 Compound 400
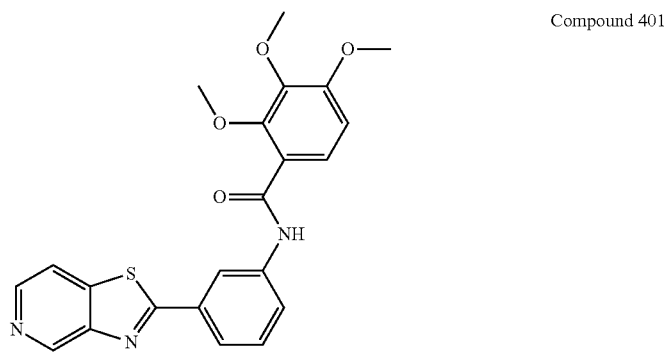 Compound 401

TABLE 1-continued
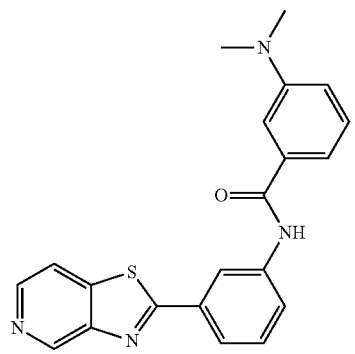 [SMILES: CN(C)c1cccc(C(=O)Nc2cccc(-c3nc4cnccc4s3)c2)c1]
Compound 402
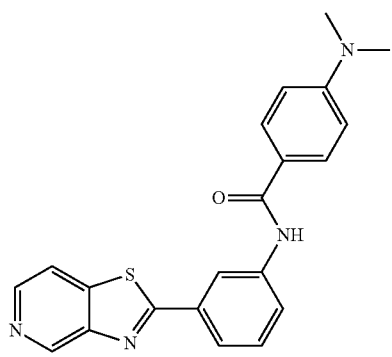 [SMILES: CN(C)c1ccc(C(=O)Nc2cccc(-c3nc4cnccc4s3)c2)cc1]
Compound 403
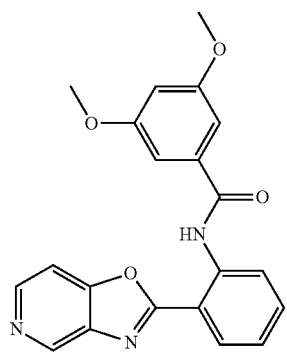 [SMILES: COc1cc(OC)cc(C(=O)Nc2ccccc2-c2nc3cnccc3o2)c1]
Compound 404
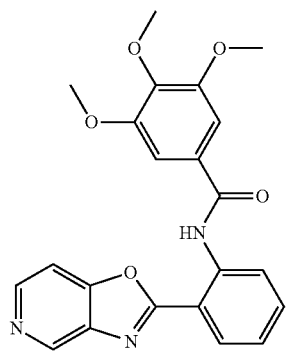 [SMILES: COc1cc(C(=O)Nc2ccccc2-c2nc3cnccc3o2)cc(OC)c1OC]
Compound 405

TABLE 1-continued
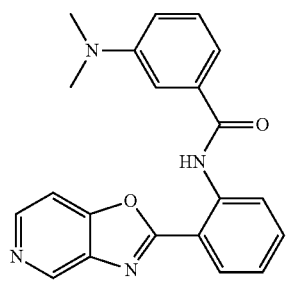 [SMILES: CN(C)c1cccc(C(=O)Nc2ccccc2-c2nc3cnccc3o2)c1]
Compound 406
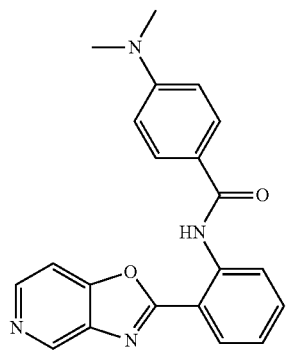 [SMILES: CN(C)c1ccc(C(=O)Nc2ccccc2-c2nc3cnccc3o2)cc1]
Compound 407
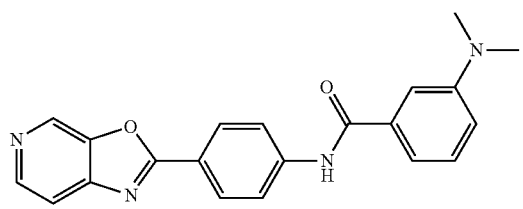 [SMILES: CN(C)c1cccc(C(=O)Nc2ccc(-c3nc4ccncc4o3)cc2)c1]
Compound 408
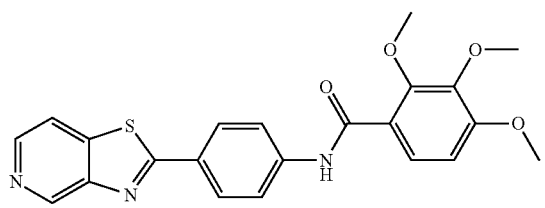
Compound 409
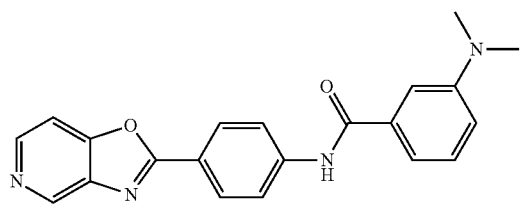
Compound 410
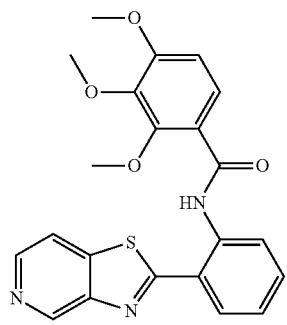
Compound 411

TABLE 1-continued
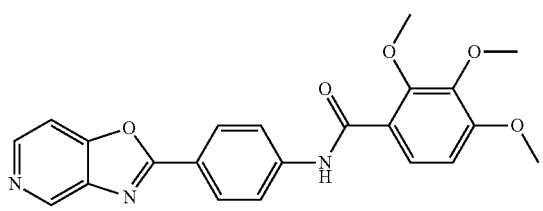 [SMILES: COc1ccc(C(=O)Nc2ccc(-c3nc4cnccc4s3)cc2)c(OC)c1OC]
Compound 412
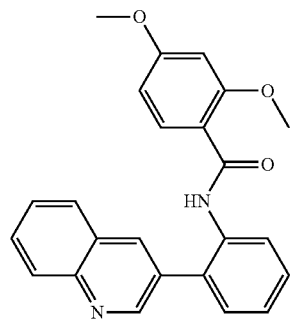 [SMILES: COc1ccc(C(=O)Nc2ccccc2-c2cnc3ccccc3c2)c(OC)c1]
Compound 413
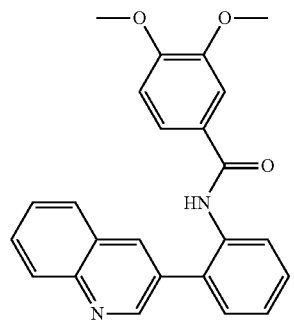 [SMILES: COc1ccc(C(=O)Nc2ccccc2-c2cnc3ccccc3c2)cc1OC]
Compound 414
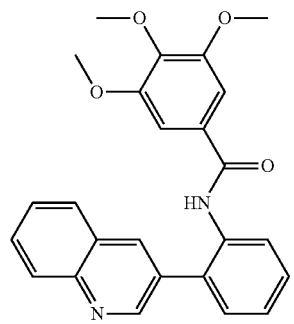 [SMILES: COc1cc(C(=O)Nc2ccccc2-c2cnc3ccccc3c2)cc(OC)c1OC]
Compound 415
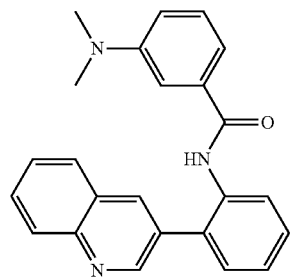 [SMILES: CN(C)c1cccc(C(=O)Nc2ccccc2-c2cnc3ccccc3c2)c1]
Compound 416

TABLE 1-continued
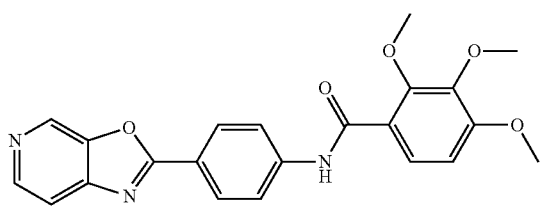
Compound 419
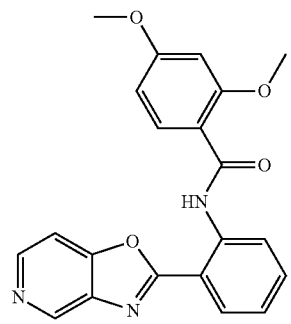 [SMILES: COc1ccc(C(=O)Nc2ccccc2-c2nc3cnccc3o2)c(OC)c1]
Compound 420
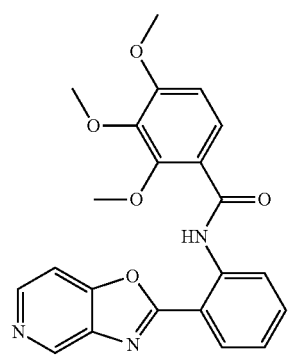 [SMILES: COc1ccc(C(=O)Nc2ccccc2-c2nc3cnccc3o2)c(OC)c1OC]
Compound 421
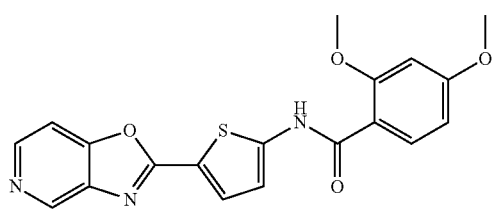 [SMILES: COc1ccc(C(=O)Nc2ccc(-c3nc4cnccc4o3)s2)c(OC)c1]
Compound 422
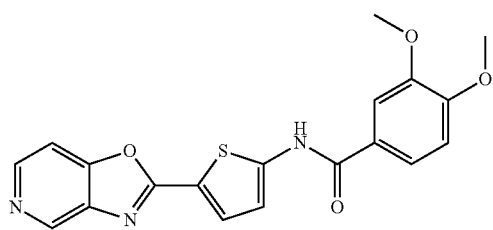 [SMILES: COc1ccc(C(=O)Nc2ccc(-c3nc4cnccc4o3)s2)cc1OC]
Compound 423
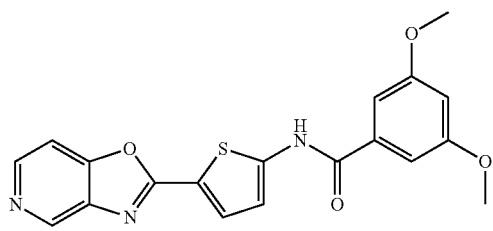
Compound 424

TABLE 1-continued
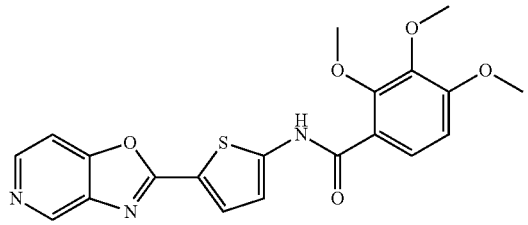
Compound 425
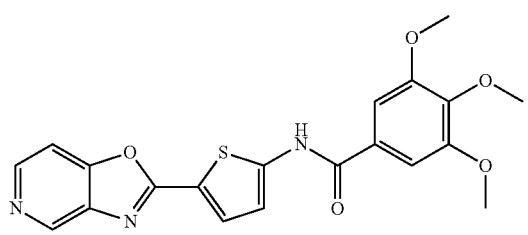
Compound 426
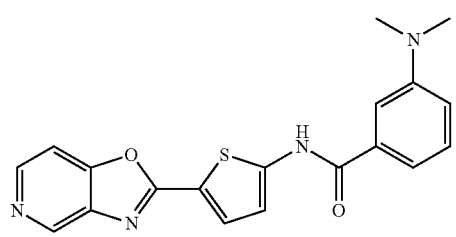
Compound 427
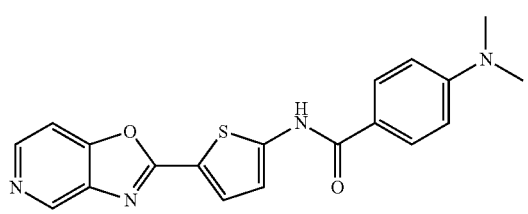
Compound 428
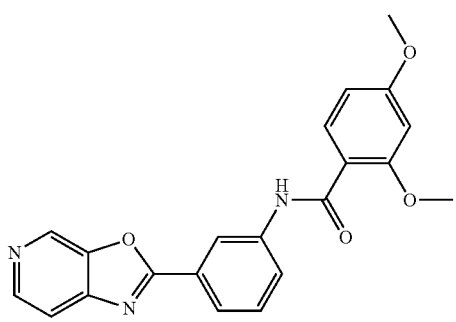
Compound 429
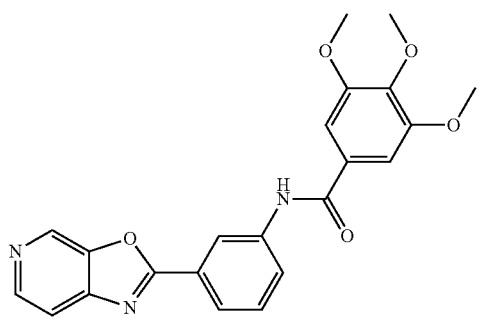 [SMILES: COc1cc(C(=O)Nc2cccc(-c3nc4ccncc4o3)c2)cc(OC)c1OC]
Compound 430

TABLE 1-continued
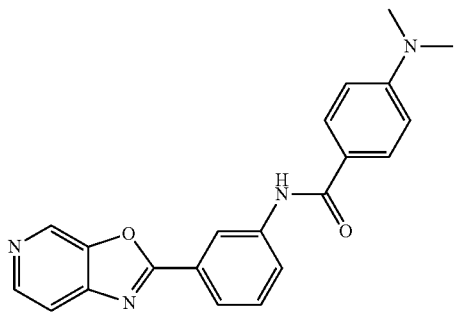 [SMILES: CN(C)c1ccc(C(=O)Nc2cccc(-c3nc4ccncc4o3)c2)cc1]
Compound 431
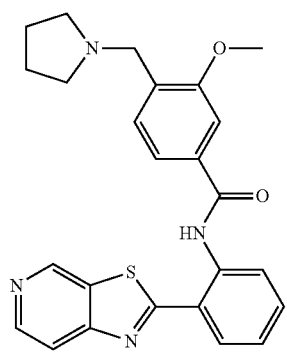 [SMILES: COc1cc(C(=O)Nc2ccccc2-c2nc3ccncc3s2)ccc1CN1CCCC1]
Compound 436
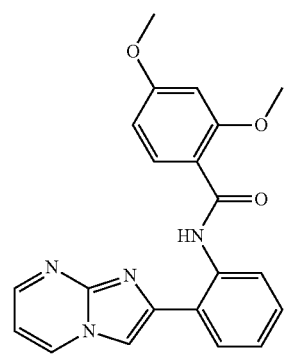 [SMILES: COc1ccc(C(=O)Nc2ccccc2-c2cn3cccnc3n2)c(OC)c1]
Compound 437
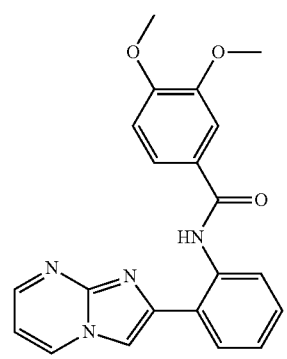 [SMILES: COc1ccc(C(=O)Nc2ccccc2-c2cn3cccnc3n2)cc1OC]
Compound 438

TABLE 1-continued
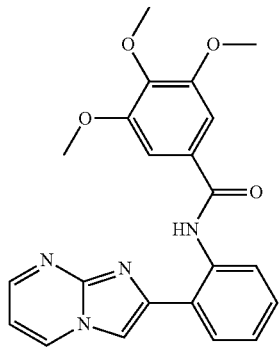 [SMILES: COc1cc(C(=O)Nc2ccccc2-c2cn3cccnc3n2)cc(OC)c1OC]
Compound 439
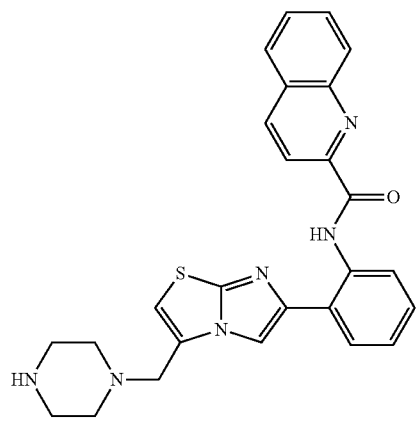 [SMILES: O=C(Nc1ccccc1-c1cn2c(CN3CCNCC3)csc2n1)c1ccc2ccccc2n1]
Compound 440
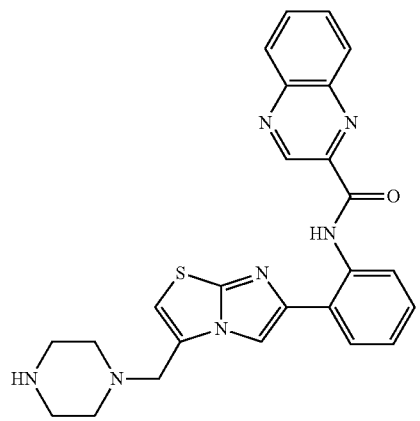 [SMILES: O=C(Nc1ccccc1-c1cn2c(CN3CCNCC3)csc2n1)c1cnc2ccccc2n1]
Compound 441
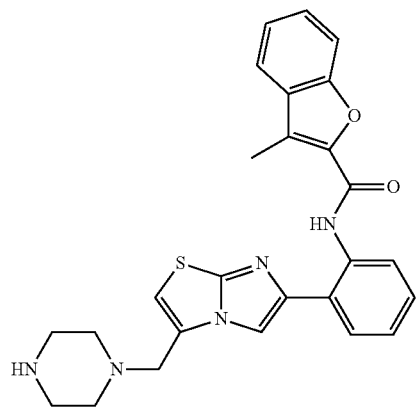 [SMILES: Cc1c(C(=O)Nc2ccccc2-c2cn3c(CN4CCNCC4)csc3n2)oc2ccccc12]
Compound 442

TABLE 1-continued
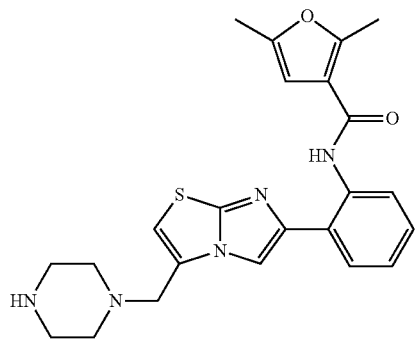 [SMILES: Cc1cc(C(=O)Nc2ccccc2-c2cn3c(CN4CCNCC4)csc3n2)c(C)o1]
Compound 443
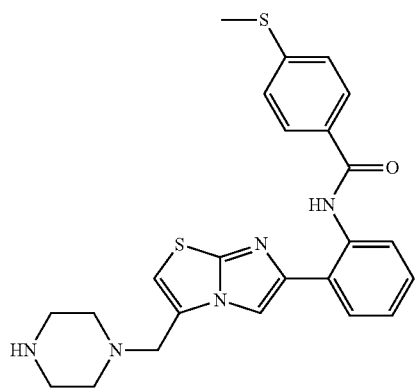 [SMILES: CSc1ccc(C(=O)Nc2ccccc2-c2cn3c(CN4CCNCC4)csc3n2)cc1]
Compound 444
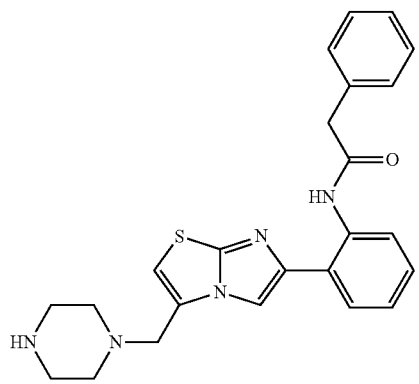 [SMILES: O=C(Cc1ccccc1)Nc1ccccc1-c1cn2c(CN3CCNCC3)csc2n1]
Compound 445
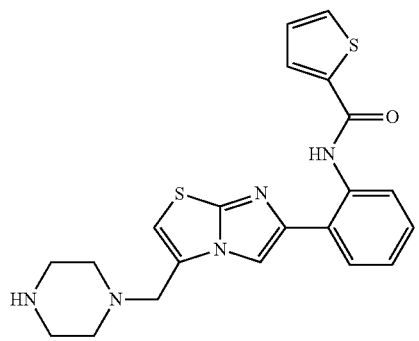 [SMILES: O=C(Nc1ccccc1-c1cn2c(CN3CCNCC3)csc2n1)c1cccs1]
Compound 446

TABLE 1-continued
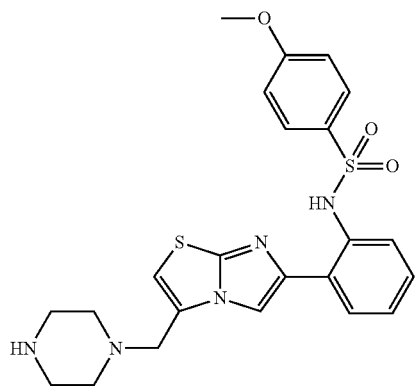 [SMILES: COc1ccc(S(=O)(=O)Nc2ccccc2-c2cn3c(CN4CCNCC4)csc3n2)cc1]
Compound 447
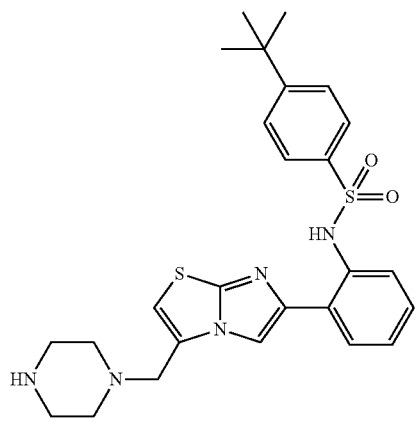 [SMILES: CC(C)(C)c1ccc(S(=O)(=O)Nc2ccccc2-c2cn3c(CN4CCNCC4)csc3n2)cc1]
Compound 448
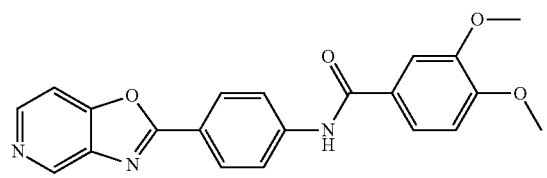 [SMILES: COc1ccc(C(=O)Nc2ccc(-c3nc4cnccc4o3)cc2)cc1OC]
Compound 449
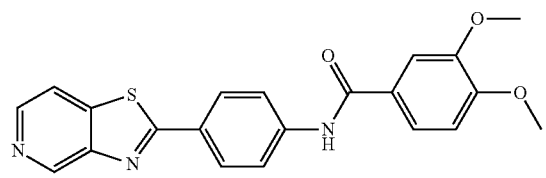
Compound 450
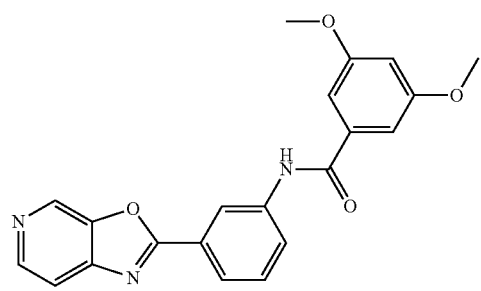
Compound 451

TABLE 1-continued
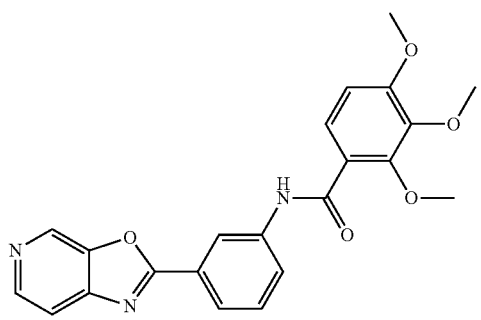 [SMILES: COc1ccc(C(=O)Nc2cccc(-c3nc4ccncc4o3)c2)c(OC)c1OC]
Compound 452
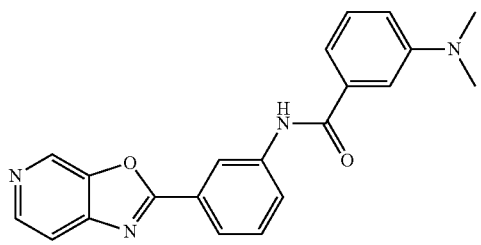 [SMILES: CN(C)c1cccc(C(=O)Nc2cccc(-c3nc4ccncc4o3)c2)c1]
Compound 453
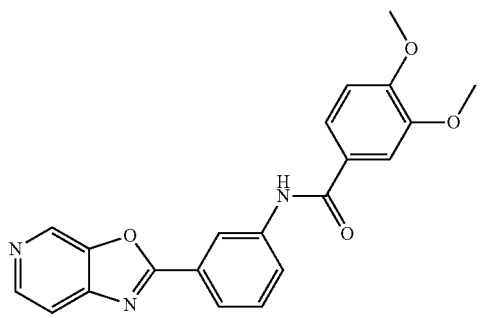 [SMILES: COc1ccc(C(=O)Nc2cccc(-c3nc4ccncc4o3)c2)cc1OC]
Compound 454
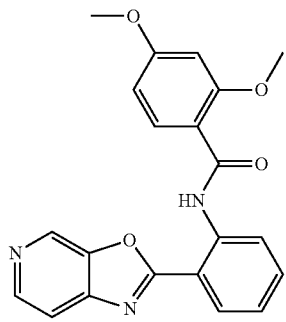 [SMILES: COc1ccc(C(=O)Nc2ccccc2-c2nc3ccncc3o2)c(OC)c1]
Compound 455
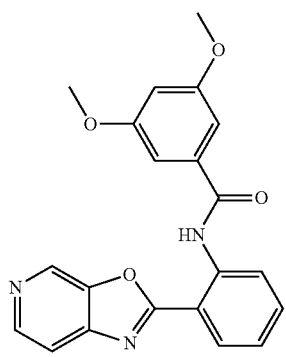
Compound 456

TABLE 1-continued
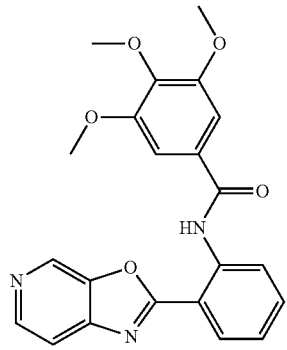 [SMILES: COc1cc(C(=O)Nc2ccccc2-c2nc3ccncc3o2)cc(OC)c1OC]
Compound 457
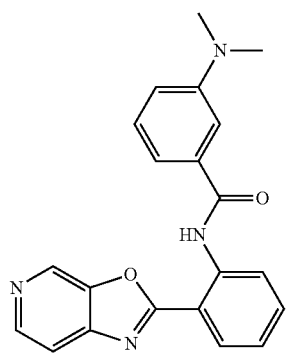 [SMILES: CN(C)c1cccc(C(=O)Nc2ccccc2-c2nc3ccncc3o2)c1]
Compound 458
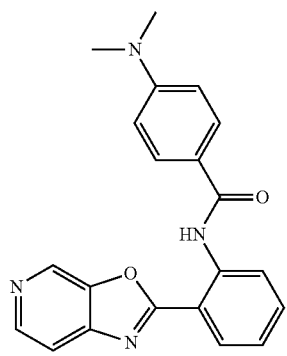 [SMILES: CN(C)c1ccc(C(=O)Nc2ccccc2-c2nc3ccncc3o2)cc1]
Compound 459
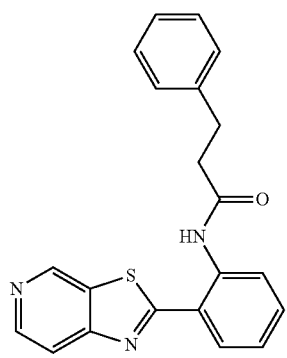 [SMILES: O=C(CCc1ccccc1)Nc1ccccc1-c1nc2ccncc2s1]
Compound 460

TABLE 1-continued
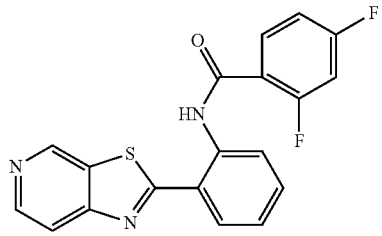 [SMILES: O=C(Nc1ccccc1-c1nc2ccncc2s1)c1ccc(F)cc1F]
Compound 461
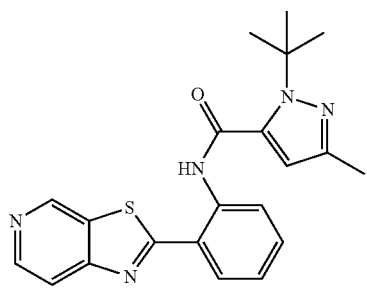 [SMILES: Cc1cc(C(=O)Nc2ccccc2-c2nc3ccncc3s2)n(C(C)(C)C)n1]
Compound 462
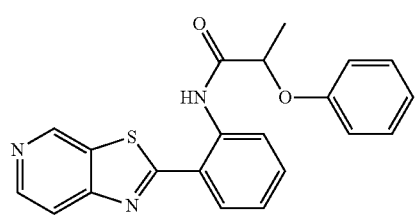 [SMILES: CC(Oc1ccccc1)C(=O)Nc1ccccc1-c1nc2ccncc2s1]
Compound 463
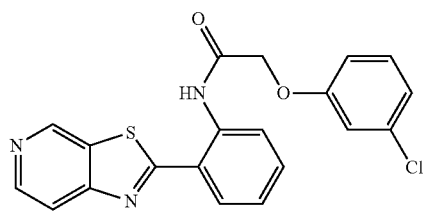 [SMILES: O=C(COc1cccc(Cl)c1)Nc1ccccc1-c1nc2ccncc2s1]
Compound 465
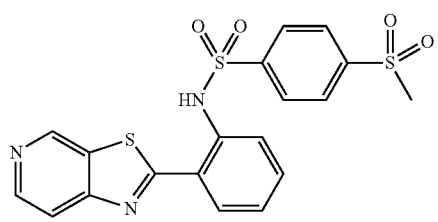 [SMILES: CS(=O)(=O)c1ccc(S(=O)(=O)Nc2ccccc2-c2nc3ccncc3s2)cc1]
Compound 466
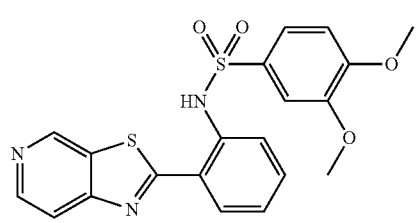 [SMILES: COc1ccc(S(=O)(=O)Nc2ccccc2-c2nc3ccncc3s2)cc1OC]
Compound 467

TABLE 1-continued
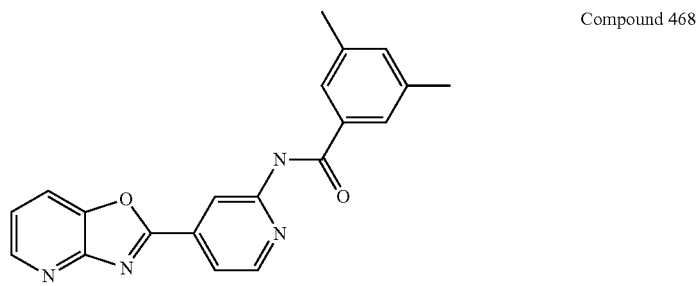
Compound 468
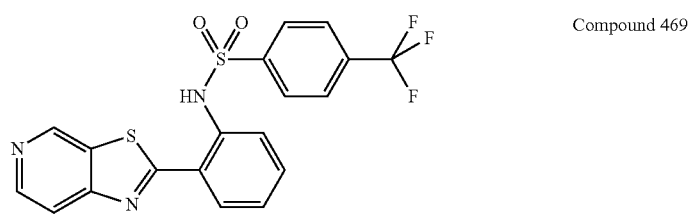
Compound 469
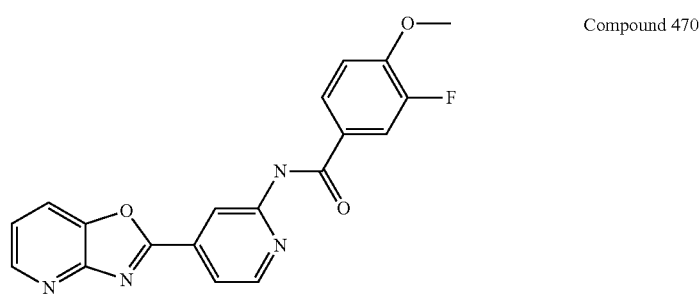
Compound 470
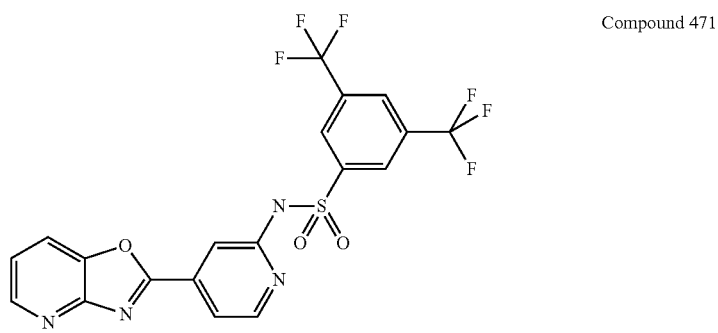
Compound 471
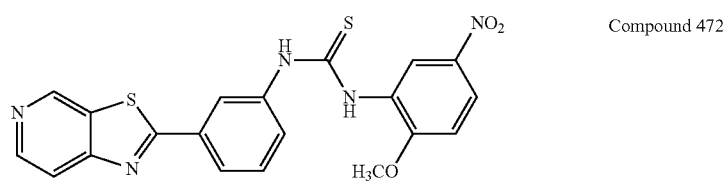
Compound 472
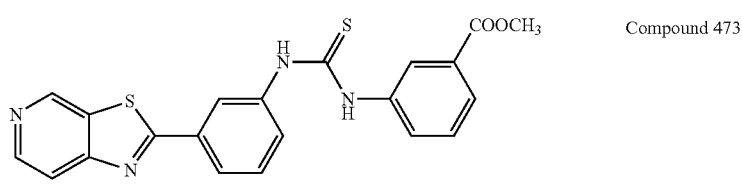
Compound 473

TABLE 1-continued
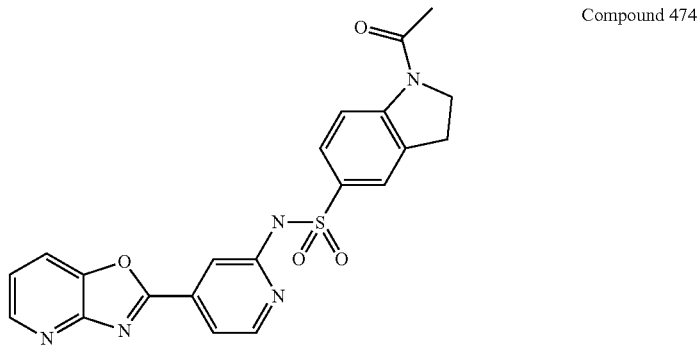
Compound 474
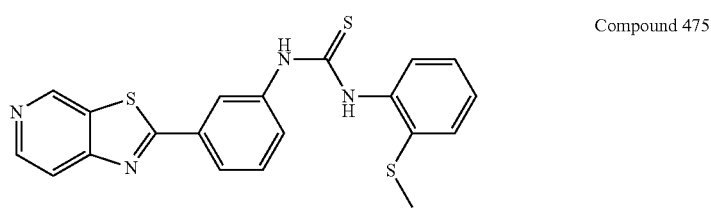
Compound 475
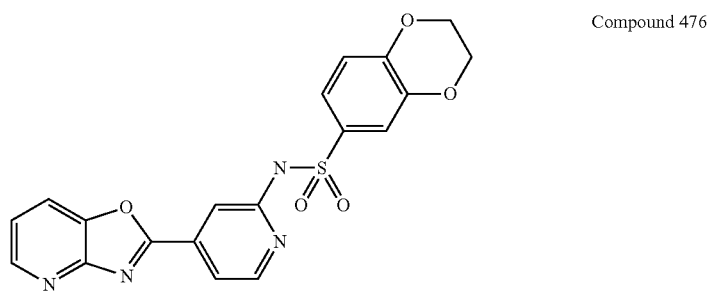
Compound 476
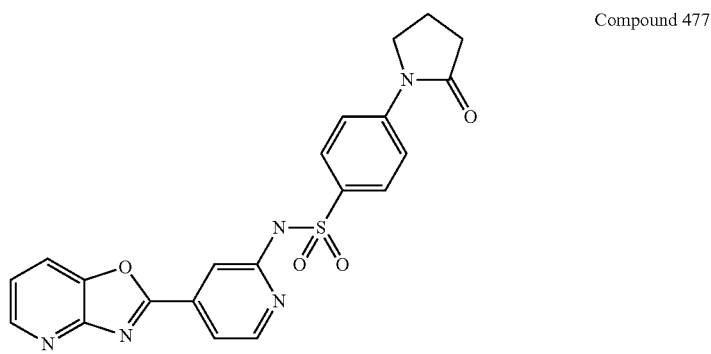
Compound 477
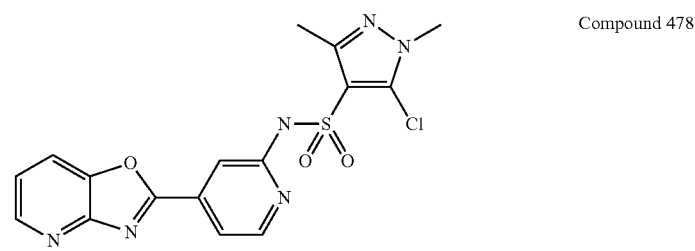
Compound 478

TABLE 1-continued
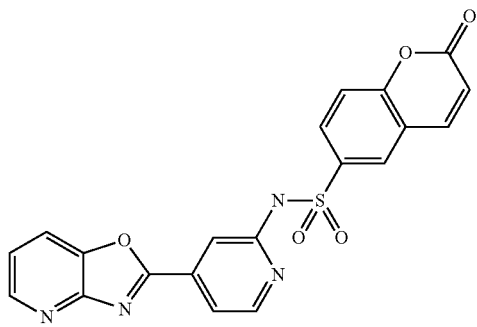 [SMILES: O=c1ccc2cc(S(=O)(=O)Nc3cc(-c4nc5ncccc5o4)ccn3)ccc2o1]
Compound 479
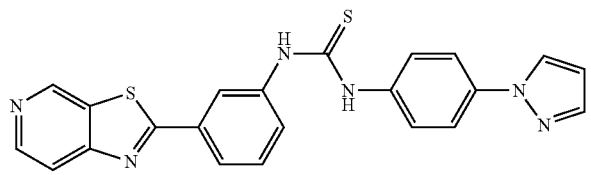 [SMILES: S=C(Nc1ccc(-n2cccn2)cc1)Nc1cccc(-c2nc3ccncc3s2)c1]
Compound 481
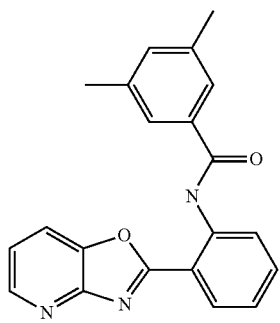 [SMILES: Cc1cc(C)cc(C(=O)Nc2ccccc2-c2nc3ncccc3o2)c1]
Compound 482
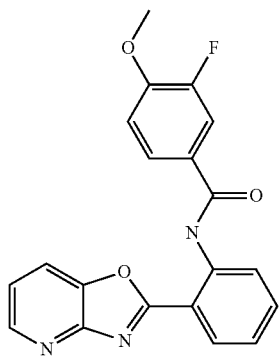 [SMILES: COc1ccc(C(=O)Nc2ccccc2-c2nc3ncccc3o2)cc1F]
Compound 483
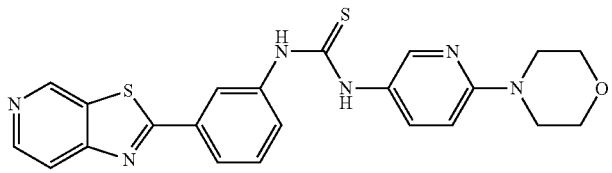 [SMILES: S=C(Nc1ccc(N2CCOCC2)nc1)Nc1cccc(-c2nc3ccncc3s2)c1]
Compound 484
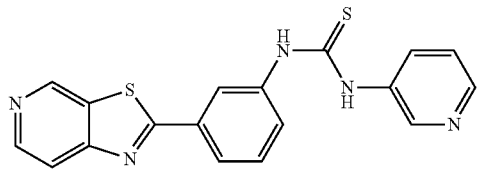 [SMILES: S=C(Nc1cccnc1)Nc1cccc(-c2nc3ccncc3s2)c1]
Compound 485

TABLE 1-continued
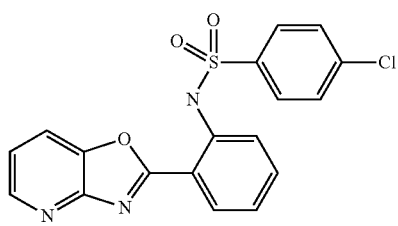 [SMILES: O=S(=O)(Nc1ccccc1-c1nc2ncccc2o1)c1ccc(Cl)cc1] Compound 486
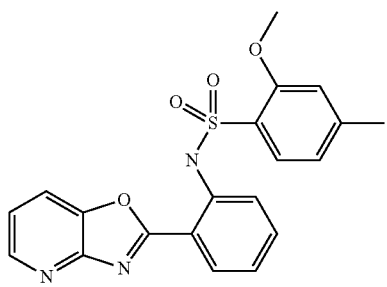 [SMILES: COc1cc(C)ccc1S(=O)(=O)Nc1ccccc1-c1nc2ncccc2o1] Compound 487
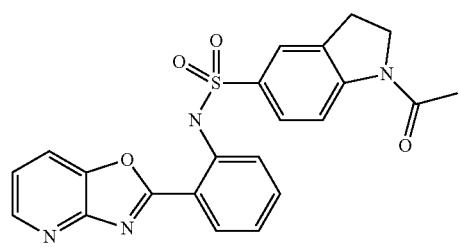 [SMILES: CC(=O)N1CCc2cc(S(=O)(=O)Nc3ccccc3-c3nc4ncccc4o3)ccc21] Compound 488
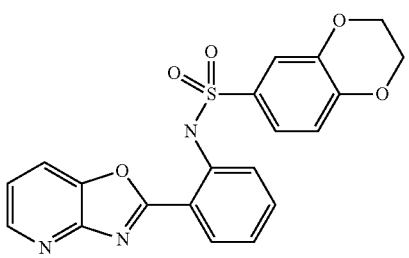 Compound 489
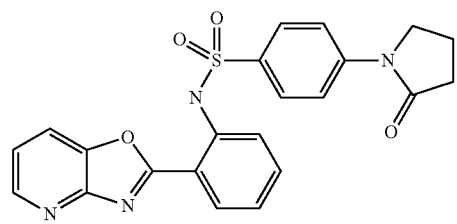 [SMILES: O=C1CCCN1c1ccc(S(=O)(=O)Nc2ccccc2-c2nc3ncccc3o2)cc1] Compound 490
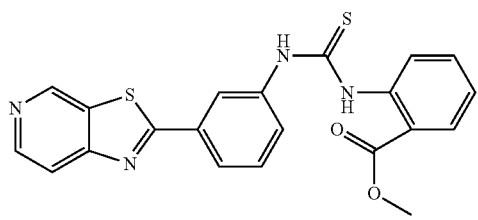 [SMILES: COC(=O)c1ccccc1NC(=S)Nc1cccc(-c2nc3ccncc3s2)c1] Compound 491

TABLE 1-continued
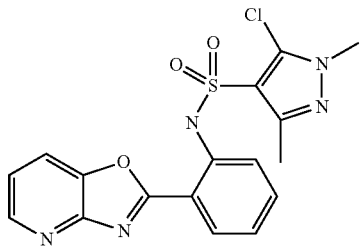 [SMILES: Cc1nn(C)c(Cl)c1S(=O)(=O)Nc1ccccc1-c1nc2ncccc2o1] Compound 492
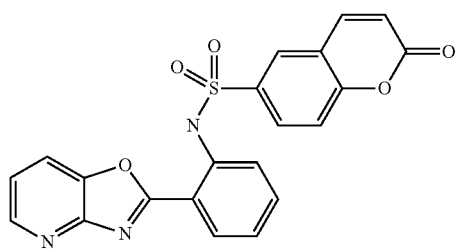 [SMILES: O=c1ccc2cc(S(=O)(=O)Nc3ccccc3-c3nc4ncccc4o3)ccc2o1] Compound 493
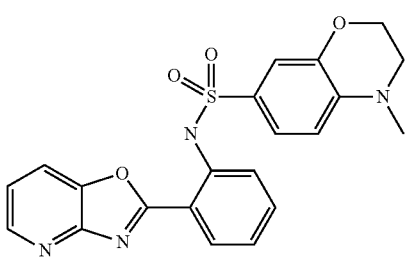 [SMILES: CN1CCOc2cc(S(=O)(=O)Nc3ccccc3-c3nc4ncccc4o3)ccc21] Compound 494
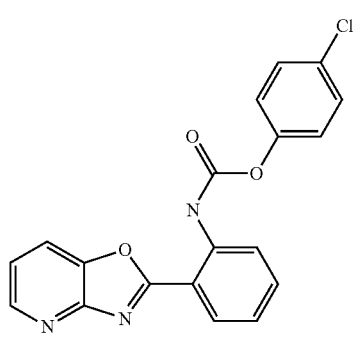 [SMILES: O=C(Nc1ccccc1-c1nc2ncccc2o1)Oc1ccc(Cl)cc1] Compound 495
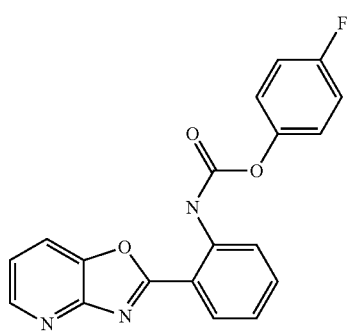 [SMILES: O=C(Nc1ccccc1-c1nc2ncccc2o1)Oc1ccc(F)cc1] Compound 496

TABLE 1-continued
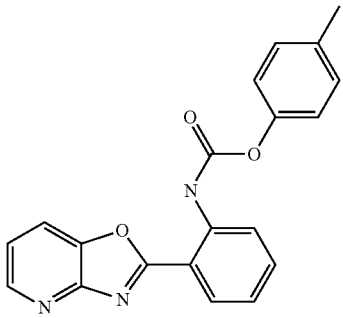 [SMILES: Cc1ccc(OC(=O)Nc2ccccc2-c2nc3ncccc3o2)cc1]
Compound 497
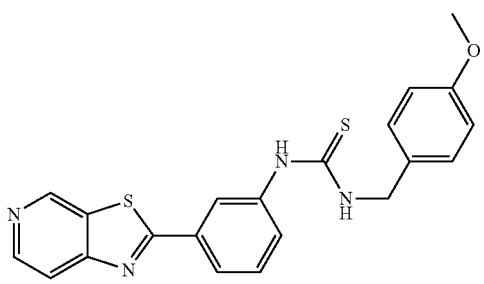 [SMILES: COc1ccc(CNC(=S)Nc2cccc(-c3nc4ccncc4s3)c2)cc1]
Compound 498
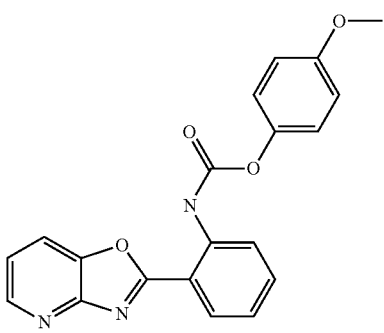 [SMILES: COc1ccc(OC(=O)Nc2ccccc2-c2nc3ncccc3o2)cc1]
Compound 499
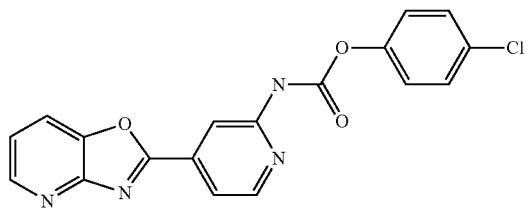 [SMILES: O=C(Nc1cc(-c2nc3ncccc3o2)ccn1)Oc1ccc(Cl)cc1]
Compound 490
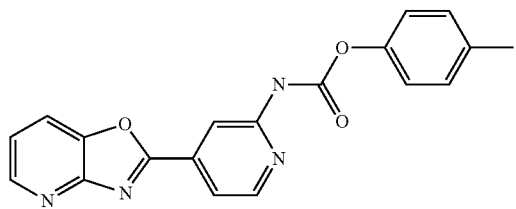 [SMILES: Cc1ccc(OC(=O)Nc2cc(-c3nc4ncccc4o3)ccn2)cc1]
Compound 501
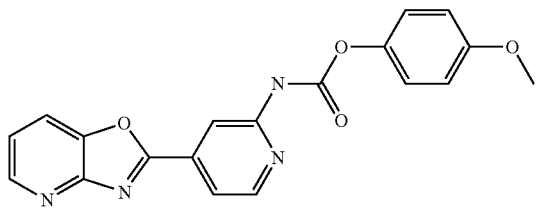 [SMILES: COc1ccc(OC(=O)Nc2cc(-c3nc4ncccc4o3)ccn2)cc1]
Compound 502

TABLE 1-continued
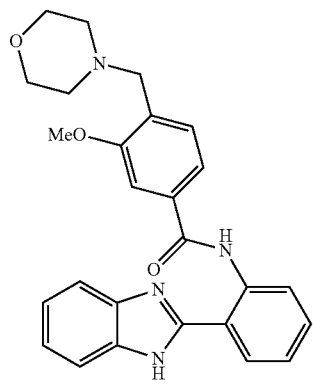 [SMILES: COc1cc(C(=O)Nc2ccccc2-c2nc3ccccc3[nH]2)ccc1CN1CCOCC1]
Compound 503
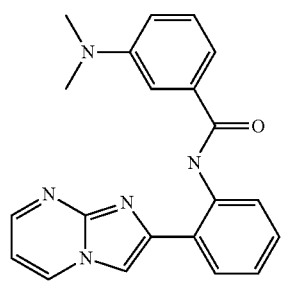 [SMILES: CN(C)c1cccc(C(=O)Nc2ccccc2-c2cn3cccnc3n2)c1]
Compound 504
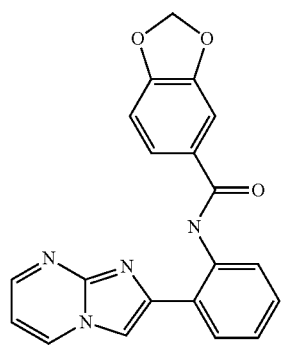 [SMILES: O=C(Nc1ccccc1-c1cn2cccnc2n1)c1ccc2c(c1)OCO2]
Compound 505
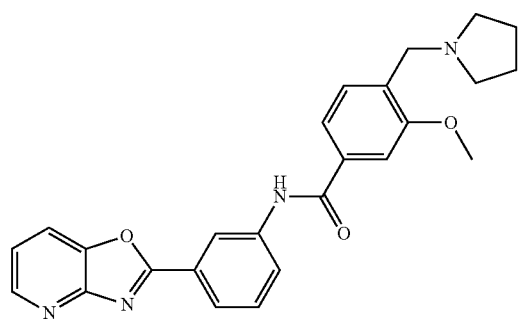 [SMILES: COc1cc(C(=O)Nc2cccc(-c3nc4ncccc4o3)c2)ccc1CN1CCCC1]
Compound 506

TABLE 1-continued
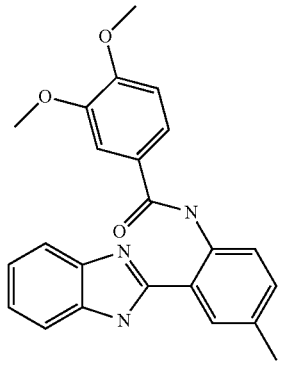 [SMILES: COc1ccc(C(=O)Nc2ccc(C)cc2-c2nc3ccccc3[nH]2)cc1OC]
Compound 507
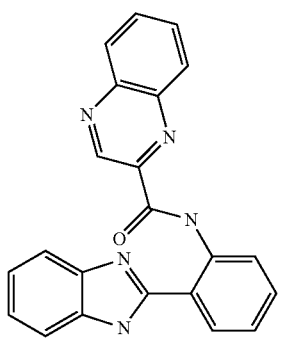 [SMILES: O=C(Nc1ccccc1-c1nc2ccccc2[nH]1)c1cnc2ccccc2n1]
Compound 508
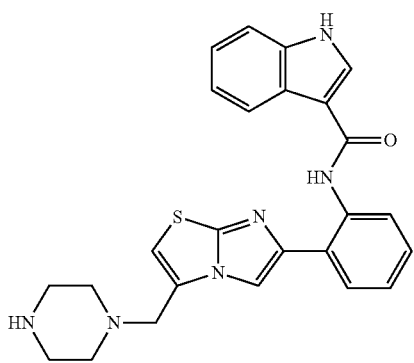 [SMILES: O=C(Nc1ccccc1-c1cn2c(CN3CCNCC3)csc2n1)c1c[nH]c2ccccc12]
Compound 510
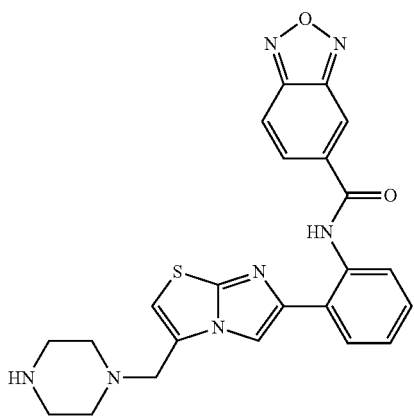 [SMILES: O=C(Nc1ccccc1-c1cn2c(CN3CCNCC3)csc2n1)c1ccc2nonc2c1]
Compound 511

TABLE 1-continued
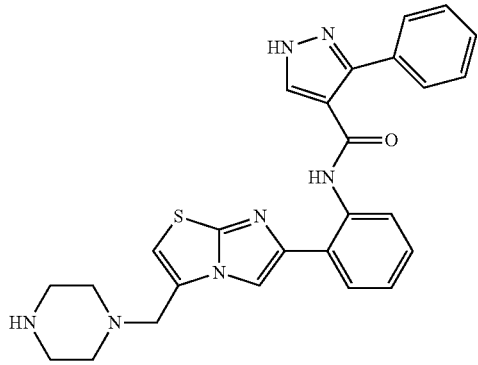 [SMILES: O=C(Nc1ccccc1-c1cn2c(CN3CCNCC3)csc2n1)c1c[nH]nc1-c1ccccc1]
Compound 512
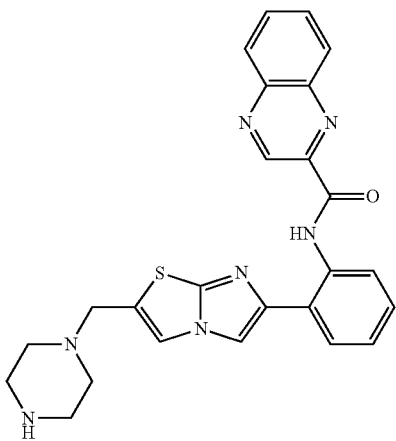 [SMILES: O=C(Nc1ccccc1-c1cn2cc(CN3CCNCC3)sc2n1)c1cnc2ccccc2n1]
Compound 513
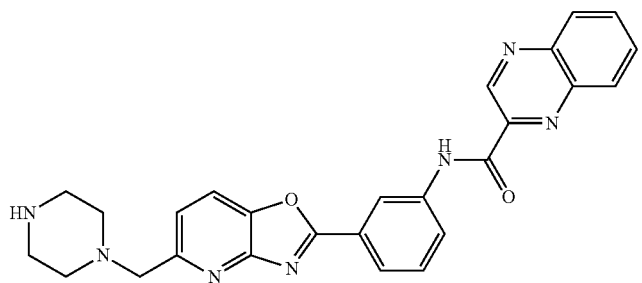 [SMILES: O=C(Nc1cccc(-c2nc3nc(CN4CCNCC4)ccc3o2)c1)c1cnc2ccccc2n1]
Compound 514
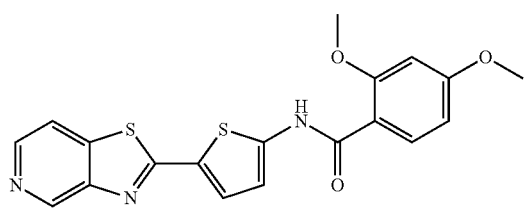 [SMILES: COc1ccc(C(=O)Nc2ccc(-c3nc4cnccc4s3)s2)c(OC)c1]
Compound 515
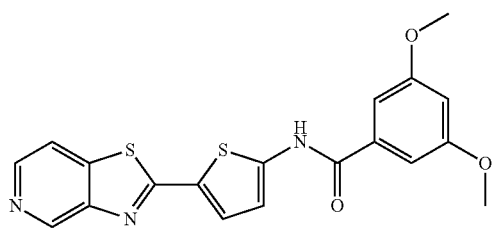 [SMILES: COc1cc(OC)cc(C(=O)Nc2ccc(-c3nc4cnccc4s3)s2)c1]
Compound 516

TABLE 1-continued
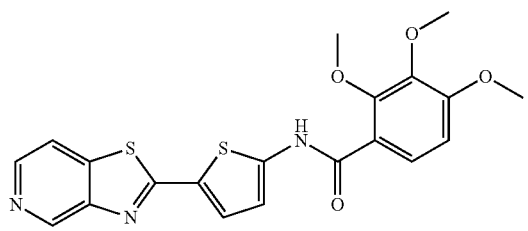 [SMILES: COc1ccc(C(=O)Nc2ccc(-c3nc4cnccc4s3)s2)c(OC)c1OC]
Compound 517
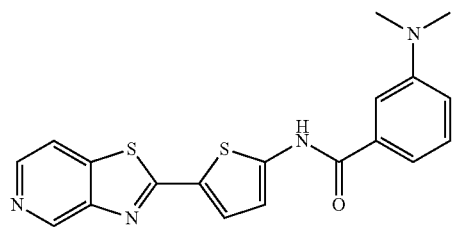 [SMILES: CN(C)c1cccc(C(=O)Nc2ccc(-c3nc4cnccc4s3)s2)c1]
Compound 518
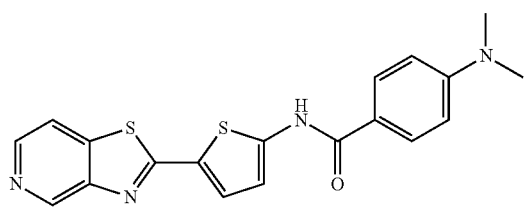 [SMILES: CN(C)c1ccc(C(=O)Nc2ccc(-c3nc4cnccc4s3)s2)cc1]
Compound 519
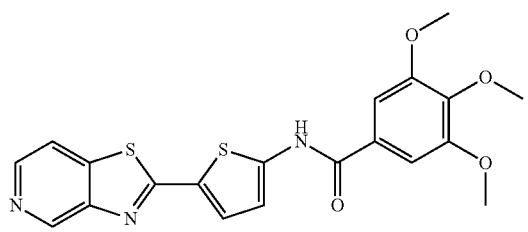 [SMILES: COc1cc(C(=O)Nc2ccc(-c3nc4cnccc4s3)s2)cc(OC)c1OC]
Compound 520
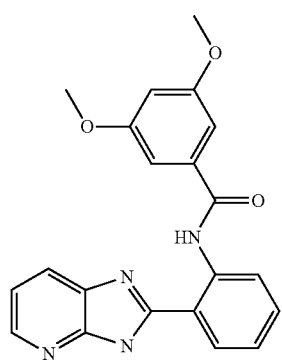 [SMILES: COc1cc(OC)cc(C(=O)Nc2ccccc2-c2nc3cccnc3[nH]2)c1]
Compound 521
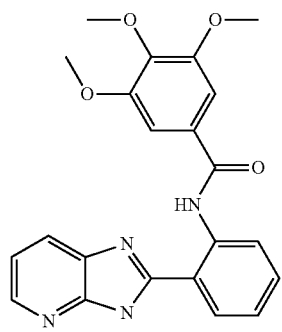 [SMILES: COc1cc(C(=O)Nc2ccccc2-c2nc3cccnc3[nH]2)cc(OC)c1OC]
Compound 522

TABLE 1-continued
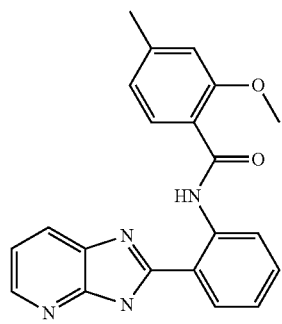 [SMILES: COc1cc(C)ccc1C(=O)Nc1ccccc1-c1nc2cccnc2[nH]1]
Compound 523
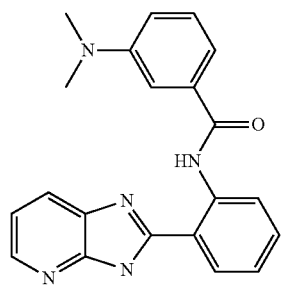 [SMILES: CN(C)c1cccc(C(=O)Nc2ccccc2-c2nc3cccnc3[nH]2)c1]
Compound 524
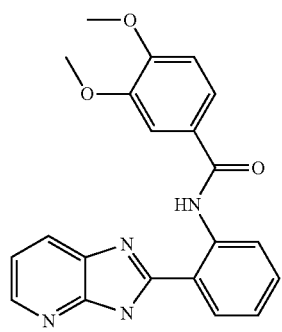 [SMILES: COc1ccc(C(=O)Nc2ccccc2-c2nc3cccnc3[nH]2)cc1OC]
Compound 525
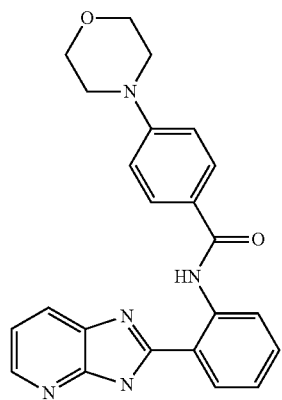 [SMILES: O=C(Nc1ccccc1-c1nc2cccnc2[nH]1)c1ccc(N2CCOCC2)cc1]
Compound 526

TABLE 1-continued
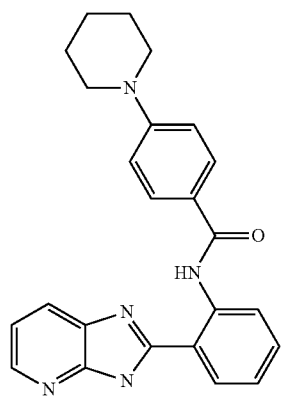 [SMILES: O=C(Nc1ccccc1-c1nc2cccnc2[nH]1)c1ccc(N2CCCCC2)cc1]
Compound 527
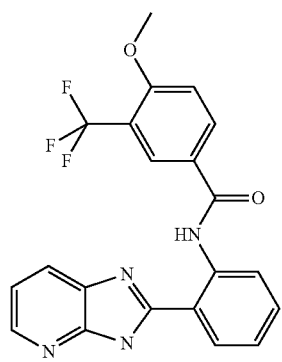 [SMILES: COc1ccc(C(=O)Nc2ccccc2-c2nc3cccnc3[nH]2)cc1C(F)(F)F]
Compound 528
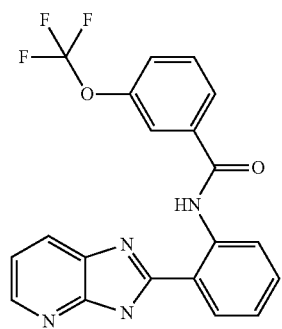 [SMILES: O=C(Nc1ccccc1-c1nc2cccnc2[nH]1)c1cccc(OC(F)(F)F)c1]
Compound 529
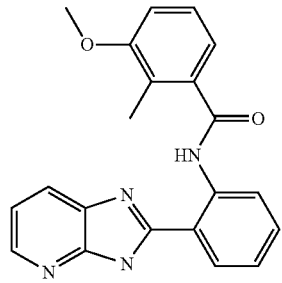 [SMILES: COc1cccc(C(=O)Nc2ccccc2-c2nc3cccnc3[nH]2)c1C]
Compound 530

TABLE 1-continued
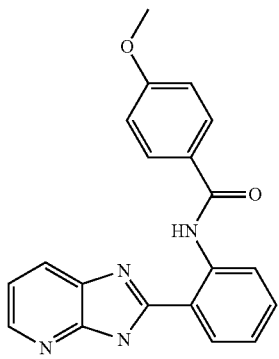 [SMILES: COc1ccc(C(=O)Nc2ccccc2-c2nc3cccnc3[nH]2)cc1]
Compound 531
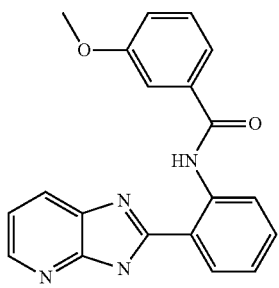 [SMILES: COc1cccc(C(=O)Nc2ccccc2-c2nc3cccnc3[nH]2)c1]
Compound 532
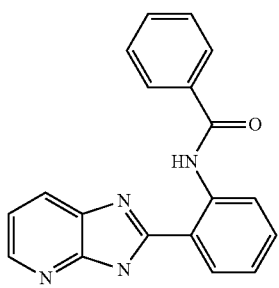 [SMILES: O=C(Nc1ccccc1-c1nc2cccnc2[nH]1)c1ccccc1]
Compound 533
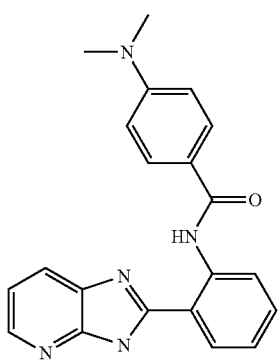 [SMILES: CN(C)c1ccc(C(=O)Nc2ccccc2-c2nc3cccnc3[nH]2)cc1]
Compound 534
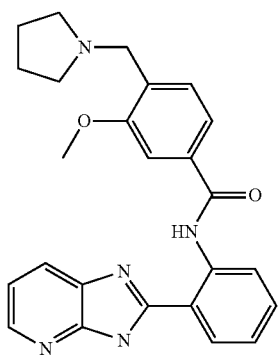 [SMILES: COc1cc(C(=O)Nc2ccccc2-c2nc3cccnc3[nH]2)ccc1CN1CCCC1]
Compound 535

TABLE 1-continued
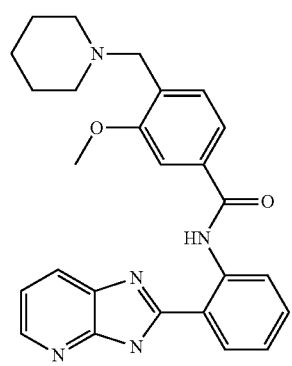 [SMILES: COc1cc(C(=O)Nc2ccccc2-c2nc3cccnc3[nH]2)ccc1CN1CCCCC1]
Compound 536
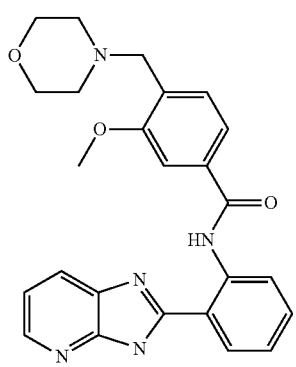 [SMILES: COc1cc(C(=O)Nc2ccccc2-c2nc3cccnc3[nH]2)ccc1CN1CCOCC1]
Compound 537
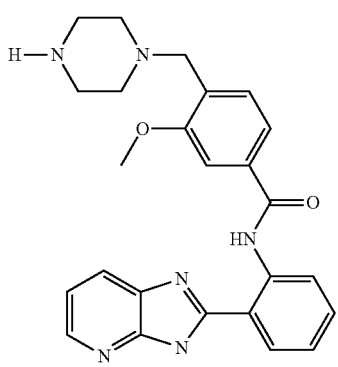 [SMILES: COc1cc(C(=O)Nc2ccccc2-c2nc3cccnc3[nH]2)ccc1CN1CCNCC1]
Compound 538
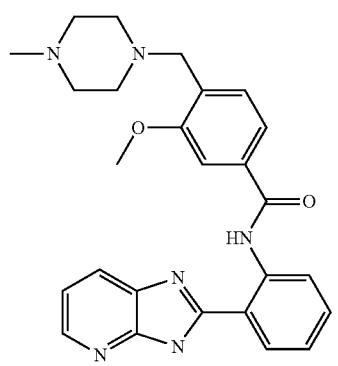 [SMILES: COc1cc(C(=O)Nc2ccccc2-c2nc3cccnc3[nH]2)ccc1CN1CCN(C)CC1]
Compound 539

TABLE 1-continued
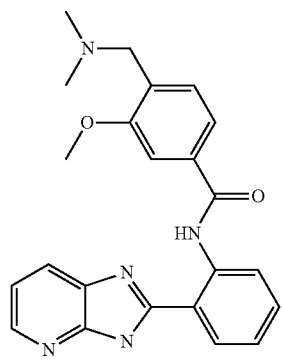 [SMILES: COc1cc(C(=O)Nc2ccccc2-c2nc3cccnc3[nH]2)ccc1CN(C)C]
Compound 540
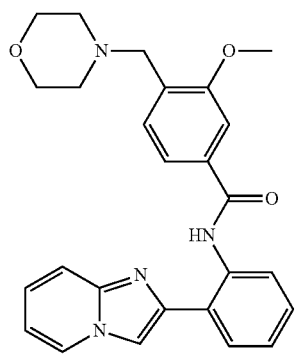 [SMILES: COc1cc(C(=O)Nc2ccccc2-c2cn3ccccc3n2)ccc1CN1CCOCC1]
Compound 541
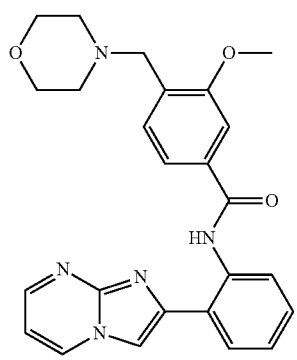 [SMILES: COc1cc(C(=O)Nc2ccccc2-c2cn3cccnc3n2)ccc1CN1CCOCC1]
Compound 542
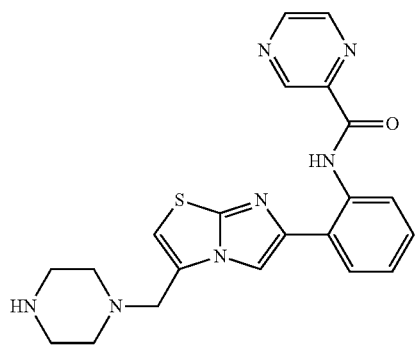 [SMILES: O=C(Nc1ccccc1-c1cn2c(CN3CCNCC3)csc2n1)c1cnccn1]
Compound 543

TABLE 1-continued
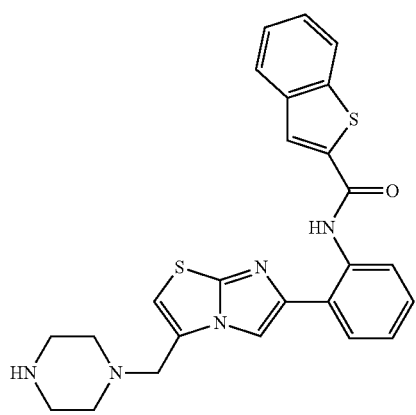 [SMILES: O=C(Nc1ccccc1-c1cn2c(CN3CCNCC3)csc2n1)c1cc2ccccc2s1]
Compound 544
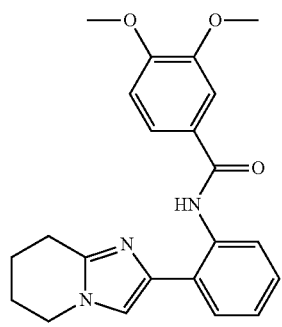 [SMILES: COc1ccc(C(=O)Nc2ccccc2-c2cn3c(n2)CCCC3)cc1OC]
Compound 545
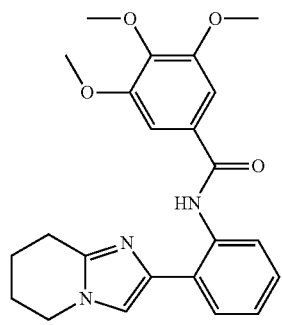 [SMILES: COc1cc(C(=O)Nc2ccccc2-c2cn3c(n2)CCCC3)cc(OC)c1OC]
Compound 546
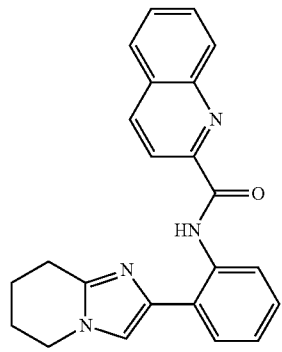 [SMILES: O=C(Nc1ccccc1-c1cn2c(n1)CCCC2)c1ccc2ccccc2n1]
Compound 547

TABLE 1-continued
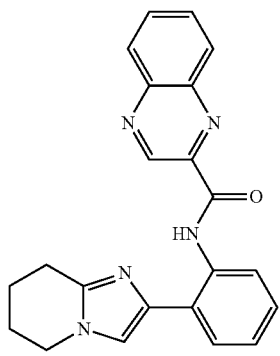 [SMILES: O=C(Nc1ccccc1-c1cn2c(n1)CCCC2)c1cnc2ccccc2n1]
Compound 548
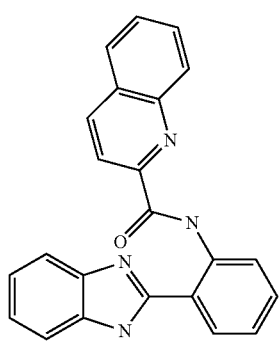 [SMILES: O=C(Nc1ccccc1-c1nc2ccccc2[nH]1)c1ccc2ccccc2n1]
Compound 556
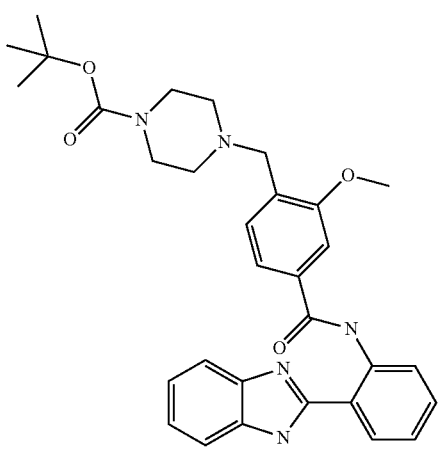 [SMILES: COc1cc(C(=O)Nc2ccccc2-c2nc3ccccc3[nH]2)ccc1CN1CCN(C(=O)OC(C)(C)C)CC1]
Compound 557
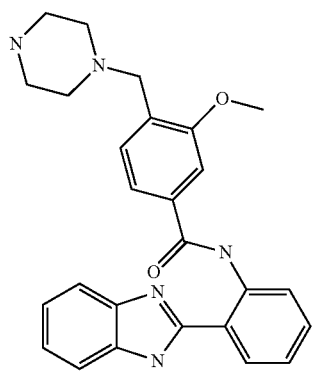 [SMILES: COc1cc(C(=O)Nc2ccccc2-c2nc3ccccc3[nH]2)ccc1CN1CCNCC1]
Compound 558

TABLE 1-continued
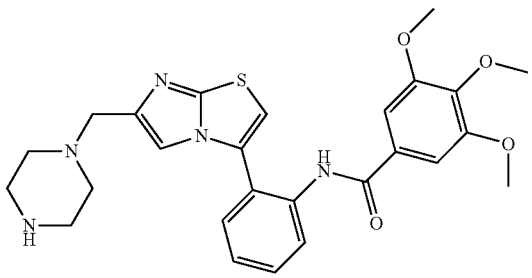 [SMILES: COc1cc(C(=O)Nc2ccccc2-c2csc3nc(CN4CCNCC4)cn23)cc(OC)c1OC]
Compound 559
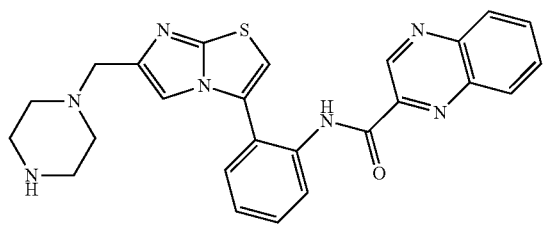 [SMILES: O=C(Nc1ccccc1-c1csc2nc(CN3CCNCC3)cn12)c1cnc2ccccc2n1]
Compound 560
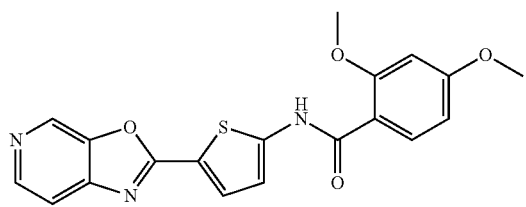 [SMILES: COc1ccc(C(=O)Nc2ccc(-c3nc4ccncc4o3)s2)c(OC)c1]
Compound 561
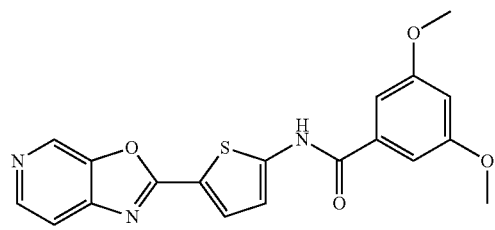 [SMILES: COc1cc(OC)cc(C(=O)Nc2ccc(-c3nc4ccncc4o3)s2)c1]
Compound 562
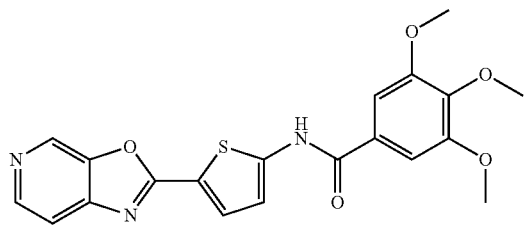 [SMILES: COc1cc(C(=O)Nc2ccc(-c3nc4ccncc4o3)s2)cc(OC)c1OC]
Compound 563
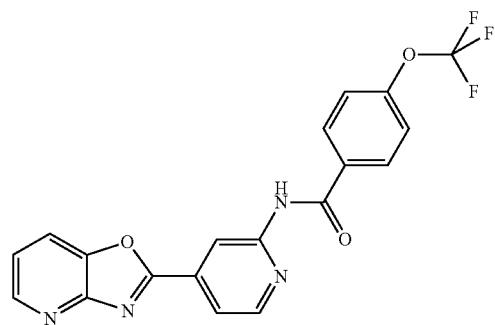 [SMILES: O=C(Nc1cc(-c2nc3ncccc3o2)ccn1)c1ccc(OC(F)(F)F)cc1]
Compound 565

TABLE 1-continued
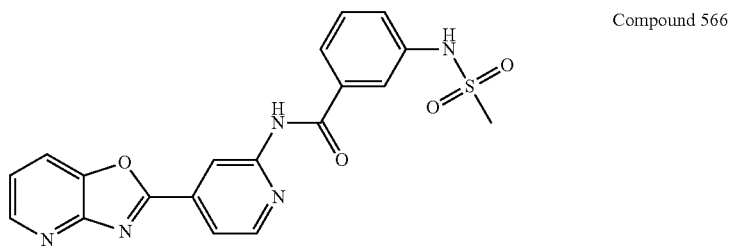
Compound 566
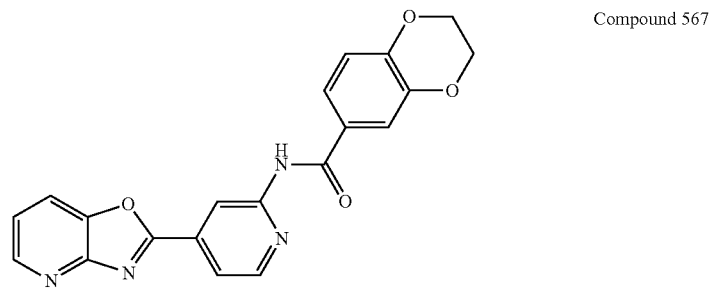
Compound 567
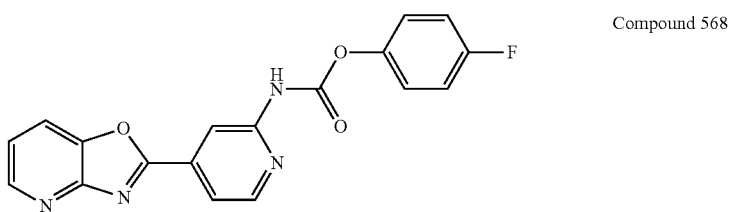
Compound 568
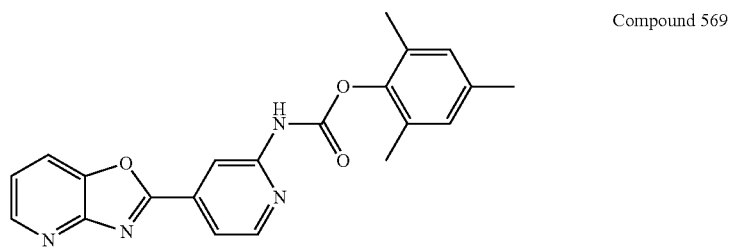
Compound 569
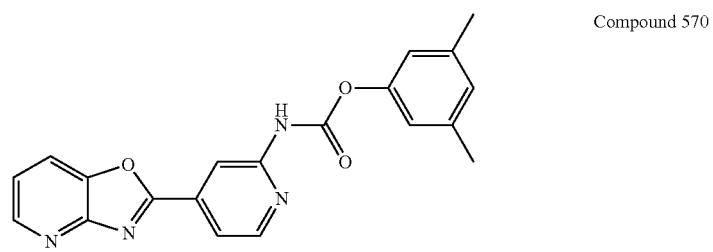
Compound 570
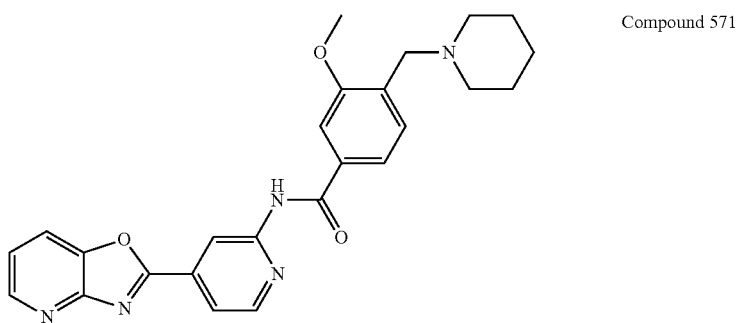
Compound 571

TABLE 1-continued
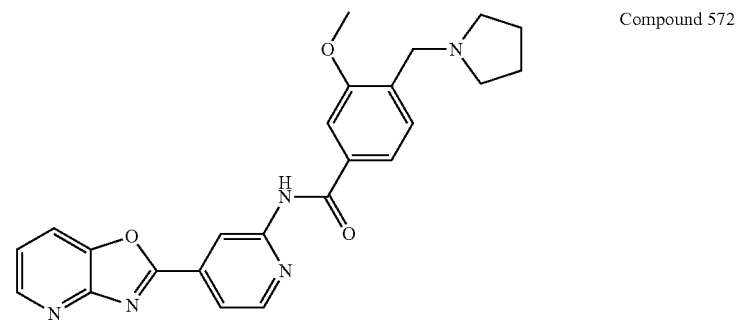
Compound 572
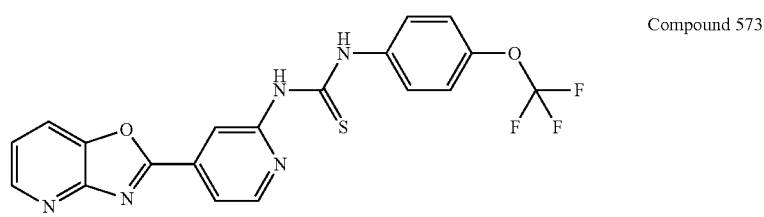
Compound 573
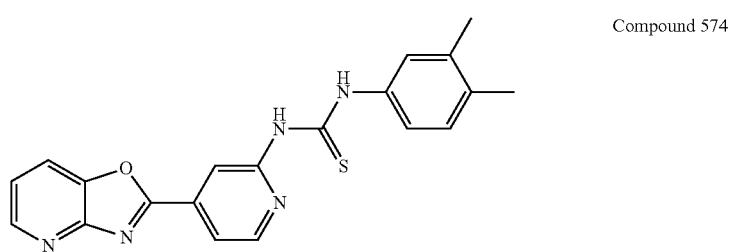
Compound 574
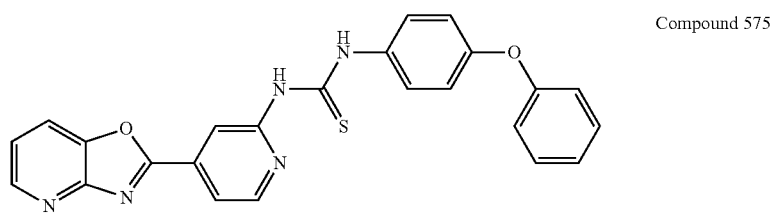
Compound 575
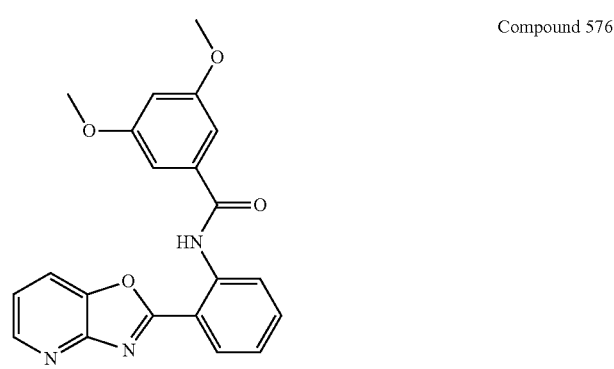
Compound 576

TABLE 1-continued
| | |
|---|---|
| 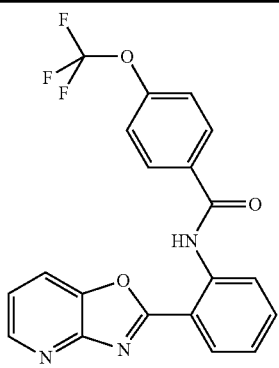 | Compound 577 |
| 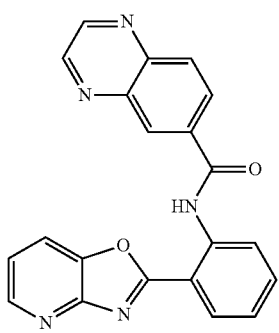 [SMILES: O=C(Nc1ccccc1-c1nc2ncccc2o1)c1ccc2nccnc2c1] | Compound 578 |
| 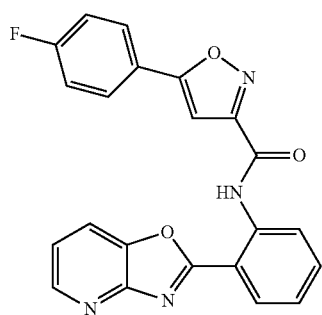 [SMILES: O=C(Nc1ccccc1-c1nc2ncccc2o1)c1cc(-c2ccc(F)cc2)on1] | Compound 579 |
| 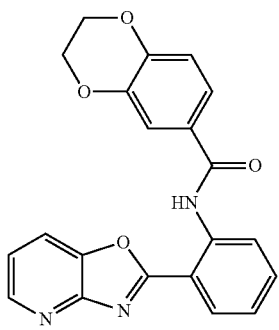 [SMILES: O=C(Nc1ccccc1-c1nc2ncccc2o1)c1ccc2c(c1)OCCO2] | Compound 580 |
| 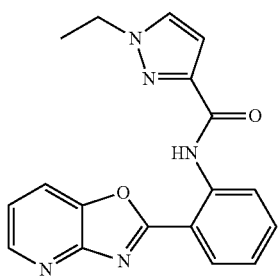 [SMILES: CCn1ccc(C(=O)Nc2ccccc2-c2nc3ncccc3o2)n1] | Compound 581 |

TABLE 1-continued
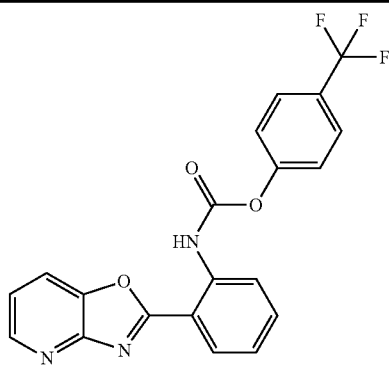
Compound 582
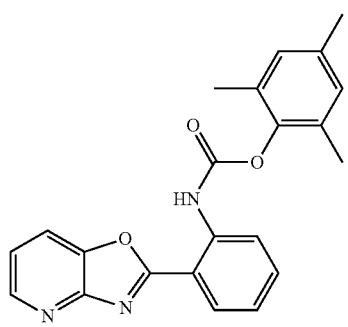 [SMILES: Cc1cc(C)c(OC(=O)Nc2ccccc2-c2nc3ncccc3o2)c(C)c1]
Compound 583
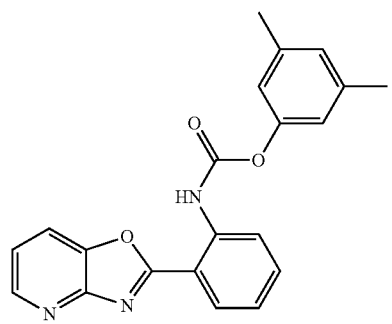 [SMILES: Cc1cc(C)cc(OC(=O)Nc2ccccc2-c2nc3ncccc3o2)c1]
Compound 584
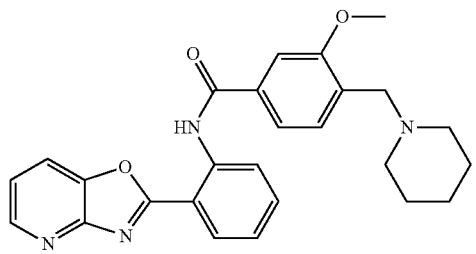 [SMILES: COc1cc(C(=O)Nc2ccccc2-c2nc3ncccc3o2)ccc1CN1CCCCC1]
Compound 585
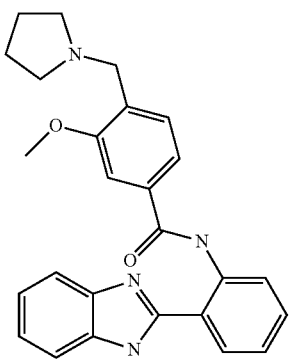 [SMILES: COc1cc(C(=O)Nc2ccccc2-c2nc3ccccc3[nH]2)ccc1CN1CCCC1]
Compound 587

TABLE 1-continued
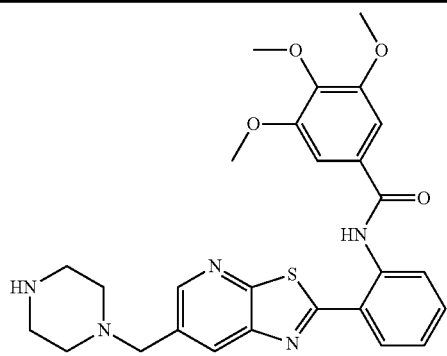
Compound 588
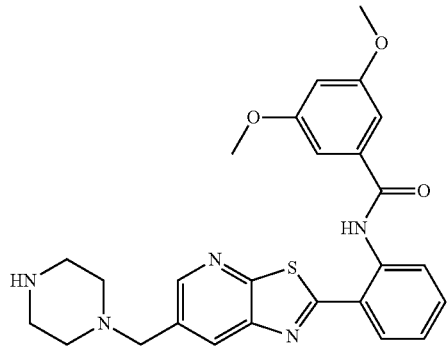 [SMILES: COc1cc(OC)cc(C(=O)Nc2ccccc2-c2nc3cc(CN4CCNCC4)cnc3s2)c1]
Compound 589
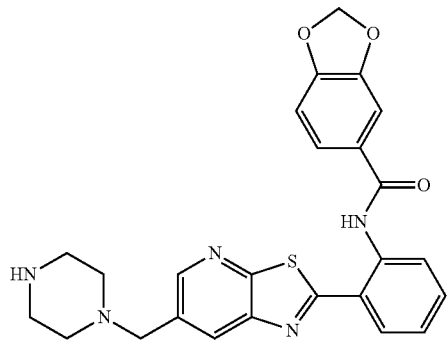 [SMILES: O=C(Nc1ccccc1-c1nc2cc(CN3CCNCC3)cnc2s1)c1ccc2c(c1)OCO2]
Compound 590
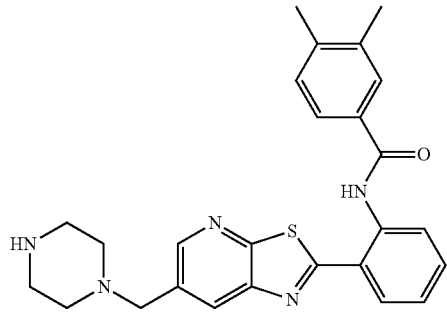 [SMILES: Cc1ccc(C(=O)Nc2ccccc2-c2nc3cc(CN4CCNCC4)cnc3s2)cc1C]
Compound 591
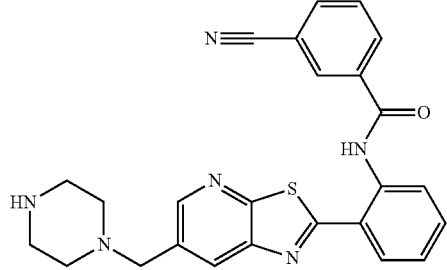 [SMILES: N#Cc1cccc(C(=O)Nc2ccccc2-c2nc3cc(CN4CCNCC4)cnc3s2)c1]
Compound 592

TABLE 1-continued
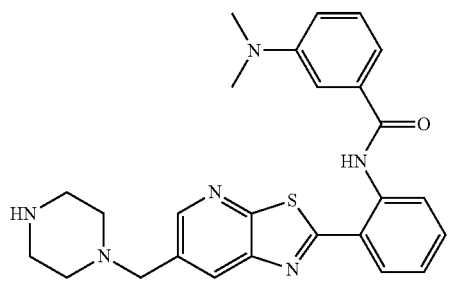 [SMILES: CN(C)c1cccc(C(=O)Nc2ccccc2-c2nc3cc(CN4CCNCC4)cnc3s2)c1]
Compound 593
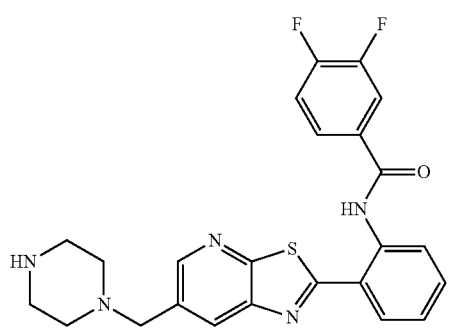 [SMILES: O=C(Nc1ccccc1-c1nc2cc(CN3CCNCC3)cnc2s1)c1ccc(F)c(F)c1]
Compound 594
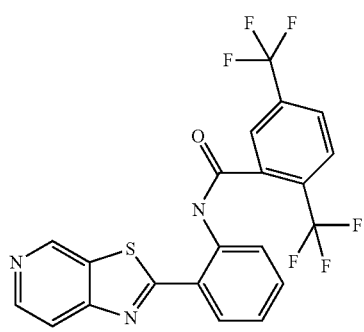 [SMILES: O=C(Nc1ccccc1-c1nc2ccncc2s1)c1cc(C(F)(F)F)ccc1C(F)(F)F]
Compound 596
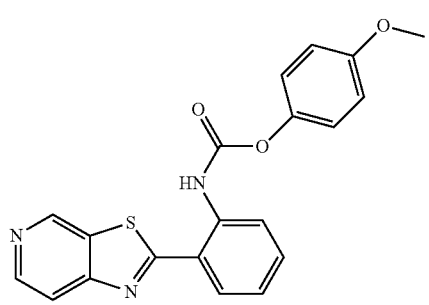 [SMILES: COc1ccc(OC(=O)Nc2ccccc2-c2nc3ccncc3s2)cc1]
Compound 597
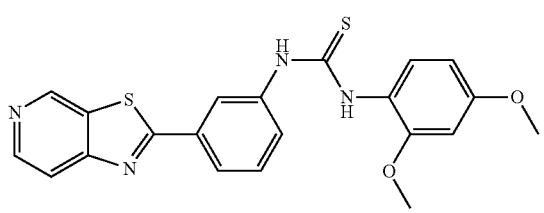 [SMILES: COc1ccc(NC(=S)Nc2cccc(-c3nc4ccncc4s3)c2)c(OC)c1]
Compound 599

TABLE 1-continued
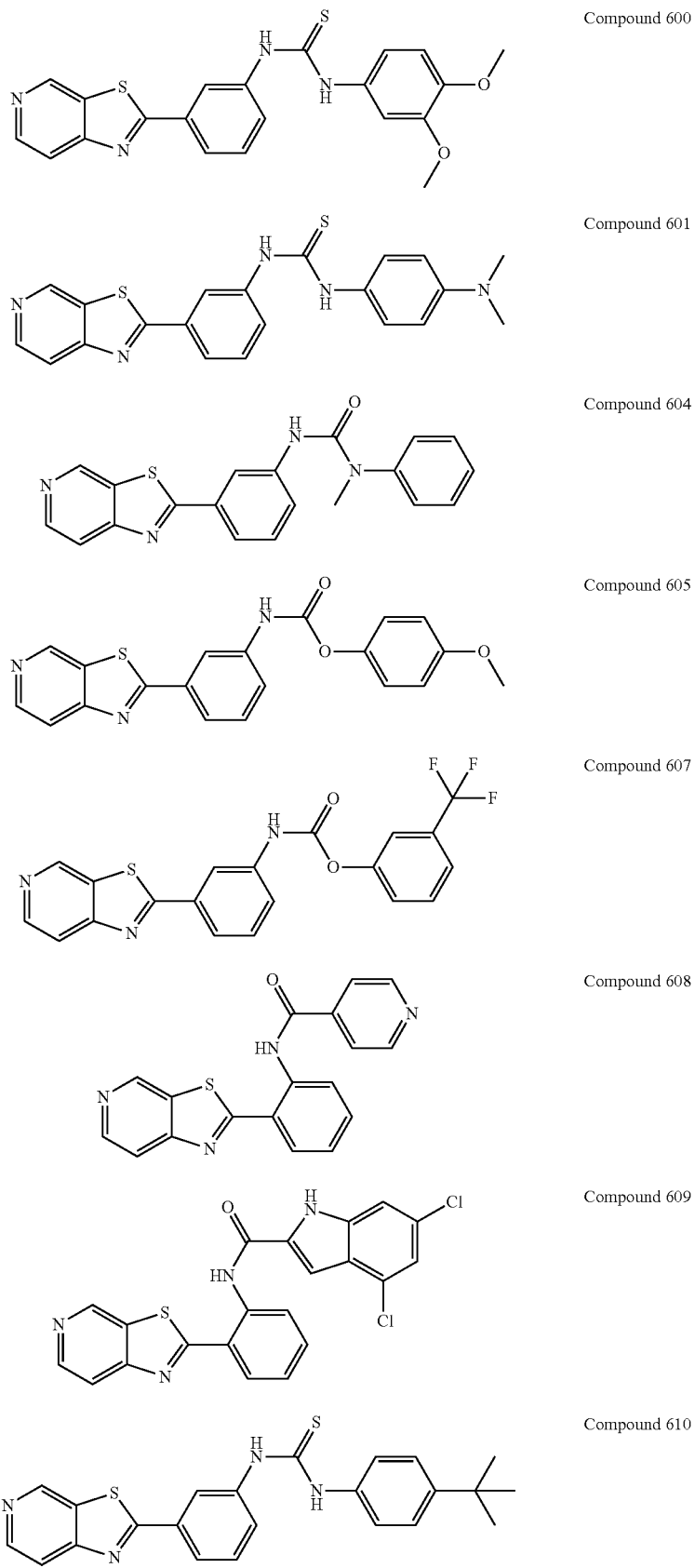
| | |
|---|---|
| | Compound 600 |
| | Compound 601 |
| | Compound 604 |
| | Compound 605 |
| | Compound 607 |
| | Compound 608 |
| | Compound 609 |
| | Compound 610 |

TABLE 1-continued
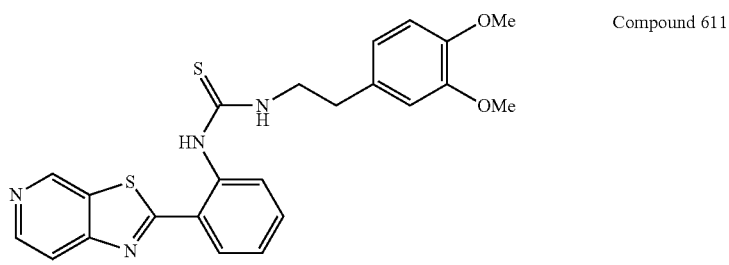
Compound 611
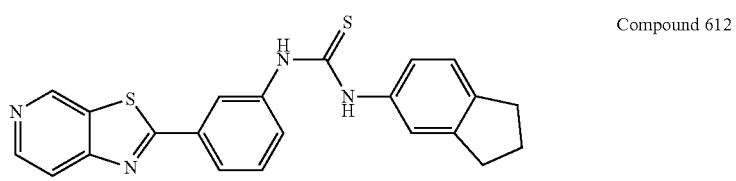
Compound 612
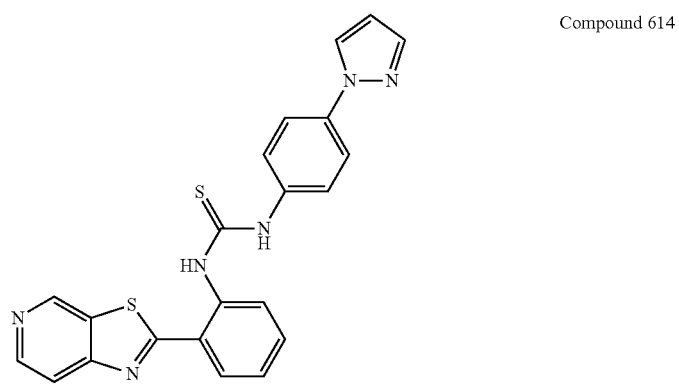
Compound 614
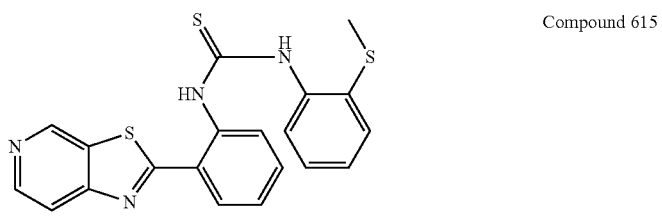
Compound 615
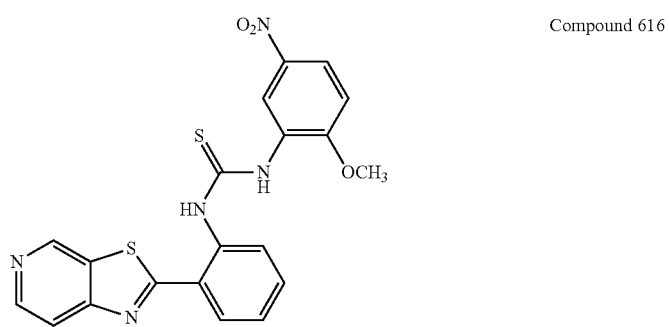
Compound 616

TABLE 1-continued
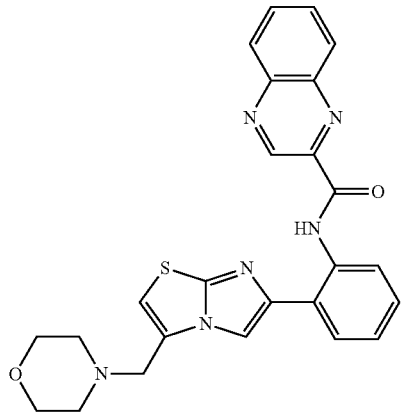 [SMILES: O=C(Nc1ccccc1-c1cn2c(CN3CCOCC3)csc2n1)c1cnc2ccccc2n1]
Compound 617
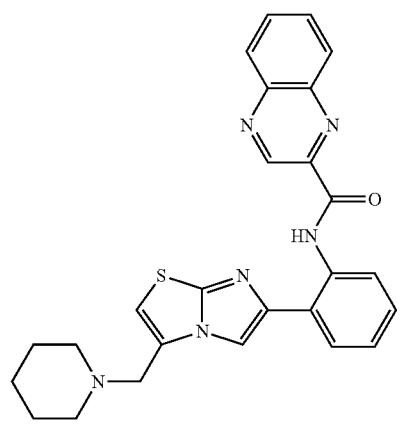 [SMILES: O=C(Nc1ccccc1-c1cn2c(CN3CCCCC3)csc2n1)c1cnc2ccccc2n1]
Compound 618
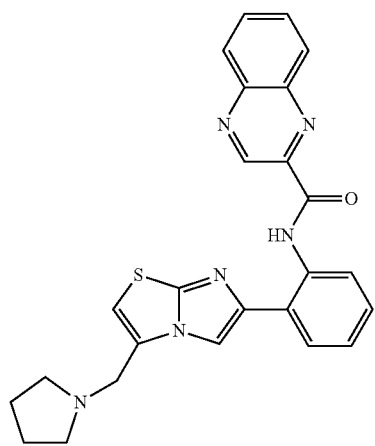 [SMILES: O=C(Nc1ccccc1-c1cn2c(CN3CCCC3)csc2n1)c1cnc2ccccc2n1]
Compound 619

TABLE 1-continued
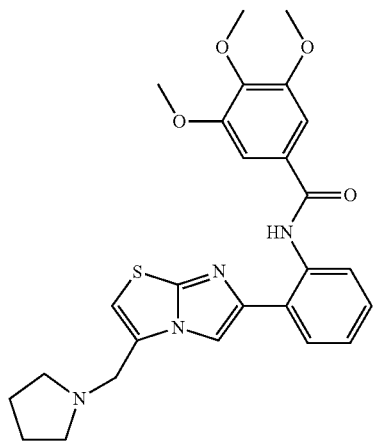 [SMILES: COc1cc(C(=O)Nc2ccccc2-c2cn3c(CN4CCCC4)csc3n2)cc(OC)c1OC]
Compound 620
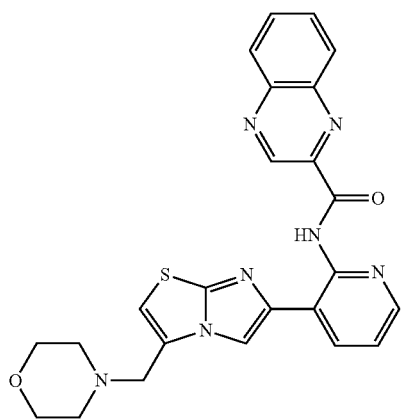 [SMILES: O=C(Nc1ncccc1-c1cn2c(CN3CCOCC3)csc2n1)c1cnc2ccccc2n1]
Compound 621
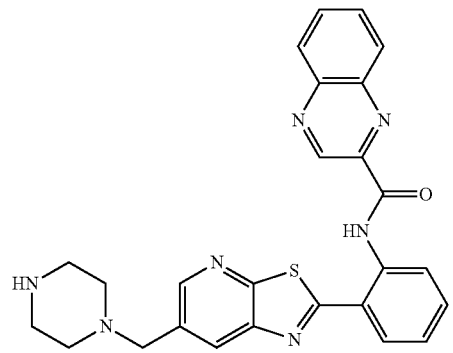 [SMILES: O=C(Nc1ccccc1-c1nc2cc(CN3CCNCC3)cnc2s1)c1cnc2ccccc2n1]
Compound 622
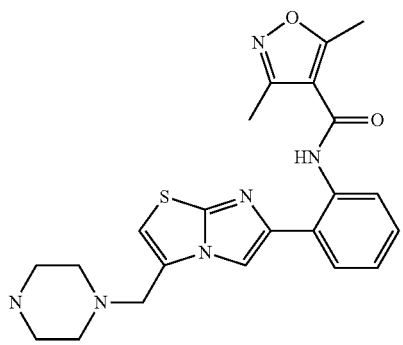 [SMILES: Cc1noc(C)c1C(=O)Nc1ccccc1-c1cn2c(CN3CCNCC3)csc2n1]
Compound 623

TABLE 1-continued
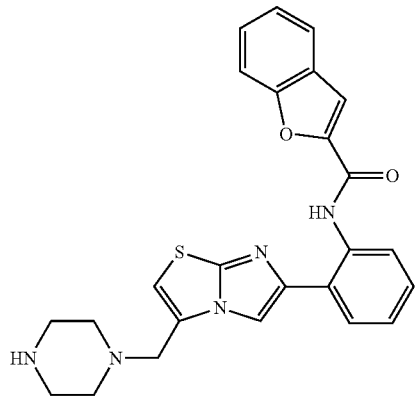 [SMILES: O=C(Nc1ccccc1-c1cn2c(CN3CCNCC3)csc2n1)c1cc2ccccc2o1]
Compound 624
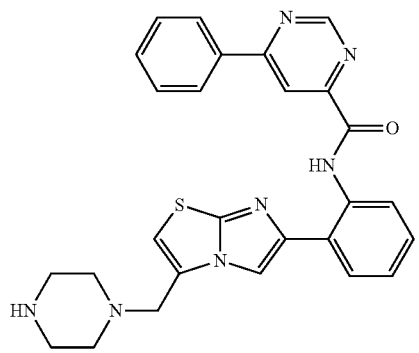 [SMILES: O=C(Nc1ccccc1-c1cn2c(CN3CCNCC3)csc2n1)c1cc(-c2ccccc2)ncn1]
Compound 625
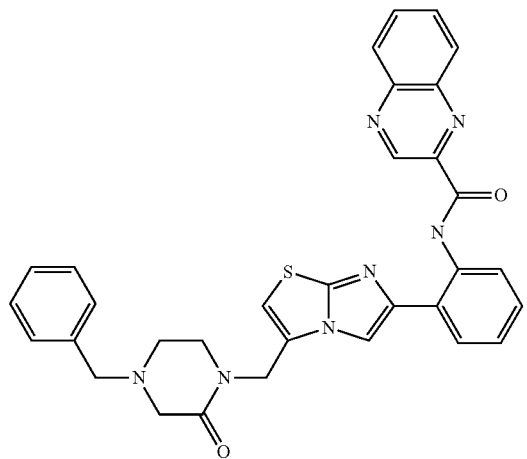 [SMILES: O=C(Nc1ccccc1-c1cn2c(CN3CCN(Cc4ccccc4)CC3=O)csc2n1)c1cnc2ccccc2n1]
Compound 628
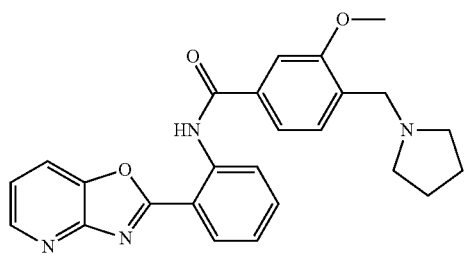 [SMILES: COc1cc(C(=O)Nc2ccccc2-c2nc3ncccc3o2)ccc1CN1CCCC1]
Compound 629

TABLE 1-continued
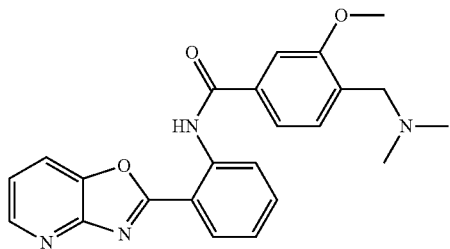 [SMILES: COc1cc(C(=O)Nc2ccccc2-c2nc3ncccc3o2)ccc1CN(C)C]
Compound 630
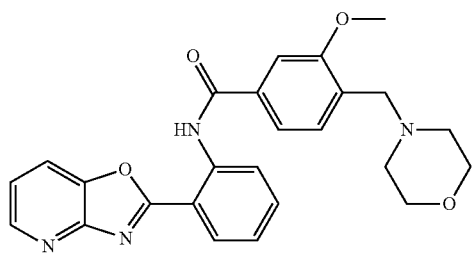 [SMILES: COc1cc(C(=O)Nc2ccccc2-c2nc3ncccc3o2)ccc1CN1CCOCC1]
Compound 631
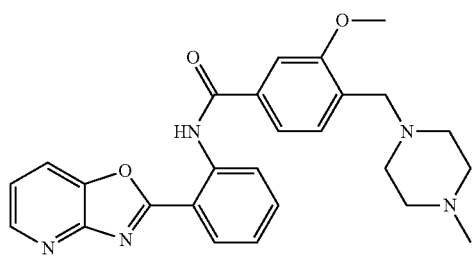
Compound 632
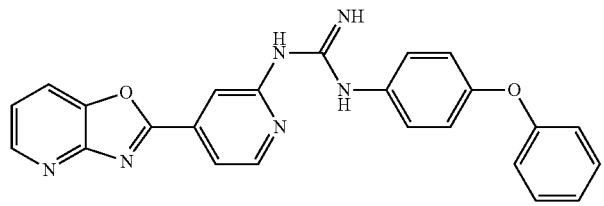 [SMILES: N=C(Nc1ccc(Oc2ccccc2)cc1)Nc1cc(-c2nc3ncccc3o2)ccn1]
Compound 633
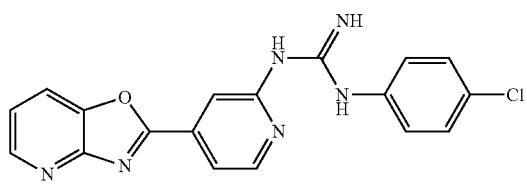 [SMILES: N=C(Nc1ccc(Cl)cc1)Nc1cc(-c2nc3ncccc3o2)ccn1]
Compound 634
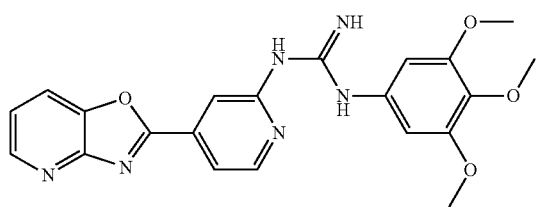 [SMILES: COc1cc(NC(=N)Nc2cc(-c3nc4ncccc4o3)ccn2)cc(OC)c1OC]
Compound 635

TABLE 1-continued
| | |
|---|---|
| 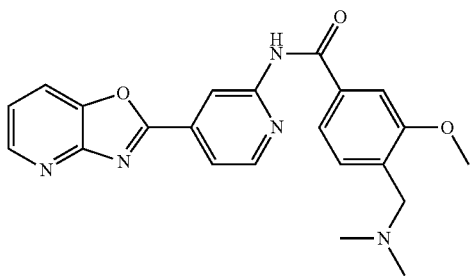 [SMILES: COc1cc(C(=O)Nc2cc(-c3nc4ncccc4o3)ccn2)ccc1CN(C)C] | Compound 636 |
| 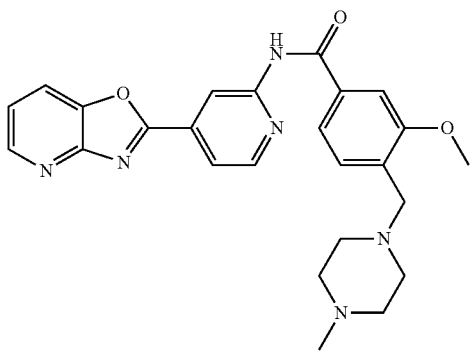 [SMILES: COc1cc(C(=O)Nc2cc(-c3nc4ncccc4o3)ccn2)ccc1CN1CCN(C)CC1] | Compound 637 |
| 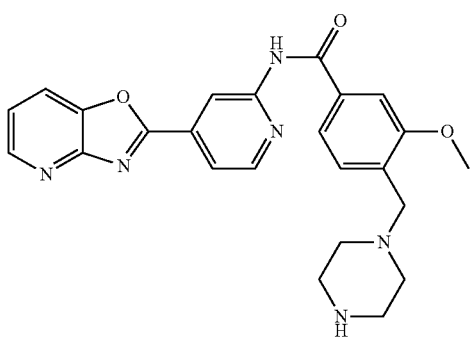 [SMILES: COc1cc(C(=O)Nc2cc(-c3nc4ncccc4o3)ccn2)ccc1CN1CCNCC1] | Compound 638 |
| 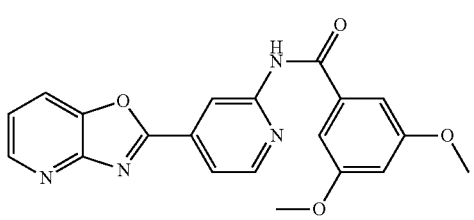 [SMILES: COc1cc(OC)cc(C(=O)Nc2cc(-c3nc4ncccc4o3)ccn2)c1] | Compound 639 |
| 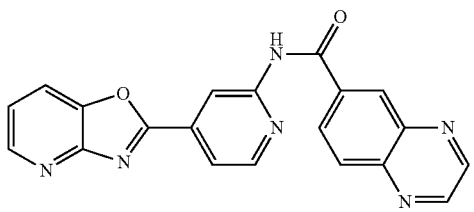 [SMILES: O=C(Nc1cc(-c2nc3ncccc3o2)ccn1)c1ccc2nccnc2c1] | Compound 640 |
| 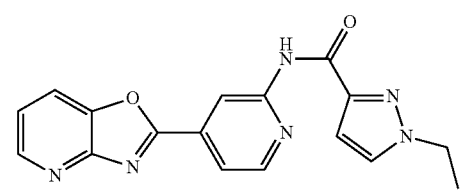 [SMILES: CCn1ccc(C(=O)Nc2cc(-c3nc4ncccc4o3)ccn2)n1] | Compound 641 |

TABLE 1-continued
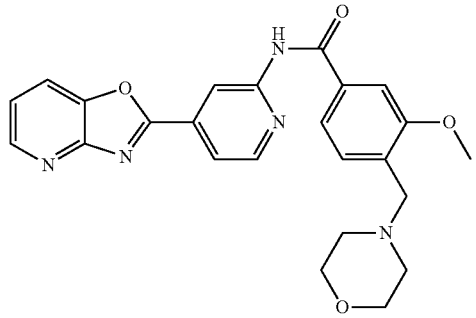 [SMILES: COc1cc(C(=O)Nc2cc(-c3nc4ncccc4o3)ccn2)ccc1CN1CCOCC1]
Compound 642
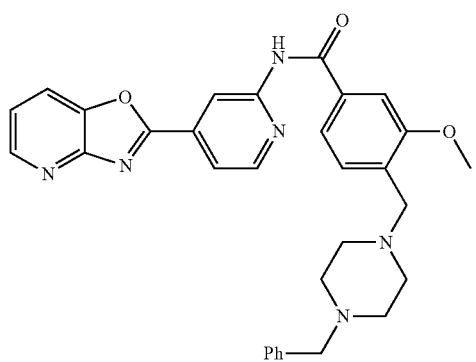 [SMILES: COc1cc(C(=O)Nc2cc(-c3nc4ncccc4o3)ccn2)ccc1CN1CCN(Cc2ccccc2)CC1]
Compound 643
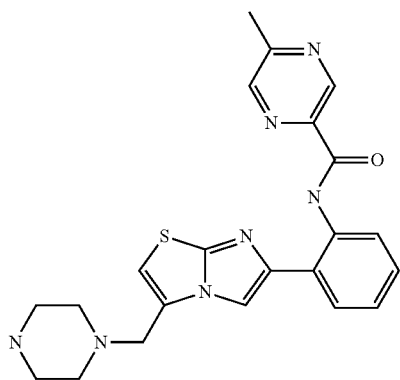 [SMILES: Cc1cnc(C(=O)Nc2ccccc2-c2cn3c(CN4CCNCC4)csc3n2)cn1]
Compound 644
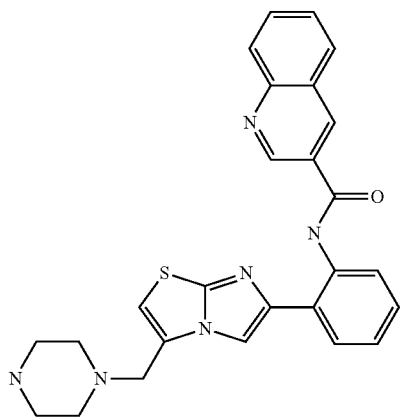 [SMILES: O=C(Nc1ccccc1-c1cn2c(CN3CCNCC3)csc2n1)c1cnc2ccccc2c1]
Compound 645

TABLE 1-continued
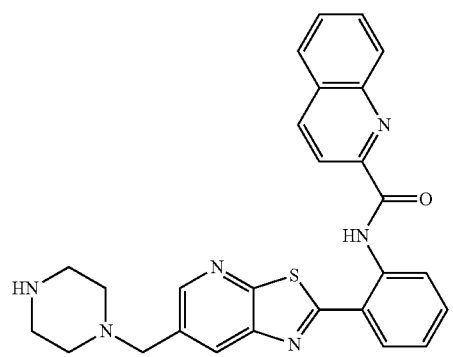 [SMILES: O=C(Nc1ccccc1-c1nc2cc(CN3CCNCC3)cnc2s1)c1ccc2ccccc2n1]
Compound 646
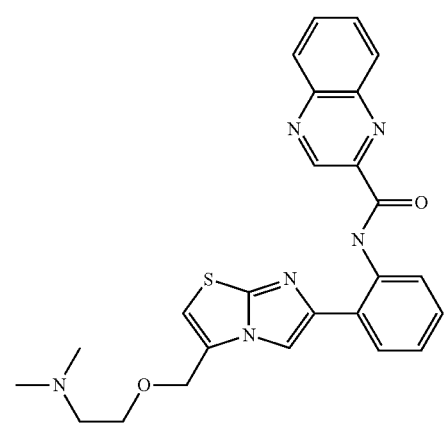 [SMILES: CN(C)CCOCc1csc2nc(-c3ccccc3NC(=O)c3cnc4ccccc4n3)cn12]
Compound 647
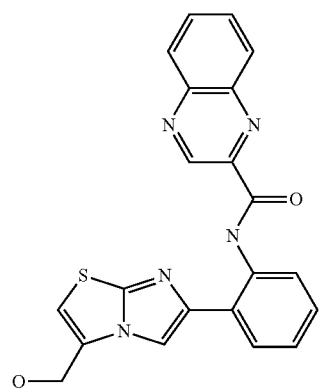 [SMILES: O=C(Nc1ccccc1-c1cn2c(CO)csc2n1)c1cnc2ccccc2n1]
Compound 648

TABLE 1-continued
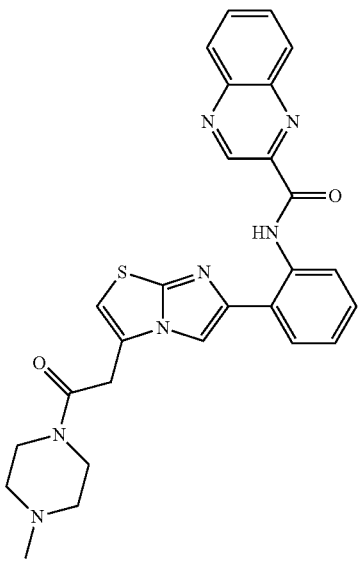 [SMILES: CN1CCN(C(=O)Cc2csc3nc(-c4ccccc4NC(=O)c4cnc5ccccc5n4)cn23)CC1]
Compound 649
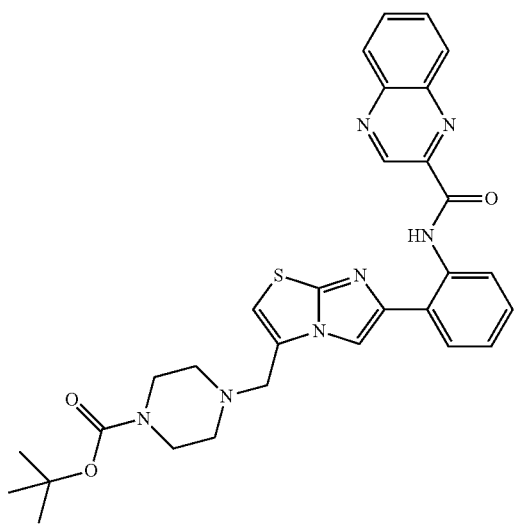 [SMILES: CC(C)(C)OC(=O)N1CCN(Cc2csc3nc(-c4ccccc4NC(=O)c4cnc5ccccc5n4)cn23)CC1]
Compound 650
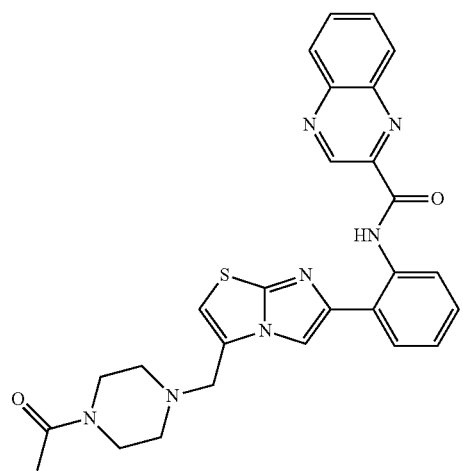 [SMILES: CC(=O)N1CCN(Cc2csc3nc(-c4ccccc4NC(=O)c4cnc5ccccc5n4)cn23)CC1]
Compound 651

TABLE 1-continued
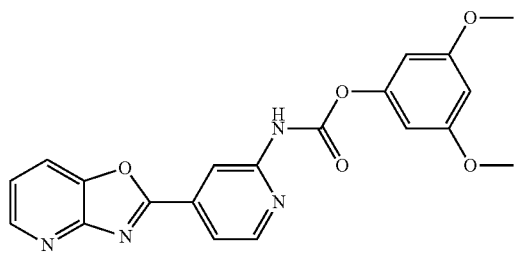 [SMILES: COc1cc(OC)cc(OC(=O)Nc2cc(-c3nc4ncccc4o3)ccn2)c1]
Compound 655
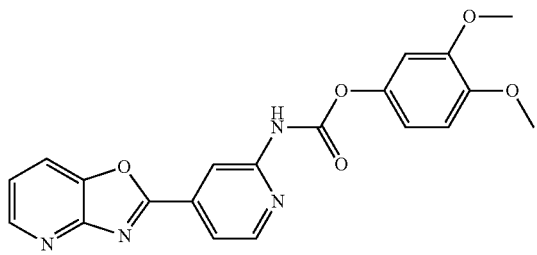 [SMILES: COc1ccc(OC(=O)Nc2cc(-c3nc4ncccc4o3)ccn2)cc1OC]
Compound 656
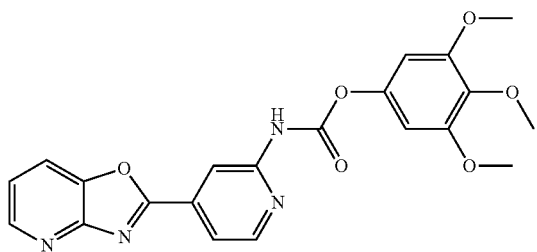 [SMILES: COc1cc(OC(=O)Nc2cc(-c3nc4ncccc4o3)ccn2)cc(OC)c1OC]
Compound 657
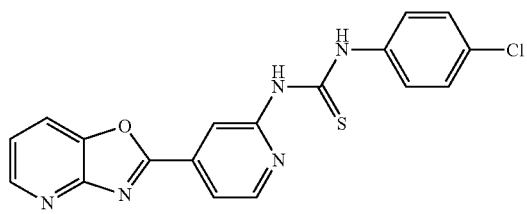 [SMILES: S=C(Nc1ccc(Cl)cc1)Nc1cc(-c2nc3ncccc3o2)ccn1]
Compound 658
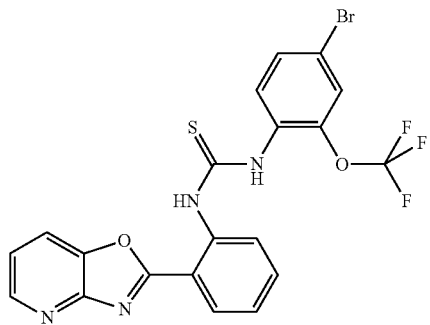 [SMILES: FC(F)(F)Oc1cc(Br)ccc1NC(=S)Nc1ccccc1-c1nc2ncccc2o1]
Compound 659
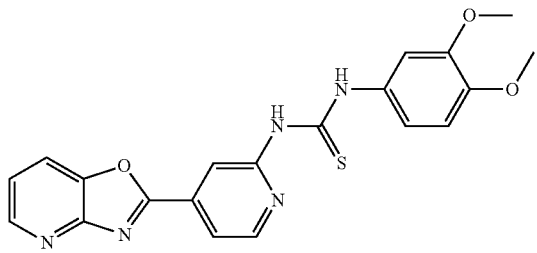 [SMILES: COc1ccc(NC(=S)Nc2cc(-c3nc4ncccc4o3)ccn2)cc1OC]
Compound 660

TABLE 1-continued
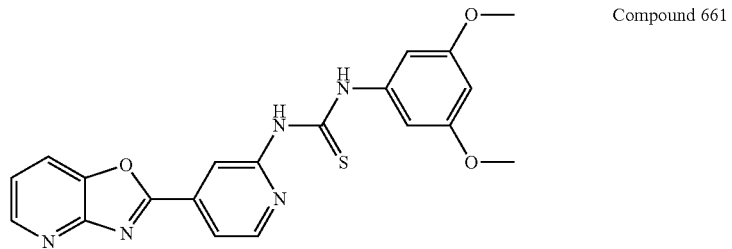
Compound 661
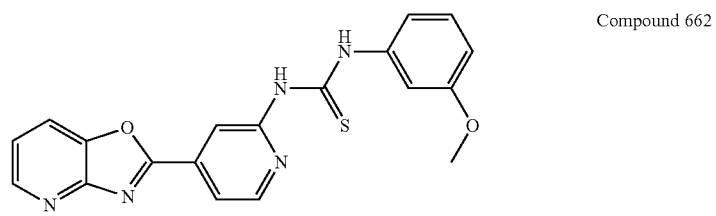
Compound 662
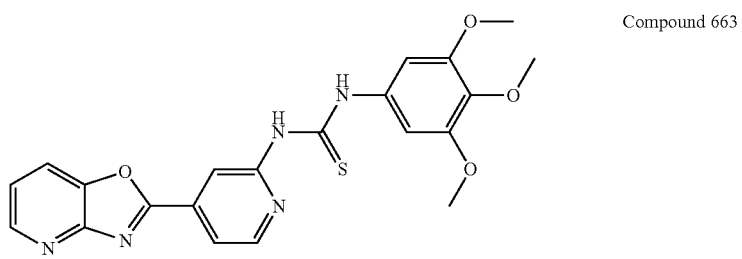
Compound 663
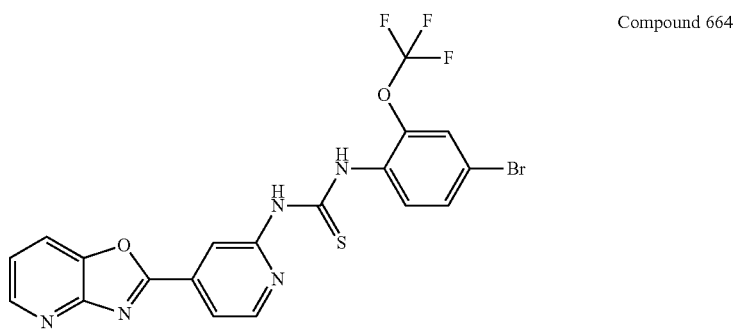
Compound 664
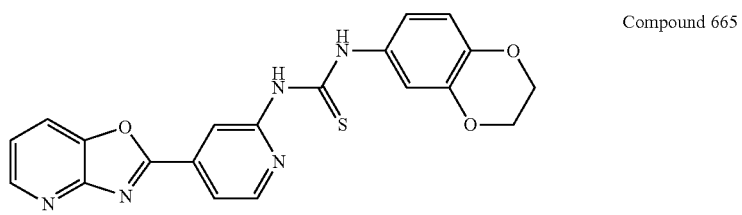
Compound 665
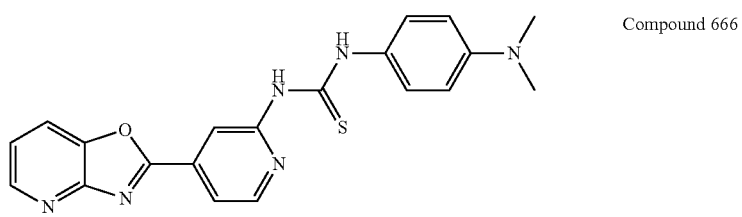
Compound 666

TABLE 1-continued
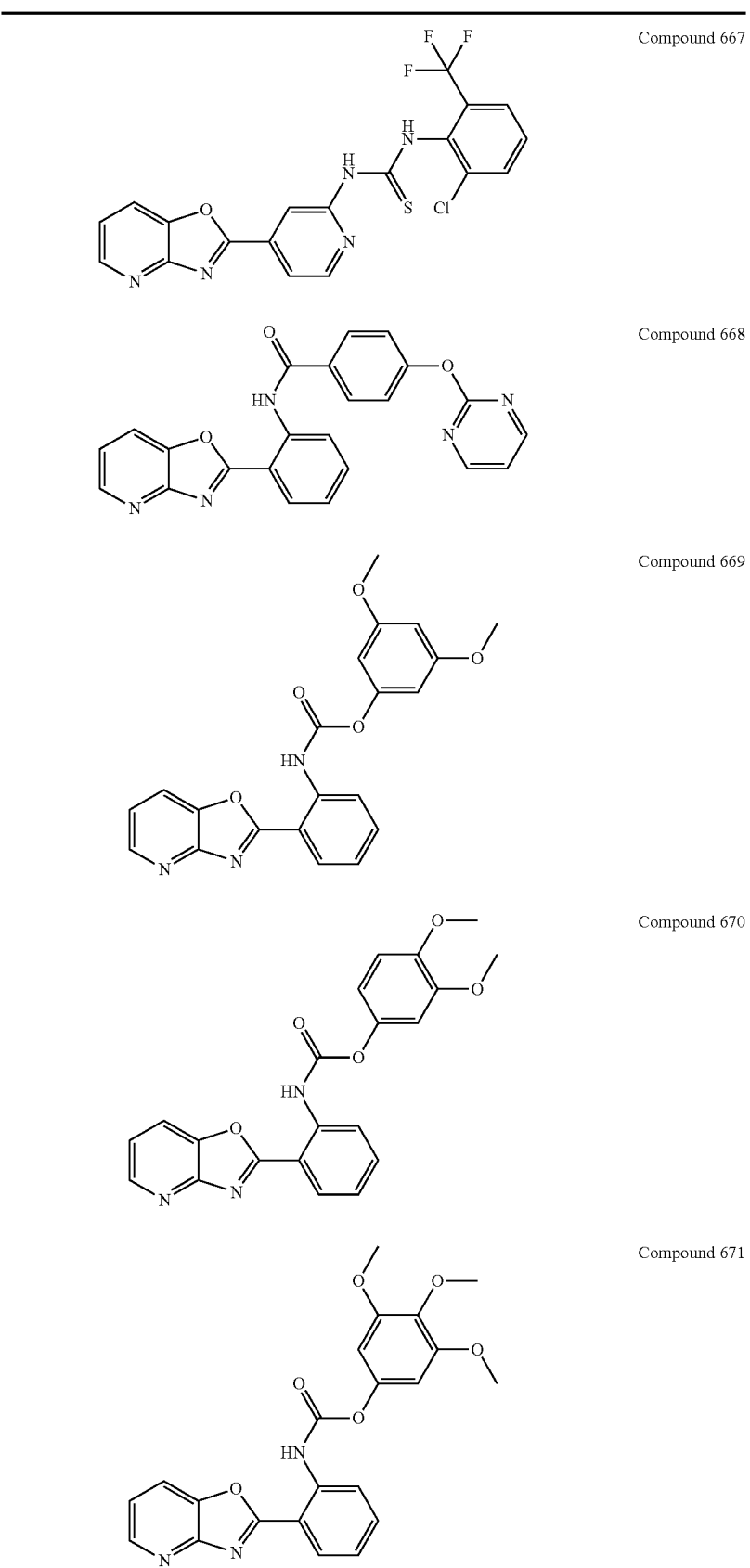
Compound 667
Compound 668
Compound 669
Compound 670
Compound 671

TABLE 1-continued
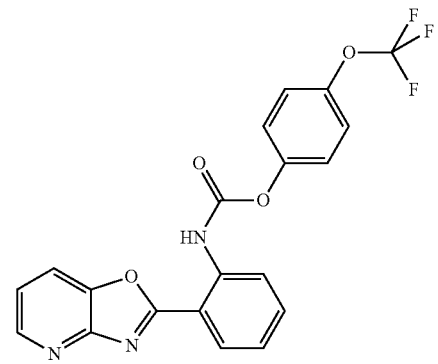 [SMILES: O=C(Nc1ccccc1-c1nc2ncccc2o1)Oc1ccc(OC(F)(F)F)cc1]
Compound 672
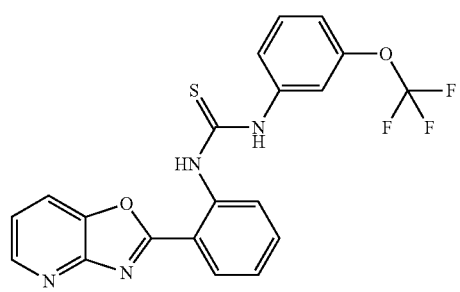 [SMILES: FC(F)(F)Oc1cccc(NC(=S)Nc2ccccc2-c2nc3ncccc3o2)c1]
Compound 673
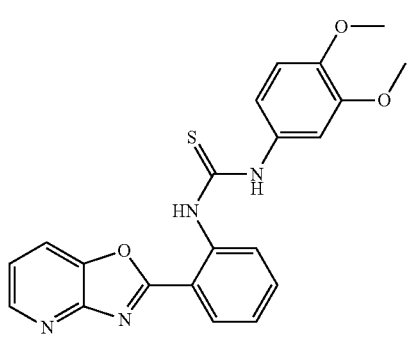 [SMILES: COc1ccc(NC(=S)Nc2ccccc2-c2nc3ncccc3o2)cc1OC]
Compound 674
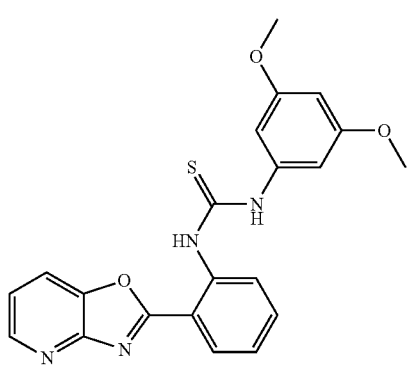 [SMILES: COc1cc(NC(=S)Nc2ccccc2-c2nc3ncccc3o2)cc(OC)c1]
Compound 675

TABLE 1-continued
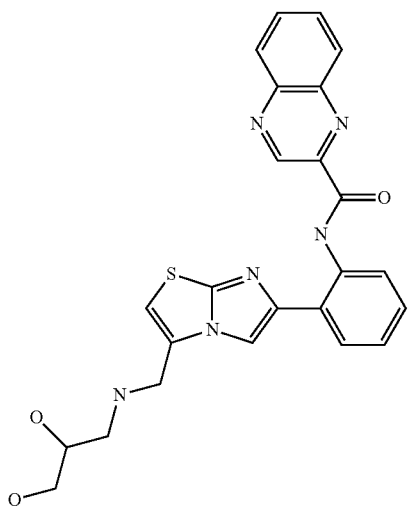
Compound 676
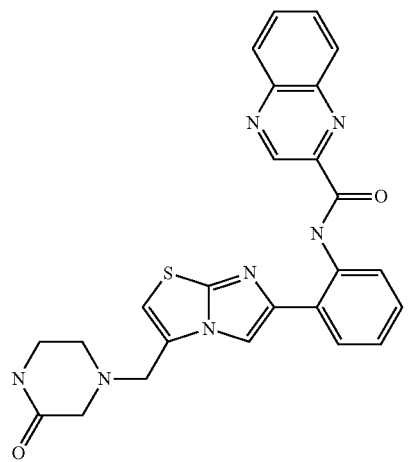 [SMILES: O=C1CN(Cc2csc3nc(-c4ccccc4NC(=O)c4cnc5ccccc5n4)cn23)CCN1]
Compound 677
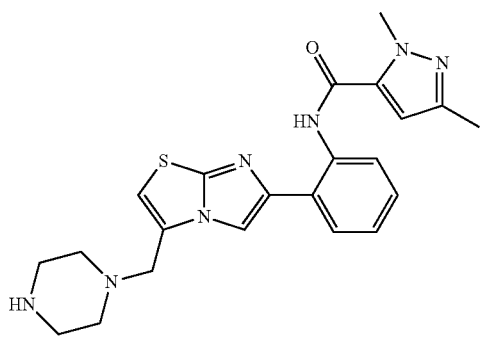 [SMILES: Cc1cc(C(=O)Nc2ccccc2-c2cn3c(CN4CCNCC4)csc3n2)n(C)n1]
Compound 678
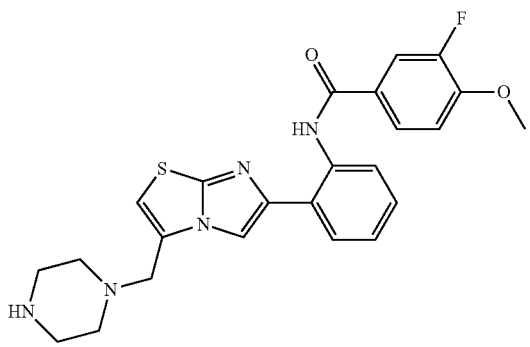 [SMILES: COc1ccc(C(=O)Nc2ccccc2-c2cn3c(CN4CCNCC4)csc3n2)cc1F]
Compound 679

TABLE 1-continued
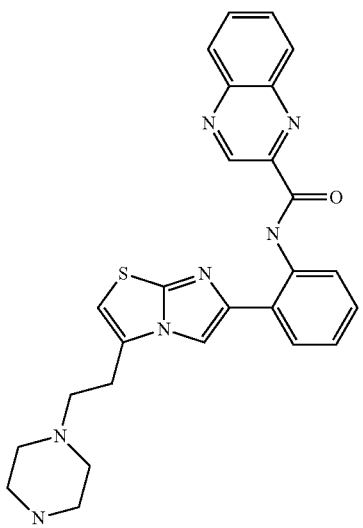 [SMILES: O=C(Nc1ccccc1-c1cn2c(CCN3CCNCC3)csc2n1)c1cnc2ccccc2n1]
Compound 680
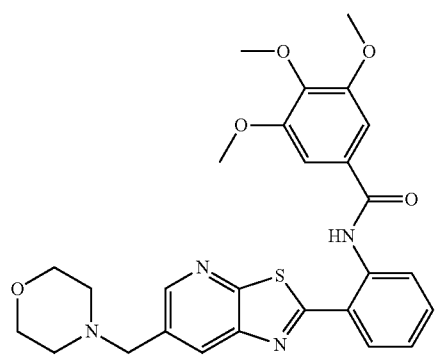 [SMILES: COc1cc(C(=O)Nc2ccccc2-c2nc3cc(CN4CCOCC4)cnc3s2)cc(OC)c1OC]
Compound 681
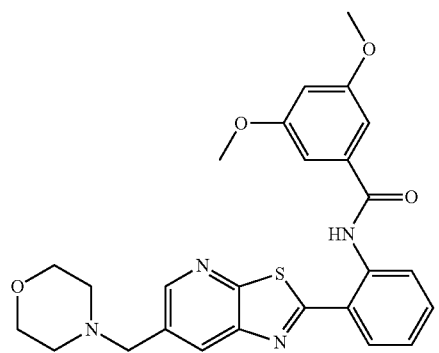 [SMILES: COc1cc(OC)cc(C(=O)Nc2ccccc2-c2nc3cc(CN4CCOCC4)cnc3s2)c1]
Compound 682
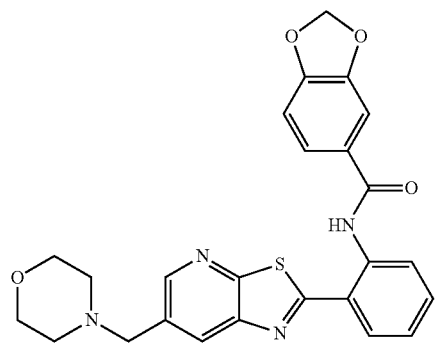 [SMILES: O=C(Nc1ccccc1-c1nc2cc(CN3CCOCC3)cnc2s1)c1ccc2c(c1)OCO2]
Compound 683

TABLE 1-continued
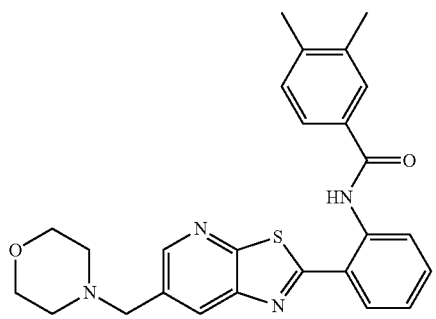 [SMILES: Cc1ccc(C(=O)Nc2ccccc2-c2nc3cc(CN4CCOCC4)cnc3s2)cc1C]
Compound 684
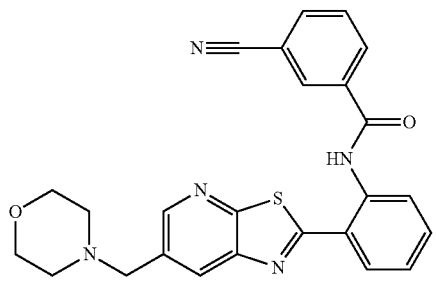 [SMILES: N#Cc1cccc(C(=O)Nc2ccccc2-c2nc3cc(CN4CCOCC4)cnc3s2)c1]
Compound 685
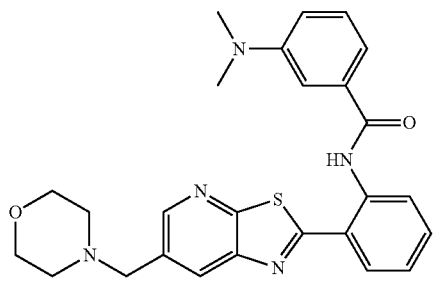 [SMILES: CN(C)c1cccc(C(=O)Nc2ccccc2-c2nc3cc(CN4CCOCC4)cnc3s2)c1]
Compound 686
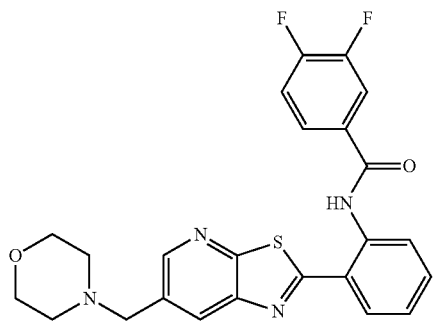 [SMILES: O=C(Nc1ccccc1-c1nc2cc(CN3CCOCC3)cnc2s1)c1ccc(F)c(F)c1]
Compound 687
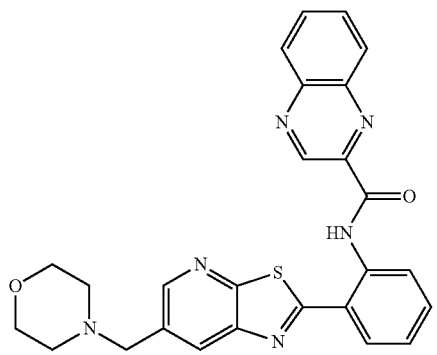 [SMILES: O=C(Nc1ccccc1-c1nc2cc(CN3CCOCC3)cnc2s1)c1cnc2ccccc2n1]
Compound 688

TABLE 1-continued
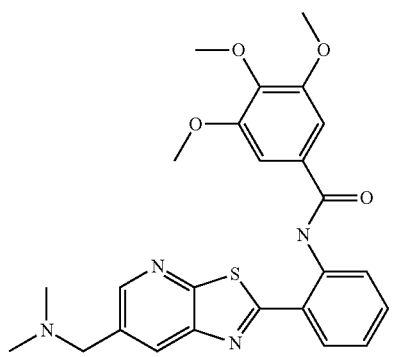 [SMILES: COc1cc(C(=O)Nc2ccccc2-c2nc3cc(CN(C)C)cnc3s2)cc(OC)c1OC]
Compound 689
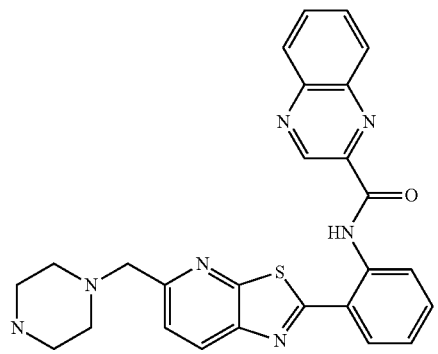 [SMILES: O=C(Nc1ccccc1-c1nc2ccc(CN3CCNCC3)nc2s1)c1cnc2ccccc2n1]
Compound 690
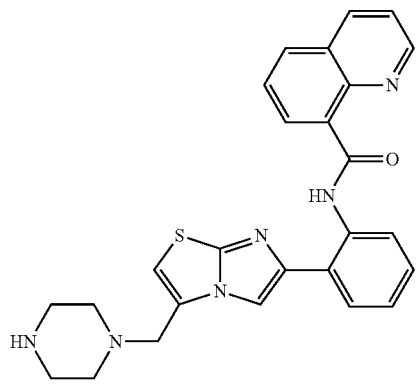 [SMILES: O=C(Nc1ccccc1-c1cn2c(CN3CCNCC3)csc2n1)c1cccc2cccnc12]
Compound 692
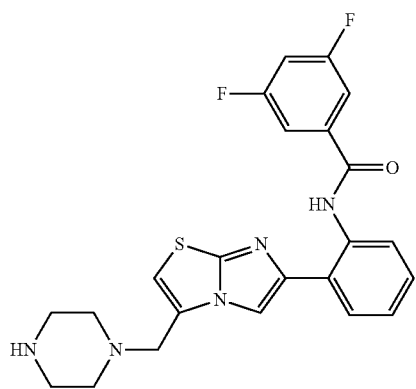 [SMILES: O=C(Nc1ccccc1-c1cn2c(CN3CCNCC3)csc2n1)c1cc(F)cc(F)c1]
Compound 695

TABLE 1-continued
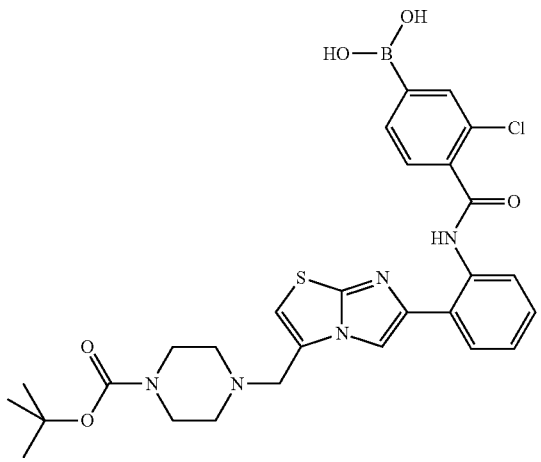 [SMILES: CC(C)(C)OC(=O)N1CCN(Cc2csc3nc(-c4ccccc4NC(=O)c4ccc(B(O)O)cc4Cl)cn23)CC1]
Compound 697
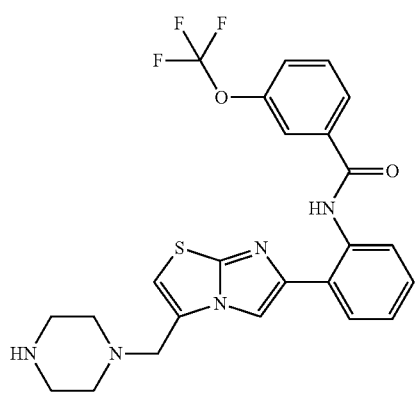 [SMILES: O=C(Nc1ccccc1-c1cn2c(CN3CCNCC3)csc2n1)c1cccc(OC(F)(F)F)c1]
Compound 698
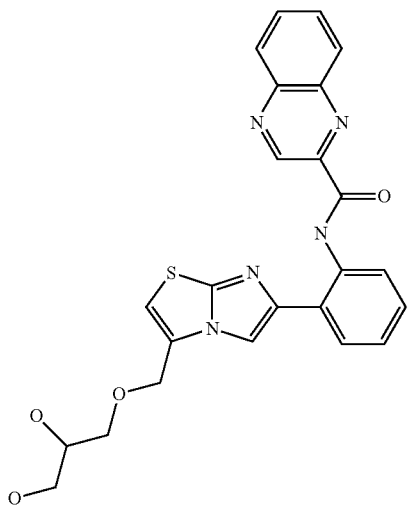 [SMILES: O=C(Nc1ccccc1-c1cn2c(COCC(O)CO)csc2n1)c1cnc2ccccc2n1]
Compound 699

TABLE 1-continued
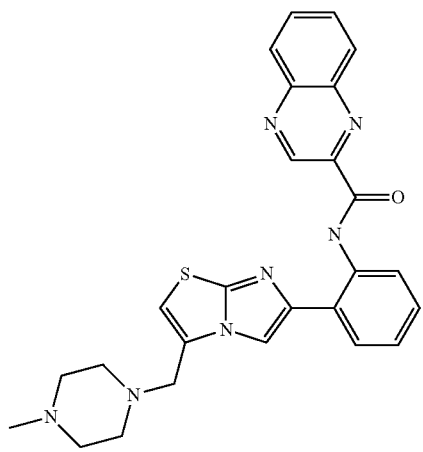 [SMILES: CN1CCN(Cc2csc3nc(-c4ccccc4NC(=O)c4cnc5ccccc5n4)cn23)CC1]
Compound 700
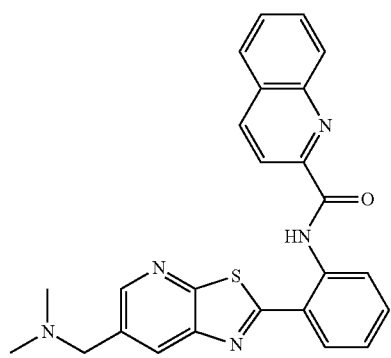 [SMILES: CN(C)Cc1cnc2sc(-c3ccccc3NC(=O)c3ccc4ccccc4n3)nc2c1]
Compound 701
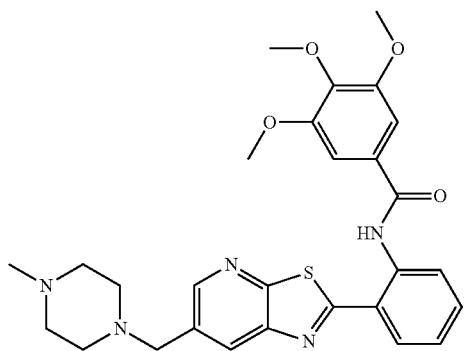 [SMILES: COc1cc(C(=O)Nc2ccccc2-c2nc3cc(CN4CCN(C)CC4)cnc3s2)cc(OC)c1OC]
Compound 702
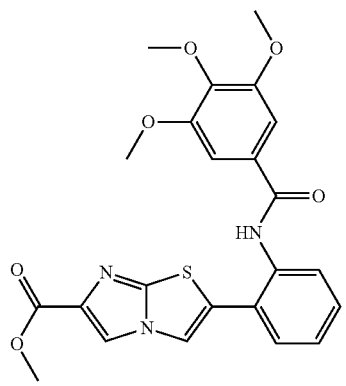 [SMILES: COC(=O)c1cn2cc(-c3ccccc3NC(=O)c3cc(OC)c(OC)c(OC)c3)sc2n1]
Compound 703

TABLE 1-continued
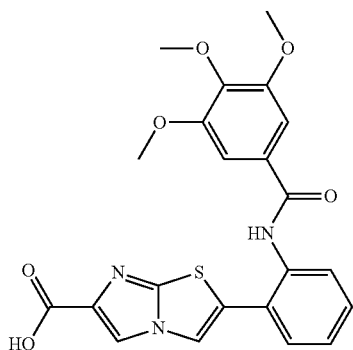 [SMILES: COc1cc(C(=O)Nc2ccccc2-c2cn3cc(C(=O)O)nc3s2)cc(OC)c1OC]
Compound 704
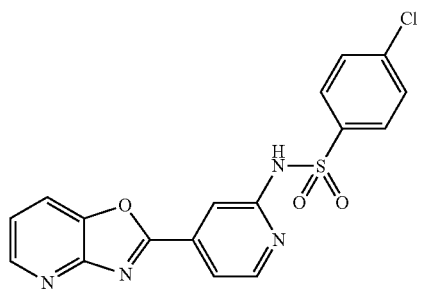 [SMILES: O=S(=O)(Nc1cc(-c2nc3ncccc3o2)ccn1)c1ccc(Cl)cc1]
Compound 705
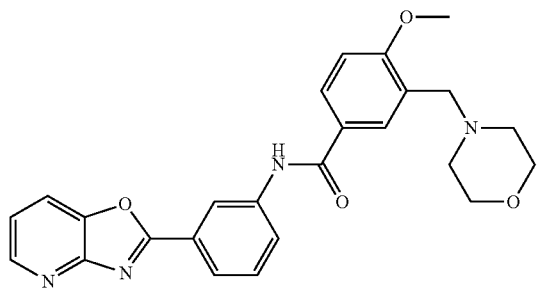 [SMILES: COc1ccc(C(=O)Nc2cccc(-c3nc4ncccc4o3)c2)cc1CN1CCOCC1]
Compound 706
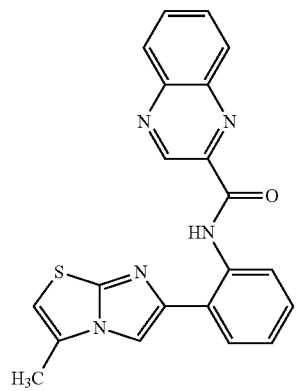 [SMILES: Cc1csc2nc(-c3ccccc3NC(=O)c3cnc4ccccc4n3)cn12]
Compound 707

TABLE 1-continued
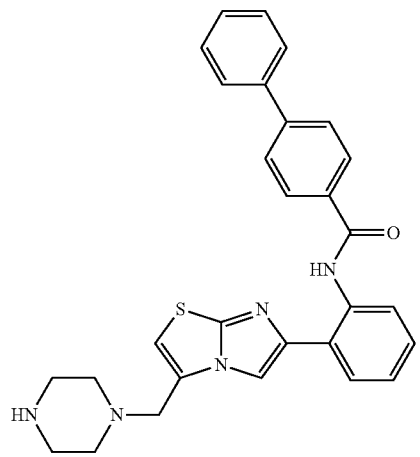 [SMILES: O=C(Nc1ccccc1-c1cn2c(CN3CCNCC3)csc2n1)c1ccc(-c2ccccc2)cc1]
Compound 708
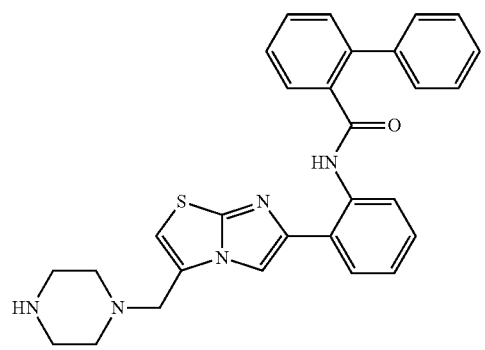 [SMILES: O=C(Nc1ccccc1-c1cn2c(CN3CCNCC3)csc2n1)c1ccccc1-c1ccccc1]
Compound 709
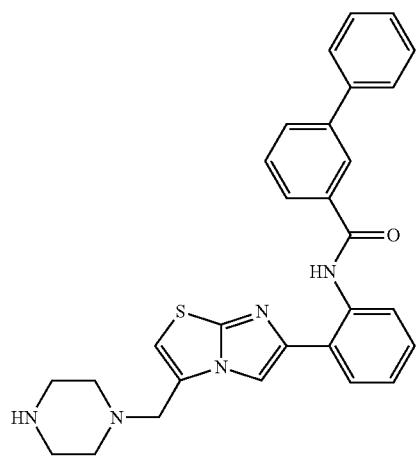 [SMILES: O=C(Nc1ccccc1-c1cn2c(CN3CCNCC3)csc2n1)c1cccc(-c2ccccc2)c1]
Compound 710

TABLE 1-continued
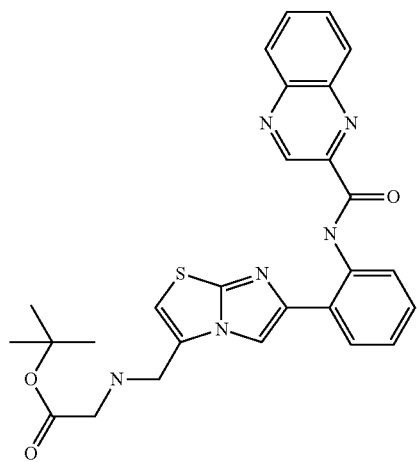 [SMILES: CC(C)(C)OC(=O)CNCc1csc2nc(-c3ccccc3NC(=O)c3cnc4ccccc4n3)cn12]
Compound 711
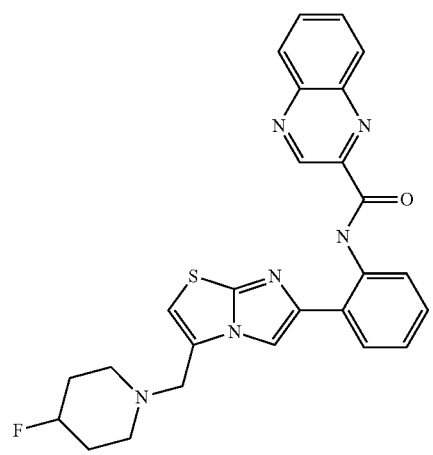 [SMILES: O=C(Nc1ccccc1-c1cn2c(CN3CCC(F)CC3)csc2n1)c1cnc2ccccc2n1]
Compound 714
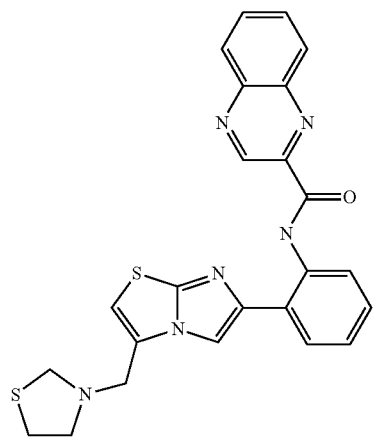 [SMILES: O=C(Nc1ccccc1-c1cn2c(CN3CCSC3)csc2n1)c1cnc2ccccc2n1]
Compound 715

TABLE 1-continued
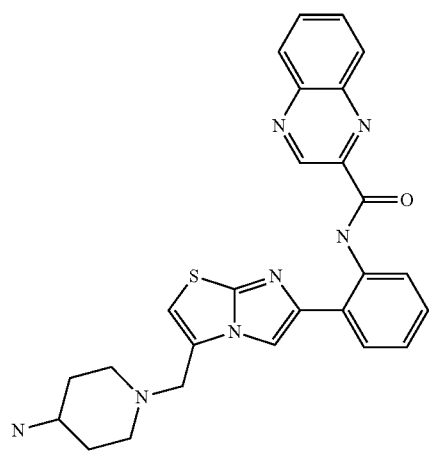 [SMILES: NC1CCN(Cc2csc3nc(-c4ccccc4NC(=O)c4cnc5ccccc5n4)cn23)CC1]
Compound 716
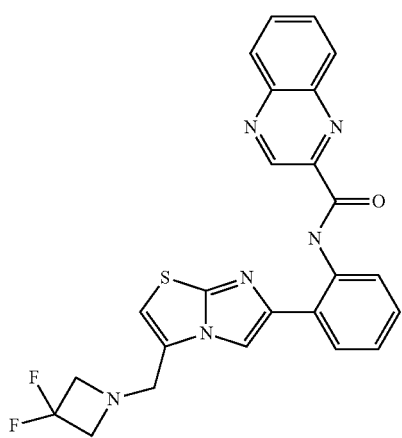 [SMILES: O=C(Nc1ccccc1-c1cn2c(CN3CC(F)(F)C3)csc2n1)c1cnc2ccccc2n1]
Compound 717
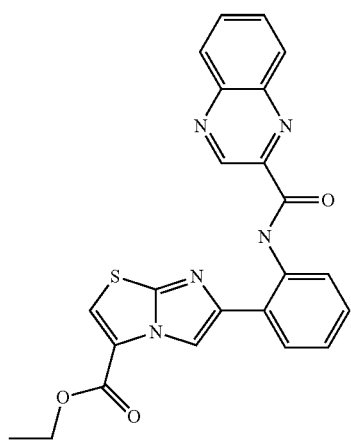 [SMILES: CCOC(=O)c1csc2nc(-c3ccccc3NC(=O)c3cnc4ccccc4n3)cn12]
Compound 718

TABLE 1-continued
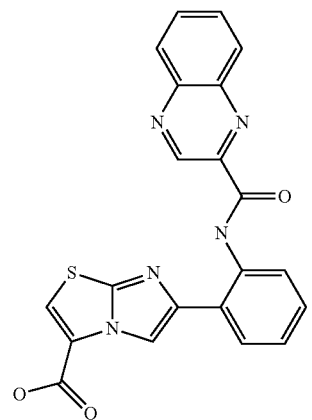 [SMILES: O=C(Nc1ccccc1-c1cn2c(C(=O)O)csc2n1)c1cnc2ccccc2n1]
Compound 719
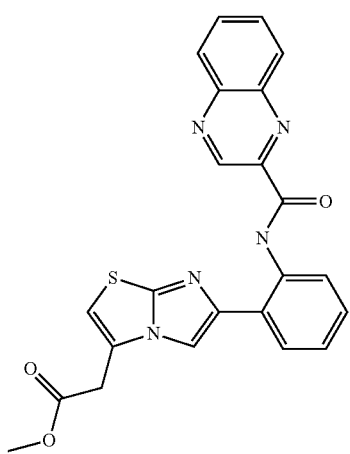 [SMILES: COC(=O)Cc1csc2nc(-c3ccccc3NC(=O)c3cnc4ccccc4n3)cn12]
Compound 720
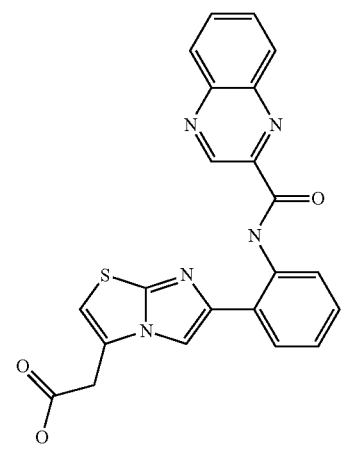 [SMILES: O=C(O)Cc1csc2nc(-c3ccccc3NC(=O)c3cnc4ccccc4n3)cn12]
Compound 721

TABLE 1-continued
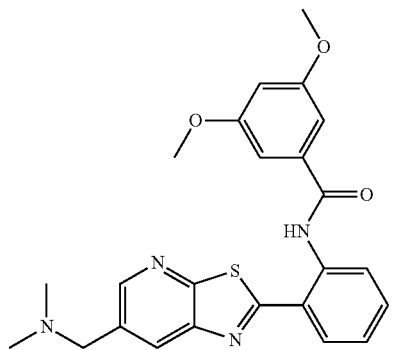 [SMILES: COc1cc(OC)cc(C(=O)Nc2ccccc2-c2nc3cc(CN(C)C)cnc3s2)c1]
Compound 722
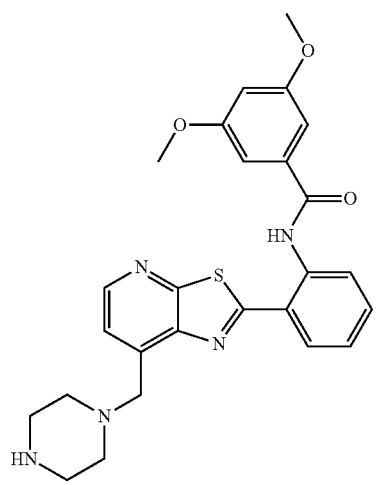 [SMILES: COc1cc(OC)cc(C(=O)Nc2ccccc2-c2nc3c(CN4CCNCC4)ccnc3s2)c1]
Compound 723
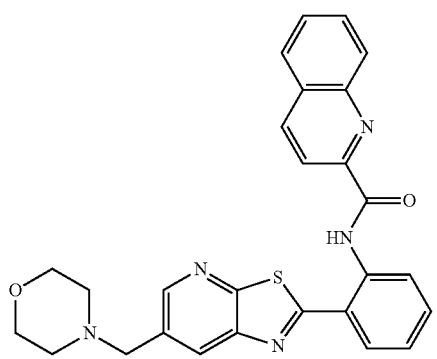 [SMILES: O=C(Nc1ccccc1-c1nc2cc(CN3CCOCC3)cnc2s1)c1ccc2ccccc2n1]
Compound 724
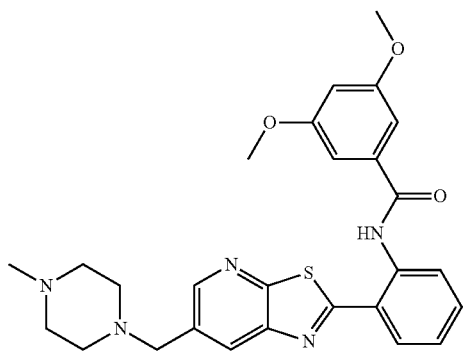 [SMILES: COc1cc(OC)cc(C(=O)Nc2ccccc2-c2nc3cc(CN4CCN(C)CC4)cnc3s2)c1]
Compound 725

TABLE 1-continued
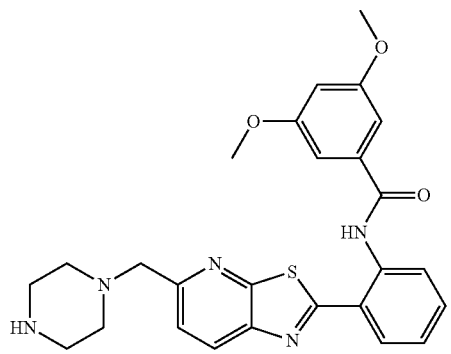 [SMILES: COc1cc(OC)cc(C(=O)Nc2ccccc2-c2nc3ccc(CN4CCNCC4)nc3s2)c1]
Compound 726
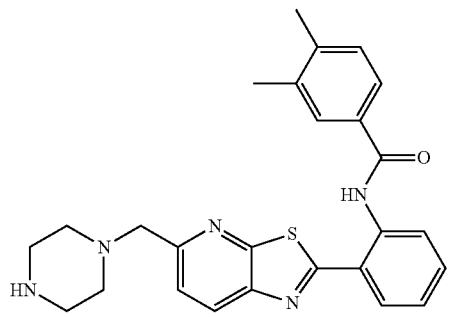 [SMILES: Cc1ccc(C(=O)Nc2ccccc2-c2nc3ccc(CN4CCNCC4)nc3s2)cc1C]
Compound 727
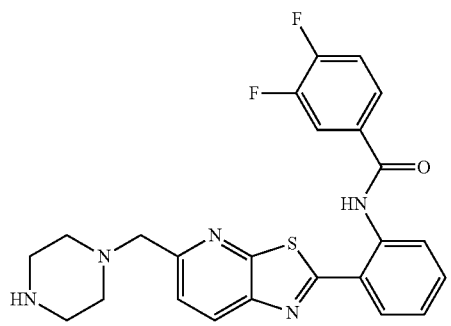 [SMILES: O=C(Nc1ccccc1-c1nc2ccc(CN3CCNCC3)nc2s1)c1ccc(F)c(F)c1]
Compound 728
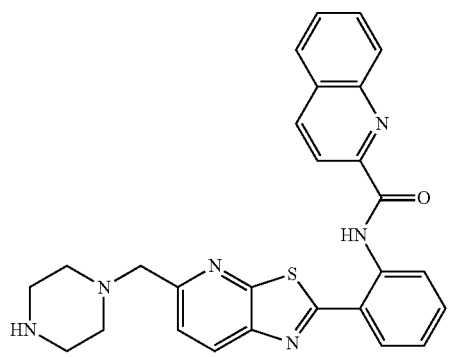 [SMILES: O=C(Nc1ccccc1-c1nc2ccc(CN3CCNCC3)nc2s1)c1ccc2ccccc2n1]
Compound 729

TABLE 1-continued
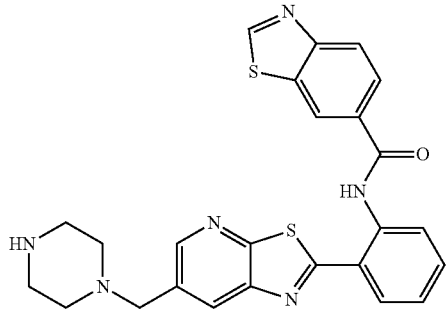 [SMILES: O=C(Nc1ccccc1-c1nc2cc(CN3CCNCC3)cnc2s1)c1ccc2ncsc2c1]
Compound 730
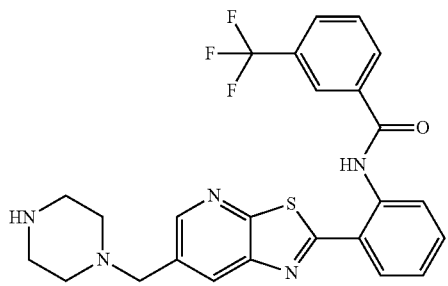 [SMILES: O=C(Nc1ccccc1-c1nc2cc(CN3CCNCC3)cnc2s1)c1cccc(C(F)(F)F)c1]
Compound 731
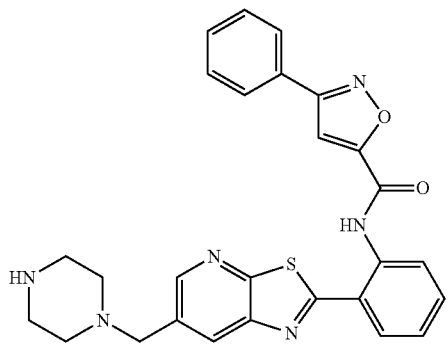 [SMILES: O=C(Nc1ccccc1-c1nc2cc(CN3CCNCC3)cnc2s1)c1cc(-c2ccccc2)no1]
Compound 732
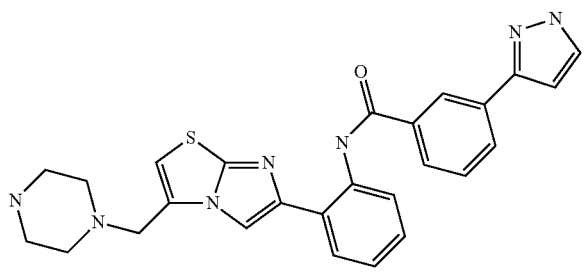 [SMILES: O=C(Nc1ccccc1-c1cn2c(CN3CCNCC3)csc2n1)c1cccc(-c2cc[nH]n2)c1]
Compound 733
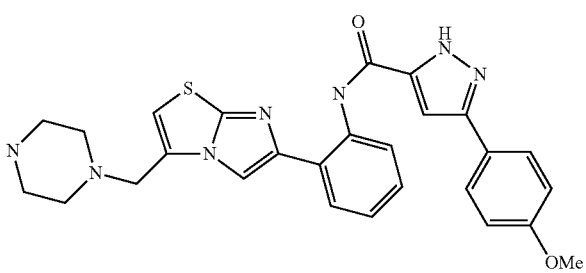 [SMILES: COc1ccc(-c2cc(C(=O)Nc3ccccc3-c3cn4c(CN5CCNCC5)csc4n3)[nH]n2)cc1]
Compound 735

TABLE 1-continued
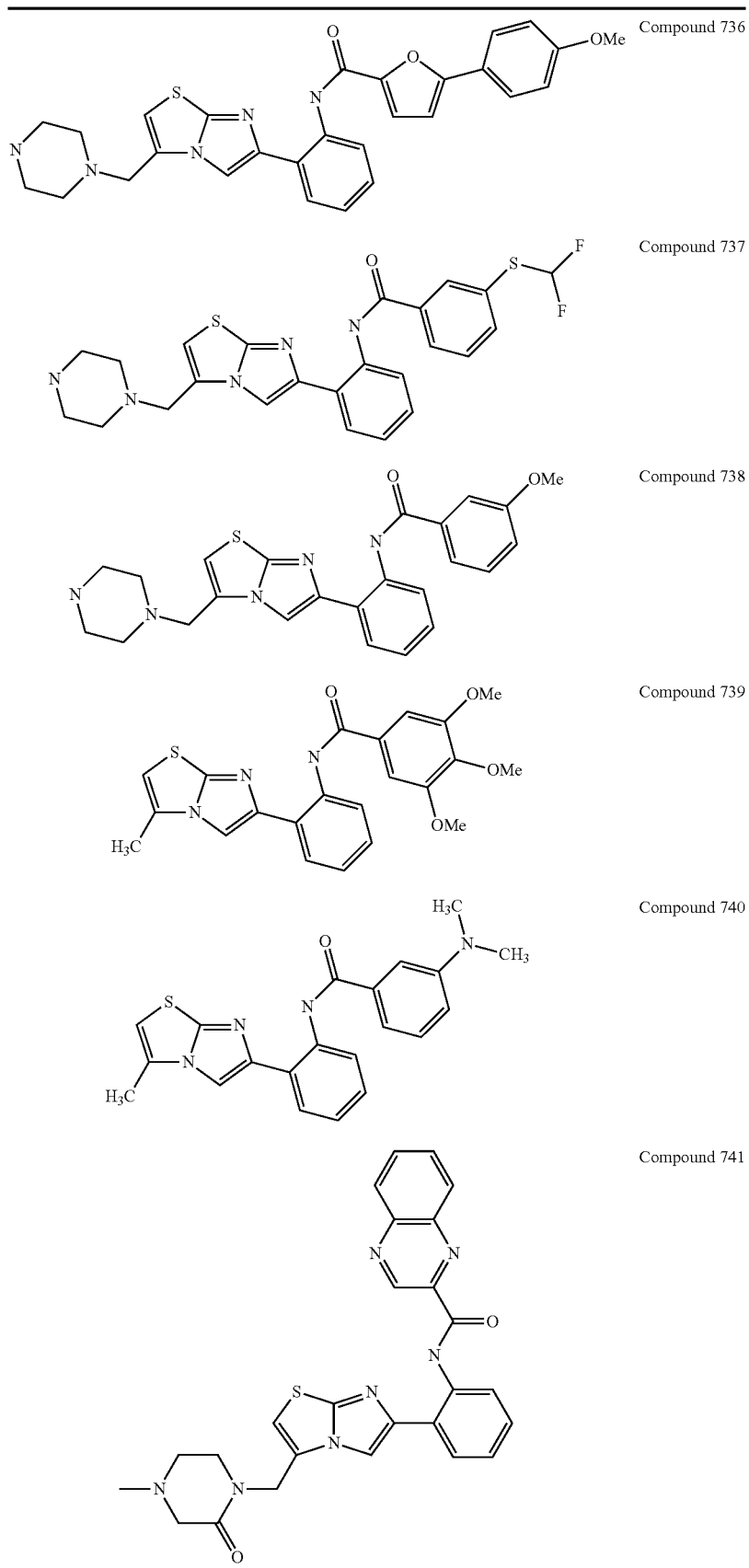
Compound 736
Compound 737
Compound 738
Compound 739
Compound 740
Compound 741

TABLE 1-continued
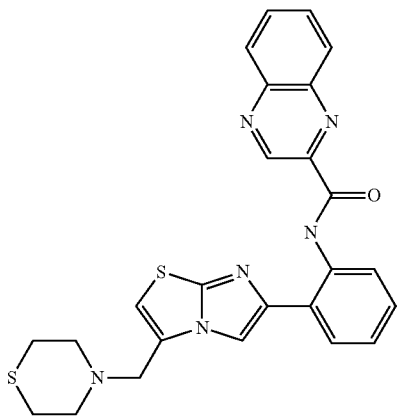 [SMILES: O=C(Nc1ccccc1-c1cn2c(CN3CCSCC3)csc2n1)c1cnc2ccccc2n1]
Compound 742
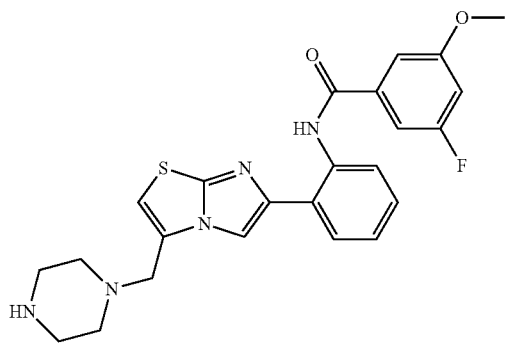 [SMILES: COc1cc(F)cc(C(=O)Nc2ccccc2-c2cn3c(CN4CCNCC4)csc3n2)c1]
Compound 743
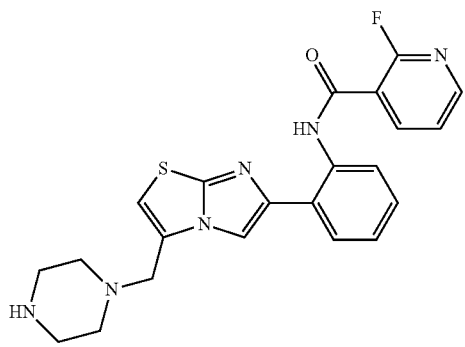 [SMILES: O=C(Nc1ccccc1-c1cn2c(CN3CCNCC3)csc2n1)c1cccnc1F]
Compound 744
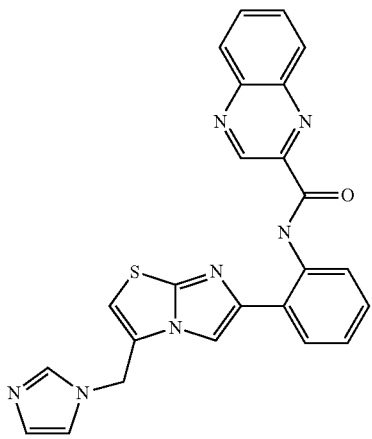 [SMILES: O=C(Nc1ccccc1-c1cn2c(Cn3ccnc3)csc2n1)c1cnc2ccccc2n1]
Compound 745

Non-limiting examples of suitable SIRT1 activators include, e.g.,

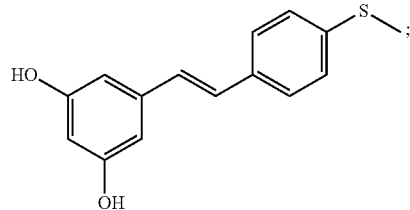
BML-230

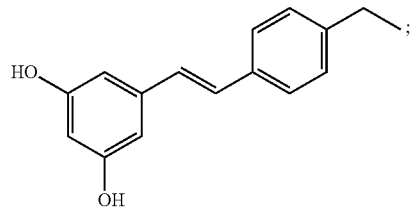
BML-225

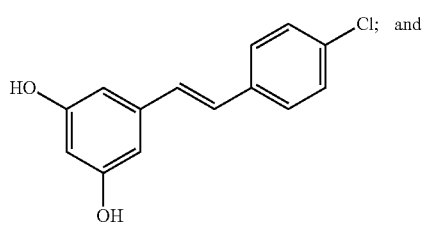
BML-217; and

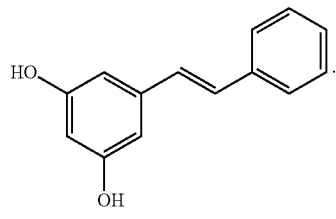
Pinosylivin

Other suitable SIRT1 activators include, e.g.,

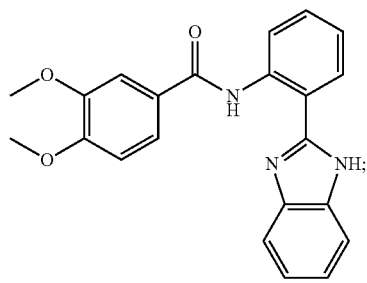

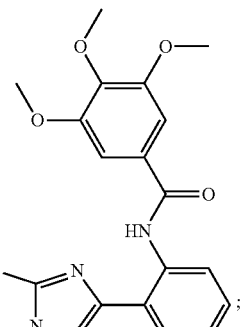
SR1460

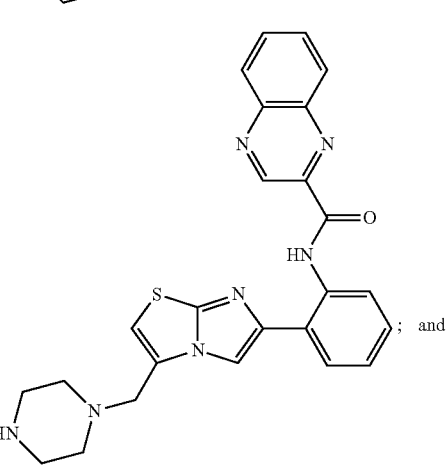
SR1720; and

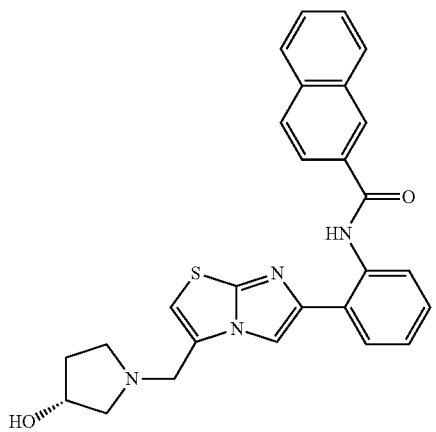
SRT-2183

SRT1720, SRT1460, and SRT2183 are selective SIRT1 activators. See, e.g., Milne et al. (2007) *Nature* 450:712.

Also suitable for use are SIRT1 activators that are quinoxaline compounds. Suitable quinoxaline SIRT1 activators include, e.g., 3-benzenesulfonyl-1-(4-fluoro-phenyl)-1H-pyrrolo[2,3-b]quinoxalin-2ylamine; 2-amino-1-(2-ethyl-phenyl)-1H-pyrrolo[2,3-b]quinoxaline-3-carboxylic acid (tetrahydro-furan-2-ylmethyl)-amine; 2-amino-1-(3-methoxy-propyl)-1H-pyrrolo[2,3-b]quinoxaline-3-carboxylic acid cyclopentylamide. See, e.g., Nayagam et al. (2006) *J. Biolmolec. Screening* 11:959.

Other suitable SIRT1 activators include, e.g., stilbene compounds, e.g., ester analogs of resveratrol, e.g., as described in U.S. Patent Publication No. 2008/0255382. For example, suitable SIRT1 activators include, e.g., ester analogs of 3,5, 4'-trihydroxy-trans-stilbene.

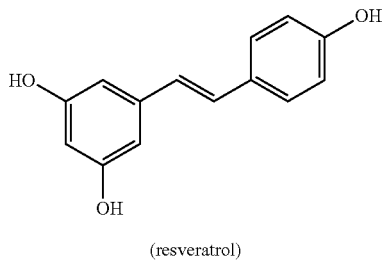 [SMILES: Oc1ccc(/C=C/c2cc(O)cc(O)c2)cc1]

(resveratrol)

Ester analogs include compounds of the formula:

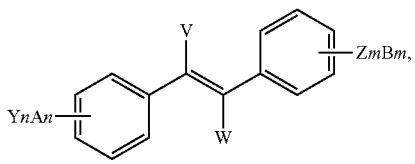

where each Y and each Z is independently —O (ethers), —O—C=O; —C=O—O (esters); —O—C=O—O (carbonates); —O—C=O—NH; —O=O—NR; —NH—C=O—O; —NR—C=O—O (carbamates); —NH—C=P; —NR—C=O; —C=O—NH; —C=O—NR (primary and secondary amides)-NH; —NR (primary and secondary amines); —N (heterocyclic rings); —S (thiol ethers); and halogen;

where each n and each m is independently 1, 2, 3, 4, or 5;

where each A and each B is independently H, R, or absent;

where each V and each W is independently H, straight or branched alkyl of from 1 to 6 carbon atoms, cycloalkyl of from 3 to 8 carbon atoms, alkoxy, phenyl, benzyl, or halogen, and where R is an alkyl with at least one carbon atom, an aryl, or an aralkyl.

Suitable SIRT1 activators include, e.g., 4'-acetoxy-3,5-bis (methoxymethoxy)stilbene; 4'-acetoxy-3,5-dihydroxystilbene; 3,5-diacetoxy-4'-chloroacetoxy stilbene; 3,5-diacetoxy-4'-hydroxy stilbene; 3,4'-diacetoxy-5-hydroxystilbene; 3-acetoxy-4'5-dihydroxystilbene; and 3,4, 5'-triacetoxystilbene.

Suitable SIRT1 activators include compounds of any one of Formulas I-VI as described in U.S. Patent Publication No. 2009/0012080. For example, a suitable SIRT1 activator is a compound of the formula:

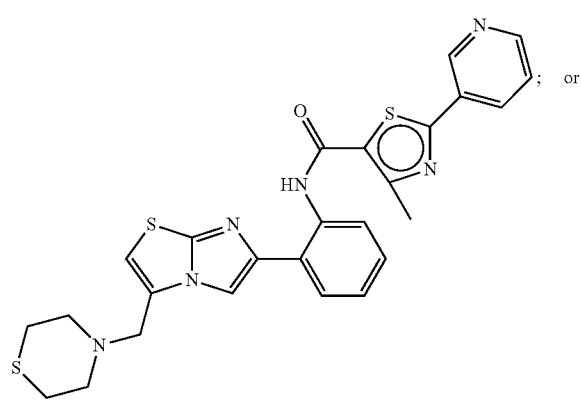

; or

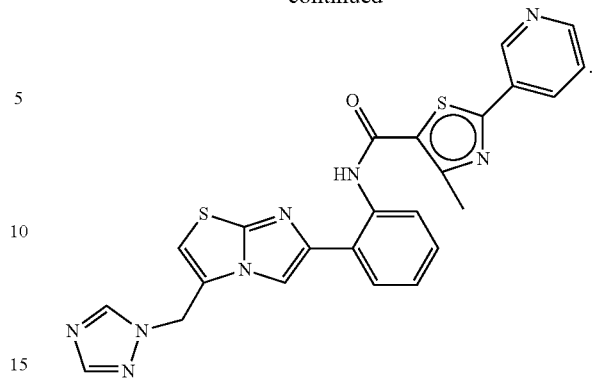

For example, a suitable SIRT1 activator is 4-methyl-N-(2 (3-morpholinomethyl)imidazol[2,1-b]thiazol-6-yl)phenyl)-2-(pyridin-3-yl)thiazol-5-carboxamide, or a pharmaceutically acceptable salt thereof.

In certain cases, an agent that decreases Ac-Tau levels is not a SIRT1 activator.

HDAC6

Histone deacetylases (HDAC) (EC number 3.5.1) are a class of enzymes that remove acetyl groups from an s-N-acetyl lysine amino acid on a histone. HDAC6 (mRNA GenBank accession no.: NM_006044.2, protein GenBank accession no.: NP_006035.2) is a cytoplasmic, microtubule-associated enzyme. HDAC6 deacetylates tubulin, Hsp90, and cortactin, and forms complexes with other partner proteins.

As described herein, HDAC6 deacetylates Tau. Overexpression of HDAC6 decreases the levels of Ac-Tau. Agents that increase the activity of HDAC6, for example, a nucleic acid comprising a nucleotide sequence encoding HDAC6, are suitable for use in a subject method. Non-limiting examples of suitable HDAC activators include, e.g., theophylline (3,7-dihydro-1,3-dimethyl-1H-purine-2,6-dione); theophylline analogs; and the like.

SIRT2

As described herein, SIRT2 deacetylates Tau. Agents that increase the activity of SIRT2, e.g., a nucleic acid comprising a nucleotide sequence encoding SIRT2, are suitable for use in a subject method.

Nucleotide sequences encoding SIRT2 polypeptides are known in the art. See, e.g., GenBank Accession No. NM_012237 (*Homo sapiens*); GenBank Accession No. NM_022432 (*Mus musculus*); NM_001008368.1 (*Rattus norvegicus*); and GenBank Accession No. XM_001168375.1 (*Pan troglodytes*).

Agents that Inhibit Acetylation of Tau

Agents that inhibit Tau acetylation include agents that inhibit the activity of a polypeptide that acetylates a Tau polypeptide. Polypeptides that acetylate a Tau polypeptide include an acetyltransferase, e.g., a histone acetyltransferase, e.g., p300. Agents that inhibit the activity of a polypeptide that acetylates a Tau polypeptide include agents that inhibit the activity of p300. In certain cases, the agent specifically inhibits the activity of p300 in acetylating Tau, e.g., the agent does not substantially inhibit any other acetyltransferase such as serotonin N-acetyltransferase, or a histone actyltransferase such as pCAF, GCN5 (e.g., GenBank Accession No. AAC50641), Rtt109, Sas, and MOZ.

p300

P300 is also known as E1A binding protein p300 (EP300). p300 (mRNA, GenBank accession no. NM_001429.3; protein, GenBank accession no. NP_001420.2) functions as histone acetyltransferase. As shown in the Examples section, p300 also acetylates Tau.

A p300 polypeptide includes a polypeptide that acetylates Tau, and that comprises an amino acid sequence at least about 75%, at least about 80%, at least about 85%, at least about 90%, at least about 95%, at least about 98%, at least about 99%, or 100%, amino acid sequence identity to a contiguous stretch of from about 1800 amino acids to about 2000 amino acids, from about 2000 amino acids to about 2200 amino acids, or from about 2200 amino acids to about 2414 amino acids, of the amino acid sequence set forth in SEQ ID NO:12.

p300 Inhibitors

As described herein, p300 acetylates Tau and increases Tau stability, resulting in increase in the steady state levels of Tau. Agents that inhibit the activity of p300 that are suitable for use in a subject method include, but are not limited to, isothiazolone-based histone acetyltransferase (HAT) inhibitors; Lys-CoA; a Lys-CoA derivative comprising a peptide of from about 5 amino acids to about 20 amino acids in length covalently linked to the lysine; Curcumin; anacardic acid; a polyprenylated benzophenone known as garcinol; a p300 specific siRNA; a compound as described in U.S. Pat. No. 6,369,030; a p300 inhibitor as described in U.S. Patent Publication No. 2009/0076155; a 4-hydroxyquinoline compound as described in Mai et al. (2009) Bioorg. Med. Chem. Lett. 19:1132; etc. The structure of Lys-CoA is shown as Compound 1 in Zheng et al. (2005) J. Am. Chem. Soc. 127:17182 (see below). In some embodiments, a suitable p300 inhibitor is a selective p300 inhibitor. In some embodiments, a suitable p300 inhibitor is cell-permeable. Cell-permeable, selective p300 inhibitors that are suitable for use include those described in Zheng et al. (2005) J. Am. Chem. Soc. 127:17182.

For example, suitable p300 inhibitors include Compounds 1-8, where the parent formula is:

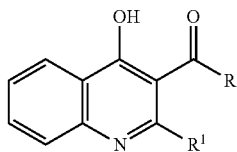

where
in Compound 1, R=OC$_2$H$_5$ and R$^1$ =CH$_3$;
in Compound 2, R=OH and R$^1$ =CH$_3$;
in Compound 3, R=OC$_2$H$_5$ and R$^1$ =C$_6$H$_{11}$;
in Compound 4, R=OC$_2$H$_5$ and R$^1$ =C$_{10}$H$_{21}$;
in Compound 5, R=OH and R$^1$ =C$_{10}$H$_{21}$;
in Compound 6, R=OC$_2$H$_5$ and R$^1$ =C$_{15}$H$_{31}$; and
in Compound 7, R=OH and R$^1$ =C$_{15}$H$_{31}$.
See, e.g., Mai et al. (2009) Bioorg. Med. Chem. Lett. 19:1132.

For example, suitable p300 inhibitors include Compounds 2-6, as shown below, of the formula:

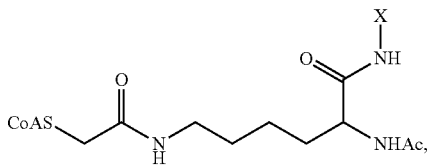

where
in Compound 1 (Lys-CoA), X=H;
in Compound 2, X=YGRKKRRQRRR—CO$_2$H (SEQ ID NO:13);
in Compound 3, X=YGRKKRRQRRRGYK—NH$_2$ (SEQ ID NO:14);
in Compound 4, X=Ahx-R-Ahx-RR-Ahx-RR-Ahx-RR-Ahx-K—NH$_2$ (SEQ ID NO:15);
in Compound 5, X=GRRRRRRRRRGK—NH$_2$ (SEQ ID NO:16); and
in Compound 6, X=Ahx-RRRRRRRRR—NH$_2$ (SEQ ID NO:17);
and where Ahx is 6-aminohexanoic acid.

A number of p300 inhibitors are known in the art. A suitable p300 inhibitor can decrease the enzymatic activity of a p300 polypeptide (e.g., the activity of the p300 polypeptide in acetylating a Tau polypeptide) by at least about 5%, at least about 10%, at least about 15%, at least about 20%, at least about 25%, at least about 30%, at least about 40%, at least about 50%, at least about 60%, at least about 70%, at least about 80%, or more than 80%, compared to the activity of the p300 polypeptide in the absence of the inhibitor.

A suitable p300 inhibitor can inhibit p300 enzymatic activity at an IC$_{50}$ (half maximal inhibitory concentration) of from about 1 nM to about 1 mM, e.g., from about 1 nM to about 10 nM, from about 10 nM to about 15 nM, from about 15 nM to about 25 nM, from about 25 nM to about 50 nM, from about 50 nM to about 75 nM, from about 75 nM to about 100 nM, from about 100 nM to about 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 450 nM, from about 450 nM to about 500 nM, from about 500 nM to about 750 nM, from about 750 nM to about 1 µM, from about 1 µM to about 10 µM, from about 10 µM to about 25 µM, from about 25 µM to about 50 µM, from about 50 µM to about 75 µM, from about 75 µM to about 100 µM, from about 100 µM to about 250 µM from about 250 µM to about 500 µM, or from about 500 µM to about 1 mM.

Suitable p300 inhibitors include compounds such as C646, C375, and C146. The structures of C646, C375, and C146 are shown below.

A

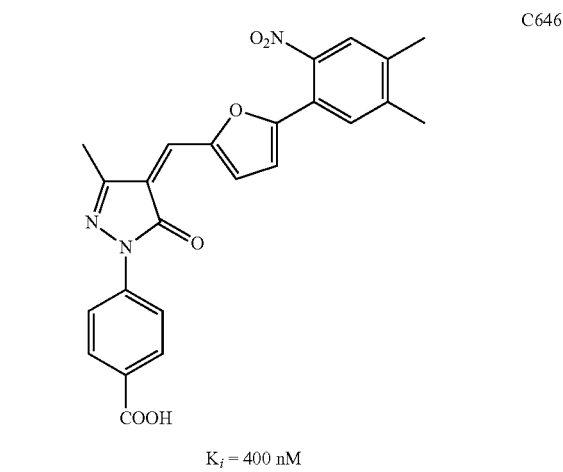

$K_i$ = 400 nM

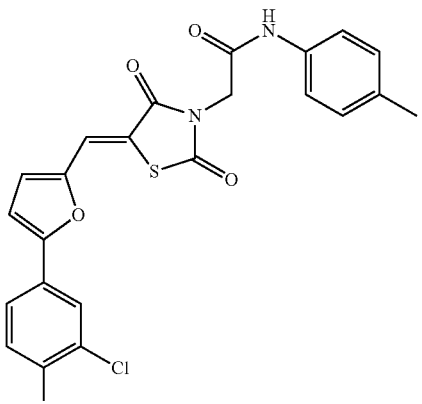

$K_i$ = 4.8 µM

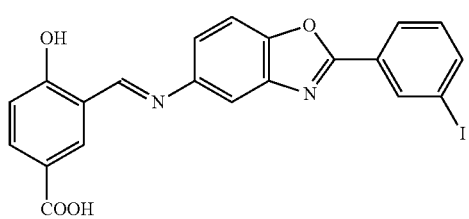

$K_i$ = 4.7 µM

Suitable p300 inhibitors include N-alkyl- and N-aryl-substituted isothiazolones; such compounds have been identified as inhibitors of p300 (35-90% inhibition at 35 µmol/L) (Stimson et al. (Oct. 1, 2005) Mol Cancer Ther 4:1521). These N-substituted isothiazolones-based compounds are shown in Tables 2 and 3.

TABLE 2

Parent Structure:

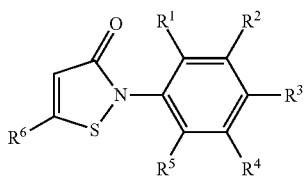

| Compound | $R^1$ | $R^2$ | $R^3$ | $R^4$ | $R^5$ | $R^6$ |
|---|---|---|---|---|---|---|
| 1 | $NO_2$ | H | H | H | H | H |
| 2 | H | $NO_2$ | H | H | H | H |
| 3 | H | H | $NO_2$ | H | H | H |
| 4 | H | H | $NO_2$ | H | H | Cl |
| 5 | H | $NO_2$ | Cl | H | H | H |
| 6 | OMe | H | H | H | H | H |
| 7 | H | H | OMe | H | H | H |
| 8 | Cl | H | H | H | H | H |
| 9 | H | Cl | H | H | H | H |
| 10 | H | H | Cl | H | H | H |
| 11 | Cl | H | H | Cl | H | H |
| 12 | Cl | H | H | Cl | H | Cl |
| 13 | Cl | H | Cl | H | H | H |
| 14 | Cl | Cl | H | H | H | H |
| 15 | $CH_3$ | H | H | H | H | H |
| 16 | H | $CH_3$ | H | H | H | H |
| 17 | H | H | $CH_3$ | H | H | H |
| 18 | $CO_2Et$ | H | H | H | H | H |
| 19 | H | $CO_2Et$ | H | H | H | H |

TABLE 2-continued

Parent Structure:

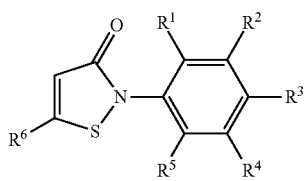

| Compound | $R^1$ | $R^2$ | $R^3$ | $R^4$ | $R^5$ | $R^6$ |
|---|---|---|---|---|---|---|
| 20 | H | H | $CO_2Et$ | H | H | H |
| 21 | $CF_3$ | H | H | H | H | H |
| 22 | H | $CF_3$ | H | H | H | H |
| 23 | H | $CF_3$ | H | H | H | Cl |
| 24 | H | $CF_3$ | F | H | H | H |
| 25 | H | $CF_3$ | F | H | H | Cl |
| 26 | H | Cl | $CH_3$ | H | H | H |
| 27 | H | OPh | H | H | H | H |

TABLE 3

Parent Structure:

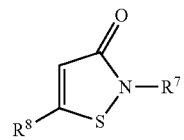

| Compound | $R^7$ | $R^8$ |
|---|---|---|
| 28 | iPr | H |
| 29 | cyclopropyl | H |
| 30 | benzyl | H |
| 31 | Et | H |
| 32 | Et | Cl |
| 33 | decyl | H |
| 34 | $CH_2CH_2OPh$ | H |
| 35 | $CH_2CH_2OPh$ | Cl |

CBP

In some embodiments, a subject method involves use of a CREB-binding protein (CBP) inhibitor. In some embodiments, a p300 inhibitor also inhibits a CBP polypeptide.

CBP polypeptides are known in the art. For example, GenBank Accession No. NP_004371.2 provides an amino acid sequence of *Homo sapiens* CBP; GenBank Accession No. XP_523285.2 provides an amino acid sequence of *Pan troglodytes* CBP; GenBank Accession No. XP_001095225.1 provides an amino acid sequence of *Macaca mulatta* CBP; GenBank Accession No. NP_596872.3 provides an amino acid sequence of *Rattus norvegicus* CBP; and GenBank Accession No. NP_001020603.1 provides an amino acid sequence of *Mus musculus* CBP. The amino acid sequence set forth in GenBank Accession No. NP_004371.2 is provided herewith as SEQ ID NO:53.

Methods of Treating a Tauopathy

The present disclosure provides a method for treating a tauopathy in an individual. The method comprising administering to an individual in need thereof an effective amount of an agent that reduces the level of acetylated Tau in the cell, e.g., an agent that inhibits the acetyltransferase activity of an acetyltransferase that acetylates a Tau polypeptide, an agent that increases the deacetylase activity of a deacetylase that deacetylates an acetylated Tau polypeptide, etc.

Tauopathies are neurodegenerative diseases that are characterized, at least in part, by pathological aggregation of Tau protein, e.g., in neurofibrillary tangles. Examples of tauopathies include frontotemporal dementia, Alzheimer's disease, progressive supranuclear palsy, corticobasal degeneration, Down syndrome, dementia pugilistica, inclusion-body myositis, and frontotemporal lobar degeneration, also known as Pick's disease. Exemplary tauopathies include: diseases showing coexistence of tau and amyloid pathologies, e.g., Alzheimer's disease, Creutzfeldt-Jakob disease, dementia pugilistica, Down's syndrome, Gerstmann-Sträussler-Scheinker disease, inclusion body myositis, and prion protein cerebral amyloid angiopathy; diseases without distinct amyloid pathology, e.g., amyotrophic lateral sclerosis/Parkinsonism-dementia complex, argyrophilic grain dementia, corticobasal degeneration, diffuse neurofibrillary tangles with calcification, frontotemporal dementia with Parkinsonism linked to chromosome 17, Hallevorden-Spatz disease, multiple system atrophy, Niemann-Pick disease type C, Pick's disease, progressive subcortical gliosis, progressive supranuclear palsy, subacute sclerosing panencephalitis, and tangle-predominant Alzheimer's disease.

In some embodiments, a subject method involves administration of an agent that inhibits acetylation of a Tau polypeptide. As explained above, agents that reduce Tau acetylation include agents that inhibit the activity of a polypeptide that acetylates a Tau polypeptide. Polypeptides that acetylate a Tau polypeptide include histone acetyltransferases, e.g., p300. Several agents that inhibit the activity of p300 are disclosed above, for example in Table 2.

In some embodiments, a subject method involves administration of an agent that increases deacetylation of an Ac-Tau polypeptide. As discussed above, agents that increase Tau deacetylation include agents that increase the activity of a polypeptide that deacetylates an Ac-Tau polypeptide. Polypeptides that deacetylate Tau include, e.g., SIRT1, SIRT2, HDAC 6, etc. Agents that increase the activity of a polypeptide that deacetylates an acetylated Tau polypeptide include, e.g., agents that increase the activity of SIRT1. Several activators of SIRT1 are provided above, for example in Table 1. Agents that increase the activity of a polypeptide that deacetylates an acetylated Tau polypeptide include, e.g., agents that increase the activity of SIRT2. Agents that increase the activity of a polypeptide that deacetylates an acetylated Tau polypeptide include, e.g., agents that increase the activity of HDAC6.

In some embodiments, a subject method involves administration of an agent that inhibits acetylation of a Tau polypeptide and an agent that increases deacetylation of an Ac-Tau polypeptide. In addition to the individual administration of an agent(s) that increases Ac-Tau polypeptide deacetylation and of an agent(s) that decreases Tau polypeptide acetylation, a combination therapy may be used in treating a tauopathy. For example, a combination of a SIRT1 activator (or a SIRT2 activator or an HDAC6 activator) and a p300 (or CBP) inhibitor may be used in a combination therapy for treating a tauopathy. A combination therapy is in some embodiments more effective in treating a tauopathy than administering a Tau-deacetylase polypeptide or an inhibitor of a Tau-acetyltransferase in monotherapy. Agents that inhibit acetylation of a Tau polypeptide and/or agents that increase deacetylation of Ac-Tau polypeptide are referred to herein as "active agents" or "active agent." In some embodiments, an agent that inhibits acetylation of a Tau polypeptide and an agent that increases deacetylation of an Ac-Tau polypeptide, when administered in combination therapy, provide for a synergistic effect.

A subject method for treating a tauopathy in an individual generally involves administering an effective amount of an agent that inhibits acetylation of a Tau polypeptide in a neuronal cell and/or an agent that increases deacetylation of an Ac-Tau polypeptide in a cell that produces Tau (e.g., a neuronal cell and/or a glial cell) in the individual. In some embodiments, a subject method involves monotherapy, e.g., administration of an effective amount of a single active agent, e.g., an agent that inhibits acetylation of a Tau polypeptide in a cell that produces Tau (e.g., a neuronal cell and/or a glial cell). In some embodiments, a subject method involves monotherapy, e.g., administration of an effective amount of a single active agent, e.g., an agent that increases deacetylation of an Ac-Tau polypeptide in a cell that produces Tau (e.g., a neuronal cell and/or a glial cell). In some embodiments, a subject method involves a combination therapy, e.g., administration of an agent that inhibits acetylation of a Tau polypeptide in a cell (e.g., a neuron; a glial cell) and an agent that increases deacetylation of an Ac-Tau polypeptide in a cell (e.g., a neuron; a glial cell) in combined effective amounts.

An effective amount of an active agent is an amount that is effective to ameliorate at least one symptom of a tauopathy, e.g., to alleviate an adverse symptom and/or to increase a normal function that was impaired as a result of the tauopathy. For example, in some embodiments, an effective amount of an active agent is an amount that is effective to reduce the number of neurofibrillary lesions in the brain of an individual having a tauopathy. Where a subject method involves combination therapy, combined effective amounts of the active agents are amounts that, in combination, are effective to reduce the number of neurofibrillary lesions in the brain of an individual having a tauopathy. In some embodiments, an effective amount of an active agent is an amount that is effective to increase a cognitive function in the individual. Where a subject method involves combination therapy, combined effective amounts of the active agents are amounts that, in combination, are effective to increase a cognitive function in the individual.

Formulations, Dosages, and Routes of Administration

An active agent (e.g., an agent that inhibits acetylation of a Tau polypeptide; an agent that increases deacetylation of Ac-Tau polypeptide) can be incorporated into a variety of formulations for therapeutic administration. More particularly, an active agent can be formulated into pharmaceutical compositions by combination with appropriate pharmaceutically acceptable carriers or diluents, and may be formulated into preparations in solid, semi-solid, liquid or gaseous forms, such as, powders, granules, solutions, injections, inhalants, gels, hydrogels, microspheres, etc. As such, administration of an active agent can be achieved in various ways, including local, such as delivery into the affected tissue, oral, catheter mediated, intrathecal, buccal, parenteral, intraperitoneal, intradermal, transdermal, intracheal, etc., administration. The active agent may be systemic after administration or may be localized by the use of regional administration, intramural administration, or use of an implant that acts to retain the active dose at the site of implantation.

In some embodiments, an active agent(s) is formulated to cross the blood brain barrier (BBB). One strategy for drug delivery through the blood brain barrier (BBB) entails disruption of the BBB, either by osmotic means such as mannitol or leukotrienes, or biochemically by the use of vasoactive substances such as bradykinin A BBB disrupting agent can be co-administered with an active agent when the compositions are administered by intravascular injection. Other strategies to go through the BBB may entail the use of endogenous transport systems, including carrier-mediated transporters such as glucose and amino acid carriers, receptor-mediated transcytosis for insulin or transferrin, and active efflux transporters such as p-glycoprotein. Active transport moieties may also be conjugated to an active agent for use in the methods disclosed herein to facilitate transport across the epithelial wall of the blood vessel. Alternatively, drug delivery behind the BBB is by intrathecal delivery of therapeutics directly to the cranium, as through an Ommaya reservoir.

Pharmaceutical compositions can include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, phosphate buffered saline (PBS), Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see. Langer, Science 249:1527-1533 (1990).

The pharmaceutical compositions can be administered for prophylactic and/or therapeutic treatments. Toxicity and therapeutic efficacy of the active agent can be determined according to standard pharmaceutical procedures in cell cultures and/or experimental animals, including, for example, determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred.

The data obtained from cell culture and/or animal studies can be used in formulating a range of dosages for humans. The dosage of the active agent typically lines within a range of circulating concentrations that include the ED50 with low toxicity. The dosage can vary within this range depending upon the dosage form employed and the route of administration utilized.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under Good Manufacturing Practice (GMP) conditions.

The effective amount of an active agent(s) to be given to a particular patient will depend on a variety of factors, several of which will be different from patient to patient. A competent clinician will be able to determine an effective amount of an active agent to administer to a patient to treat a tauopathy. Utilizing LD50 animal data, and other information available for the inhibitor, a clinician can determine the maximum safe dose for an individual, depending on the route of administration. For instance, an intravenously administered dose may be more than an intrathecally administered dose, given the greater body of fluid into which the therapeutic composition is being administered. Similarly, compositions which are rapidly cleared from the body may be administered at higher doses, or in repeated doses, in order to maintain a therapeutic concentration. Utilizing ordinary skill, the competent clinician will be able to optimize the dosage of a particular therapeutic in the course of routine clinical trials.

Formulations

In carrying out a subject treatment method (e.g., reducing the level of acetylated Tau polypeptide in a cell (e.g., a neuron; a glial cell) in an individual; treating a tauopathy), an active agent(s) may be administered to the host using any convenient means capable of resulting in the desired physiological effect (e.g., reduction in the level of acetylated Tau polypeptide in a neuronal cell and/or a glial cell in an individual; increase in cognitive function; reduction in neurofibrillary lesions; reduction in adverse effect of a tauopathy; etc.). Thus, the agent can be incorporated into a variety of formulations for therapeutic administration. More particularly, an active agent can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, an active agent(s) can be administered in the form of its (their) pharmaceutically acceptable salts, or the active agent may also be used alone or in appropriate association, as well as in combination, with other pharmaceutically active compounds. The following methods and excipients are merely exemplary and are in no way limiting.

For oral preparations, an active agent can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

An active agent can be formulated into preparations for injection by dissolving, suspending or emulsifying the active agent in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

An active agent can be utilized in aerosol formulation to be administered via inhalation. The compounds of the present invention can be formulated into pressurized acceptable propellants such as dichlorodifluoromethane, propane, nitrogen and the like.

Furthermore, an active agent can be made into suppositories by mixing with a variety of bases such as emulsifying bases or water-soluble bases. An active agent can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more active agents. Similarly, unit dosage forms for injection or intravenous administration may comprise the active agent(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of an active agent calculated in an amount sufficient to produce the desired effect in association with a pharmaceutically acceptable diluent, carrier or vehicle. The specifications for a unit dosage form of an active agent depend on the particular active agent employed and the effect to be achieved, and the pharmacodynamics associated with each active agent in the host.

Other modes of administration will also find use with the subject invention. For instance, an active agent can be formulated in suppositories and, in some cases, aerosol and intranasal compositions. For suppositories, the vehicle composition will include traditional binders and carriers such as, polyalkylene glycols, or triglycerides. Such suppositories may be formed from mixtures containing the active ingredient in the range of about 0.5% to about 10% (w/w), e.g., about 1% to about 2%.

Intranasal formulations will usually include vehicles that neither cause irritation to the nasal mucosa nor significantly disturb ciliary function. Diluents such as water, aqueous saline or other known substances can be employed. The nasal formulations may also contain preservatives such as, but not limited to, chlorobutanol and benzalkonium chloride. A surfactant may be present to enhance absorption of an active agent by the nasal mucosa.

An active agent can be administered as injectables. Typically, injectable compositions are prepared as liquid solutions or suspensions; solid forms suitable for solution in, or suspension in, liquid vehicles prior to injection may also be prepared. The preparation may also be emulsified or the active agent encapsulated in liposome vehicles.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the active agent adequate to achieve the desired state in the subject being treated.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Oral Formulations

In some embodiments, an active agent is formulated for oral delivery to an individual in need of such an agent.

For oral delivery, a formulation comprising an active agent will in some embodiments include an enteric-soluble coating material. Suitable enteric-soluble coating material include hydroxypropyl methylcellulose acetate succinate (HPMCAS), hydroxypropyl methyl cellulose phthalate (HPMCP), cellulose acetate phthalate (CAP), polyvinyl phthalic acetate (PVPA), Eudragit™, and shellac.

As one non-limiting example of a suitable oral formulation, an active agent is formulated with one or more pharmaceutical excipients and coated with an enteric coating, as described in U.S. Pat. No. 6,346,269. For example, a solution comprising an active agent and a stabilizer is coated onto a core comprising pharmaceutically acceptable excipients, to form an active agent-coated core; a sub-coating layer is applied to the active agent-coated core, which is then coated with an enteric coating layer. The core generally includes pharmaceutically inactive components such as lactose, a starch, mannitol, sodium carboxymethyl cellulose, sodium starch glycolate, sodium chloride, potassium chloride, pigments, salts of alginic acid, talc, titanium dioxide, stearic acid, stearate, micro-crystalline cellulose, glycerin, polyethylene glycol, triethyl citrate, tributyl citrate, propanyl triacetate, dibasic calcium phosphate, tribasic sodium phosphate, calcium sulfate, cyclodextrin, and castor oil. Suitable solvents for an active agent include aqueous solvents. Suitable stabilizers include alkali-metals and alkaline earth metals, bases of phosphates and organic acid salts and organic amines. The sub-coating layer comprises one or more of an adhesive, a plasticizer, and an anti-tackiness agent. Suitable anti-tackiness agents include talc, stearic acid, stearate, sodium stearyl fumarate, glyceryl behenate, kaolin and aerosil. Suitable adhesives include polyvinyl pyrrolidone (PVP), gelatin, hydroxyethyl cellulose (HEC), hydroxypropyl cellulose (HPC), hydroxypropyl methyl cellulose (HPMC), vinyl acetate (VA), polyvinyl alcohol (PVA), methyl cellulose (MC), ethyl cellulose (EC), hydroxypropyl methyl cellulose phthalate (HPMCP), cellulose acetate phthalates (CAP), xanthan gum, alginic acid, salts of alginic acid, Eudragit™, copolymer of methyl acrylic acid/methyl methacrylate with polyvinyl acetate phthalate (PVAP). Suitable plasticizers include glycerin, polyethylene glycol, triethyl citrate, tributyl citrate, propanyl triacetate and castor oil. Suitable enteric-soluble coating material include hydroxypropyl methylcellulose acetate succinate (HPMCAS), hydroxypropyl methyl cellulose phthalate(HPMCP), cellulose acetate phthalate (CAP), polyvinyl phthalic acetate (PVPA), Eudragit™ and shellac.

Suitable oral formulations also include an active agent, formulated with any of the following: microgranules (see, e.g., U.S. Pat. No. 6,458,398); biodegradable macromers (see, e.g., U.S. Pat. No. 6,703,037); biodegradable hydrogels (see, e.g., Graham and McNeill (1989) *Biomaterials* 5:27-36); biodegradable particulate vectors (see, e.g., U.S. Pat. No. 5,736,371); bioabsorbable lactone polymers (see, e.g., U.S. Pat. No. 5,631,015); slow release protein polymers (see, e.g., U.S. Pat. No. 6,699,504; Pelias Technologies, Inc.); a poly (lactide-co-glycolide/polyethylene glycol block copolymer (see, e.g., U.S. Pat. No. 6,630,155; Atrix Laboratories, Inc.); a composition comprising a biocompatible polymer and particles of metal cation-stabilized agent dispersed within the polymer (see, e.g., U.S. Pat. No. 6,379,701; Alkermes Controlled Therapeutics, Inc.); and microspheres (see, e.g., U.S. Pat. No. 6,303,148; Octoplus, B.V.).

Suitable oral formulations also include an active agent formulated with any of the following: a carrier such as Emisphere® (Emisphere Technologies, Inc.); TIMERx, a hydrophilic matrix combining xanthan and locust bean gums which, in the presence of dextrose, form a strong binder gel in water (Penwest); Geminex™ (Penwest); Procise™ (GlaxoSmithKline); SAVIT™ (Mistral Pharma Inc.); RingCap™ (Alza Corp.); Smartrix® (Smartrix Technologies, Inc.); SQZgel™ (MacroMed, Inc.); Geomatrix™ (Skye Pharma, Inc.); Oros® Tri-layer (Alza Corporation); and the like.

Also suitable for use are formulations such as those described in U.S. Pat. No. 6,296,842 (Alkermes Controlled Therapeutics, Inc.); U.S. Pat. No. 6,187,330 (Scios, Inc.); and the like.

Also suitable for use herein are formulations comprising an intestinal absorption enhancing agent. Suitable intestinal absorption enhancers include, but are not limited to, calcium chelators (e.g., citrate, ethylenediamine tetracetic acid); surfactants (e.g., sodium dodecyl sulfate, bile salts, palmitoylcarnitine, and sodium salts of fatty acids); toxins (e.g., zonula occludens toxin); and the like.

Controlled Release Formulations

In some embodiments, an active agent is formulated in a controlled release formulation.

Controlled release formulations suitable for use can be taken to mean any one of a number of extended release dosage forms. The following terms may be considered to be substantially equivalent to controlled release, for the purposes of the present disclosure: continuous release, controlled release, delayed release, depot, gradual release, long-term release, programmed release, prolonged release, proportionate release, protracted release, repository, retard, slow release, spaced release, sustained release, time coat, timed release, delayed action, extended action, layered-time action, long acting, prolonged action, repeated action, slowing acting, sustained action, sustained-action medications, and extended release. Further discussions of these terms may be found in Lesczek Krowczynski, *Extended-Release Dosage Forms*, 1987 (CRC Press, Inc.).

The various controlled release technologies cover a very broad spectrum of drug dosage forms. Controlled release technologies include, but are not limited to physical systems and chemical systems.

Physical systems include, but are not limited to, reservoir systems with rate-controlling membranes, such as microencapsulation, macroencapsulation, and membrane systems; reservoir systems without rate-controlling membranes, such as hollow fibers, ultra microporous cellulose triacetate, and porous polymeric substrates and foams; monolithic systems, including those systems physically dissolved in non-porous, polymeric, or elastomeric matrices (e.g., nonerodible, erodible, environmental agent ingression, and degradable), and materials physically dispersed in non-porous, polymeric, or elastomeric matrices (e.g., nonerodible, erodible, environmental agent ingression, and degradable); laminated structures, including reservoir layers chemically similar or dissimilar to outer control layers; and other physical methods, such as osmotic pumps, or adsorption onto ion-exchange resins.

Chemical systems include, but are not limited to, chemical erosion of polymer matrices (e.g., heterogeneous, or homogeneous erosion), or biological erosion of a polymer matrix (e.g., heterogeneous, or homogeneous). Additional discussion of categories of systems for controlled release may be found in Agis F. Kydonieus, *Controlled Release Technologies: Methods, Theory and Applications*, 1980 (CRC Press, Inc.).

There are a number of controlled release drug formulations that are developed for oral administration. These include, but are not limited to, osmotic pressure-controlled gastrointestinal delivery systems; hydrodynamic pressure-controlled gastrointestinal delivery systems; membrane permeation-controlled gastrointestinal delivery systems, which include microporous membrane permeation-controlled gastrointestinal delivery devices; gastric fluid-resistant intestine targeted controlled-release gastrointestinal delivery devices; gel diffusion-controlled gastrointestinal delivery systems; and ion-exchange-controlled gastrointestinal delivery systems, which include cationic and anionic drugs. Additional information regarding controlled release drug delivery systems may be found in Yie W. Chien, *Novel Drug Delivery Systems*, 1992 (Marcel Dekker, Inc.). Some of these formulations will now be discussed in more detail.

Enteric coatings are applied to tablets to prevent the release of drugs in the stomach either to reduce the risk of unpleasant side effects or to maintain the stability of the drug which might otherwise be subject to degradation of expose to the gastric environment. Most polymers that are used for this purpose are polyacids that function by virtue or the fact that their solubility in aqueous medium is pH-dependent, and they require conditions with a pH higher than normally encountered in the stomach.

One exemplary type of oral controlled release structure is enteric coating of a solid or liquid dosage form. The enteric coatings are designed to disintegrate in intestinal fluid for ready absorption. Delay of absorption of the active agent that is incorporated into a formulation with an enteric coating is dependent on the rate of transfer through the gastrointestinal tract, and so the rate of gastric emptying is an important factor. Some investigators have reported that a multiple-unit type dosage form, such as granules, may be superior to a single-unit type. Therefore, in one exemplary embodiment, an active agent may be contained in an enterically coated multiple-unit dosage form. In an exemplary embodiment, an active agent dosage form is prepared by spray-coating granules of an active agent-enteric coating agent solid dispersion on an inert core material. These granules can result in prolonged absorption of the drug with good bioavailability.

Typical enteric coating agents include, but are not limited to, hydroxypropylmethylcellulose phthalate, methacrylic acid-methacrylic acid ester copolymer, polyvinyl acetate-phthalate and cellulose acetate phthalate. Akihiko Hasegawa, *Application of solid dispersions of Nifedipine with enteric coating agent to prepare a sustained-release dosage form*, Chem. Pharm. Bull. 33: 1615-1619 (1985). Various enteric coating materials may be selected on the basis of testing to achieve an enteric coated dosage form designed ab initio to have an optimal combination of dissolution time, coating thicknesses and diametral crushing strength. S. C. Porter et al., *The Properties of Enteric Tablet Coatings Made From Polyvinyl Acetate-phthalate and Cellulose acetate Phthalate*, J. Pharm. Pharmacol. 22:42p (1970).

Another type of useful oral controlled release structure is a solid dispersion. A solid dispersion may be defined as a dispersion of one or more active ingredients in an inert carrier or matrix in the solid state prepared by the melting (fusion), solvent, or melting-solvent method. Akihiko Hasegawa, *Super Saturation Mechanism of Drugs from Solid Dispersions with Enteric Coating Agents*, Chem. Pharm. Bull. 36: 4941-4950 (1998). The solid dispersions may be also called solid-state dispersions. The term "coprecipitates" may also be used to refer to those preparations obtained by the solvent methods.

The selection of the carrier may have an influence on the dissolution characteristics of the dispersed active agent because the dissolution rate of a component from a surface may be affected by other components in a multiple component mixture. For example, a water-soluble carrier may result in a fast release of the active agent from the matrix, or a poorly soluble or insoluble carrier may lead to a slower release of the active agent from the matrix. The solubility of the active agent may also be increased owing to some interaction with the carriers.

Examples of carriers useful in solid dispersions include, but are not limited to, water-soluble polymers such as polyethylene glycol, polyvinylpyrrolidone, and hydroxypropylmethyl-cellulose. Alternative carriers include phosphatidylcholine. Phosphatidylcholine is an amphoteric but water-insoluble lipid, which may improve the solubility of otherwise insoluble active agents in an amorphous state in phosphatidylcholine solid dispersions.

Other carriers include polyoxyethylene hydrogenated castor oil. Poorly water-soluble active agents may be included in a solid dispersion system with an enteric polymer such as hydroxypropylmethylcellulose phthalate and carboxymethylethylcellulose, and a non-enteric polymer, hydroxypropylmethylcellulose. Another solid dispersion dosage form includes incorporation of the active agent with ethyl cellulose and stearic acid in different ratios.

There are various methods commonly known for preparing solid dispersions. These include, but are not limited to, the melting method, the solvent method and the melting-solvent method.

Another controlled release dosage form is a complex between an ion exchange resin and an active agent. Ion exchange resin-drug complexes have been used to formulate sustained-release products of acidic and basic drugs. In one exemplary embodiment, a polymeric film coating is provided to the ion exchange resin-drug complex particles, making drug release from these particles diffusion controlled. See Y. Raghunathan et al., *Sustained-released drug delivery system I: Coded ion-exchange resin systems for phenylpropanolamine and other drugs*, J. Pharm. Sciences 70: 379-384 (1981).

Injectable microspheres are another controlled release dosage form. Injectable micro spheres may be prepared by non-aqueous phase separation techniques, and spray-drying techniques. Microspheres may be prepared using polylactic acid or copoly(lactic/glycolic acid). Shigeyuki Takada, *Utilization of an Amorphous Form of a Water-Soluble GPIIb/IIIa Antagonist for Controlled Release From Biodegradable Micro spheres*, Pharm. Res. 14:1146-1150 (1997), and ethyl cellulose, Yoshiyuki Koida, *Studies on Dissolution Mechanism of Drugs from Ethyl Cellulose Microcapsules*, Chem. Pharm. Bull. 35:1538-1545 (1987).

Other controlled release technologies that may be used include, but are not limited to, SODAS (Spheroidal Oral Drug Absorption System), INDAS (Insoluble Drug Absorption System), IPDAS (Intestinal Protective Drug Absorption System), MODAS (Multiporous Oral Drug Absorption System), EFVAS (Effervescent Drug Absorption System), PRODAS (Programmable Oral Drug Absorption System), and DUREDAS (Dual Release Drug Absorption System) available from Elan Pharmaceutical Technologies. SODAS are multi particulate dosage forms utilizing controlled release beads. INDAS are a family of drug delivery technologies designed to increase the solubility of poorly soluble drugs. IPDAS are multi particulate tablet formation utilizing a combination of high density controlled release beads and an immediate release granulate. MODAS are controlled release single unit dosage forms. Each tablet consists of an inner core surrounded by a semipermeable multiparous membrane that controls the rate of drug release. EFVAS is an effervescent drug absorption system. PRODAS is a family of multi particulate formulations utilizing combinations of immediate release and controlled release mini-tablets. DUREDAS is a bilayer tablet formulation providing dual release rates within the one dosage form. Although these dosage forms are known to one of skill, certain of these dosage forms will now be discussed in more detail.

INDAS was developed specifically to improve the solubility and absorption characteristics of poorly water soluble drugs. Solubility and, in particular, dissolution within the fluids of the gastrointestinal tract is a key factor in determining the overall oral bioavailability of poorly water soluble drug. By enhancing solubility, one can increase the overall bioavailability of a drug with resulting reductions in dosage.

IPDAS is a multi-particulate tablet technology that may enhance the gastrointestinal tolerability of potential irritant and ulcerogenic drugs. Intestinal protection is facilitated by the multi-particulate nature of the IPDAS formulation which promotes dispersion of an irritant lipoate throughout the gastrointestinal tract. Controlled release characteristics of the individual beads may avoid high concentration of active agent being both released locally and absorbed systemically. The combination of both approaches serves to minimize the potential harm of the active agent with resultant benefits to patients.

IPDAS is composed of numerous high density controlled release beads. Each bead may be manufactured by a two step process that involves the initial production of a micromatrix with embedded active agent and the subsequent coating of this micromatrix with polymer solutions that form a rate-limiting semipermeable membrane in vivo. Once an IPDAS tablet is ingested, it may disintegrate and liberate the beads in the stomach. These beads may subsequently pass into the duodenum and along the gastrointestinal tract, e.g., in a controlled and gradual manner, independent of the feeding state. Release of the active agent occurs by diffusion process through the micromatrix and subsequently through the pores in the rate controlling semipermeable membrane. The release rate from the IPDAS tablet may be customized to deliver a drug-specific absorption profile associated with optimized clinical benefit. Should a fast onset of activity be necessary, an immediate release granulate may be included in the tablet. The tablet may be broken prior to administration, without substantially compromising drug release, if a reduced dose is required for individual titration.

MODAS is a drug delivery system that may be used to control the absorption of water soluble agents. Physically MODAS is a non-disintegrating table formulation that manipulates drug release by a process of rate limiting diffusion by a semipermeable membrane formed in vivo. The diffusion process essentially dictates the rate of presentation of drug to the gastrointestinal fluids, such that the uptake into the body is controlled. Because of the minimal use of excipients, MODAS can readily accommodate small dosage size forms. Each MODAS tablet begins as a core containing active drug plus excipients. This core is coated with a solution of insoluble polymers and soluble excipients. Once the tablet is ingested, the fluid of the gastrointestinal tract may dissolve the soluble excipients in the outer coating leaving substantially the insoluble polymer. What results is a network of tiny, narrow channels connecting fluid from the gastrointestinal tract to the inner drug core of water soluble drug. This fluid passes through these channels, into the core, dissolving the drug, and the resultant solution of drug may diffuse out in a controlled manner. This may permit both controlled dissolution and absorption. An advantage of this system is that the drug releasing pores of the tablet are distributed over substantially the entire surface of the tablet. This facilitates uniform drug absorption reduces aggressive unidirectional drug delivery. MODAS represents a very flexible dosage form in that both the inner core and the outer semipermeable membrane may be altered to suit the individual delivery requirements of a drug. In particular, the addition of excipients to the inner core may help to produce a microenvironment within the tablet that facilitates more predictable release and absorption rates. The addition of an immediate release outer coating may allow for development of combination products.

Additionally, PRODAS may be used to deliver an active agent. PRODAS is a multi particulate drug delivery technology based on the production of controlled release mini tablets in the size range of 1.5 to 4 mm in diameter. The PRODAS technology is a hybrid of multi particulate and hydrophilic matrix tablet approaches, and may incorporate, in one dosage form, the benefits of both these drug delivery systems.

In its most basic form, PRODAS involves the direct compression of an immediate release granulate to produce individual mini tablets that contain an active agent. These mini tablets are subsequently incorporated into hard gels and capsules that represent the final dosage form. A more beneficial use of this technology is in the production of controlled release formulations. In this case, the incorporation of various polymer combinations within the granulate may delay the release rate of drugs from each of the individual mini tablets. These mini tablets may subsequently be coated with controlled release polymer solutions to provide additional delayed release properties. The additional coating may be necessary in the case of highly water soluble drugs or drugs that are perhaps gastroirritants where release can be delayed until the formulation reaches more distal regions of the gastrointestinal tract. One value of PRODAS technology lies in the inherent flexibility to formulation whereby combinations of mini tablets, each with different release rates, are incorporated into one dosage form. As well as potentially permitting controlled absorption over a specific period, this also may permit targeted delivery of drug to specific sites of absorption throughout the gastrointestinal tract. Combination products also may be possible using mini tablets formulated with different active ingredients.

DUREDAS is a bilayer tableting technology that may be used to formulate an active agent. DUREDAS was developed to provide for two different release rates, or dual release of a drug from one dosage form. The term bilayer refers to two separate direct compression events that take place during the tableting process. In an exemplary embodiment, an immediate release granulate is first compressed, being followed by the addition of a controlled release element which is then compressed onto this initial tablet. This may give rise to the characteristic bilayer seen in the final dosage form.

The controlled release properties may be provided by a combination of hydrophilic polymers. In certain cases, a rapid release of an active agent may be desirable in order to facilitate a fast onset of therapeutic affect. Hence one layer of the tablet may be formulated as an immediate release granulate. By contrast, the second layer of the tablet may release the drug in a controlled manner, e.g., through the use of hydrophilic polymers. This controlled release may result from a combination of diffusion and erosion through the hydrophilic polymer matrix.

A further extension of DUREDAS technology is the production of controlled release combination dosage forms. In this instance, two different active agents may be incorporated into the bilayer tablet and the release of drug from each layer controlled to maximize therapeutic affect of the combination.

An active agent can be incorporated into any one of the aforementioned controlled released dosage forms, or other conventional dosage forms. The amount of active agent contained in each dose can be adjusted, to meet the needs of the individual patient, and the indication. One of skill in the art and reading this disclosure will readily recognize how to adjust the level of active agent and the release rates in a controlled release formulation, in order to optimize delivery of an active agent and its bioavailability.

Inhalational Formulations

An active agent will in some embodiments be administered to a patient by means of a pharmaceutical delivery system for the inhalation route. An active agent may be formulated in a form suitable for administration by inhalation. The inhalational route of administration provides the advantage that the inhaled drug can bypass the blood-brain barrier. The pharmaceutical delivery system is one that is suitable for respiratory therapy by delivery of an active agent to mucosal linings of the bronchi. An active agent can be delivered by a system that depends on the power of a compressed gas to expel the active agent from a container. An aerosol or pressurized package can be employed for this purpose.

As used herein, the term "aerosol" is used in its conventional sense as referring to very fine liquid or solid particles carries by a propellant gas under pressure to a site of therapeutic application. When a pharmaceutical aerosol is employed in this invention, the aerosol contains an active agent, which can be dissolved, suspended, or emulsified in a mixture of a fluid carrier and a propellant. The aerosol can be in the form of a solution, suspension, emulsion, powder, or semi-solid preparation. Aerosols employed in the present invention are intended for administration as fine, solid particles or as liquid mists via the respiratory tract of a patient. Various types of propellants known to one of skill in the art can be utilized. Suitable propellants include, but are not limited to, hydrocarbons or other suitable gas. In the case of the pressurized aerosol, the dosage unit may be determined by providing a value to deliver a metered amount.

An active agent can also be formulated for delivery with a nebulizer, which is an instrument that generates very fine liquid particles of substantially uniform size in a gas. For example, a liquid containing an active agent is dispersed as droplets. The small droplets can be carried by a current of air through an outlet tube of the nebulizer. The resulting mist penetrates into the respiratory tract of the patient.

A powder composition containing an active agent, with or without a lubricant, carrier, or propellant, can be administered to a mammal in need of therapy. This embodiment can be carried out with a conventional device for administering a powder pharmaceutical composition by inhalation. For example, a powder mixture of the active agent and a suitable powder base such as lactose or starch may be presented in unit dosage form in for example capsular or cartridges, e.g. gelatin, or blister packs, from which the powder may be administered with the aid of an inhaler.

There are several different types of inhalation methodologies which can be employed in connection with the present disclosure. An active agent can be formulated in basically three different types of formulations for inhalation. First, an active agent can be formulated with low boiling point propellants. Such formulations are generally administered by conventional meter dose inhalers (MDI's). However, conventional MDI's can be modified so as to increase the ability to obtain repeatable dosing by utilizing technology which measures the inspiratory volume and flow rate of the patient as discussed within U.S. Pat. Nos. 5,404,871 and 5,542,410.

Alternatively, an active agent can be formulated in aqueous or ethanolic solutions and delivered by conventional nebulizers. In some embodiments, such solution formulations are aerosolized using devices and systems such as disclosed within U.S. Pat. Nos. 5,497,763; 5,544,646; 5,718,222; and 5,660,166.

An active agent can be formulated into dry powder formulations. Such formulations can be administered by simply inhaling the dry powder formulation after creating an aerosol mist of the powder. Technology for carrying such out is described within U.S. Pat. No. 5,775,320 issued Jul. 7, 1998 and U.S. Pat. No. 5,740,794 issued Apr. 21, 1998.

Dosages

Although the dosage used will vary depending on the clinical goals to be achieved, a suitable dosage range is one which provides up to about 1 μg to about 1,000 μg or about 10,000 μg of an active agent and can be administered in a single dose. Alternatively, a target dosage of an active agent can be considered to be about in the range of about 0.1-1000 μM, about 0.5-500 μM, about 1-100 μM, or about 5-50 μM in a sample of host blood drawn within the first 24-48 hours after administration of the agent.

Those of skill will readily appreciate that dose levels can vary as a function of the specific compound, the severity of the symptoms and the susceptibility of the subject to side effects. Preferred dosages for a given compound are readily determinable by those of skill in the art by a variety of means.

Routes of Administration

An active agent is administered to an individual using any available method and route suitable for drug delivery, including in vivo and ex vivo methods, as well as systemic and localized routes of administration.

Conventional and pharmaceutically acceptable routes of administration include intranasal, intramuscular, intratracheal, subcutaneous, intradermal, topical application, intravenous, rectal, nasal, oral and other enteral and parenteral routes of administration. Routes of administration may be combined, if desired, or adjusted depending upon the agent and/or the desired effect. The active agent can be administered in a single dose or in multiple doses. In some embodiments, the active agent is administered orally. In other specific embodiments, the active agent is administered via an inhalational route. In some embodiments, the active agent is administered intranasally.

The active agent can be administered to a host using any available conventional methods and routes suitable for delivery of conventional drugs, including systemic or localized routes. In general, routes of administration contemplated by the present disclosure include, but are not necessarily limited to, enteral, parenteral, and inhalational routes.

Parenteral routes of administration other than inhalation administration include, but are not necessarily limited to, topical, transdermal, subcutaneous, intramuscular, intraorbital, intracapsular, intraspinal, intrasternal, and intravenous routes, i.e., any route of administration other than through the alimentary canal. Parenteral administration can be carried to effect systemic or local delivery of the agent. Where systemic delivery is desired, administration typically involves invasive or systemically absorbed topical or mucosal administration of pharmaceutical preparations.

The active agent can also be delivered to the subject by enteral administration. Enteral routes of administration include, but are not necessarily limited to, oral and rectal (e.g., using a suppository) delivery.

Methods of administration of the active agent through the skin or mucosa include, but are not necessarily limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" which deliver their product continuously via electric pulses through unbroken skin for periods of several days or more.

By treatment is meant at least an amelioration of the symptoms associated with the pathological condition afflicting the host, where amelioration is used in a broad sense to refer to at least a reduction in the magnitude of a parameter, e.g. symptom, associated with the pathological condition being treated, such as a tauopathy. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

A variety of subjects (wherein the term "subject" is used interchangeably herein with the terms "individual," "host," and "patient") are treatable according to the subject methods. Generally such subjects are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the subject will be a human.

Subjects Suitable for Treatment

Individuals suitable for treatment with a subject treatment method include individuals who have been diagnosed with a tauopathy; individuals who have a tauopathy and who have been treated with an agent other than an agent discussed herein and who have either failed to respond to such treatment or who initially responded and subsequently relapsed.

Diagnostic Methods

The present disclosure provides a method of diagnosing a cognitive impairment disorder in an individual. The method generally involves detecting a level of acetylated Tau polypeptide in a biological sample obtained from an individual. A level of acetylated Tau polypeptide that is higher than a normal control level indicates that the individual has a cognitive impairment disorder. The present disclosure also provides a method of determining the risk that an individual will develop a cognitive impairment disorder. The method generally involves detecting a level of acetylated Tau polypeptide in a biological sample obtained from an individual. A level of acetylated Tau polypeptide that is higher than a normal control level indicates that the individual is at greater risk than the general population of developing a cognitive impairment disorder.

A level of acetylated Tau polypeptide in a biological sample (e.g., a biological sample that comprises a neuronal cell and/or a glial cell; a biological sample derived from a neuronal cell and/or a glial cell (e.g., a neuronal cell lysate; a glial cell lysate); etc.) that is at least about 10% higher, at least about 15% higher at least about 20% higher, at least about 25% higher, at least about 50% higher, at least about 2-fold higher, at least about 5-fold higher, at least about 10-fold higher, or more than 10-fold higher, than a normal control level, indicates that the individual from whom the biological sample was obtained has or is at greater risk than the general population of having, a cognitive impairment disorder.

Mild cognitive impairment (MCI, also known as incipient dementia, or isolated memory impairment) is a diagnosis given to individuals who have cognitive impairments beyond that expected for their age and education, but that do not interfere significantly with their daily activities. MCI is considered to be the boundary or transitional stage between normal aging and dementia. Although MCI can present with a variety of symptoms, when memory loss is the predominant symptom it is termed "amnestic MCI" and is frequently seen as a risk factor for Alzheimer's disease. Studies suggest that individuals with amnestic MCI tend to progress to probable Alzheimer's disease at a rate of approximately 10% to 15% per year. Additionally, when individuals have impairments in domains other than memory it is classified as non-amnestic single- or multiple-domain MCI and these individuals are believed to be more likely to convert to other dementias (e.g., dementia with Lewy bodies).

Since MCI is a risk factor for Alzheimer's disease, diagnosis of MCI leads to diagnosis of early-stage Alzheimer's disease. The diagnosis of MCI requires considerable clinical judgment, and a comprehensive clinical assessment including clinical observation, neuroimaging, blood tests and neuropsychological. A level of Ac-Tau polypeptide that is higher than a normal control level indicates that the individual has a cognitive impairment disorder. Thus, measurement of Ac-Tau polypeptide may be used to detect and diagnose MCI and tauopathies, such as, Alzheimer's disease.

The level of Ac-Tau polypeptide may be determined by using a reagent specific for Ac-Tau, such as, an antibody that recognizes the acetylated form of Tau but not the non acetylated-Tau polypeptide (e.g., Anti-Ac-Tau: Ab708 described below). Ac-Tau specific antibodies may be generated using a standard immunization protocol. For example, a Tau peptide acetylated at one or more lysine residues (e.g., Lys-163, and/or, Lys-174, and/or Lys-190 of Tau isoform 2) may be used to immunize an appropriate host animal (e.g., rabbit, goat, sheep, etc.). At about 10 days after the second booster immunization, antibody titers may be determined using ELISA. Usually two booster immunizations are sufficient for obtaining high antibody titers.

A number of biological samples may be used to detect Ac-Tau levels. For example, cerebrospinal fluid, plasma, serum, blood, urine, brain biopsy sample, may be used to determine the Ac-Tau levels of an individual. The obtained sample may be supplemented with an enzyme inhibitor at the time of or after the collection of the sample in order to prevent the change of a Tau protein (fragmentation, dephosphorylation, deacetylation, etc.) or the coagulation of the blood in the sample. Enzyme inhibitors that can be utilized include: phosphatase inhibitors, such as, EDTA, EGTA, okadaic acid, pyrophosphoric acid, phosphate, sodium fluoride, β-glycerophosphoric acid, and cyclosporine A; and protease inhibitors such as aprotinin, antipain, pepstatin, leupeptin, EDTA, EGTA, PMSF (phenylmethanesulfonyl fluoride), and TLCK (tosyl lysine chloromethyl ketone). The samples may be obtained and tested fresh or the samples may be stored before determining Ac-Tau levels. The samples may be stored at, for example, at 4° C. or lower, for example, at −20° C. or lower.

A corresponding biological sample from an age matched non-demented individual, e.g., an individual with normal cognitive abilities, is used as a control. In addition, Ac-Tau levels may be normalized with reference to a normalization control, for example, a protein that is known to be present at comparable levels between patients with MCI and normal individuals, such as, GAPDH (glyceraldehyde-3-phosphate dehydrogenase), HPRT1 (hypoxanthine phosphoribosyltransferase-1).

Ac-Tau levels may be measured using anti-Ac-Tau antibody, for example, in an immunoassay, such as, enzyme linked immunosorbent assay (ELISA), radioimmunoassay (RIA), protein blot (Western blot) assay, and the like. In exemplary embodiments, sandwich ELISA may be used. If Ac-Tau protein is measured by the sandwich ELISA method or the like, an antibody used in combination with the antibody specific to a Ac-Tau protein is an antibody that recognizes a tau protein regardless of kind of isoforms and acetylation status (hereinafter, which is also referred to as a "nonspecific anti-tau protein antibody") is used. Specific examples of the non-specific anti-tau protein antibody include anti-tau protein monoclonal antibodies HT7 (that binds to amino acid numbers 159-163 of a Tau protein) and BT2 (that binds to amino acid numbers 193-198 of a Tau protein) commercially available from Innogenetics.

Screening Methods

The present disclosure provides a method of identifying a candidate agent suitable for use in treating a tauopathy. A subject screening method is generally an in vitro method, and can be carried out in a cell in vitro, or in an in vitro cell-free assay system.

In some cases, the method involves: a) contacting a sample with a test agent, where the sample comprises: i) an enzyme that deacetylates acetylated Tau; and ii) an acetylated Tau polypeptide; and b) determining the effect of the test agent on the degree of acetylation of the Tau polypeptide. A test agent that increases deacetylation of the Tau polypeptide is a candidate agent for treating a tauopathy. The method can be carried out in vitro in a cell-based assay, e.g., using a cell that produces an enzyme that deacetylates acetylated Tau and an acetylated Tau polypeptide, where the method involves contacting the cell with a test agent. The method can be carried out in vitro in a cell-free assay system, e.g., where the enzyme that deacetylates acetylated Tau and the acetylated Tau polypeptide are contacted with a test agent in a cell-free system.

In other cases, the method involves: a) contacting a sample with a test agent, where the sample comprises: i) an enzyme that acetylates a Tau polypeptide; and ii) a non-acetylated Tau polypeptide; and b) determining the effect of the agent on the degree of acetylation of the Tau polypeptide. A test agent that inhibits acetylation of the Tau polypeptide is a candidate agent for treating a tauopathy. The method can be carried out in vitro in a cell-based assay, e.g., using a cell that produces an enzyme that acetylates a Tau polypeptide and a non-acetylated Tau polypeptide, where the method involves contacting the cell with a test agent. The method can be carried out in vitro in a cell-free assay system, e.g., where the enzyme that acetylates Tau and the non-acetylated Tau polypeptide are contacted with a test agent in a cell-free system.

A subject screening method generally includes appropriate controls, e.g., a control sample that lacks the test agent. Generally a plurality of assay mixtures is run in parallel with different agent concentrations to obtain a differential response to the various concentrations. Typically, one of these concentrations serves as a negative control, i.e. at zero concentration or below the level of detection.

A variety of other reagents may be included in the screening assay. These include reagents such as salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The components of the assay mixture are added in any order that provides for the requisite binding or other activity. Incubations are performed at any suitable temperature, typically between 4° C. and 40° C. Incubation periods are selected for optimum activity, but may also be optimized to facilitate rapid high-throughput screening. Typically between 0.1 and 1 hour will be sufficient.

As used herein, the term "determining" refers to both quantitative and qualitative determinations and as such, the term "determining" is used interchangeably herein with "assaying," "measuring," and the like.

The terms "candidate agent," "test agent," "agent", "substance" and "compound" are used interchangeably herein. Candidate agents encompass numerous chemical classes, including synthetic, semi-synthetic, and naturally occurring inorganic or organic molecules. Candidate agents include those found in large libraries of synthetic or natural compounds. For example, synthetic compound libraries are commercially available from Maybridge Chemical Co. (Trevillet, Cornwall, UK), ComGenex (South San Francisco, Calif.), and MicroSource (New Milford, Conn.). A rare chemical library is available from Aldrich (Milwaukee, Wis.) and can also be used. Alternatively, libraries of natural compounds in the form of bacterial, fungal, plant and animal extracts are available from Pan Labs (Bothell, Wash.) or are readily producible.

Candidate agents may be small organic or inorganic compounds having a molecular weight of more than 50 daltons and less than about 2,500 daltons. Candidate agents may comprise functional groups necessary for structural interaction with proteins, e.g., hydrogen bonding, and may include at least an amine, carbonyl, hydroxyl or carboxyl group, and may contain at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

A test agent can be a small molecule. The test molecules may be individual small molecules of choice or in some cases, the small molecule test agents to be screened come from a combinatorial library, i.e., a collection of diverse chemical compounds generated by either chemical synthesis or biological synthesis by combining a number of chemical "building blocks." For example, a linear combinatorial chemical library such as a polypeptide library is formed by combining a set of chemical building blocks called amino acids in every possible way for a given compound length (i.e., the number of amino acids in a polypeptide compound). Millions of chemical compounds can be synthesized through such combinatorial mixing of chemical building blocks. Indeed, theoretically, the systematic, combinatorial mixing of 100 interchangeable chemical building blocks results in the synthesis of 100 million tetrameric compounds or 10 billion pentameric compounds. See, e.g., Gallop et al., (1994), J. Med. Chem., 37(9), 1233-1251. Preparation and screening of combinatorial chemical libraries are well known in the art. Combinatorial chemical libraries include, but are not limited to: diversomers such as hydantoins, benzodiazepines, and dipeptides, as described in, e.g., Hobbs et al., (1993), Proc. Natl. Acad. Sci. U.S.A., 90:6909-6913; analogous organic syntheses of small compound libraries, as described in Chen et al., (1994), J. Amer. Chem. Soc., 116:2661-2662; Oligocarbamates, as described in Cho, et al., (1993), Science, 261:1303-1305; peptidyl phosphonates, as described in Campbell et al., (1994), J. Org. Chem., 59: 658-660; and small organic molecule libraries containing, e.g., thiazolidinones and metathiazanones (U.S. Pat. No. 5,549,974), pyrrolidines (U.S. Pat. Nos. 5,525,735 and 5,519,134), benzodiazepines (U.S. Pat. No. 5,288,514).

Numerous combinatorial libraries are commercially available from, e.g., ComGenex (Princeton, N.J.); Asinex (Moscow, Russia); Tripos, Inc. (St. Louis, Mo.); ChemStar, Ltd. (Moscow, Russia); 3D Pharmaceuticals (Exton, Pa.); and Martek Biosciences (Columbia, Md.).

Cell-based In Vitro Assay

As noted above, in some embodiments, a subject screening method is a cell-based in vitro assay. As noted above, in some embodiments, a subject screening method involves contacting a cell that produces a deacetylase, and an acetylated Tau polypeptide, with a test agent; and determining the effect of the test agent on the level of Ac-Tau polypeptide in the cell. As noted above, in some embodiments, a subject screening method involves contacting a cell that produces an enzyme that acetylates a Tau polypeptide, and a non-acetylated Tau polypeptide, with a test agent; and determining the effect of the test agent on the level of Ac-Tau polypeptide in the cell.

A test agent that reduces the level of acetylated Tau in the cell by at least about 10%, at least about 15%, at least about 20%, at least about 25%, at least about 30%, at least about 40%, at least about 50%, at least about 60%, at least about 70%, at least about 80%, or more than 80%, compared to the level of acetylated Tau polypeptide in the cell in the absence of the test agent, is considered a candidate agent for treating a tauopathy.

A number of different types of cells can be used, for example, mouse embryonic fibroblasts (MEFs); primary neuronal cultures, such as cortical neurons; a neuronal cell line (e.g., an immortalized neuronal cell line); and the like. In certain cases, the screening is carried out using a primary neuronal culture, where the neuron is obtained from a human donor, a non-human primate, a rodent, etc. In alternative embodiments, the neuron is obtained by differentiation of an embryonic stem cell, or a neuronal cell line, such as, PC12, or a neuroblastoma cell line, etc.

Suitable cell lines include, but are not limited to, a human glioma cell line, e.g., SVGp12 (ATCC CRL-8621), CCF-STTG1 (ATCC CRL-1718), SW 1088 (ATCC HTB-12), SW 1783 (ATCC HTB-13), LLN-18 (ATCC CRL-2610), LNZTA3WT4 (ATCC CRL-11543), LNZTA3WT11 (ATCC CRL-11544), U-138 MG (ATCC HTB-16), U-87 MG (ATCC HTB-14), H4 (ATCC HTB-148), and LN-229 (ATCC CRL-2611); a human medulloblastoma-derived cell line, e.g., D342 Med (ATCC HTB-187), Daoy (ATCC HTB-186), D283 Med (ATCC HTB-185); a human tumor-derived neuronal-like cell, e.g., PFSK-1 (ATCC CRL-2060), SK-N-DZ (ATCCCRL-2149), SK-N-AS (ATCC CRL-2137), SK-N-FI (ATCC CRL-2142), IMR-32 (ATCC CCL-127), etc.; a mouse neuronal cell line, e.g., BC3H1 (ATCC CRL-1443), EOC1 (ATCC CRL-2467), C8-D30 (ATCC CRL-2534), C8-S (ATCC CRL-2535), Neuro-2a (ATCC CCL-131), NB41A3 (ATCC CCL-147), SW10 (ATCC CRL-2766), NG108-15 (ATCC HB-12317); a rat neuronal cell line, e.g., PC-12 (ATCC CRL-1721), CTX TNA2 (ATCC CRL-2006), C6 (ATCC CCL-107), F98 (ATCC CRL-2397), RG2 (ATCC CRL-2433), B35 (ATCC CRL-2754), R3 (ATCC CRL-2764), SCP (ATCC CRL-1700), OA1 (ATCC CRL-6538).

One or more of the deacetylase, acetyltransferase, and Tau (acetylated or non-acetylated) can be endogenous to the cells utilized in the screen. In some embodiments, one or more of the deacetylase, acetyltransferase, and Tau (acetylated or non-acetylated) is provided exogenously, for example, by genetically modifying a host cell with a nucleic acid (e.g., an expression construct(s)) comprising a nucleotide sequence(s) encoding one or more of the polypeptides; the genetically modified host cell is contacted with a test agent. When provided exogenously, the deacetylase can be a deacetylase known to deacetylate Ac-Tau and the acetyltransferase can be an acetyltransferase known to acetylate non-acetylated Tau to generate Ac-Tau.

In certain embodiments, the acetyltransferase is a p300 polypeptide (mRNA GenBank accession no.:

NM_001429.3. protein GenBank accession no.: NP_001420.2). In certain cases, a nucleic acid (e.g., an expression construct) comprising a nucleotide sequence that encodes a p300 polypeptide is introduced into a host cell, where the nucleotide sequence encodes a p300 polypeptide that acetylates a Tau polypeptide and comprises an amino acid sequence that has at least about 75%, at least about 80%, at least about 85%, at least about 90%, at least about 95%, at least about 98%, at least about 99%, or 100%, amino acid sequence identity to a contiguous stretch of from about 1800 amino acids to about 2000 amino acids, from about 2000 amino acids to about 2200 amino acids, or from about 2200 amino acids to about 2414 amino acids, of the amino acid sequence set forth in SEQ ID NO:12. In these embodiments, the host cell is genetically modified with the p300 polypeptide-encoding expression construct.

In certain cases, a nucleic acid (e.g., an expression construct) comprising a nucleotide sequence that encodes a deacetylase is introduced into a host cell, where the nucleotide sequence encodes a SIRT1 polypeptide that i) deacetylates an acetylated Tau polypeptide and ii) comprises an amino acid sequence having at least about 75%, at least about 80%, at least about 85%, at least about 90%, at least about 95%, at least about 98%, at least about 99%, or 100%, amino acid sequence identity to a contiguous stretch of from about 400 amino acids to about 450 amino acids, or from about 450 amino acids to about 555 amino acids, of the amino acid sequence set forth in SEQ ID NO:9 (GenBank AAH12499; *Homo sapiens* SIRT1); or where the nucleotide sequence encodes a SIRT1 polypeptide that i) deacetylates an acetylated Tau polypeptide and ii) comprises an amino acid sequence having at least about 75%, at least about 80%, at least about 85%, at least about 90%, at least about 95%, at least about 98%, at least about 99%, or 100%, amino acid sequence identity to a contiguous stretch of from about 500 amino acids to about 600 amino acids, from about 600 amino acids to about 700 amino acids, or from about 700 amino acids to about 747 amino acids, of the amino acid sequence set forth in SEQ ID NO:10 (GenBank NP_036370; *Homo sapiens* SIRT1 isoform a); or where the nucleotide sequence encodes a SIRT1 polypeptide that i) deacetylates an acetylated Tau polypeptide and ii) comprises an amino acid sequence having at least about 75%, at least about 80%, at least about 85%, at least about 90%, at least about 95%, at least about 98%, at least about 99%, or 100%, amino acid sequence identity to a contiguous stretch of from about 300 amino acids to about 400 amino acids, or from about 400 amino acids to about 452 amino acids, of the amino acid sequence set forth in SEQ ID NO:11 (GenBank NP_001135970; *Homo sapiens* SIRT1 isoform b). In these embodiments, the host cell is genetically modified with the SIRT1 polypeptide-encoding expression construct.

In certain cases, a nucleic acid (e.g., an expression construct) comprising a nucleotide sequence that encodes a Tau polypeptide is introduced into the cell, where the nucleotide sequence encodes a Tau polypeptide that comprises an amino acid sequence having at least about 75%, at least about 80%, at least about 85%, at least about 90%, at least about 95%, at least about 98%, at least about 99%, or 100%, amino acid sequence identity to a contiguous stretch of about 350 amino acids of any one of the amino acid sequences set forth in SEQ ID NOs:1-6; or where the nucleotide sequence encodes a Tau polypeptide that comprises an amino acid sequence having at least about 75%, at least about 80%, at least about 85%, at least about 90%, at least about 95%, at least about 98%, at least about 99%, or 100%, amino acid sequence identity to a contiguous stretch of from about 350 amino acids to 383 amino acids of the amino acid sequence set forth in SEQ ID NO:2 (*Homo sapiens* Tau isoform 3); or where the nucleotide sequence encodes a Tau polypeptide that comprises an amino acid sequence having at least about 75%, at least about 80%, at least about 85%, at least about 90%, at least about 95%, at least about 98%, at least about 99%, or 100%, amino acid sequence identity to a contiguous stretch of from about 350 amino acids to about 412 amino acids of the amino acid sequence set forth in SEQ ID NO:4 (*Homo sapiens* Tau isoform 5); or where the nucleotide sequence encodes a Tau polypeptide that comprises an amino acid sequence having at least about 75%, at least about 80%, at least about 85%, at least about 90%, at least about 95%, at least about 98%, at least about 99%, or 100%, amino acid sequence identity to a contiguous stretch of from about 350 amino acids to about 400 amino acids, or from about 400 amino acids to about 441 amino acids, of the amino acid sequence set forth in SEQ ID NO:1 (*Homo sapiens* Tau isoform 2); or where the nucleotide sequence encodes a Tau polypeptide that comprises an amino acid sequence having at least about 75%, at least about 80%, at least about 85%, at least about 90%, at least about 95%, at least about 98%, at least about 99%, or 100%, amino acid sequence identity to a contiguous stretch of from about 350 amino acids to about 400 amino acids, from about 400 amino acids to about 500 amino acids, from about 500 amino acids to about 600 amino acids, from about 600 amino acids to about 700 amino acids, or from about 700 amino acids to about 758 amino acids, of the amino acid sequence set forth in SEQ ID NO:5 (*Homo sapiens* Tau isoform 1); or where the nucleotide sequence encodes a Tau polypeptide that comprises an amino acid sequence having at least about 75%, at least about 80%, at least about 85%, at least about 90%, at least about 95%, at least about 98%, at least about 99%, or 100%, amino acid sequence identity to a contiguous stretch of from about 350 amino acids to about 400 amino acids, from about 400 amino acids to about 500 amino acids, from about 500 amino acids to about 600 amino acids, from about 600 amino acids to about 700 amino acids, or from about 700 amino acids to about 776 amino acids, of the amino acid sequence set forth in SEQ ID NO:6 (*Homo sapiens* Tau isoform 6).

A nucleotide sequence encoding, for example, an acetyltransferase (e.g., a p300 polypeptide), and/or a Tau polypeptide, and/or a deacetylase (e.g., a SIRT1 polypeptide) can be introduced into a suitable expression vector. The expression vector is introduced into a suitable host cell. Expression vectors generally have convenient restriction sites located near the promoter sequence to provide for the insertion of polynucleotide sequences. Transcription cassettes may be prepared comprising a transcription initiation region, a nucleotide sequence encoding a polypeptide (e.g., an acetyltransferase (e.g., a p300 polypeptide), a Tau polypeptide, or a deacetylase (e.g., a SIRT1 polypeptide)), and a transcriptional termination region. The transcription cassettes may be introduced into a variety of vectors, e.g. plasmid; retrovirus, e.g. lentivirus; adenovirus; and the like, where the vectors are able to transiently or stably be maintained in the cells, usually for a period of at least about one day, more usually for a period of at least about several days to several weeks.

The Tau polypeptide can be a fusion protein, e.g., a polypeptide comprising Tau and a fusion partner. Suitable fusion partners include peptides and polypeptides that confer enhanced stability in vivo (e.g., enhanced serum half-life); provide ease of purification, e.g., (His)$_n$, e.g., 6His, and the like; provide for secretion of the fusion protein from a cell; provide an epitope tag, e.g., glutathione-S-transferase (GST), hemagglutinin (HA; e.g., CYPYDVPDYA; SEQ ID NO:18), FLAG (e.g., DYKDDDDK; SEQ ID NO:19), c-myc (e.g., CEQKLISEEDL; SEQ ID NO:20), and the like; provide a detectable signal, e.g., an enzyme that generates a detectable product (e.g., β-galactosidase, luciferase), or a protein that is itself detectable, e.g., a green fluorescent protein, etc.; provides for multimerization, e.g., a multimerization domain such as an Fc portion of an immunoglobulin; and the like.

The various manipulations to generate an expression construct may be carried out in vitro or may be performed in an appropriate host cell, e.g. *Escherichia coli*. After each manipulation, the resulting construct may be cloned, the vector isolated, and the DNA screened or sequenced to ensure the correctness of the construct. The sequence may be screened by restriction analysis, sequencing, or the like.

Determining the effect of a test agent is generally carried out by determining the level of acetylated Tau polypeptide in the cell. Ac-Tau levels can be measured using anti-Ac-Tau antibody specific for Ac-Tau ("anti-Ac-Tau antibody"), for example, in an immunoassay, such as, ELISA, RIA, protein blot (Western blot) assay, and the like. The anti-Ac-Tau antibody can comprise a detectable label, and binding of the anti-Ac-Tau to acetylated Tau can be determined by detecting the label. Alternatively, binding of the anti-Ac-Tau antibody to acetylated Tau can be detected using a detectably labeled secondary antibody that binds to the anti-Ac-Tau antibody. The cell can be cultured in a liquid culture medium that includes a radiolabelled acetyl donor compound, such that any acetylated Tau produced by the cell comprises a radiolabelled acetyl group, where the level of acetylated Tau is carried out by detecting radiolabelled acetylated Tau. The level of Ac-Tau can be measured in an intact cell, or in a cell lysate, or using Ac-Tau isolated from the cell.

Cell-free In Vitro Assay

As noted above, in some embodiments, a subject screening method is carried out in an in vitro cell-free assay system. As noted above, in some embodiments, a subject screening method involves contacting i) an enzyme that deacetylates acetylated Tau; and ii) an acetylated Tau polypeptide with a test agent in a cell-free system. As noted above, in some embodiments, a subject screening method involves contacting i) an enzyme that acetylates a Tau polypeptide; and ii) a non-acetylated Tau polypeptide with a test agent in a cell-free system.

The polypeptides used (e.g., an enzyme that deacetylates acetylated Tau and an acetylated Tau polypeptide; or an enzyme that acetylates a Tau polypeptide and a non-acetylated Tau polypeptide) can be purified, e.g., where the polypeptides are at least about 75%, at least about 80%, at least about 85%, at least about 90%, at least about 95%, at least about 98%, or at least about 99% pure, e.g., free of other macromolecules and/or contaminants. The polypeptides can be produced recombinantly, then purified; the polypeptides can be purified from a naturally-occurring source of the polypeptides; or the polypeptides can be synthesized (e.g., using a cell-free chemical synthesis method).

A test agent that reduces the level of acetylated Tau by at least about 10%, at least about 15%, at least about 20%, at least about 25%, at least about 30%, at least about 40%, at least about 50%, at least about 60%, at least about 70%, at least about 80%, or more than 80%, compared to the level of acetylated Tau polypeptide in the absence of the test agent, is considered a candidate agent for treating a tauopathy.

A suitable enzyme that deacetylates acetylated Tau is as described above. For example, a suitable enzyme is a polypeptide that deacetylates an acetylated Tau polypeptide in a neuronal cell, and that comprises an amino acid sequence having at least about 75%, at least about 80%, at least about 85%, at least about 90%, at least about 95%, at least about 98%, at least about 99%, or 100%, amino acid sequence identity to a contiguous stretch of from about 400 amino acids to about 450 amino acids, or from about 450 amino acids to about 555 amino acids, of the amino acid sequence set forth in SEQ ID NO:9 (GenBank AAH12499; *Homo sapiens* SIRT1); or is a polypeptide that deacetylates an acetylated Tau polypeptide in a neuronal cell, and that comprises an amino acid sequence having at least about 75%, at least about 80%, at least about 85%, at least about 90%, at least about 95%, at least about 98%, at least about 99%, or 100%, amino acid sequence identity to a contiguous stretch of from about 500 amino acids to about 600 amino acids, from about 600 amino acids to about 700 amino acids, or from about 700 amino acids to about 747 amino acids, of the amino acid sequence set forth in SEQ ID NO:10 (GenBank NP_036370; *Homo sapiens* SIRT1 isoform a); or is a polypeptide that deacetylates an acetylated Tau polypeptide in a neuronal cell, and that comprises an amino acid sequence having at least about 75%, at least about 80%, at least about 85%, at least about 90%, at least about 95%, at least about 98%, at least about 99%, or 100%, amino acid sequence identity to a contiguous stretch of from about 300 amino acids to about 400 amino acids, or from about 400 amino acids to about 452 amino acids, of the amino acid sequence set forth in SEQ ID NO:11 (GenBank NP_001135970; *Homo sapiens* SIRT1 isoform b).

A suitable enzyme that acetylates a Tau polypeptide includes an acetyltransferase that acetylates Tau and that comprises an amino acid sequence at least about 75%, at least about 80%, at least about 85%, at least about 90%, at least about 95%, at least about 98%, at least about 99%, or 100%, amino acid sequence identity to a contiguous stretch of from about 1800 amino acids to about 2000 amino acids, from about 2000 amino acids to about 2200 amino acids, or from about 2200 amino acids to about 2414 amino acids, of the amino acid sequence set forth in SEQ ID NO:12.

A suitable Tau polypeptide includes a polypeptide that comprises an amino acid sequence having at least about 75%, at least about 80%, at least about 85%, at least about 90%, at least about 95%, at least about 98%, at least about 99%, or 100%, amino acid sequence identity to a contiguous stretch of about 350 amino acids of any one of the amino acid sequences set forth in SEQ ID NOs:1-6; or that comprises an amino acid sequence having at least about 75%, at least about 80%, at least about 85%, at least about 90%, at least about 95%, at least about 98%, at least about 99%, or 100%, amino acid sequence identity to a contiguous stretch of from about 350 amino acids to 383 amino acids of the amino acid sequence set forth in SEQ ID NO:2 (*Homo sapiens* Tau isoform 3); or that comprises an amino acid sequence having at least about 75%, at least about 80%, at least about 85%, at least about 90%, at least about 95%, at least about 98%, at least about 99%, or 100%, amino acid sequence identity to a contiguous stretch of from about 350 amino acids to about 412 amino acids of the amino acid sequence set forth in SEQ ID NO:4 (*Homo sapiens* Tau isoform 5); or that comprises an amino acid sequence having at least about 75%, at least about 80%, at least about 85%, at least about 90%, at least about 95%, at least about 98%, at least about 99%, or 100%, amino acid sequence identity to a contiguous stretch of from about 350 amino acids to about 400 amino acids, or from about 400 amino acids to about 441 amino acids, of the amino acid sequence set forth in SEQ ID NO:1 (*Homo sapiens* Tau isoform 2); or that comprises an amino acid sequence having at least about 75%, at least about 80%, at least about 85%, at least about 90%, at least about 95%, at least about 98%, at least about 99%, or 100%, amino acid sequence identity to a contiguous stretch of from about 350 amino acids to about 400 amino acids, from about 400 amino acids to about 500 amino acids, from about 500 amino acids to about 600 amino acids, from about 600 amino acids to about 700 amino acids, or from about 700 amino acids to about 758 amino acids, of the amino acid sequence set forth in SEQ ID NO:5 (*Homo sapiens* Tau isoform 1); or that comprises an amino acid sequence having at least about 75%, at least about 80%, at least about 85%, at least about 90%, at least about 95%, at least about 98%, at least about 99%, or 100%, amino acid sequence identity to a contiguous stretch of from about 350 amino acids to about 400 amino acids, from about 400 amino acids to about 500 amino acids, from about 500 amino acids to about 600 amino acids, from about 600 amino acids to about 700 amino acids, or from about 700 amino acids to about 776 amino acids, of the amino acid sequence set forth in SEQ ID NO:6 (*Homo sapiens* Tau isoform 6).

Acetylated Tau polypeptide can be produced recombinantly, e.g., in a neuronal cell line that produces a Tau polypeptide and an enzyme that acetylates a Tau polypeptide. Acetylated Tau polypeptide can also be produced by chemically acetylating a non-acetylated Tau polypeptide in vitro.

Determining the effect of a test agent is generally carried out by determining the level of acetylated Tau polypeptide. Ac-Tau levels can be measured using anti-Ac-Tau antibody specific for Ac-Tau ("anti-Ac-Tau antibody"), for example, in an immunoassay, such as, ELISA, RIA, protein blot (Western blot) assay, and the like. The anti-Ac-Tau antibody can comprise a detectable label, and binding of the anti-Ac-Tau to acetylated Tau can be determined by detecting the label. Alternatively, binding of the anti-Ac-Tau antibody to acetylated Tau can be detected using a detectably labeled secondary antibody that binds to the anti-Ac-Tau antibody. In some embodiments, the acetylated Tau polypeptide is produced by a cell that is cultured in a liquid medium comprising a radiolabelled acetyl donor, such that the acetylated Tau produced by the cell comprises one, two, three, or more radiolabelled acetyl groups. The determining step can in these cases be carried out by determining the amount of radioactively labeled Tau polypeptide.

In Vivo Screening

A candidate agent identified by an in vitro screening assay as described above can be tested for its ability to decrease Ac-Tau polypeptide levels in a neuron and/or a glial cell in vivo. Alternatively, one can assess test agents for those that decrease Ac-Tau polypeptide levels in vivo.

A non-human model for cognitive impairment can be used to screen test agents to identify candidate agents that decrease the level of Ac-Tau polypeptides. Exemplary non-human models include transgenic animal models for Alzheimer's disease; transgenic animal models overexpressing human Tau, transgenic animal models showing cognitive impairment and/or tau-positive neurofibrillary tangles. A number of such non-human animal models are known in the art. A transgenic non-human animal model refers to a non-human animal (e.g., a rodent) which contain a transgene which is involved in human neurodegenerative diseases, such as tauopathies, which present with dementia, such as Alzheimer's disease, and includes the following exemplary transgenic non-human animals: LID mice (Yakar S, et al, 1999, Proc Natl Acad Sci USA 96; 7324-7329). transgenic animals carriers of mutations in presenilins and beta amyloid (Hock B J, Jr., Lamb B T, 2001, Trends Genet. 17: S7-12), animals carriers of other mutations and alterations (US20030229907, Transgenic non-human mammals with progressive neurologic disease; US20030145343, Transgenic animals expressing human p25; US20030131364, Method for producing transgenic animal models with modulated phenotype and animals produced therefrom; US20030101467, Transgenic animal model for Alzheimer's disease; US200030093822, Transgenic animal model of neurodegenerative disorders; U.S. Pat. No. 6,717,031, Method for selecting a transgenic mouse model of Alzheimer's disease; U.S. Pat. No. 6,593,512. Transgenic mouse expressing human tau gene; U.S. Pat. No. 6,563,015, Transgenic mice expressing mutant human APP and forming congo red staining plaques; U.S. Pat. No. 6,455,757, Transgenic mice expressing human APP and TGF-beta demonstrate cerebrovascular amyloid deposits; U.S. Pat. No. 6,452,065, Transgenic mouse expressing non-native wild-type and familial Alzheimer's Disease mutant presenilin 1 protein on native presenilin 1 null background; WO03053136, Triple transgenic model of Alzheimer disease: WO03046172. In general, any animal model for tauopathy that has a higher than normal level of Ac-Tau and/or Tau may be used in an in vivo screening assay to identify compounds that lower level of Tau and/or Ac-Tau.

In addition to determining the levels of Ac-Tau present in the non-human animal model, these non-human animal models can also be used to assess the efficacy of a candidate agent identified via a subject in vitro screening method(s). Efficacy of a candidate agent may tested in a animal model for MCI, for example, by assessing improvement in symptoms associated with tauopathy, such as, cognition.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); wt, wild type; and the like.

Example 1

Acetylation of Tau Inhibits its Degradation and Contributes to Tauopathy

Experimental Procedures

Chemicals and Reagents

C646 was from Chembridge (San Diego, Calif.). C37 (inactive analog of C646) was synthesized. EX527 (Tocris Bioscience, Ellisville, Mo.), resveratrol (EMD Chemicals, Gibbstown, N.J.), MG-132 (Sigma, St. Louis, Mo.), cycloheximide (Sigma), Aβ42 peptide (rPeptide, Bogart, Ga.), and recombinant tau (rPeptide) were purchased. Aβ42 oligomers were prepared as described. Chen et al. (2005) *J. Biol. Chem.* 280:40364.

Primary Antibodies

Two rabbit polyclonal anti-ac-tau antisera were generated against two acetylated peptides of tau (Abgent, San Diego, Calif.). PHF1 antibody was a gift. Other antibodies were obtained and used at the indicated concentrations: Tau 5 (1:5000; Abcam, Cambridge, Mass.), anti-p300 (1:500; Santa Cruz Biotechnology, Santa Cruz, Calif.), anti-GAPDH (1:10000; Sigma), anti-tubulin (1:10000; Sigma), anti-FLAG (1:2000; Sigma), AT8 for p-tau (1:500; Thermo Fisher Scientific, Rockford, Ill.), anti-Sir2 (1:2000; Millipore, Billerica, Mass.), anti-hemagglutinin (anti-HA) (1:1000; Cell Signaling Technology, Danvers, Mass.). Secondary antibodies: peroxidase-conjugated goat anti-rabbit and anti-mouse IgGs (1:2000; GE Healthcare, Piscataway, N.J.).

Expression Plasmids

For expression in HEK293T cells, cDNAs encoding hTauwt, hTau2KR (K174R, K180R), hTau3KR (K163R, K174R, K180 R), p300, SIRT1, H363Y (SIRT1), SIRT2, HDAC5, HDAC6, and HA-ubiquitin were cloned into pcDNA3.1 vector (Invitrogen). For protein expression in bacteria, hTauwt cDNA was cloned into pGEX4T-1 vector for GST-fusion protein expression. For expression in primary neurons, cDNAs encoding hTauwt, hTau3KR, hTauP301, and cre recombinase were cloned into lentiviral FUGW vectors.

Mice

All procedures involving animals were in compliance with the policies of the Animal Care and Use Committee at the University of California, San Francisco. PS19 mice were obtained from Jackson Laboratory (Bar Harbor, Me.). The hT-PAC-N line was a gift. SIRT-null and SIRT1$^{F/F}$ mice were provided by Fred Alt (Harvard Medical School).

Cell Cultures and Transient Transfections

HEK293T cells and MEFs were grown at 37° C. in Dulbecco's modified Eagles medium (DMEM) supplemented with 10% fetal bovine serum, 100 U/ml penicillin, and 100 µg/ml streptomycin. For overexpression, transfections were performed with Lipofectamine 2000 (Invitrogen). For siRNA oligonucleotide transfection, HEK 293T cells were seeded at 1×10$^5$ cells/well on 12-well culture plates. After 12 h, cells were transfected with 10 nM ON-TARGETplus SMARTpool siRNA (Thermo Scientific-Dharmacon, Chicago, Ill.) with Lipofectamine RNAiMAX transfection reagent (Invitrogen), according to the manufacturer's protocol. SIRT1 siRNA (L-094699-01), SIRT2 siRNA (L-004826-00), HDAC6 siRNA (L-003499-00), p300 siRNA (L-003486-00), and PCAF siRNA (L-005055-00) were used to target specific cellular genes; siControl Non-Targeting siRNA#1 (Dharmacon) was used as a negative control. About 48 h after siRNA transfection, plasmid pcDNA3.1-hTauwt was transfected into the same culture plates. Cells were harvested 24 h later for real-time RT-PCR or western blot analyses.

Primary Neuronal Cultures and Lentiviral Infections

Primary cultures were established from cortices of Sprague-Dawley rat pups (Charles River Laboratories) or SIRT1$^{F/F}$ mice on postnatal day 0 or 1. Purified cells were plated at 160,000 cells/ml in Neurobasal medium supplemented with B27 (Invitrogen) on poly-ornithine coated plates. All treatments were performed at 7-13 DIV in Neurobasal medium supplemented with N2 (Invitrogen) unless noted otherwise.

Lentivirus was generated, purified, and used for infection as described. Chen et al. (2005) supra. Recombinant lentivirus was produced by co-transfection of the shuttle vector (FUGW), two helper plasmids, delta8.9 packaging vector, and VSV-G envelope vector into 293T cells and purified by ultracentrifugation. Viral titers were measured by p24 enzyme-linked immunosorbent assays at the Gladstone-UCSF Laboratory of Clinical Virology.

Homogenization of Cells and Tissues and Western Blot Analyses

Cells or human or mouse brain tissues were lysed in RIPA buffer containing protease inhibitor cocktail (Sigma), 1 mM phenylmethyl sulfonyl fluoride (PMSF) (Sigma), phosphatase inhibitor cocktail (Roche), and HDAC inhibitors, including 5 mM nicotinamide (Sigma) and 1 µM trichostatin A (Sigma). After sonication, lysates from human or mouse brain tissues were centrifuged at 170,000 g at 4° C. for 15 min and at 18,000 g at 4° C. for 10 min. Supernatants were collected and analyzed by western blot. Bands in immunoblots were visualized by enhanced chemiluminescence (Pierce) and quantified by densitometry and Quantity One 4.0 software (Bio-Rad, Hercules, Calif.).

In Vitro Acetylation Assays

The reactions were performed as described. Pagans et al. (2005) PLoS Biol 3:e41. Briefly, 1 µg of human recombinant tau, 2 nM of acetyl CoA (Sigma), and 1 µl of purified GST-p300 in acetylation buffer (50 mM HEPES, pH 8.0, 10% glycerol, 1 mM dithiothreitol (DTT), and 10 mM Na butyrate) were incubated for 30 min at 30° C. with constant shaking. Reactions were stopped by adding 2×LDS sampling buffer (Invitrogen), followed by sodium dodecyl sulfate-polyacrylamide gel electrophoresis (SDS-PAGE) and western blot analyses.

MALDI-TOF Analyses

Samples from in vitro acetylation reactions were run on SDS-polyacrylamide gels and stained with Coomassie Blue. The band at approximately 65 kDa was cut out and sent to Stanford Mass Spectrometry Laboratory for analyses. In-gel digestion was done with Promega MS grade trypsin overnight. Before digestion, the gel slices were cut into approximately 1 mm×1 mm cubes, reduced with 5 mM dithiothreitol (DTT) and alkylated with acrylamide. Peptides were extracted and dried down using a speed-vac before reconstitution and analysis.

Nano reversed-phase high performance liquid chromatography (HPLC) was done with an Eksigent 2D nanoLC (Eksigent, Dublin, Calif.) with buffer A consisting of 0.1% formic acid in water and buffer B consisting of 0.1% formic acid in acetonitrile. A fused silica column self packed with Duragel C18 (Peeke, Redwood City, Calif.) matrix was used with a linear gradient from 5% B to 40% B over 80 min at a flow rate of 450 nl/min. The nanoHPLC was interfaced with an Advion Nanomate (Ithaca, N.Y.) for nano-electrospray ionization into the mass spectrometer. The mass spectrometer was a LCQ Deca XP Plus (Thermo Scientific), which was set in data dependent acquisition mode to perform MS/MS on the top three most intense ions with a dynamic exclusion setting of two. The DTA files were extracted from the raw data and systematically searched with Mascot. At least two peptides with a probability >95% were needed for the assignment of a protein.

In Vitro Deacetylation Assays

The reactions were modified from established procedures. Pagans et al. (2005) supra. HEK293T cells were transfected with human FLAG-tagged SIRT1 plasmid or mock plasmid with Lipofectamine 2000 (Invitrogen). After 24 h, cells were lysed in lysis buffer (50 mM Tris-HCl, pH 7.5, 0.5 mM EDTA, 0.5% NP-40, 150 mM NaCl, and protease inhibitor cocktails). After centrifugation at 13,000 rpm at 4° C. for 10 min, equal amounts of supernatant proteins were immunoprecipitated with FLAG M2 agarose beads (Sigma) for 3 h at 4° C. Immuoprecipitated beads were washed twice in lysis buffer and once in deacetylation buffer (50 mM Tris-HCl, pH 9.0, 4 mM MgCl$_2$, and 0.2 mM DTT) and incubated with in vitro ac-tau in deacetylation buffer at 30° C. for 3 h with constant shaking. Reactions were stopped by adding 2×LDS sampling buffer (Invitrogen) and analyzed by western blot.

In Vivo Ubiquitination Assays

Procedures were modified from a published study. Oh et al. (2009) Nat Cell Biol 11:295. HEK293T cells were transfected with expression vectors encoding FLAG-tagged human tau and HA-ubiquitin with or without Myc-SIRT1 (wildtype or H363Y mutant). After 2 h of incubation, cells were treated with EX527, resveratrol, or dimethylsulfoxide (DMSO) in Dulbecco's modified Eagle's medium and incubated for 20 h. MG-132 (20 µM) was added and incubated for 4 h. Cells were lysed in ubiquitination buffer (20 mM Tris-HCl, pH 7.5, 0.1 mM EDTA, 0.2% Triton X-100, 150 mM NaCl, and protease inhibitor cocktail). Supernatant proteins were immunoprecipitated with FLAG M2 agarose beads (Sigma) for 3 h at 4° C. Reactions were washed at least three times with ubiquitination buffer and analyzed by SDS-PAGE and western blot with anti-HA antibody (Cell Signaling Technology).

Purification of GST Fusion Proteins and Interaction Assays

Full-length cDNA encoding human tau was subcloned into pGEX-4T-1 bacterial expression vector (Sigma) and transformed in the BL21 (DE3) strain. After induction with 100 µM isopropyl β-D-1-thiogalactopyranoside, bacterial cells were harvested and sonicated in phosphate-buffered saline with 1 mM EDTA, 0.5% Triton X-100, and protease inhibitor cocktail (Sigma). Glutathione-S-transferase (GST)-tagged human tau or GST protein was purified with glutathione-agarose beads (GenScript).

In GST pull-down assays, bead-bound forms of purified GST-tau were incubated with lysates from HEK293T cells that were not transfected (for interaction with endogenous SIRT1) or transfected with FLAG-tagged human SIRT1. Beads were washed at least three times with lysis buffer containing Triton X-100 or Nonidet-40 and analyzed by SDS-PAGE and western blot with anti-SIRT1 antibody (Millipore) or anti-FLAG antibody (Sigma).

In coimmunoprecipitation assays, HEK293T cells were transfected with pcDNA3.1-hTau-FLAG. Triton X-100-solubilized lysates were incubated with FLAG M2 agarose beads for 3 h at 4° C. Beads were washed at least three times with lysis buffer containing Triton X-100 (0.5%) and analyzed by SDS-PAGE and western blot with anti-SIRT1 antibody (Millipore) or anti-FLAG antibody (Sigma).

Characterization of C646, a Selective p300 Inhibitor

C646 was identified as one of the putative inhibitors of p300 by a computational docking screen. Bowers et al. (2010) Chem Biol 17:471. A convenient spectrophotometric assay was performed to validate it as a p300 inhibitor (Kim et al. (2000) Anal Biochem 280:308), followed by a series of secondary assays. In the coupled spectrophotometric assay, the acetyltransferase reaction product CoASH becomes a substrate for alphaketoglutarate dehydrogenase, which converts NAD to NADH, resulting in an increase of UV absorbance at 340 nm. Kim et al. (2000), supra. A radioactive p300 HAT assay was subsequently performed to directly measure the IC$_{50}$ of C646. The specific inhibition of p300 versus other acetyltransferases by C646 was further examined. These acetyltransferases included serotonin N-acetyltransferase, and the HATs pCAF, GCN5, Rtt109, Sas, and MOZ.

Data Analyses

Statistical analyses were conducted with Graphpad Prism. Differences among multiple (≥3) means with one variable were evaluated by one-way ANOVA and the Tukey-Kramer posthoc test. Differences between two means were assessed with the paired or unpaired two-tailed t test. $P<0.05$ was considered significant.

Results

Tau is Acetylated in Vitro and in Vivo

To demonstrate that tau is acetylated, recombinant tau was incubated with recombinant acetyltransferase p300 or pCAF (p300/CBP-associated factor) with $^{14}$C-acetyl-coenzyme A. Incubation with p300, not pCAF, led to tau acetylation, while both p300 and pCAF were active in transferring acetyl groups to histones as expected (FIG. 1A). Matrix-assisted laser desorption/ionization-time of flight (MALDI-TOF) spectrometry identified multiple lysines that were acetylated by p300 in vitro. A total of 23 putatively acetylated lysines were detected out of 383 residues (~86.8% coverage; Table 4) throughout the tau sequence (2N4R, 441 amino acids). A few putative acetylated lysines were in the N- and C-terminal regions; 13 were in microtubule-binding domains (FIG. 1B and Table 4). Putative acetylated N-terminal lysines (e.g., lysines 163, 174, and 180) appeared to be acetylated in all mass spectrometry (MS) analyses. Those in the microtubule-binding domains appeared to be acetylated in a subset of MS analyses, suggesting variable acetylation at these sites in vitro (Table 4).

TABLE 4

| Peptide position (Tau441) | Peptide sequence | SEQQUEST XCorr Score | Modifications identified by spectrum | Acetylation observed in peptides |
|---|---|---|---|---|
| 2-24 | AEPRQEFEVMEDHAGTYGLGDRK (SEQ ID NO: 21) | 4.20 | | none |
| 24-44 | KDQGGYTMHQDQEGDTDAGLK (SEQ ID NO: 22) | 4.09 | Oxidation (+16) | none |
| 45-67 | ESPLQTPTEDGSEEPGSETSDAK (SEQ ID NO: 23) | 4.90 | | none |
| 68-87 | STPTAEDVTAPLVDEGAPGK (SEQ ID NO: 24) | 3.17 | | none |
| 144-155 | GADGKTKIATPR (SEQ ID NO: 25) | 2.98 | Acetyl (+42) | all |
| 156-170 | GAAPPGQKGQANATR (SEQ ID NO: 26) | 3.02 | Acetyl (+42) | all |

TABLE 4-continued

| Peptide position (Tau441) | Peptide sequence | SEQQUEST XCorr Score | Modifications identified by spectrum | Acetylation observed in peptides |
|---|---|---|---|---|
| 171-190 | IPAKTPPAPKTPPSSGEPPK (SEQ ID NO: 27) | 3.16 | Acetyl (+42) | all |
| 175-194 | TPPAPKTPPSSGEPPKSGDR (SEQ ID NO: 28) | 2.59 | Acetyl (+42) | all |
| 181-194 | TPPSSGEPPKSGDR (SEQ ID NO: 29) | 3.60 | | none |
| 212-225 | TPSLPTPPTREPKK (SEQ ID NO: 30) | 3.76 | | none |
| 243-259 | LQTAPVPMPDLK\*NVK\*SK (SEQ ID NO: 31) | 3.49 | Acetyl (+42) | some |
| 255-267 | NVK\*SK\*IGSTENLK (SEQ ID NO: 32) | 2.95 | Acetyl (+42) | some |
| 258-267 | SKIGSTENLK\* (SEQ ID NO:33) | 2.61 | Acetyl (+42) | some |
| 260-280 | IGSTENLKHQPGGGKVQIINK\* (SEQ ID NO: 34) | 6.28 | Acetyl (+42) | some |
| 268-280 | HQPGGGKVQIINK (SEQ ID NO: 35) | 3.39 | Acetyl (+42) | some |
| 275-290 | VQIINK\*K\*LDLSNVQSK (SEQ ID NO: 36) | 3.86 | Acetyl (+42) | some |
| 281-294 | KLDLSNVQSK\*CGSK (SEQ ID NO: 37) | 3.46 | Acetyl (+42) | some |
| 282-294 | LDLSNVQSK\*CGSK (SEQ ID NO: 38) | 2.85 | Acetyl (+42) | some |
| 295-317 | DNIK\*HVPGGGSVQIVYKPVDLSK (SEQ ID NO: 39) | 6.74 | Acetyl (+42) | some |
| 299-321 | HVPGGGSVQIVYKPVDLSK\*VTSK (SEQ ID NO: 40) | 5.63 | Acetyl (+42) | some |
| 308-321 | IVYKPVDLSKVTSK\* (SEQ ID NO: 41) | 3.42 | Acetyl (+42) | some |
| 318-340 | VTSK\*CGSLGNIHHKPGGGQVEVK (SEQ ID NO: 42) | 5.32 | Acetyl (+42) | some |
| 350-370 | VQSK\*IGSLDNITHVPGGGNK\*K (SEQ ID NO: 43) | 5.08 | Acetyl (+42) | some |
| 354-370 | IGSLDNITHVPGGGNK\*K (SEQ ID NO: 44) | 4.13 | Acetyl (+42) | some |
| 354-375 | IGSLDNITHVPGGGNK\*K\*IETHK (SEQ ID NO: 45) | 6.50 | Acetyl (+42) | some |
| 370-379 | KIETHK\*LTFR (SEQ ID NO: 46) | 3.64 | Acetyl (+42) | some |
| 380-395 | ENAKAKTDHGAEIVYK (SEQ ID NO: 47) | 4.58 | Acetyl (+42) | all |
| 384-406 | AKTDHGAEIVYK\*SPVVSGDTSPR (SEQ ID NO: 48) | 3.63 | Acetyl (+42) | all (AK), some (YK) |
| 386-406 | TDHGAEIVYK\*SPVVSGDTSPR (SEQ ID NO: 49) | 4.91 | Acetyl (+42) | some |
| 407-438 | HLSNVSSTGSIDMVDSPQLATLADEVSASLAK (SEQ ID NO: 50) | 5.50 | Oxidation (+16), | none |
| 419-438 | MVDSPQLATLADEVSASLAK (SEQ ID NO: 51) | 4.19 | Oxidation (+16), not acetylated | none |

Table 4 depicts putative modification of human tau peptides in the presence of p300. Only peptides with lysines are shown. Total coverage: 383/441 (86.8%) from three independent analyses. The putative acetylated lysines are bolded and underlined. Shown are the highest SEQUEST XCorr scores for each peptide among multiple observations. The cut-off of the XCorr score is 2.5. Lysines are also observed to be non-acetylated.

To examine tau acetylation in vivo, a polyclonal antibody (anti-ac-tau, Ab708) was generated using a synthetic tau peptide (amino acids 160-182 for 2N4R tau isoform; underlined in FIG. 10) containing acetylated lysines at positions 163 and 174 and 180. A control antibody was generated (anti-tau, Ab707) using the same peptide with nonacetylated lysines. To test the specificity of Ab708 against ac-tau, recombinant human tau (441; 2N4R isoform) was incubated with glutathione S-transferase (GST) alone or GST-p300 Immunoblotting with Ab708 detected strong tau signals after incubation with GST-p300, but not with GST alone (FIG. 1C). In contrast, Ab707 or Tau 5 antibody detected similar levels of total tau (t-tau) with either GST or GST-p300 (FIG. 1C). Thus, Ab708 specifically recognizes tau acetylated by p300 under cell-free conditions. In HEK293T cells transfected with tau, overexpression of p300 markedly elevated the levels of ac-tau detected with Ab708 while the increase in the levels of t-tau was modest, suggesting that Ab708 preferentially recognizes p300-induced ac-tau in cultured cells (FIG. 1D). Mutation of lysines 163, 174 and 180 (Tau3KR) reduced ac-tau levels relative to t-tau levels in HEK293T cells (FIG. 1E). A smaller yet still significant reduction was also observed when two lysines were mutated in Tau2KR(K174R/K180R) (FIG. 1E). These findings suggest that Ab708 recognizes human tau acetylated at positions 163, 174 or 180 and possibly other acetylated lysines on tau, but not nonacetylated tau.

To detect ac-tau in vivo, western blots were performed with brain lysates from transgenic mice expressing human tau cDNA (1N4R) with P301S mutation (P19) (Yoshiyama et al. (2007) Neuron 53:337) or from transgenic mice expressing the entire human wildtype MAPT (hT-PAC-N) with 0N3R and 0N4R as the two predominant tau isoforms (McMillan et al. (2008) J Comp Neurol 511:788). Human and mouse tau differ at three positions in the region used to generate Ab708 and Ab707 (FIG. 10). Ab708 detected specific signals in lysates from P19 and hT-PAC-N mice, but not those from nontransgenic (NTG) littermates (FIG. 1F). These findings suggest that Ab708 recognizes various isoforms of human ac-tau, but not mouse ac-tau. The control antibody Ab707, which recognizes human t-tau, does not recognize mouse tau either. Endogenous tau in NTG mice was detected with Tau 5 antibody (FIG. 1F).

Rat tau is more similar to human tau than mouse tau in the region used to generate Ab708 (FIG. 10). Ab708 detected endogenous ac-tau in rat primary cortical neurons (FIG. 1G). Levels of ac-tau/t-tau gradually increased as neurons matured from 5-12 days in vitro (DIV), suggesting that tau acetylation is regulated developmentally (FIG. 1G). However, the isoforms of rat tau detected by Ab708 remain to be defined.

FIGS. 1A-G. Tau is Acetylated in Vitro and in Vivo. (A) Acetylation of h-tau (2N4R) by p300 but not pCAF under cell-free conditions, as shown by autoradiography. (B) MALDI-TOF spectrometry identified ac-lysines on h-tau by p300 in vitro. Red: lysines (K) with acetyl group. Underlined: sequence covered by MS analysis. Blue box: microtubule-binding domains. (C-E) Ab708 specifically recognizes ac-tau. (C) Ab708 only recognized recombinant tau acetylated by GST-p300, not nonacetylated tau with GST alone. Similar levels of t-tau were detected with Ab707 and Tau 5 antibody. (D) Overexpressing p300 markedly enhanced ac-tau, detected with Ab708, in HEK293T cells. Levels of t-tau, detected with Tau 5, were similar with or without p300. Blots are representative of >5 experiments. (E) Putatively acetylated lysine sites recognized by Ab708. Ac-tau/t-tau levels in HEK293T cells expressing wildtype tau were set as 1. n=4. *, P=0.012;  P=0.003; *, P=0.0003 (one-way ANOVA with Tukey-Kramer posthoc analysis). (F) Ab708 recognizes human ac-tau in brains of PS19 or hT-PAC-N transgenic mice, not in non-transgenic (NTG) littermates. Human t-tau was detected with Ab707 antibody; human and mouse t-tau was detected with Tau 5 antibody. See FIG. 10 for the sequence similarity among human, mouse and rat tau. (G) Levels of Ab708-positive ac-tau were elevated in primary rat neurons as they matured in culture (DIV=5-12). n=2-7 from 2-3 independent experiments. *, P<0.001 (DIV5 vs. DIV8 or DIV12); , P<0.01 (DIV5 vs. DIV9-11). Values are means±SEM (E, G).

Acetylation of Tau by p300 Acetyltransferase

To determine the role of endogenous p300 or pCAF in tau acetylation, HEK293T cells expressing human tau cDNA (2N4R) were transfected with siRNAs targeting p300 or pCAF (FIG. 2A) and the effects on ac-tau or t-tau were assessed Inhibiting p300 significantly reduced levels of ac-tau, but not t-tau (FIG. 2B, 2C). In contrast, inhibiting pCAF had no effects (FIG. 2B, 2C). These findings are consistent with the results of in vitro studies (FIG. 1A). Next, primary neurons were treated with C646, a pyrazolone-containing small-molecule inhibitor of p300 with a Ki of 400 nM. Bowers et al. (2010) supra. Under cell-free conditions, C646 at 10 µM inhibits p300 in a highly selective manner (86% inhibition vs. <10% for the six other acetyltransferases). Bowers et al. (2010), supra Inhibition of p300 with C646 (20 µM) drastically reduced levels of ac-tau in primary neurons within 8 h. The levels of t-tau remained unchanged (FIG. 2D). p300 is a transcriptional coactivator. Goodman and Smolik (2000) Genes Dev 14:1553. However, C646 treatment for 8 h did not suppress tau transcripts as quantified with real-time reverse transcription-polymerase chain reaction (RT-PCR). Thus short-term (8 h) inhibition of p300 deacetylates tau without affecting t-tau levels. Extended treatment with C646 for 20 h lowered the levels of ac-tau relative to the t-tau (ac-tau/t-tau), but also those of t-tau (FIG. 2E).

FIGS. 2A-E. Tau is Acetylated by p300 Acetyltransferase. (A-C) Inhibiting p300, not pCAF, reduced ac-tau in HEK293T cells. (A) Inhibition of p300 or pCAF expression by siRNA transfections. Levels of p300/GAPDH or pCAF/GAPDH in control siRNA-transfected cells were set as 1. *, P=0.0006 (p300 vs. control) or P<0.0001 (pCAF vs. control). (B) Representative western blots (from three experiments) showing levels of p300 or pCAF, ac-tau, t-tau, and GAPDH in cells transfected with control siRNA (CTRL) or siRNA targeting p300 or pCAF. (C) Inhibition of p300, not pCAF, reduced ac-tau levels. Levels of ac-tau/GAPDH or t-tau/GAPDH in control siRNA-transfected cells were set as 1. n=5-6. , P=0.008 (paired t test). (D) Inhibiting p300 acutely with C646 (20 µM for 8 h) eliminated ac-tau without affecting t-tau levels in primary rat cortical neurons. Left: Representative western blot from three experiments. Right: Ac-tau/t-tau levels in vehicle-treated cells were set as 1. n=3. ***, P=0.0001 (unpaired t test). (E) Extended treatment with C646 (20 µM for 20 h) lowered t-tau in primary cortical neuron. Blots are representative of two experiments. Values are means±SEM (A, C-E).

Deacetylation of Tau by SIRT1 in Cultures

To investigate the enzymes that deacetylate tau, an expression vector encoding FLAG-tagged SIRT1, SIRT2, HDAC5, or HDAC6 was transfected into HEK293T cells expressing human tau. All HDACs were expressed at high levels (FIG. 3A). Although expressed at lower levels than SIRT1 and SIRT2, HDAC6 eliminated tubulin acetylation (Hubbert et al. (2002) Nature 417:455), suggesting sufficient expression (FIG. 3B). Overexpression of SIRT1 reduced levels of Ab708-positive ac-tau. SIRT2 and HDAC6 overexpression also lowered ac-tau, although to lesser extents (FIG. 3B, 3C). Levels of t-tau were also reduced in cells overexpressing SIRT1 and HDAC6. Nevertheless, the ac-tau/t-tau ratio was significantly reduced by SIRT1 overexpression (FIG. 3D). The modest reduction in ac-tau/t-tau induced by HDAC6 or SIRT2 overexpression was not statistically significant (FIG. 3D).

Figure 3E:
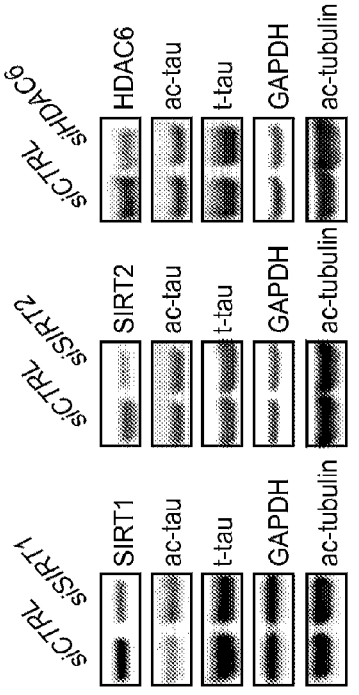
Figure 3G:
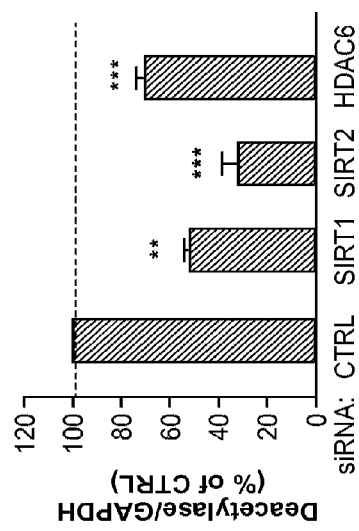
Figure 3F:
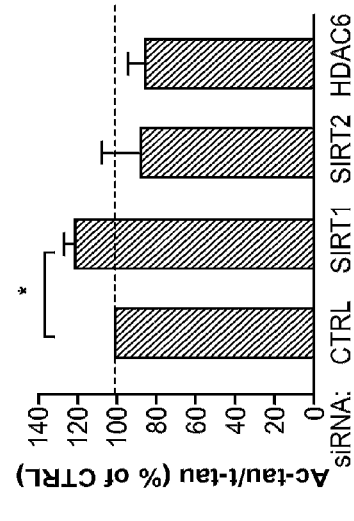
Figure 3H:
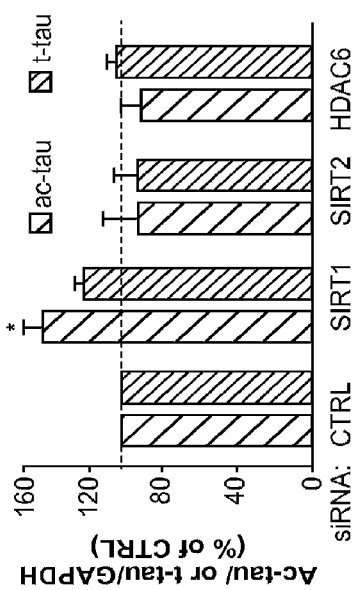

To examine the effects of endogenous HDACs on ac-tau, expression of SIRT1, SIRT2, or HDAC6 was inhibited with siRNAs (FIG. 3E). Relative to control siRNA, target siRNAs significantly reduced levels of SIRT1, SIRT2, and HDAC6. Despite modest inhibition, HDAC6 increased ac-tubulin levels (FIG. 3F). However, only inhibition of SIRT1 increased ac-tau levels, suggesting the involvement of endogenous SIRT1 in deacetylating tau (FIG. 3G). Consistent with the observation that SIRT1 overexpression reduced t-tau, SIRT1 inhibition led to a trend of increase in t-tau (FIG. 3G). Nevertheless, inhibition of SIRT1, not SIRT2 or HDAC6, significantly elevated levels of ac-tau relative to t-tau (ac-tau/t-tau) (FIG. 3H). These results provided direct support that SIRT1 is involved in tau deacetylation. Our findings so far do not support a prominent role of SIRT2 or HDAC6, which both deacetylate tubulin (Hubbert et al. (2002) supra; North et al. (2003) Mol. Cell. 11:437), in tau deacetylation. However, their involvement cannot be ruled out since only partial silencing of SIRT2 or HDAC6 was achieved with siRNA transfections.

Figure 3I:
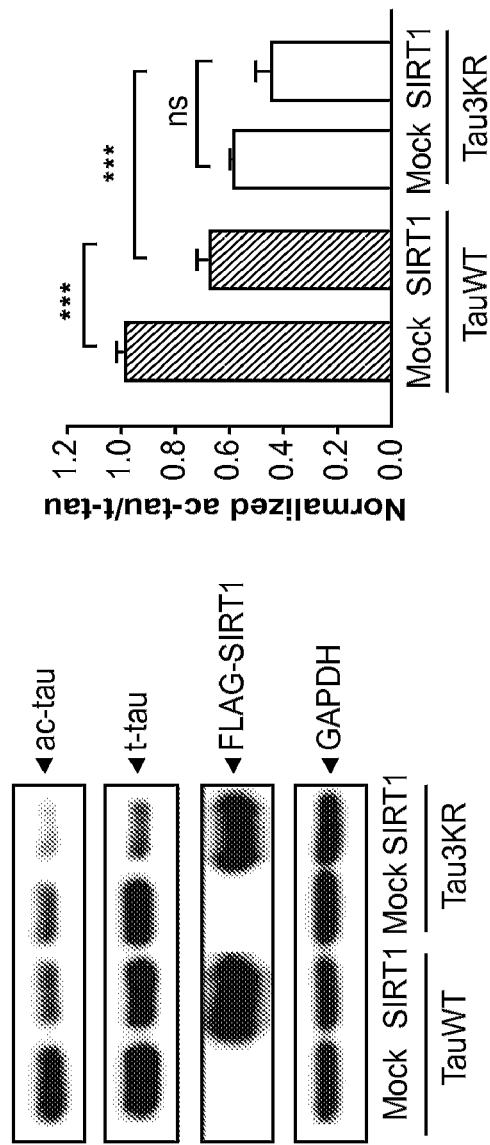

To further investigate the role of SIRT1 in tau deacetylation, low-passage mouse embryonic fibroblasts (MEF) with (SIRT1$^{+/+}$) or without SIRT1 (SIRT1$^{-/-}$) were transfected with human tau cDNA. Deleting SIRT1 significantly raised ac-tau levels. The increase in t-tau did not reach statistical significance, suggesting SIRT1 deacetylates tau in MEFs. In HEK293T cells, when lysines 163, 174, and 180 were mutated to arginines (Tau3KR), levels of ac-tau were significantly reduced (FIG. 3I). SIRT1 overexpression reduced ac-tau in TauWT cells, but the reduction was much attenuated in Tau3KR cells (FIG. 3I). These results implicate SIRT1 in deacetylating lysines 163, 174, and 180. However, SIRT1 reduced ac-tau to lower levels in Tau3KR cells than in TauWT cells, indicating that SIRT1 could deacetylate additional lysine residues besides those at positions 163, 174, and 180 (FIG. 3I).

FIGS. 3A-I. SIRT1 Deacetylates Tau in Culture. (A-D) SIRT1 overexpression lowered ac-tau levels in HEK293T cells. (A) Western blot showing expression of FLAG-tagged SIRT1, SIRT2, HDAC5, or HDAC6 with an anti-FLAG antibody. Blots are representative of 2-3 experiments. (B) Western blot showing levels of ac-tau, t-tau, tubulin, and ac-tubulin in cells overexpressing SIRT1, SIRT2, HDAC5, or HDAC6. Blots are representative of 2-3 experiments. (C) Overexpression of SIRT1, SIRT2 or HDAC6 significantly reduced levels of ac-tau/GAPDH. Levels of t-tau were also reduced by SIRT1 or HDAC6 overexpression. n=9-18 from 6-10 independent experiments. *, P<0.001 (Mock vs. SIRT1 or Mock vs. HDAC6); , P<0.01 (Mock vs. SIRT2) (two-way ANOVA and Bonferroni posthoc test). (D) Overexpression of SIRT1 significantly reduced ac-tau/t-tau. n=9-18 from 6-10 independent experiments, *, P<0.001 (Mock vs. SIRT1) (one-way ANOVA and Tukey-Kramer posthoc test). (E-H) Inhibition of SIRT1 elevated ac-tau in HEK293T cells. (E) Inhibition of SIRT1, SIRT2, or HDAC6 expression mediated by siRNA transfections. n=4-6 from 2-3 experiments. , P=0.0015; ***, P=0.0001 (SIRT2 vs. control) or P=0.001 (HDAC6 vs. control) (paired t test). (F) Western blot showing levels of ac-tau, t-tau, tubulin, and ac-tubulin in cells transfected with control siRNA or siRNA targeting SIRT1, SIRT2, or HDAC6. Blots are representative of 2-3 experiments. (G-H) Inhibition of SIRT1, significantly elevated levels of ac-tau/GAPDH (G) or ac-tau/t-tau (H). n=4-6 from 2-3 experiments. *, P<0.05 (paired t test). Levels of deacetylase/GAPDH (E), ac-tau or t-tau/GAPDH (G), and ac-tau/t-tau (H) in control siRNA-transfected cells were set as 1. (I) Deacetylation of Tau3KR by SIRT1. Left: Representative western blot showing levels of ac-tau, t-tau, FLAG-tagged SIRT1, and GAPDH. Right: Ac-tau/t-tau levels in mock-transfected cells expressing wildtype tau were set as 1. n=10-20 from 4-10 independent experiments. ***, P<0.001; ns, not significant (one-way ANOVA and Tukey-Kramer posthoc analysis). Values are means±SEM (C-E, G-I).

SIRT1 Reduces Tau Acetylation in Primary Neurons and In Vivo

In primary neurons, ac-tau/t-tau increased as the neurons matured (FIG. 1G) but levels of full-length SIRT1 decreased (FIG. 4A). Consistent with the notion that SIRT1 deactylates tau, levels of SIRT1 negatively correlated with levels of ac-tau/t-tau in primary neurons during development (FIG. 4B). To investigate if SIRT1 negatively regulates tau acetylation in neurons, SIRT1 was deleted in neurons by infecting neurons from SIRT1 conditional knockout mice (SIRT1$^{F/F}$) (Chua et al. (2005) Cell Metab 2:67) with a lentiviral vector expressing cre recombinase (Lenti-cre) (FIG. 4C). Controls were infection with an empty vector (Lenti-con). SIRT1$^{F/F}$ neurons were also infected with a lentiviral vector expressing human tau. Deleting SIRT1 significantly elevated levels of acetylated human tau relative to t-tau (FIG. 4C), indicating that SIRT1 deacetylates tau in neurons.

To examine the effects of SIRT1 deletion on the acetylation of mouse tau in vivo, another ac-tau-specific antibody targeting the microtubule-binding region (264-287), which is 100% conserved between mouse and human (FIG. 4D), was developed. Recombinant tau was incubated with p300 to induce acetylation. Like Ab708, antibody 9AB recognized recombinant tau acetylated by GST-p300, but not tau incubated with GST alone, suggesting that 9AB does not cross-react with non-ac-tau. In HEK293T cells, overexpression of p300 markedly elevated levels of ac-tau detected with 9AB, but only modestly those of t-tau. Thus, 9AB also preferentially recognizes p300-induced ac-tau in cultured cells (FIG. 4E). In mouse brains, 9AB detected low levels of ac-tau, which was absent in tau$^{-/-}$ mice. To delete SIRT1, SIRT1$^{+/-}$ mice were crossed on an outbred background, which partially rescued the embryonic lethality of SIRT1-null mice on the inbred background. Chen et al. (2003) Proc. Natl. Acad. Sci. USA 100:10794. Deleting SIRT1 significantly enhanced levels of ac-tau in the brain, providing direct evidence that SIRT1 deacetylates tau in vivo (FIG. 4F).

FIGS. 4A-F. SIRT1 Reduces Tau Acetylation in Neurons and In Vivo (A) Western blot showing expression of SIRT1 in primary cortical neurons during maturation in culture (DIV5-11). Blots are representative of 2-3 independent cultures. (B) Levels of endogenous ac-tau relative to t-tau correlated negatively with levels of SIRT1 in primary rat neuronal cultures (DIV5-9). Levels of SIRT1 or ac-tau/t-tau at DIV=5 were set as 1. n=20 independent measurements. P=0.0007, Pearson correlation coefficient $r^2$=0.4791. (C) Deleting SIRT1 in neurons elevated levels of ac-tau relative to t-tau. Neurons cultured from SIRT1$^{F/F}$ mice were infected with control virus or virus expressing cre recombinase (Lenti-cre). Both cultures were also infected with a lentiviral vector expressing h-tau. n=8. P=0.001, (unpaired t test). (D) Acetyl-specific antibody (9AB) recognized tau acetylated by GST-p300, but not non-ac-tau. Also shown is the sequence of the antigen used to generate 9AB. (E) Overexpressing p300 enhanced 9AB-positive ac-tau in HEK293T cells. Levels of t-tau, detected with Tau 5, were similar with or without p300 overexpression. Blots are representative of three independent experiments. (F) Deletion of SIRT1 elevated ac-tau relative to t-tau in the brain. Left: Representative western blots showing levels of ac-tau, t-tau, and GAPDH. Right: Levels of ac-tau/t-tau in SIRT1$^{+/+}$, SIRT1$^{+/-}$, and SIRT1$^{-/-}$ brains. n=3-6 mice/genotype. *, P=0.02 (SIRT1$^{+/-}$ vs. SIRT1$^{-/-}$) (one-way ANOVA and Tukey-Kramer posthoc test). Values are means±SEM (C, F).

SIRT1 Interacts with Tau Directly

Figure 5A:
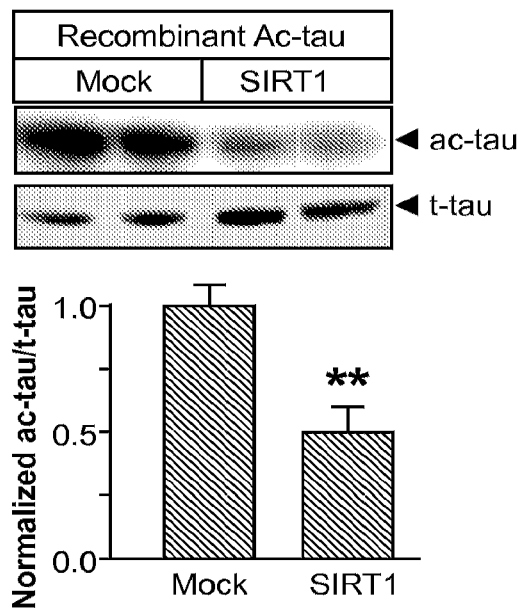
FIGS. 5A-C depict SIRT1 interaction with Tau.
Figure 5B:
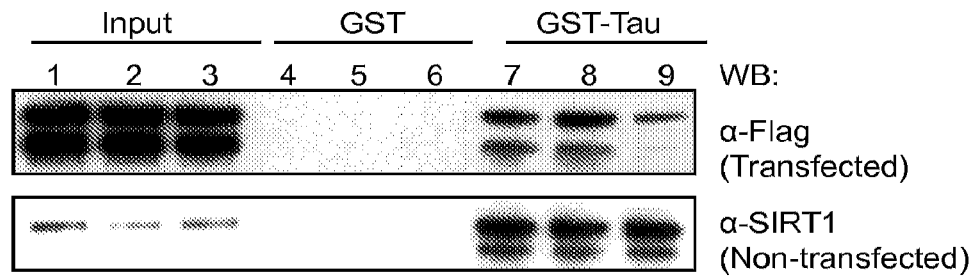

Although mainly localized in the nucleus, SIRT1 can be shuttled to the cytoplasm. To determine if SIRT1 directly deacetylates tau, in vitro deacetylation assays were performed. Recombinant tau acetylated by p300 was incubated with SIRT1 immunoprecipitated from SIRT1-overexpressing HEK293T cells. Ac-tau/t-tau levels were significantly lower in the presence of immunoprecipitated SIRT1 (FIG. 5A). To confirm that SIRT1 interacts with tau directly in vivo, GST pull-down assays were performed. Bead-bound GST-tau, not GST alone, interacted with FLAG-SIRT1 expressed in HEK293T cells or endogenous SIRT1 in nontransfected cells (FIG. 5B). Moreover, in coimmunoprecipitation assays, after immunoprecipitation with an anti-FLAG antibody, endogenous SIRT1 was detected with an anti-SIRT1 antibody, and tau was detected with a pan-tau antibody (Tau 5) in HEK293T cells expressing FLAG-tagged tau (FIG. 5C).

Figure 5C:
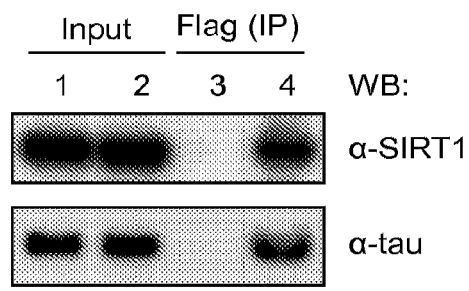

FIGS. 5A-C. SIRT1 Interacts with Tau. (A) SIRT1 directly deacetylated ac-tau in vitro. Ac-tau/t-tau levels in the absence of immunoprecipitated SIRT1 were set as 1. Ac-tau was detected with Ab708 antibody. n=5 from two experiments. **, P=0.0063 (unpaired t test). (B) GST pull-down assays. GST-tau protein (lanes 7-9) or GST alone (lanes 4-6) was incubated with lysates of cells transfected with FLAG-tagged SIRT1 or of nontransfected cells. Lanes 1, 4 and 7: 0.1% Triton X-100; lanes 2, 5, and 8: 0.5% Triton X-100; lanes 3, 6, and 9: 0.5% NP-40. Data shown are representative of two experiments. The lower band is likely to represent the cleavage product of SIRT1 observed previously. Ohsawa and Miura (2006) *FEBS Lett* 580:5875. (C) Communoprecipitation assays. HEK293T cells were transfected with a plasmid encoding FLAG-tagged human tau. Cell lysates were collected 24 h later, immunoprecipitated with an anti-FLAG antibody, and immunoblotted with Tau 5 or an anti-SIRT1 antibody. Lanes 1-2: input; lane 3: no primary antibody; lane 4: anti-FLAG antibody. Values are means±SEM (A).

SIRT1 Deficiency Increases Tau Acetylation and Suppresses Degradation of p-Tau

As a class III lysine deacetylase, SIRT1 supports and promotes longevity in diverse organisms. Besides regulating endocrine and behavioral responses to caloric restriction, SIRT1 has been strongly implicated in neurodegenerative diseases. Gan and Mucke (2008) *Neuron* 58:10. In AD brains, SIRT1 levels are significantly reduced, and the reduction appears to correlate with tau accumulation and aggregation. Thus, deficient SIRT1 activity may contribute to tauopathy. In primary neurons, inhibiting SIRT1 with a specific inhibitor EX527 (Napper et al. (2005) *J Med Chem* 48:8045) markedly increased ac-tau, AT8-positive p-tau, as well as t-tau (FIG. 6A). Levels of ac-tau or p-tau relative to t-tau were significantly increased with EX527 treatments (FIG. 6A). Thus, the increase in ac-tau induced by SIRT1 deficiency is accompanied by accumulation of pathogenic p-tau in primary neurons. In mouse brains, deleting SIRT1, which elevated ac-tau, also increased AT8-positive p-tau (FIG. 6B).

How might elevated tau acetylation lead to higher levels of p-tau? Acetylation of lysines can preclude its ubiquitination and stabilize proteins that are normally degraded by the UPS, including p53, Runx3, β-catenin, and other regulatory factors. Since tau is ubiquitinated and the degradation of tau, especially p-tau, involves the proteasome-mediated pathway, it was hypothesized that acetylation precludes tau ubiquitination and suppresses its degradation.

Figure 6E:
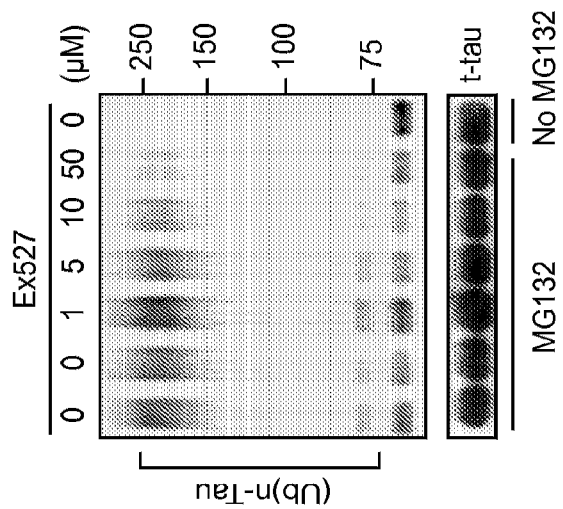
Figure 6D:
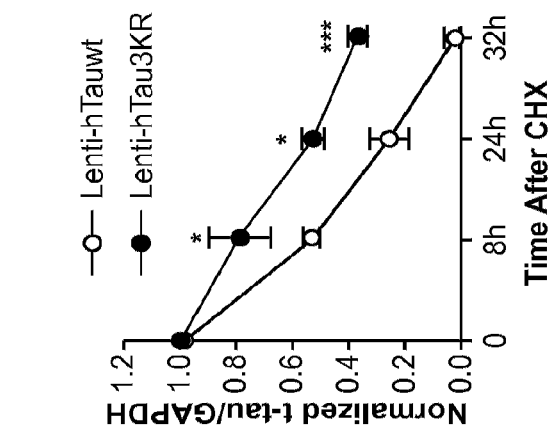
Figure 6C:
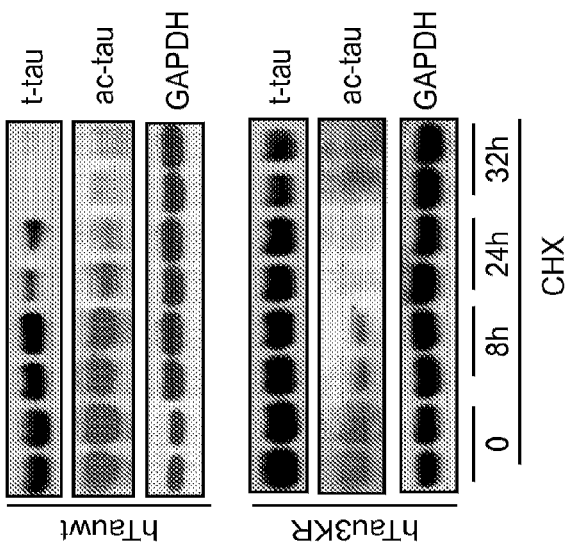

To test this hypothesis, the involvement of acetylated lysines in regulating protein turnover was assessed. The turnover rates of human wildtype tau (hTauwt) and human tau3KR (hTau3KR) were compared. Primary cortical neurons were infected with Lenti-hTauwt and Lenti-hTau3KR and treated with CHX (FIG. 6C). Infection of Lenti-hTau3KR resulted in much weaker Ab708-positive signal than that of Lenti-hTauwt, providing further support that Ab708 recognizes acetylation of lysines 163, 174, and 180. Mutating these three lysines to arginines significantly increased the half-life of tau, possibly by permanently blocking ubiquitination at the three sites (FIG. 6D). These results support the notion that the acetylated lysines can be ubiquitinated.

To directly test if enhancing acetylation can block ubiquitination, HEK293T cells were transfected with expression plasmids encoding tau and hemagglutinin (HA)-tagged ubiquitin and then treated with EX527 to inhibit SIRT1 and with MG132 to block the proteasome-mediated degradation. Ubiquitinated tau was immunoprecipitated with an anti-FLAG antibody and detected with an anti-HA antibody. EX527 prevented polyubiquitination of tau in a dose-dependent manner, indicating that tau ubiquitination is suppressed by enhanced acetylation (FIG. 6E). EX527 also elevated ac-tau levels as expected (FIG. 6F). In contrast, SIRT1-mediated deacetylation appears to enhance tau ubquitination. Treatment with resveratrol, which may be indirectly involved in activating SIRT1, significantly increased tau ubiquitination in cells transfected with wildtype SIRT1, but not those with H363Y mutant.

It was then directly examined whether enhancing acetylation of tau slows the turnover of endogenous tau. Primary neurons were treated with EX527 to enhance tau acetylation and with cycloheximide (CHX) to inhibit translation of new proteins. Endogenous rat tau in primary neurons had a half-life of around 5 h Inhibiting SIRT1 with EX527 slowed tau turnover and increased the half-life of t-tau in a dose-dependent manner (FIG. 6G, 6H). Consistent with this notion, ac-tau appears to be degraded slower than that of t-tau. In primary neurons, CHX markedly reduced t-tau levels after 5 h, whereas ac-tau levels were only slightly reduced after 8 h. Moreover, inhibition of SIRT1 with 10 μM of EX527 blocked the turnover of ac-tau, leading its accumulation (FIG. 6I, 6J). Higher dose of EX527 (50 μM) resulted in more pronounced accumulation of ac-tau (FIG. 6I). Treatment with EX527 also blocked the degradation of AT8-positive p-tau in a dose-dependent manner (FIG. 6K).

FIGS. 6A-K. Acetylation Slows Tau Turnover by Inhibiting its Ubiquitination.

(A) Inhibiting SIRT1 with EX527 (50 μM) elevated ac-tau and p-tau in rat primary neurons (DIV=10). Left: Representative western blots. p-tau was detected with ATB. Right:

Levels of ac-tau/t-tau or p-tau/t-tau in vehicle-treated cells were set as 1. n=6 independent treatments. ***, P<0.001; *, P<0.05 (paired t test). (B) Deletion of SIRT1 elevated AT8-positive p-tau in the brain. n=3-4 mice/genotype. *, P<0.05 (SIRT1$^{+/+}$ vs. SIRT1$^{-/-}$) (one-way ANOVA and Tukey-Kramer posthoc test). (C and D) Tau3KR was more stable than wildtype tau in primary neurons. Cells were infected with Lenti-hTauwt or Lenti-hTau3KR and treated with CHX for 8-32 h 4 days after infection (DIV=9). (C) Representative western blot of 2 experiments showing ac-tau, t-tau, and GAPDH. (D) The turnover of t-tau was slower in cells expressing Tau3KR. t-tau/GAPDH levels in cells harvested at time 0 were set as 1. n=3-5 from 2 experiments. *, P=0.04 (8 h), P=0.015 (24 h); *, P<0.0001 (32 h) (unpaired t test for each time-point). (E and F) SIRT1 inhibitor EX527 (1-50 µM) suppressed tau ubiquitination and elevated ac-tau in a dose-dependent manner. Blots are representative of 3 experiments. (G-K) The SIRT1 inhibitor EX527 increases the half-life of tau in rat primary neurons (DIV=8) in a dose-dependent manner. Neurons were treated with CHX for 0-8 h in the presence or absence of EX527 (10-50 µM). Representative western blots of 3 experiments showing the turnover of t-tau (G), ac-tau (I), or p-tau (K) in neurons with or without EX527. (H and J) The turnover of t-tau (H) or ac-tau (J) was markedly slowed by treatment of EX527. Levels of t-tau/tubulin or ac-tau/tubulin in cells harvested at time 0 were set as 1. n=3. , P<0.01; ***, P<0.001 (two-way ANOVA, EX527-treated vs. vehicle-treated). Values are means±SEM (A-B, D, G, I).

Elevation of Tau Acetylation in Pathological Conditions

Figure 7A:
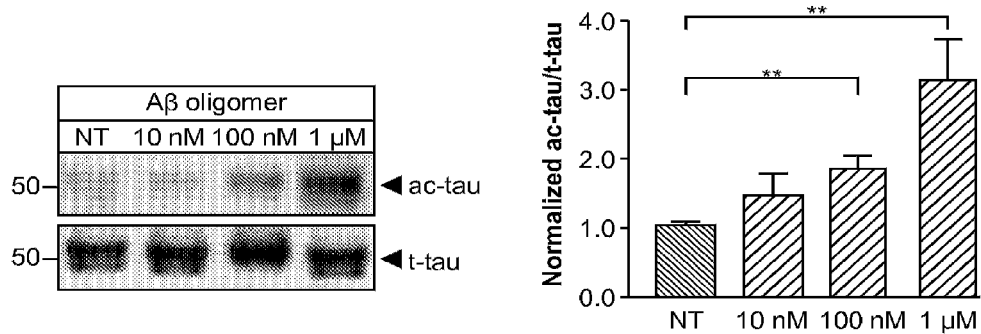
FIGS. 7A-D depict elevated Tau acetylation under pathological conditions.
Figure 7B:
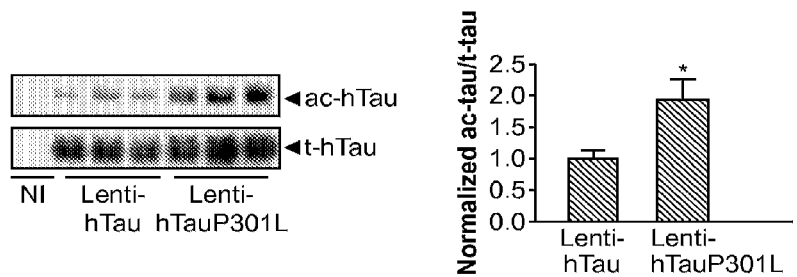

Since degradation of tau was slowed by its acetylation, it was hypothesized that acetylation is a critical early event that contributes to accumulation of p-tau that is normally degraded via the proteasome-mediated pathway. In primary neurons, treatment with low levels of amyloid β (Aβ) oligomers, a key pathogen in AD, increased levels of ac-tau in a dose-dependent manner (FIG. 7A). Higher levels of ac-tau were observed in primary neurons expressing human tau carrying FTD-linked mutation (hTauP301L) than those expressing similar levels of hTauwt (FIG. 7B). These findings suggest that tau acetylation is elevated by stress, such as Aβ accumulation, or FTD-linked mutations.

Figure 7C:
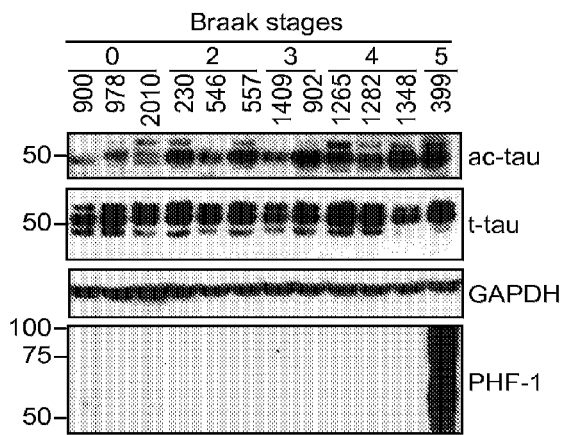
Figure 7D:
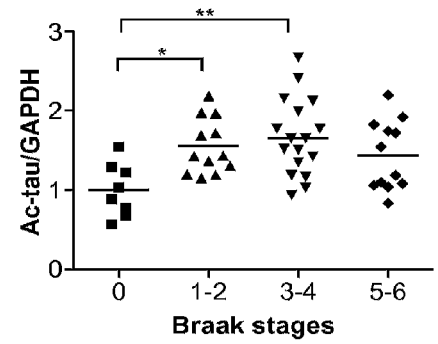

Tau acetylation in the frontal cortex of patients with various degrees of tau pathology was examined. Braak and Braak (1991) *Neuropathol. Berl.* 82:239. Patients at Braak stages 1-2 or 3-4 had significantly higher levels of ac-tau in the soluble fraction of the brain lysates than patients at Braak stage 0 (FIG. 7C). Ab708 can recognize various human tau isoforms in transgenic mice overexpressing human tau (FIG. 1D). However, unlike Tau 5, which detects all isoforms, Ab708 appears to detect some isoforms preferentially in AD brains (FIG. 7C). Hyperphosphorylated tau detected with PHF-1 (FIG. 1D) or AT8 was observed only in patients at stages 5-6, consistent with lack of significant NFTs in the frontal cortex of patients at earlier Braak stages (Braak and Braak (1991) supra). Thus, these findings support the notion that enhanced tau acetylation precedes hyperphosphorylation of tau and NFT formation. However, in patients at Braak stages 5-6, especially those at stage 6, with NFTs in the frontal cortex, levels of ac-tau were slightly lower than patients at mild to moderate stages. This end-stage reduction might be explained by severe loss of neurons, or sequestration of ac-tau in the NFTs, thus remaining in the insoluble fractions of the lysates.

FIGS. 7A-D. Tau Acetylation is Elevated under Pathological Conditions. (A) Tau acetylation was increased by low levels of Aβ oligomers in primary cortical neurons (DIV=11). n=5 from 3 experiments. **, P=0.003 (one-way ANOVA and Tukey-Kramer posthoc test). (B) Tau acetylation was associated with familial MAPT mutations in primary neurons (DIV=13). Ac-tau/t-tau levels in neurons infected with Lenti-hTauwt were set as 1. n=9 from three experiments. *, P=0.013 (unpaired t test). (C) Representative western blots showing levels of ac-tau, t-tau, and hyperphosphorylated tau in human brains (Bm-22, superior temporal gyrus) at different Braak stages (0-5). (D) Ac-tau levels were elevated in patients with mild (Braak stages 1-2) to moderate (Braak stages 3-4) levels of tau pathology. n=8-18 cases/Braak range. *, P<0.05; **, P<0.01, one-way ANOVA Tukey-Kramer posthoc analyses. Values are means±SEM (A, B, D).

Reducing Tau Acetylation Eliminates p-Tau Induced by FTD-linked Mutation

To test the hypothesis that tau acetylation contributes to p-tau accumulation, it was determined if inhibiting tau acetylation eliminates p-tau and protects against tauopathy. Inhibiting p300 in primary neurons with the small molecule C646 eliminated ac-tau without affecting t-tau levels (FIG. 8A). Strikingly, pathogenic tau phosphorylated at serine 202, detected with AT8 antibody, was also abolished within 2 h treatment with C646. Its inactive analog C37 had no effects (FIG. 8B). These results suggest that deacetylation preferentially enhances degradation of p-tau, consistent with the observation that p-tau species are selectively degraded via the UPS pathway In primary neurons expressing hTauP301L, a cellular model of tauopathy, AT8-positive p-tau was also diminished by C646 treatment (FIG. 8C). Reducing tau improves cognitive function in mouse models of AD and FTDP-17 (Roberson et al. (2007) *Science* 316:750; and Santacruz et al. (2005) *Science* 309:476) and protects against excitotoxicity (Roberson et al. (2007) supra). These results implicate modulating lysine acetylation as a new therapeutic strategy to reduce levels of tau, especially pathogenic forms of p-tau, in neurodegenerative tauopathies.

FIGS. 8A-D. Reducing Tau Acetylation Eliminates p-Tau. (A) C646 (20 µM) eliminated ac-tau and AT8-positive p-tau within 2 h in primary cortical neurons (DIV=9). Representative western blot of two experiments. (B) C646 (20 µM) eliminated p-tau. Levels of p-tau/GAPDH in non-treated cells were set as 1. n=4. *, P<0.0001 (unpaired t test). (C) C646 (20 µM) eliminated AT8-positive p-tau in primary neurons expressing hTauP301L (DIV=12). Left, Representative western blot of two experiments. Right, Levels of p-tau/GAPDH in cells treated with control compound (C37) were set as 1. n=7. *, P=0.0001 (unpaired t test). (D) Hypothetical model of how tau acetylation may contribute to tau-mediated neurodegeneration. Dashed lines and factors in grey indicate pathways not yet tested. Values are means±SEM (B-C).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for reducing the level of an acetylated Tau polypeptide in a cell, the method comprising contacting the cell with an agent that increases the activity of a polypeptide that deacetylates a Tau polypeptide in the cell and/or an agent that decreases the activity of a polypeptide that acetylates a Tau polypeptide in the cell.

2. The method of claim 1, wherein the method comprises contacting the cell with an agent that increases the activity of a polypeptide that deacetylates a Tau polypeptide in the cell and an agent that decreases the activity of a polypeptide that acetylates a Tau polypeptide in the cell.

3. The method of claim 1, wherein the cell is a neuron.

4. The method of claim 1, wherein the cell is a glial cell.

5. The method of claim 1, wherein the agent is not a sirtuin activator.

6. The method of claim 1, wherein the agent is a p300 inhibitor or a CBP inhibitor.

7. The method of claim 1, wherein the agent is an activator of SIRT1, SIRT2, or HDAC6.

8. The method of claim 1, wherein said contacting reduces the level of phosphorylated Tau polypeptide in the cell.

9. The method of claim 1, wherein said contacting increases the level of active Tau polypeptide in the cell.

10. A method for treating a tauopathy in an individual, the method comprising administering to the individual an effective amount of an agent that reduces the level of acetylated Tau in a neuron or a glial cell in the individual.

11. The method of claim 10, wherein the administering comprises administering to the individual an agent that increases the activity of a polypeptide that deacetylates a Tau polypeptide in a neuronal cell or a glial cell and an agent that decreases the activity of a polypeptide that acetylates a Tau polypeptide in a neuronal cell or a glial cell in combined effective amounts to treat the tauopathy.

12. The method of claim 10, wherein the tauopathy is frontotemporal dementia, Alzheimer's disease, progressive supranuclear palsy, corticobasal degeneration, Down syndrome, dementia pugilistica, inclusion-body myositis, or frontotemporal lobar degeneration.

13. The method of claim 10, wherein the agent that reduces the level of acetylated Tau is a P300/CBP inhibitor.

14. The method of claim 10, wherein the agent that reduces the level of acetylated Tau is a SIRT1 activator.

15. The method of claim 10, wherein said administering reduces the level of phosphorylated Tau in a neuron or glial cell in the individual.

16. The method of claim 10, wherein said administering increases the level of active Tau in a neuron or glial cell in the individual.

17. A method of diagnosing a cognitive impairment disorder in an individual, the method comprising detecting a level of acetylated Tau polypeptide in a biological sample obtained from the individual, wherein a level of acetylated Tau polypeptide that is higher than a normal control level indicates that the individual has a cognitive impairment disorder.

18. The method of claim 17, wherein the biological sample is cerebrospinal fluid, blood, plasma, or serum.

* * * * *

SEQUENCE LISTING

<160> NUMBER OF SEQ ID NOS: 53

<210> SEQ ID NO 1
<211> LENGTH: 441
<212> TYPE: PRT
<213> ORGANISM: Homo sapiens

<400> SEQUENCE: 1

Met Ala Glu Pro Arg Gln Glu Phe Glu Val Met Glu Asp His Ala Gly
1               5                  10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Pro Gly Gly Gly
    290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
        355                 360                 365

```
Lys Lys Ile Glu Thr His Lys Leu Thr Phe Arg Glu Asn Ala Lys Ala
370                 375                 380
Lys Thr Asp His Gly Ala Glu Ile Val Tyr Lys Ser Pro Val Val Ser
385                 390                 395                 400
Gly Asp Thr Ser Pro Arg His Leu Ser Asn Val Ser Ser Thr Gly Ser
                405                 410                 415
Ile Asp Met Val Asp Ser Pro Gln Leu Ala Thr Leu Ala Asp Glu Val
            420                 425                 430
Ser Ala Ser Leu Ala Lys Gln Gly Leu
            435                 440

<210> SEQ ID NO 2
<211> LENGTH: 383
<212> TYPE: PRT
<213> ORGANISM: Homo sapiens

<400> SEQUENCE: 2

Met Ala Glu Pro Arg Gln Glu Phe Glu Val Met Glu Asp His Ala Gly
1               5                   10                  15
Thr Tyr Gly Leu Gly Asp Arg Lys Asp Gln Gly Gly Tyr Thr Met His
                20                  25                  30
Gln Asp Gln Glu Gly Asp Thr Asp Ala Gly Leu Lys Ala Glu Glu Ala
            35                  40                  45
Gly Ile Gly Asp Thr Pro Ser Leu Glu Asp Glu Ala Ala Gly His Val
        50                  55                  60
Thr Gln Ala Arg Met Val Ser Lys Ser Lys Asp Gly Thr Gly Ser Asp
65                  70                  75                  80
Asp Lys Lys Ala Lys Gly Ala Asp Gly Lys Thr Lys Ile Ala Thr Pro
                85                  90                  95
Arg Gly Ala Ala Pro Pro Gly Gln Lys Gly Gln Ala Asn Ala Thr Arg
            100                 105                 110
Ile Pro Ala Lys Thr Pro Pro Ala Pro Lys Thr Pro Pro Ser Ser Gly
        115                 120                 125
Glu Pro Pro Lys Ser Gly Asp Arg Ser Gly Tyr Ser Ser Pro Gly Ser
130                 135                 140
Pro Gly Thr Pro Gly Ser Arg Ser Arg Thr Pro Ser Leu Pro Thr Pro
145                 150                 155                 160
Pro Thr Arg Glu Pro Lys Lys Val Ala Val Val Arg Thr Pro Pro Lys
                165                 170                 175
Ser Pro Ser Ser Ala Lys Ser Arg Leu Gln Thr Ala Pro Val Pro Met
            180                 185                 190
Pro Asp Leu Lys Asn Val Lys Ser Lys Ile Gly Ser Thr Glu Asn Leu
        195                 200                 205
Lys His Gln Pro Gly Gly Gly Lys Val Gln Ile Ile Asn Lys Lys Leu
    210                 215                 220
Asp Leu Ser Asn Val Gln Ser Lys Cys Gly Ser Lys Asp Asn Ile Lys
225                 230                 235                 240
His Val Pro Gly Gly Gly Ser Val Gln Ile Val Tyr Lys Pro Val Asp
                245                 250                 255
Leu Ser Lys Val Thr Ser Lys Cys Gly Ser Leu Gly Asn Ile His His
            260                 265                 270
Lys Pro Gly Gly Gly Gln Val Glu Val Lys Ser Glu Lys Leu Asp Phe
        275                 280                 285
Lys Asp Arg Val Gln Ser Lys Ile Gly Ser Leu Asp Asn Ile Thr His
    290                 295                 300
```

```
Val Pro Gly Gly Gly Asn Lys Lys Ile Glu Thr His Lys Leu Thr Phe
305                 310                 315                 320

Arg Glu Asn Ala Lys Ala Lys Thr Asp His Gly Ala Glu Ile Val Tyr
                325                 330                 335

Lys Ser Pro Val Val Ser Gly Asp Thr Ser Pro Arg His Leu Ser Asn
                340                 345                 350

Val Ser Ser Thr Gly Ser Ile Asp Met Val Asp Ser Pro Gln Leu Ala
                355                 360                 365

Thr Leu Ala Asp Glu Val Ser Ala Ser Leu Ala Lys Gln Gly Leu
                370                 375                 380
```

<210> SEQ ID NO 3
<211> LENGTH: 352
<212> TYPE: PRT
<213> ORGANISM: Homo sapiens

<400> SEQUENCE: 3

```
Met Ala Glu Pro Arg Gln Glu Phe Glu Val Met Glu Asp His Ala Gly
  1               5                  10                  15

Thr Tyr Gly Leu Gly Asp Arg Lys Asp Gln Gly Gly Tyr Thr Met His
                 20                  25                  30

Gln Asp Gln Glu Gly Asp Thr Asp Ala Gly Leu Lys Ala Glu Glu Ala
                 35                  40                  45

Gly Ile Gly Asp Thr Pro Ser Leu Glu Asp Glu Ala Ala Gly His Val
             50                  55                  60

Thr Gln Ala Arg Met Val Ser Lys Ser Lys Asp Gly Thr Gly Ser Asp
 65                  70                  75                  80

Asp Lys Lys Ala Lys Gly Ala Asp Gly Lys Thr Lys Ile Ala Thr Pro
                 85                  90                  95

Arg Gly Ala Ala Pro Pro Gly Gln Lys Gly Gln Ala Asn Ala Thr Arg
                100                 105                 110

Ile Pro Ala Lys Thr Pro Pro Ala Pro Lys Thr Pro Pro Ser Ser Gly
                115                 120                 125

Glu Pro Pro Lys Ser Gly Asp Arg Ser Gly Tyr Ser Ser Pro Gly Ser
130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Val Arg Thr Pro Pro Lys
                165                 170                 175

Ser Pro Ser Ser Ala Lys Ser Arg Leu Gln Thr Ala Pro Val Pro Met
                180                 185                 190

Pro Asp Leu Lys Asn Val Lys Ser Lys Ile Gly Ser Thr Glu Asn Leu
                195                 200                 205

Lys His Gln Pro Gly Gly Gly Lys Val Gln Ile Val Tyr Lys Pro Val
210                 215                 220

Asp Leu Ser Lys Val Thr Ser Lys Cys Gly Ser Leu Gly Asn Ile His
225                 230                 235                 240

His Lys Pro Gly Gly Gly Gln Val Glu Val Lys Ser Glu Lys Leu Asp
                245                 250                 255

Phe Lys Asp Arg Val Gln Ser Lys Ile Gly Ser Leu Asp Asn Ile Thr
                260                 265                 270

His Val Pro Gly Gly Gly Asn Lys Lys Ile Glu Thr His Lys Leu Thr
                275                 280                 285

Phe Arg Glu Asn Ala Lys Ala Lys Thr Asp His Gly Ala Glu Ile Val
```

```
                290                 295                 300
Tyr Lys Ser Pro Val Val Ser Gly Asp Thr Ser Pro Arg His Leu Ser
305                 310                 315                 320

Asn Val Ser Ser Thr Gly Ser Ile Asp Met Val Asp Ser Pro Gln Leu
                325                 330                 335

Ala Thr Leu Ala Asp Glu Val Ser Ala Ser Leu Ala Lys Gln Gly Leu
                340                 345                 350

<210> SEQ ID NO 4
<211> LENGTH: 412
<212> TYPE: PRT
<213> ORGANISM: Homo sapiens

<400> SEQUENCE: 4

Met Ala Glu Pro Arg Gln Glu Phe Glu Val Met Glu Asp His Ala Gly
 1               5                  10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Glu Pro Gly Ser Glu Thr Ser
 50                  55                  60

Asp Ala Lys Ser Thr Pro Thr Ala Glu Ala Glu Glu Ala Gly Ile Gly
65                  70                  75                  80

Asp Thr Pro Ser Leu Glu Asp Glu Ala Ala Gly His Val Thr Gln Ala
                85                  90                  95

Arg Met Val Ser Lys Ser Lys Asp Gly Thr Gly Ser Asp Asp Lys Lys
            100                 105                 110

Ala Lys Gly Ala Asp Gly Lys Thr Lys Ile Ala Thr Pro Arg Gly Ala
        115                 120                 125

Ala Pro Pro Gly Gln Lys Gly Gln Ala Asn Ala Thr Arg Ile Pro Ala
    130                 135                 140

Lys Thr Pro Pro Ala Pro Lys Thr Pro Pro Ser Ser Gly Glu Pro Pro
145                 150                 155                 160

Lys Ser Gly Asp Arg Ser Gly Tyr Ser Ser Pro Gly Ser Pro Gly Thr
                165                 170                 175

Pro Gly Ser Arg Ser Arg Thr Pro Ser Leu Pro Thr Pro Pro Thr Arg
            180                 185                 190

Glu Pro Lys Lys Val Ala Val Val Arg Thr Pro Pro Lys Ser Pro Ser
        195                 200                 205

Ser Ala Lys Ser Arg Leu Gln Thr Ala Pro Val Pro Met Pro Asp Leu
    210                 215                 220

Lys Asn Val Lys Ser Lys Ile Gly Ser Thr Glu Asn Leu Lys His Gln
225                 230                 235                 240

Pro Gly Gly Gly Lys Val Gln Ile Ile Asn Lys Lys Leu Asp Leu Ser
                245                 250                 255

Asn Val Gln Ser Lys Cys Gly Ser Lys Asp Asn Ile Lys His Val Pro
            260                 265                 270

Gly Gly Gly Ser Val Gln Ile Val Tyr Lys Pro Val Asp Leu Ser Lys
        275                 280                 285

Val Thr Ser Lys Cys Gly Ser Leu Gly Asn Ile His His Lys Pro Gly
    290                 295                 300

Gly Gly Gln Val Glu Val Lys Ser Glu Lys Leu Asp Phe Lys Asp Arg
305                 310                 315                 320
```

```
Val Gln Ser Lys Ile Gly Ser Leu Asp Asn Ile Thr His Val Pro Gly
            325                 330                 335

Gly Gly Asn Lys Lys Ile Glu Thr His Lys Leu Thr Phe Arg Glu Asn
        340                 345                 350

Ala Lys Ala Lys Thr Asp His Gly Ala Glu Ile Val Tyr Lys Ser Pro
            355                 360                 365

Val Val Ser Gly Asp Thr Ser Pro Arg His Leu Ser Asn Val Ser Ser
370                 375                 380

Thr Gly Ser Ile Asp Met Val Asp Ser Pro Gln Leu Ala Thr Leu Ala
385                 390                 395                 400

Asp Glu Val Ser Ala Ser Leu Ala Lys Gln Gly Leu
            405                 410

<210> SEQ ID NO 5
<211> LENGTH: 758
<212> TYPE: PRT
<213> ORGANISM: Homo sapiens

<400> SEQUENCE: 5

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Glu Pro Glu Ser
        115                 120                 125

Gly Lys Val Val Gln Glu Gly Phe Leu Arg Glu Pro Gly Pro Pro Gly
    130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
            180                 185                 190

Leu Gly Asp Leu His Gln Glu Gly Pro Pro Leu Lys Gly Ala Gly Gly
        195                 200                 205

Lys Glu Arg Pro Gly Ser Lys Glu Glu Val Asp Glu Asp Arg Asp Val
    210                 215                 220

Asp Glu Ser Ser Pro Gln Asp Ser Pro Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
            260                 265                 270

Ser Lys Val Ser Thr Glu Ile Pro Ala Ser Glu Pro Asp Gly Pro Ser
        275                 280                 285
```

-continued

```
Val Gly Arg Ala Lys Gly Gln Asp Ala Pro Leu Glu Phe Thr Phe His
    290                 295                 300
Val Glu Ile Thr Pro Asn Val Gln Lys Glu Gln Ala His Ser Glu Glu
305                 310                 315                 320
His Leu Gly Arg Ala Ala Phe Pro Gly Ala Pro Gly Glu Gly Pro Glu
                325                 330                 335
Ala Arg Gly Pro Ser Leu Gly Glu Asp Thr Lys Glu Ala Asp Leu Pro
            340                 345                 350
Glu Pro Ser Glu Lys Gln Pro Ala Ala Ala Pro Arg Gly Lys Pro Val
        355                 360                 365
Ser Arg Val Pro Gln Leu Lys Ala Arg Met Val Ser Lys Ser Lys Asp
    370                 375                 380
Gly Thr Gly Ser Asp Asp Lys Lys Ala Lys Thr Ser Thr Arg Ser Ser
385                 390                 395                 400
Ala Lys Thr Leu Lys Asn Arg Pro Cys Leu Ser Pro Lys His Pro Thr
                405                 410                 415
Pro Gly Ser Ser Asp Pro Leu Ile Gln Pro Ser Ser Pro Ala Val Cys
            420                 425                 430
Pro Glu Pro Ser Ser Pro Lys His Val Ser Val Thr Ser Arg
        435                 440                 445
Thr Gly Ser Ser Gly Ala Lys Glu Met Lys Leu Lys Gly Ala Asp Gly
    450                 455                 460
Lys Thr Lys Ile Ala Thr Pro Arg Gly Ala Ala Pro Pro Gly Gln Lys
465                 470                 475                 480
Gly Gln Ala Asn Ala Thr Arg Ile Pro Ala Lys Thr Pro Pro Ala Pro
                485                 490                 495
Lys Thr Pro Pro Ser Ser Gly Glu Pro Pro Lys Ser Gly Asp Arg Ser
            500                 505                 510
Gly Tyr Ser Ser Pro Gly Ser Pro Gly Thr Pro Gly Ser Arg Ser Arg
        515                 520                 525
Thr Pro Ser Leu Pro Thr Pro Pro Thr Arg Glu Pro Lys Lys Val Ala
    530                 535                 540
Val Val Arg Thr Pro Pro Lys Ser Pro Ser Ala Lys Ser Arg Leu
545                 550                 555                 560
Gln Thr Ala Pro Val Pro Met Pro Asp Leu Lys Asn Val Lys Ser Lys
                565                 570                 575
Ile Gly Ser Thr Glu Asn Leu Lys His Gln Pro Gly Gly Gly Lys Val
            580                 585                 590
Gln Ile Ile Asn Lys Lys Leu Asp Leu Ser Asn Val Gln Ser Lys Cys
        595                 600                 605
Gly Ser Lys Asp Asn Ile Lys His Val Pro Gly Gly Gly Ser Val Gln
    610                 615                 620
Ile Val Tyr Lys Pro Val Asp Leu Ser Lys Val Thr Ser Lys Cys Gly
625                 630                 635                 640
Ser Leu Gly Asn Ile His His Lys Pro Gly Gly Gln Val Glu Val
                645                 650                 655
Lys Ser Glu Lys Leu Asp Phe Lys Asp Arg Val Gln Ser Lys Ile Gly
            660                 665                 670
Ser Leu Asp Asn Ile Thr His Val Pro Gly Gly Gly Asn Lys Lys Ile
        675                 680                 685
Glu Thr His Lys Leu Thr Phe Arg Glu Asn Ala Lys Ala Lys Thr Asp
    690                 695                 700
```

```
His Gly Ala Glu Ile Val Tyr Lys Ser Pro Val Ser Gly Asp Thr
705                 710                 715                 720

Ser Pro Arg His Leu Ser Asn Val Ser Ser Thr Gly Ser Ile Asp Met
            725                 730                 735

Val Asp Ser Pro Gln Leu Ala Thr Leu Ala Asp Glu Val Ser Ala Ser
            740                 745                 750

Leu Ala Lys Gln Gly Leu
        755

<210> SEQ ID NO 6
<211> LENGTH: 776
<212> TYPE: PRT
<213> ORGANISM: Homo sapiens

<400> SEQUENCE: 6

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
            85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Glu Pro Glu Ser
        115                 120                 125

Gly Lys Val Val Gln Glu Gly Phe Leu Arg Glu Pro Gly Pro Pro Gly
    130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
            165                 170                 175

Asp Thr Glu Gly Gly Arg His Ala Pro Glu Leu Leu Lys His Gln Leu
            180                 185                 190

Leu Gly Asp Leu His Gln Glu Gly Pro Pro Leu Lys Gly Ala Gly Gly
        195                 200                 205

Lys Glu Arg Pro Gly Ser Lys Glu Glu Val Asp Glu Asp Arg Asp Val
    210                 215                 220

Asp Glu Ser Ser Pro Gln Asp Ser Pro Pro Lys Ala Ser Pro Ala
225                 230                 235                 240

Gln Asp Gly Arg Pro Pro Gln Thr Ala Ala Arg Glu Ala Thr Ser Ile
            245                 250                 255

Pro Gly Phe Pro Ala Glu Gly Ala Ile Pro Leu Pro Val Asp Phe Leu
            260                 265                 270

Ser Lys Val Ser Thr Glu Ile Pro Ala Ser Glu Pro Asp Gly Pro Ser
        275                 280                 285

Val Gly Arg Ala Lys Gly Gln Asp Ala Pro Leu Glu Phe Thr Phe His
    290                 295                 300

Val Glu Ile Thr Pro Asn Val Gln Lys Glu Gln Ala His Ser Glu Glu
305                 310                 315                 320
```

```
His Leu Gly Arg Ala Ala Phe Pro Gly Ala Pro Gly Glu Gly Pro Glu
            325                 330                 335

Ala Arg Gly Pro Ser Leu Gly Glu Asp Thr Lys Glu Ala Asp Leu Pro
            340                 345                 350

Glu Pro Ser Glu Lys Gln Pro Ala Ala Ala Pro Arg Gly Lys Pro Val
            355                 360                 365

Ser Arg Val Pro Gln Leu Lys Ala Arg Met Val Ser Lys Ser Lys Asp
        370                 375                 380

Gly Thr Gly Ser Asp Asp Lys Lys Ala Lys Thr Ser Thr Arg Ser Ser
385                 390                 395                 400

Ala Lys Thr Leu Lys Asn Arg Pro Cys Leu Ser Pro Lys His Pro Thr
                405                 410                 415

Pro Gly Ser Ser Asp Pro Leu Ile Gln Pro Ser Ser Pro Ala Val Cys
            420                 425                 430

Pro Glu Pro Pro Ser Ser Pro Lys His Val Ser Ser Val Thr Ser Arg
            435                 440                 445

Thr Gly Ser Ser Gly Ala Lys Glu Met Lys Leu Lys Gly Ala Asp Gly
        450                 455                 460

Lys Thr Lys Ile Ala Thr Pro Arg Gly Ala Ala Pro Pro Gly Gln Lys
465                 470                 475                 480

Gly Gln Ala Asn Ala Thr Arg Ile Pro Ala Lys Thr Pro Pro Ala Pro
                485                 490                 495

Lys Thr Pro Pro Ser Ser Ala Thr Lys Gln Val Gln Arg Arg Pro Pro
            500                 505                 510

Pro Ala Gly Pro Arg Ser Glu Arg Gly Glu Pro Lys Ser Gly Asp
            515                 520                 525

Arg Ser Gly Tyr Ser Ser Pro Gly Ser Pro Thr Pro Gly Ser Arg
        530                 535                 540

Ser Arg Thr Pro Ser Leu Pro Thr Pro Pro Thr Arg Glu Pro Lys Lys
545                 550                 555                 560

Val Ala Val Val Arg Thr Pro Pro Lys Ser Pro Ser Ser Ala Lys Ser
                565                 570                 575

Arg Leu Gln Thr Ala Pro Val Pro Met Pro Asp Leu Lys Asn Val Lys
            580                 585                 590

Ser Lys Ile Gly Ser Thr Glu Asn Leu Lys His Gln Pro Gly Gly Gly
        595                 600                 605

Lys Val Gln Ile Ile Asn Lys Lys Leu Asp Leu Ser Asn Val Gln Ser
610                 615                 620

Lys Cys Gly Ser Lys Asp Asn Ile Lys His Val Pro Gly Gly Gly Ser
625                 630                 635                 640

Val Gln Ile Val Tyr Lys Pro Val Asp Leu Ser Lys Val Thr Ser Lys
                645                 650                 655

Cys Gly Ser Leu Gly Asn Ile His His Lys Pro Gly Gly Gly Gln Val
            660                 665                 670

Glu Val Lys Ser Glu Lys Leu Asp Phe Lys Asp Arg Val Gln Ser Lys
        675                 680                 685

Ile Gly Ser Leu Asp Asn Ile Thr His Val Pro Gly Gly Gly Asn Lys
        690                 695                 700

Lys Ile Glu Thr His Lys Leu Thr Phe Arg Glu Asn Ala Lys Ala Lys
705                 710                 715                 720

Thr Asp His Gly Ala Glu Ile Val Tyr Lys Ser Pro Val Val Ser Gly
                725                 730                 735
```

```
Asp Thr Ser Pro Arg His Leu Ser Asn Val Ser Ser Thr Gly Ser Ile
            740                 745                 750

Asp Met Val Asp Ser Pro Gln Leu Ala Thr Leu Ala Asp Glu Val Ser
        755                 760                 765

Ala Ser Leu Ala Lys Gln Gly Leu
    770                 775

<210> SEQ ID NO 7
<211> LENGTH: 432
<212> TYPE: PRT
<213> ORGANISM: Rattus norvegicus

<400> SEQUENCE: 7

Met Ala Glu Pro Arg Gln Glu Phe Asp Thr Met Glu Asp Gln Ala Gly
  1               5                  10                  15

Asp Tyr Thr Met Leu Gln Asp Gln Glu Gly Asp Met Asp His Gly Leu
             20                  25                  30

Lys Glu Ser Pro Pro Gln Pro Ala Asp Asp Gly Ser Glu Glu Pro
         35                  40                  45

Gly Ser Glu Thr Ser Asp Ala Lys Ser Thr Pro Thr Ala Glu Asp Val
 50                  55                  60

Thr Ala Pro Leu Val Glu Arg Ala Pro Asp Lys Gln Ala Thr Ala
 65                  70                  75                  80

Gln Ser His Thr Glu Ile Pro Glu Gly Thr Thr Ala Glu Glu Ala Gly
             85                  90                  95

Ile Gly Asp Thr Pro Asn Met Glu Asp Gln Ala Ala Gly His Val Thr
            100                 105                 110

Gln Ala Arg Val Ala Gly Val Ser Lys Asp Arg Thr Gly Asn Asp Glu
        115                 120                 125

Lys Lys Ala Lys Gly Ala Asp Gly Lys Thr Gly Ala Lys Ile Ala Thr
130                 135                 140

Pro Arg Gly Ala Ala Thr Pro Gly Gln Lys Gly Thr Ser Asn Ala Thr
145                 150                 155                 160

Arg Ile Pro Ala Lys Thr Thr Pro Ser Pro Lys Thr Pro Pro Gly Ser
                165                 170                 175

Gly Glu Pro Pro Lys Ser Gly Glu Arg Ser Gly Tyr Ser Ser Pro Gly
            180                 185                 190

Ser Pro Gly Thr Pro Gly Ser Arg Ser Arg Thr Pro Ser Leu Pro Thr
        195                 200                 205

Pro Pro Thr Arg Glu Pro Lys Lys Val Ala Val Val Arg Thr Pro Pro
210                 215                 220

Lys Ser Pro Ser Ala Ser Lys Ser Arg Leu Gln Thr Ala Pro Val Pro
225                 230                 235                 240

Met Pro Asp Leu Lys Asn Val Arg Ser Lys Ile Gly Ser Thr Glu Asn
                245                 250                 255

Leu Lys His Gln Pro Gly Gly Gly Lys Val Gln Ile Ile Asn Lys Lys
            260                 265                 270

Leu Asp Leu Ser Asn Val Gln Ser Lys Cys Gly Ser Lys Asp Asn Ile
        275                 280                 285

Lys His Val Pro Gly Gly Gly Ser Val Gln Ile Val Tyr Lys Pro Val
290                 295                 300

Asp Leu Ser Lys Val Thr Ser Lys Cys Gly Ser Leu Gly Asn Ile His
305                 310                 315                 320

His Lys Pro Gly Gly Gly Gln Val Glu Val Lys Ser Glu Lys Leu Asp
                325                 330                 335
```

-continued

```
Phe Lys Asp Arg Val Gln Ser Lys Ile Gly Ser Leu Asp Asn Ile Thr
            340                 345                 350
His Val Pro Gly Gly Asn Lys Ile Glu Thr His Lys Leu Thr
        355                 360                 365
Phe Arg Glu Asn Ala Lys Ala Lys Thr Asp His Gly Ala Glu Ile Val
370                 375                 380
Tyr Lys Ser Pro Val Val Ser Gly Asp Thr Ser Pro Arg His Leu Ser
385                 390                 395                 400
Asn Val Ser Ser Thr Gly Ser Ile Asp Met Val Asp Ser Pro Gln Leu
                405                 410                 415
Ala Thr Leu Ala Asp Glu Val Ser Ala Ser Leu Ala Lys Gln Gly Leu
            420                 425                 430

<210> SEQ ID NO 8
<211> LENGTH: 430
<212> TYPE: PRT
<213> ORGANISM: Mus musculus

<400> SEQUENCE: 8

Met Ala Asp Pro Arg Gln Glu Phe Asp Thr Met Glu Asp His Ala Gly
1               5                   10                  15
Asp Tyr Thr Leu Leu Gln Asp Gln Glu Gly Asp Met Asp His Gly Leu
            20                  25                  30
Lys Glu Ser Pro Pro Gln Pro Ala Asp Asp Gly Ala Glu Glu Pro
        35                  40                  45
Gly Ser Glu Thr Ser Asp Ala Lys Ser Thr Pro Thr Ala Glu Asp Val
    50                  55                  60
Thr Ala Pro Leu Val Asp Glu Arg Ala Pro Asp Lys Gln Ala Ala Ala
65                  70                  75                  80
Gln Pro His Thr Glu Ile Pro Glu Gly Ile Thr Ala Glu Glu Ala Gly
                85                  90                  95
Ile Gly Asp Thr Pro Asn Gln Glu Asp Gln Ala Ala Gly His Val Thr
            100                 105                 110
Gln Ala Arg Val Ala Ser Lys Asp Arg Thr Gly Asn Asp Glu Lys Lys
        115                 120                 125
Ala Lys Gly Ala Asp Gly Lys Thr Gly Ala Lys Ile Ala Thr Pro Arg
    130                 135                 140
Gly Ala Ala Ser Pro Ala Gln Lys Gly Thr Ser Asn Ala Thr Arg Ile
145                 150                 155                 160
Pro Ala Lys Thr Thr Pro Ser Pro Lys Thr Pro Pro Gly Ser Gly Glu
                165                 170                 175
Pro Pro Lys Ser Gly Glu Arg Ser Gly Tyr Ser Ser Pro Gly Ser Pro
            180                 185                 190
Gly Thr Pro Gly Ser Arg Ser Arg Thr Pro Ser Leu Pro Thr Pro Pro
        195                 200                 205
Thr Arg Glu Pro Lys Lys Val Ala Val Val Arg Thr Pro Pro Lys Ser
    210                 215                 220
Pro Ser Ala Ser Lys Ser Arg Leu Gln Thr Ala Pro Val Pro Met Pro
225                 230                 235                 240
Asp Leu Lys Asn Val Arg Ser Lys Ile Gly Ser Thr Glu Asn Leu Lys
                245                 250                 255
His Gln Pro Gly Gly Gly Lys Val Gln Ile Ile Asn Lys Lys Leu Asp
            260                 265                 270
Leu Ser Asn Val Gln Ser Lys Cys Gly Ser Lys Asp Asn Ile Lys His
```

```
                    275                 280                 285
Val Pro Gly Gly Ser Val Gln Ile Val Tyr Lys Pro Val Asp Leu
    290                 295                 300

Ser Lys Val Thr Ser Lys Cys Gly Ser Leu Gly Asn Ile His His Lys
305                 310                 315                 320

Pro Gly Gly Gly Gln Val Glu Val Lys Ser Glu Lys Leu Asp Phe Lys
                325                 330                 335

Asp Arg Val Gln Ser Lys Ile Gly Ser Leu Asp Asn Ile Thr His Val
                340                 345                 350

Pro Gly Gly Gly Asn Lys Lys Ile Glu Thr His Lys Leu Thr Phe Arg
                355                 360                 365

Glu Asn Ala Lys Ala Lys Thr Asp His Gly Ala Glu Ile Val Tyr Lys
370                 375                 380

Ser Pro Val Val Ser Gly Asp Thr Ser Pro Arg His Leu Ser Asn Val
385                 390                 395                 400

Ser Ser Thr Gly Ser Ile Asp Met Val Asp Ser Pro Gln Leu Ala Thr
                405                 410                 415

Leu Ala Asp Glu Val Ser Ala Ser Leu Ala Lys Gln Gly Leu
                420                 425                 430

<210> SEQ ID NO 9
<211> LENGTH: 555
<212> TYPE: PRT
<213> ORGANISM: Homo sapiens

<400> SEQUENCE: 9

Met Ile Gly Thr Asp Pro Arg Thr Ile Leu Lys Asp Leu Leu Pro Glu
  1               5                  10                  15

Thr Ile Pro Pro Pro Glu Leu Asp Asp Met Thr Leu Trp Gln Ile Val
                 20                  25                  30

Ile Asn Ile Leu Ser Glu Pro Pro Lys Arg Lys Lys Arg Lys Asp Ile
                 35                  40                  45

Asn Thr Ile Glu Asp Ala Val Lys Leu Leu Gln Glu Cys Lys Lys Ile
 50                  55                  60

Ile Val Leu Thr Gly Ala Gly Val Ser Val Ser Cys Gly Ile Pro Asp
 65                  70                  75                  80

Phe Arg Ser Arg Asp Gly Ile Tyr Ala Arg Leu Ala Val Asp Phe Pro
                 85                  90                  95

Asp Leu Pro Asp Pro Gln Ala Met Phe Asp Ile Glu Tyr Phe Arg Lys
                100                 105                 110

Asp Pro Arg Pro Phe Phe Lys Phe Ala Lys Glu Ile Tyr Pro Gly Gln
                115                 120                 125

Phe Gln Pro Ser Leu Cys His Lys Phe Ile Ala Leu Ser Asp Lys Glu
                130                 135                 140

Gly Lys Leu Leu Arg Asn Tyr Thr Gln Asn Ile Asp Thr Leu Glu Gln
145                 150                 155                 160

Val Ala Gly Ile Gln Arg Ile Ile Gln Cys His Gly Ser Phe Ala Thr
                165                 170                 175

Ala Ser Cys Leu Ile Cys Lys Tyr Lys Val Asp Cys Glu Ala Val Arg
                180                 185                 190

Gly Ala Leu Phe Ser Gln Val Val Pro Arg Cys Pro Arg Cys Pro Ala
                195                 200                 205

Asp Glu Pro Leu Ala Ile Met Lys Pro Glu Ile Val Phe Phe Gly Glu
                210                 215                 220
```

```
Asn Leu Pro Glu Gln Phe His Arg Ala Met Lys Tyr Asp Lys Asp Glu
225                 230                 235                 240

Val Asp Leu Leu Ile Val Ile Gly Ser Ser Leu Lys Val Arg Pro Val
            245                 250                 255

Ala Leu Ile Pro Ser Ser Ile Pro His Glu Val Pro Gln Ile Leu Ile
            260                 265                 270

Asn Arg Glu Pro Leu Pro His Leu His Phe Asp Val Glu Leu Leu Gly
        275                 280                 285

Asp Cys Asp Val Ile Ile Asn Glu Leu Cys His Arg Leu Gly Gly Glu
        290                 295                 300

Tyr Ala Lys Leu Cys Cys Asn Pro Val Lys Leu Ser Glu Ile Thr Glu
305                 310                 315                 320

Lys Pro Pro Arg Thr Gln Lys Glu Leu Ala Tyr Leu Ser Glu Leu Pro
                325                 330                 335

Pro Thr Pro Leu His Val Ser Glu Asp Ser Ser Ser Pro Glu Arg Thr
            340                 345                 350

Ser Pro Pro Asp Ser Ser Val Ile Val Thr Leu Leu Asp Gln Ala Ala
        355                 360                 365

Lys Ser Asn Asp Asp Leu Asp Val Ser Glu Ser Lys Gly Cys Met Glu
370                 375                 380

Glu Lys Pro Gln Glu Val Gln Thr Ser Arg Asn Val Glu Ser Ile Ala
385                 390                 395                 400

Glu Gln Met Glu Asn Pro Asp Leu Lys Asn Val Gly Ser Ser Thr Gly
                405                 410                 415

Glu Lys Asn Glu Arg Thr Ser Val Ala Gly Thr Val Lys Cys Trp
            420                 425                 430

Pro Asn Arg Val Ala Lys Glu Gln Ile Ser Arg Arg Leu Asp Gly Asn
        435                 440                 445

Gln Tyr Leu Phe Leu Pro Pro Asn Arg Tyr Ile Phe His Gly Ala Glu
    450                 455                 460

Val Tyr Ser Asp Ser Glu Asp Val Leu Ser Ser Ser Ser Cys Gly
465                 470                 475                 480

Ser Asn Ser Asp Ser Gly Thr Cys Gln Ser Pro Ser Leu Glu Glu Pro
                485                 490                 495

Met Glu Asp Glu Ser Glu Ile Glu Phe Tyr Asn Gly Leu Glu Asp
            500                 505                 510

Glu Pro Asp Val Pro Glu Arg Ala Gly Gly Ala Gly Phe Gly Thr Asp
        515                 520                 525

Gly Asp Asp Gln Glu Ala Ile Asn Glu Ala Ile Ser Val Lys Gln Glu
530                 535                 540

Val Thr Asp Met Asn Tyr Pro Ser Asn Lys Ser
545                 550                 555

<210> SEQ ID NO 10
<211> LENGTH: 747
<212> TYPE: PRT
<213> ORGANISM: Homo sapiens

<400> SEQUENCE: 10

Met Ala Asp Glu Ala Leu Ala Leu Gln Pro Gly Gly Ser Pro Ser
 1               5                  10                  15

Ala Ala Gly Ala Asp Arg Glu Ala Ala Ser Ser Pro Ala Gly Glu Pro
            20                  25                  30

Leu Arg Lys Arg Pro Arg Arg Asp Gly Pro Gly Leu Glu Arg Ser Pro
        35                  40                  45
```

```
Gly Glu Pro Gly Gly Ala Ala Pro Glu Arg Glu Val Pro Ala Ala
 50                  55                  60
Arg Gly Cys Pro Gly Ala Ala Ala Ala Leu Trp Arg Glu Ala Glu
 65                  70                  75                  80
Ala Glu Ala Ala Ala Ala Gly Gly Glu Gln Glu Ala Gln Ala Thr Ala
                     85                  90                  95
Ala Ala Gly Glu Gly Asp Asn Gly Pro Gly Leu Gln Gly Pro Ser Arg
                100                 105                 110
Glu Pro Pro Leu Ala Asp Asn Leu Tyr Asp Glu Asp Asp Asp Asp Glu
            115                 120                 125
Gly Glu Glu Glu Glu Ala Ala Ala Ala Ile Gly Tyr Arg Asp
 130                 135                 140
Asn Leu Leu Phe Gly Asp Glu Ile Ile Thr Asn Gly Phe His Ser Cys
145                 150                 155                 160
Glu Ser Asp Glu Glu Asp Arg Ala Ser His Ala Ser Ser Ser Asp Trp
                165                 170                 175
Thr Pro Arg Pro Arg Ile Gly Pro Tyr Thr Phe Val Gln Gln His Leu
                180                 185                 190
Met Ile Gly Thr Asp Pro Arg Thr Ile Leu Lys Asp Leu Leu Pro Glu
                195                 200                 205
Thr Ile Pro Pro Pro Glu Leu Asp Asp Met Thr Leu Trp Gln Ile Val
210                 215                 220
Ile Asn Ile Leu Ser Glu Pro Pro Lys Arg Lys Lys Arg Lys Asp Ile
225                 230                 235                 240
Asn Thr Ile Glu Asp Ala Val Lys Leu Leu Gln Glu Cys Lys Lys Ile
                245                 250                 255
Ile Val Leu Thr Gly Ala Gly Val Ser Val Ser Cys Gly Ile Pro Asp
                260                 265                 270
Phe Arg Ser Arg Asp Gly Ile Tyr Ala Arg Leu Ala Val Asp Phe Pro
            275                 280                 285
Asp Leu Pro Asp Pro Gln Ala Met Phe Asp Ile Glu Tyr Phe Arg Lys
            290                 295                 300
Asp Pro Arg Pro Phe Phe Lys Phe Ala Lys Glu Ile Tyr Pro Gly Gln
305                 310                 315                 320
Phe Gln Pro Ser Leu Cys His Lys Phe Ile Ala Leu Ser Asp Lys Glu
                325                 330                 335
Gly Lys Leu Leu Arg Asn Tyr Thr Gln Asn Ile Asp Thr Leu Glu Gln
                340                 345                 350
Val Ala Gly Ile Gln Arg Ile Gln Cys His Gly Ser Phe Ala Thr
            355                 360                 365
Ala Ser Cys Leu Ile Cys Lys Tyr Lys Val Asp Cys Glu Ala Val Arg
370                 375                 380
Gly Asp Ile Phe Asn Gln Val Val Pro Arg Cys Pro Arg Cys Pro Ala
385                 390                 395                 400
Asp Glu Pro Leu Ala Ile Met Lys Pro Glu Ile Val Phe Phe Gly Glu
                405                 410                 415
Asn Leu Pro Glu Gln Phe His Arg Ala Met Lys Tyr Asp Lys Asp Glu
                420                 425                 430
Val Asp Leu Leu Ile Val Ile Gly Ser Ser Leu Lys Val Arg Pro Val
            435                 440                 445
Ala Leu Ile Pro Ser Ser Ile Pro His Glu Val Pro Gln Ile Leu Ile
 450                 455                 460
```

-continued

Asn Arg Glu Pro Leu Pro His Leu His Phe Asp Val Glu Leu Leu Gly
465                 470                 475                 480

Asp Cys Asp Val Ile Ile Asn Glu Leu Cys His Arg Leu Gly Gly Glu
            485                 490                 495

Tyr Ala Lys Leu Cys Cys Asn Pro Val Lys Leu Ser Glu Ile Thr Glu
            500                 505                 510

Lys Pro Pro Arg Thr Gln Lys Glu Leu Ala Tyr Leu Ser Glu Leu Pro
            515                 520                 525

Pro Thr Pro Leu His Val Ser Glu Asp Ser Ser Pro Glu Arg Thr
            530                 535                 540

Ser Pro Pro Asp Ser Ser Val Ile Val Thr Leu Leu Asp Gln Ala Ala
545                 550                 555                 560

Lys Ser Asn Asp Leu Asp Val Ser Glu Ser Lys Gly Cys Met Glu
            565                 570                 575

Glu Lys Pro Gln Glu Val Gln Thr Ser Arg Asn Val Glu Ser Ile Ala
            580                 585                 590

Glu Gln Met Glu Asn Pro Asp Leu Lys Asn Val Gly Ser Ser Thr Gly
            595                 600                 605

Glu Lys Asn Glu Arg Thr Ser Val Ala Gly Thr Val Arg Lys Cys Trp
            610                 615                 620

Pro Asn Arg Val Ala Lys Glu Gln Ile Ser Arg Arg Leu Asp Gly Asn
625                 630                 635                 640

Gln Tyr Leu Phe Leu Pro Pro Asn Arg Tyr Ile Phe His Gly Ala Glu
            645                 650                 655

Val Tyr Ser Asp Ser Glu Asp Val Leu Ser Ser Ser Cys Gly
            660                 665                 670

Ser Asn Ser Asp Ser Gly Thr Cys Gln Ser Pro Ser Leu Glu Glu Pro
            675                 680                 685

Met Glu Asp Glu Ser Glu Ile Glu Glu Phe Tyr Asn Gly Leu Glu Asp
            690                 695                 700

Glu Pro Asp Val Pro Glu Arg Ala Gly Gly Ala Gly Phe Gly Thr Asp
705                 710                 715                 720

Gly Asp Asp Gln Glu Ala Ile Asn Glu Ala Ile Ser Val Lys Gln Glu
            725                 730                 735

Val Thr Asp Met Asn Tyr Pro Ser Asn Lys Ser
            740                 745

<210> SEQ ID NO 11
<211> LENGTH: 452
<212> TYPE: PRT
<213> ORGANISM: Homo sapiens

<400> SEQUENCE: 11

Met Phe Asp Ile Glu Tyr Phe Arg Lys Asp Pro Arg Pro Phe Phe Lys
1               5                   10                  15

Phe Ala Lys Glu Ile Tyr Pro Gly Gln Phe Gln Pro Ser Leu Cys His
            20                  25                  30

Lys Phe Ile Ala Leu Ser Asp Lys Glu Gly Lys Leu Leu Arg Asn Tyr
            35                  40                  45

Thr Gln Asn Ile Asp Thr Leu Glu Gln Val Ala Gly Ile Gln Arg Ile
            50                  55                  60

Ile Gln Cys His Gly Ser Phe Ala Thr Ala Ser Cys Leu Ile Cys Lys
65                  70                  75                  80

Tyr Lys Val Asp Cys Glu Ala Val Arg Gly Asp Ile Phe Asn Gln Val
            85                  90                  95

```
Val Pro Arg Cys Pro Arg Cys Pro Ala Asp Glu Pro Leu Ala Ile Met
            100                 105                 110
Lys Pro Glu Ile Val Phe Phe Gly Glu Asn Leu Pro Glu Gln Phe His
            115                 120                 125
Arg Ala Met Lys Tyr Asp Lys Asp Glu Val Asp Leu Leu Ile Val Ile
        130                 135                 140
Gly Ser Ser Leu Lys Val Arg Pro Val Ala Leu Ile Pro Ser Ser Ile
145                 150                 155                 160
Pro His Glu Val Pro Gln Ile Leu Ile Asn Arg Glu Pro Leu Pro His
                165                 170                 175
Leu His Phe Asp Val Glu Leu Leu Gly Asp Cys Asp Val Ile Ile Asn
            180                 185                 190
Glu Leu Cys His Arg Leu Gly Gly Glu Tyr Ala Lys Leu Cys Cys Asn
            195                 200                 205
Pro Val Lys Leu Ser Glu Ile Thr Glu Lys Pro Pro Arg Thr Gln Lys
        210                 215                 220
Glu Leu Ala Tyr Leu Ser Glu Leu Pro Pro Thr Pro Leu His Val Ser
225                 230                 235                 240
Glu Asp Ser Ser Ser Pro Glu Arg Thr Ser Pro Pro Asp Ser Ser Val
                245                 250                 255
Ile Val Thr Leu Leu Asp Gln Ala Ala Lys Ser Asn Asp Asp Leu Asp
            260                 265                 270
Val Ser Glu Ser Lys Gly Cys Met Glu Glu Lys Pro Gln Glu Val Gln
            275                 280                 285
Thr Ser Arg Asn Val Glu Ser Ile Ala Glu Gln Met Glu Asn Pro Asp
        290                 295                 300
Leu Lys Asn Val Gly Ser Ser Thr Gly Glu Lys Asn Glu Arg Thr Ser
305                 310                 315                 320
Val Ala Gly Thr Val Arg Lys Cys Trp Pro Asn Arg Val Ala Lys Glu
                325                 330                 335
Gln Ile Ser Arg Arg Leu Asp Gly Asn Gln Tyr Leu Phe Leu Pro Pro
            340                 345                 350
Asn Arg Tyr Ile Phe His Gly Ala Glu Val Tyr Ser Asp Ser Glu Asp
            355                 360                 365
Asp Val Leu Ser Ser Ser Ser Cys Gly Ser Asn Ser Asp Ser Gly Thr
        370                 375                 380
Cys Gln Ser Pro Ser Leu Glu Glu Pro Met Glu Asp Glu Ser Glu Ile
385                 390                 395                 400
Glu Glu Phe Tyr Asn Gly Leu Glu Asp Glu Pro Asp Val Pro Glu Arg
                405                 410                 415
Ala Gly Gly Ala Gly Phe Gly Thr Asp Gly Asp Gln Glu Ala Ile
            420                 425                 430
Asn Glu Ala Ile Ser Val Lys Gln Glu Val Thr Asp Met Asn Tyr Pro
        435                 440                 445
Ser Asn Lys Ser
    450

<210> SEQ ID NO 12
<211> LENGTH: 2414
<212> TYPE: PRT
<213> ORGANISM: Homo sapiens

<400> SEQUENCE: 12

Met Ala Glu Asn Val Val Glu Pro Gly Pro Pro Ser Ala Lys Arg Pro
```

-continued

```
                1               5                   10                  15
        Lys Leu Ser Ser Pro Ala Leu Ser Ala Ser Ala Ser Asp Gly Thr Asp
                        20                  25                  30
        Phe Gly Ser Leu Phe Asp Leu Glu His Asp Leu Pro Asp Glu Leu Ile
                        35                  40                  45
        Asn Ser Thr Glu Leu Gly Leu Thr Asn Gly Gly Asp Ile Asn Gln Leu
        50                      55                  60
        Gln Thr Ser Leu Gly Met Val Gln Asp Ala Ala Ser Lys His Lys Gln
        65                      70                  75                  80
        Leu Ser Glu Leu Leu Arg Ser Gly Ser Ser Pro Asn Leu Asn Met Gly
                        85                  90                  95
        Val Gly Gly Pro Gly Gln Val Met Ala Ser Gln Ala Gln Gln Ser Ser
                        100                 105                 110
        Pro Gly Leu Gly Leu Ile Asn Ser Met Val Lys Ser Pro Met Thr Gln
                        115                 120                 125
        Ala Gly Leu Thr Ser Pro Asn Met Gly Met Gly Thr Ser Gly Pro Asn
                        130                 135                 140
        Gln Gly Pro Thr Gln Ser Thr Gly Met Met Asn Ser Pro Val Asn Gln
        145                     150                 155                 160
        Pro Ala Met Gly Met Asn Thr Gly Met Asn Ala Gly Met Asn Pro Gly
                        165                 170                 175
        Met Leu Ala Ala Gly Asn Gly Gln Gly Ile Met Pro Asn Gln Val Met
                        180                 185                 190
        Asn Gly Ser Ile Gly Ala Gly Arg Gly Arg Gln Asn Met Gln Tyr Pro
                        195                 200                 205
        Asn Pro Gly Met Gly Ser Ala Gly Asn Leu Leu Thr Glu Pro Leu Gln
                        210                 215                 220
        Gln Gly Ser Pro Gln Met Gly Gly Gln Thr Gly Leu Arg Gly Pro Gln
        225                     230                 235                 240
        Pro Leu Lys Met Gly Met Met Asn Asn Pro Asn Pro Tyr Gly Ser Pro
                        245                 250                 255
        Tyr Thr Gln Asn Pro Gly Gln Gln Ile Gly Ala Ser Gly Leu Gly Leu
                        260                 265                 270
        Gln Ile Gln Thr Lys Thr Val Leu Ser Asn Asn Leu Ser Pro Phe Ala
                        275                 280                 285
        Met Asp Lys Lys Ala Val Pro Gly Gly Met Pro Asn Met Gly Gln
                        290                 295                 300
        Gln Pro Ala Pro Gln Val Gln Gln Pro Gly Leu Val Thr Pro Val Ala
        305                     310                 315                 320
        Gln Gly Met Gly Ser Gly Ala His Thr Ala Asp Pro Glu Lys Arg Lys
                        325                 330                 335
        Leu Ile Gln Gln Gln Leu Val Leu Leu Leu His Ala His Lys Cys Gln
                        340                 345                 350
        Arg Arg Glu Gln Ala Asn Gly Glu Val Arg Gln Cys Asn Leu Pro His
                        355                 360                 365
        Cys Arg Thr Met Lys Asn Val Leu Asn His Met Thr His Cys Gln Ser
                        370                 375                 380
        Gly Lys Ser Cys Gln Val Ala His Cys Ala Ser Ser Arg Gln Ile Ile
        385                     390                 395                 400
        Ser His Trp Lys Asn Cys Thr Arg His Asp Cys Pro Val Cys Leu Pro
                        405                 410                 415
        Leu Lys Asn Ala Gly Asp Lys Arg Asn Gln Gln Pro Ile Leu Thr Gly
                        420                 425                 430
```

```
Ala Pro Val Gly Leu Gly Asn Pro Ser Ser Leu Gly Val Gly Gln Gln
        435                 440                 445
Ser Ala Pro Asn Leu Ser Thr Val Ser Gln Ile Asp Pro Ser Ser Ile
450                 455                 460
Glu Arg Ala Tyr Ala Ala Leu Gly Leu Pro Tyr Gln Val Asn Gln Met
465                 470                 475                 480
Pro Thr Gln Pro Gln Val Gln Ala Lys Asn Gln Gln Asn Gln Gln Pro
                485                 490                 495
Gly Gln Ser Pro Gln Gly Met Arg Pro Met Ser Asn Met Ser Ala Ser
                500                 505                 510
Pro Met Gly Val Asn Gly Gly Val Gly Val Gln Thr Pro Ser Leu Leu
        515                 520                 525
Ser Asp Ser Met Leu His Ser Ala Ile Asn Ser Gln Asn Pro Met Met
530                 535                 540
Ser Glu Asn Ala Ser Val Pro Ser Leu Gly Pro Met Pro Thr Ala Ala
545                 550                 555                 560
Gln Pro Ser Thr Thr Gly Ile Arg Lys Gln Trp His Glu Asp Ile Thr
                565                 570                 575
Gln Asp Leu Arg Asn His Leu Val His Lys Leu Val Gln Ala Ile Phe
                580                 585                 590
Pro Thr Pro Asp Pro Ala Ala Leu Lys Asp Arg Arg Met Glu Asn Leu
        595                 600                 605
Val Ala Tyr Ala Arg Lys Val Glu Gly Asp Met Tyr Glu Ser Ala Asn
610                 615                 620
Asn Arg Ala Glu Tyr Tyr His Leu Leu Ala Glu Lys Ile Tyr Lys Ile
625                 630                 635                 640
Gln Lys Glu Leu Glu Glu Lys Arg Arg Thr Arg Leu Gln Lys Gln Asn
                645                 650                 655
Met Leu Pro Asn Ala Ala Gly Met Val Pro Val Ser Met Asn Pro Gly
                660                 665                 670
Pro Asn Met Gly Gln Pro Gln Pro Gly Met Thr Ser Asn Gly Pro Leu
        675                 680                 685
Pro Asp Pro Ser Met Ile Arg Gly Ser Val Pro Asn Gln Met Met Pro
        690                 695                 700
Arg Ile Thr Pro Gln Ser Gly Leu Asn Gln Phe Gly Gln Met Ser Met
705                 710                 715                 720
Ala Gln Pro Pro Ile Val Pro Arg Gln Thr Pro Pro Leu Gln His His
                725                 730                 735
Gly Gln Leu Ala Gln Pro Gly Ala Leu Asn Pro Pro Met Gly Tyr Gly
                740                 745                 750
Pro Arg Met Gln Gln Pro Ser Asn Gln Gly Gln Phe Leu Pro Gln Thr
        755                 760                 765
Gln Phe Pro Ser Gln Gly Met Asn Val Thr Asn Ile Pro Leu Ala Pro
        770                 775                 780
Ser Ser Gly Gln Ala Pro Val Ser Gln Ala Gln Met Ser Ser Ser Ser
785                 790                 795                 800
Cys Pro Val Asn Ser Pro Ile Met Pro Pro Gly Ser Gln Gly Ser His
                805                 810                 815
Ile His Cys Pro Gln Leu Pro Gln Pro Ala Leu His Gln Asn Ser Pro
                820                 825                 830
Ser Pro Val Pro Ser Arg Thr Pro Thr Pro His Thr Pro Pro Ser
        835                 840                 845
```

```
Ile Gly Ala Gln Gln Pro Pro Ala Thr Thr Ile Pro Ala Pro Val Pro
850                 855                 860

Thr Pro Pro Ala Met Pro Pro Gly Pro Gln Ser Gln Ala Leu His Pro
865                 870                 875                 880

Pro Pro Arg Gln Thr Pro Thr Pro Pro Thr Thr Gln Leu Pro Gln Gln
                885                 890                 895

Val Gln Pro Ser Leu Pro Ala Ala Pro Ser Ala Asp Gln Pro Gln Gln
            900                 905                 910

Gln Pro Arg Ser Gln Gln Ser Thr Ala Ala Ser Val Pro Thr Pro Thr
            915                 920                 925

Ala Pro Leu Leu Pro Pro Gln Pro Ala Thr Pro Leu Ser Gln Pro Ala
930                 935                 940

Val Ser Ile Glu Gly Gln Val Ser Asn Pro Pro Ser Thr Ser Ser Thr
945                 950                 955                 960

Glu Val Asn Ser Gln Ala Ile Ala Glu Lys Gln Pro Ser Gln Glu Val
                965                 970                 975

Lys Met Glu Ala Lys Met Glu Val Asp Gln Pro Glu Pro Ala Asp Thr
            980                 985                 990

Gln Pro Glu Asp Ile Ser Glu Ser Lys Val Glu Asp Cys Lys Met Glu
            995                 1000                1005

Ser Thr Glu Thr Glu Glu Arg Ser Thr Glu Leu Lys Thr Glu Ile Lys
    1010                1015                1020

Glu Glu Glu Asp Gln Pro Ser Thr Ser Ala Thr Gln Ser Ser Pro Ala
1025                1030                1035                1040

Pro Gly Gln Ser Lys Lys Lys Ile Phe Lys Pro Glu Glu Leu Arg Gln
                1045                1050                1055

Ala Leu Met Pro Thr Leu Glu Ala Leu Tyr Arg Gln Asp Pro Glu Ser
            1060                1065                1070

Leu Pro Phe Arg Gln Pro Val Asp Pro Gln Leu Leu Gly Ile Pro Asp
            1075                1080                1085

Tyr Phe Asp Ile Val Lys Ser Pro Met Asp Leu Ser Thr Ile Lys Arg
            1090                1095                1100

Lys Leu Asp Thr Gly Gln Tyr Gln Glu Pro Trp Gln Tyr Val Asp Asp
1105                1110                1115                1120

Ile Trp Leu Met Phe Asn Asn Ala Trp Leu Tyr Asn Arg Lys Thr Ser
                1125                1130                1135

Arg Val Tyr Lys Tyr Cys Ser Lys Leu Ser Glu Val Phe Glu Gln Glu
            1140                1145                1150

Ile Asp Pro Val Met Gln Ser Leu Gly Tyr Cys Cys Gly Arg Lys Leu
            1155                1160                1165

Glu Phe Ser Pro Gln Thr Leu Cys Cys Tyr Gly Lys Gln Leu Cys Thr
            1170                1175                1180

Ile Pro Arg Asp Ala Thr Tyr Tyr Ser Tyr Gln Asn Arg Tyr His Phe
1185                1190                1195                1200

Cys Glu Lys Cys Phe Asn Glu Ile Gln Gly Glu Ser Val Ser Leu Gly
                1205                1210                1215

Asp Asp Pro Ser Gln Pro Gln Thr Thr Ile Asn Lys Glu Gln Phe Ser
            1220                1225                1230

Lys Arg Lys Asn Asp Thr Leu Asp Pro Glu Leu Phe Val Glu Cys Thr
            1235                1240                1245

Glu Cys Gly Arg Lys Met His Gln Ile Cys Val Leu His His Glu Ile
            1250                1255                1260

Ile Trp Pro Ala Gly Phe Val Cys Asp Gly Cys Leu Lys Lys Ser Ala
```

```
                1265                1270                1275                1280
Arg Thr Arg Lys Glu Asn Lys Phe Ser Ala Lys Arg Leu Pro Ser Thr
                1285                1290                1295
Arg Leu Gly Thr Phe Leu Glu Asn Arg Val Asn Asp Phe Leu Arg Arg
                1300                1305                1310
Gln Asn His Pro Glu Ser Gly Glu Val Thr Val Arg Val His Ala
        1315                1320                1325
Ser Asp Lys Thr Val Glu Val Lys Pro Gly Met Lys Ala Arg Phe Val
        1330                1335                1340
Asp Ser Gly Glu Met Ala Glu Ser Phe Pro Tyr Arg Thr Lys Ala Leu
1345                1350                1355                1360
Phe Ala Phe Glu Glu Ile Asp Gly Val Asp Leu Cys Phe Phe Gly Met
                1365                1370                1375
His Val Gln Glu Tyr Gly Ser Asp Cys Pro Pro Asn Gln Arg Arg
        1380                1385                1390
Val Tyr Ile Ser Tyr Leu Asp Ser Val His Phe Phe Arg Pro Lys Cys
        1395                1400                1405
Leu Arg Thr Ala Val Tyr His Glu Ile Leu Ile Gly Tyr Leu Glu Tyr
        1410                1415                1420
Val Lys Lys Leu Gly Tyr Thr Thr Gly His Ile Trp Ala Cys Pro Pro
1425                1430                1435                1440
Ser Glu Gly Asp Asp Tyr Ile Phe His Cys His Pro Asp Gln Lys
                1445                1450                1455
Ile Pro Lys Pro Lys Arg Leu Gln Glu Trp Tyr Lys Lys Met Leu Asp
                1460                1465                1470
Lys Ala Val Ser Glu Arg Ile Val His Asp Tyr Lys Asp Ile Phe Lys
        1475                1480                1485
Gln Ala Thr Glu Asp Arg Leu Thr Ser Ala Lys Glu Leu Pro Tyr Phe
        1490                1495                1500
Glu Gly Asp Phe Trp Pro Asn Val Leu Glu Glu Ser Ile Lys Glu Leu
1505                1510                1515                1520
Glu Gln Glu Glu Glu Glu Arg Lys Arg Glu Glu Asn Thr Ser Asn Glu
                1525                1530                1535
Ser Thr Asp Val Thr Lys Gly Asp Ser Lys Asn Ala Lys Lys Lys Asn
                1540                1545                1550
Asn Lys Lys Thr Ser Lys Asn Lys Ser Ser Leu Ser Arg Gly Asn Lys
        1555                1560                1565
Lys Lys Pro Gly Met Pro Asn Val Ser Asn Asp Leu Ser Gln Lys Leu
        1570                1575                1580
Tyr Ala Thr Met Glu Lys His Lys Glu Val Phe Phe Val Ile Arg Leu
1585                1590                1595                1600
Ile Ala Gly Pro Ala Ala Asn Ser Leu Pro Pro Ile Val Asp Pro Asp
                1605                1610                1615
Pro Leu Ile Pro Cys Asp Leu Met Asp Gly Arg Asp Ala Phe Leu Thr
                1620                1625                1630
Leu Ala Arg Asp Lys His Leu Glu Phe Ser Ser Leu Arg Arg Ala Gln
        1635                1640                1645
Trp Ser Thr Met Cys Met Leu Val Glu Leu His Thr Gln Ser Gln Asp
        1650                1655                1660
Arg Phe Val Tyr Thr Cys Asn Glu Cys Lys His His Val Glu Thr Arg
1665                1670                1675                1680
Trp His Cys Thr Val Cys Glu Asp Tyr Asp Leu Cys Ile Thr Cys Tyr
                1685                1690                1695
```

```
Asn Thr Lys Asn His Asp His Lys Met Glu Lys Leu Gly Leu Gly Leu
                1700                1705                1710

Asp Asp Glu Ser Asn Asn Gln Ala Ala Thr Gln Ser Pro Gly
        1715                1720                1725

Asp Ser Arg Arg Leu Ser Ile Gln Arg Cys Ile Gln Ser Leu Val His
            1730                1735                1740

Ala Cys Gln Cys Arg Asn Ala Asn Cys Ser Leu Pro Ser Cys Gln Lys
1745                1750                1755                1760

Met Lys Arg Val Val Gln His Thr Lys Gly Cys Lys Arg Lys Thr Asn
                1765                1770                1775

Gly Gly Cys Pro Ile Cys Lys Gln Leu Ile Ala Leu Cys Cys Tyr His
            1780                1785                1790

Ala Lys His Cys Gln Glu Asn Lys Cys Pro Val Pro Phe Cys Leu Asn
        1795                1800                1805

Ile Lys Gln Lys Leu Arg Gln Gln Leu Gln His Arg Leu Gln Gln
    1810                1815                1820

Ala Gln Met Leu Arg Arg Arg Met Ala Ser Met Gln Arg Thr Gly Val
1825                1830                1835                1840

Val Gly Gln Gln Gln Gly Leu Pro Ser Pro Thr Pro Ala Thr Pro Thr
                1845                1850                1855

Thr Pro Thr Gly Gln Gln Pro Thr Thr Pro Gln Thr Pro Gln Pro Thr
            1860                1865                1870

Ser Gln Pro Gln Pro Thr Pro Pro Asn Ser Met Pro Pro Tyr Leu Pro
        1875                1880                1885

Arg Thr Gln Ala Ala Gly Pro Val Ser Gln Gly Lys Ala Ala Gly Gln
    1890                1895                1900

Val Thr Pro Pro Thr Pro Pro Gln Thr Ala Gln Pro Pro Leu Pro Gly
1905                1910                1915                1920

Pro Pro Pro Ala Ala Val Glu Met Ala Met Gln Ile Gln Arg Ala Ala
                1925                1930                1935

Glu Thr Gln Arg Gln Met Ala His Val Gln Ile Phe Gln Arg Pro Ile
            1940                1945                1950

Gln His Gln Met Pro Pro Met Thr Pro Met Ala Pro Met Gly Met Asn
        1955                1960                1965

Pro Pro Pro Met Thr Arg Gly Pro Ser Gly His Leu Glu Pro Gly Met
    1970                1975                1980

Gly Pro Thr Gly Met Gln Gln Pro Pro Trp Ser Gln Gly Gly Leu
1985                1990                1995                2000

Pro Gln Pro Gln Gln Leu Gln Ser Gly Met Pro Arg Pro Ala Met Met
                2005                2010                2015

Ser Val Ala Gln His Gly Gln Pro Leu Asn Met Ala Pro Gln Pro Gly
            2020                2025                2030

Leu Gly Gln Val Gly Ile Ser Pro Leu Lys Pro Gly Thr Val Ser Gln
        2035                2040                2045

Gln Ala Leu Gln Asn Leu Leu Arg Thr Leu Arg Ser Pro Ser Ser Pro
    2050                2055                2060

Leu Gln Gln Gln Gln Val Leu Ser Ile Leu His Ala Asn Pro Gln Leu
2065                2070                2075                2080

Leu Ala Ala Phe Ile Lys Gln Arg Ala Ala Lys Tyr Ala Asn Ser Asn
                2085                2090                2095

Pro Gln Pro Ile Pro Gly Gln Pro Gly Met Pro Gln Gly Gln Pro Gly
            2100                2105                2110
```

```
Leu Gln Pro Pro Thr Met Pro Gly Gln Gln Gly Val His Ser Asn Pro
        2115                2120                2125

Ala Met Gln Asn Met Asn Pro Met Gln Ala Gly Val Gln Arg Ala Gly
    2130                2135                2140

Leu Pro Gln Gln Gln Pro Gln Gln Leu Gln Pro Pro Met Gly Gly
2145                2150                2155                2160

Met Ser Pro Gln Ala Gln Gln Met Asn Met Asn His Asn Thr Met Pro
            2165                2170                2175

Ser Gln Phe Arg Asp Ile Leu Arg Arg Gln Met Met Gln Gln Gln
        2180                2185                2190

Gln Gln Gln Gly Ala Gly Pro Gly Ile Gly Pro Gly Met Ala Asn His
        2195                2200                2205

Asn Gln Phe Gln Gln Pro Gln Gly Val Gly Tyr Pro Pro Gln Gln Gln
    2210                2215                2220

Gln Arg Met Gln His His Met Gln Met Gln Gln Gly Asn Met Gly
2225                2230                2235                2240

Gln Ile Gly Gln Leu Pro Gln Ala Leu Gly Ala Glu Ala Gly Ala Ser
            2245                2250                2255

Leu Gln Ala Tyr Gln Gln Arg Leu Leu Gln Gln Gln Met Gly Ser Pro
        2260                2265                2270

Val Gln Pro Asn Pro Met Ser Pro Gln Gln His Met Leu Pro Asn Gln
        2275                2280                2285

Ala Gln Ser Pro His Leu Gln Gly Gln Gln Ile Pro Asn Ser Leu Ser
    2290                2295                2300

Asn Gln Val Arg Ser Pro Gln Pro Val Pro Ser Pro Arg Pro Gln Ser
2305                2310                2315                2320

Gln Pro Pro His Ser Ser Pro Ser Pro Arg Met Gln Pro Gln Pro Ser
            2325                2330                2335

Pro His His Val Ser Pro Gln Thr Ser Ser Pro His Pro Gly Leu Val
        2340                2345                2350

Ala Ala Gln Ala Asn Pro Met Glu Gln Gly His Phe Ala Ser Pro Asp
        2355                2360                2365

Gln Asn Ser Met Leu Ser Gln Leu Ala Ser Asn Pro Gly Met Ala Asn
    2370                2375                2380

Leu His Gly Ala Ser Ala Thr Asp Leu Gly Leu Ser Thr Asp Asn Ser
2385                2390                2395                2400

Asp Leu Asn Ser Asn Leu Ser Gln Ser Thr Leu Asp Ile His
            2405                2410

<210> SEQ ID NO 13
<211> LENGTH: 11
<212> TYPE: PRT
<213> ORGANISM: Artificial Sequence
<220> FEATURE:
<223> OTHER INFORMATION: Synthetic peptide

<400> SEQUENCE: 13

Tyr Gly Arg Lys Lys Arg Arg Gln Arg Arg
1               5                   10

<210> SEQ ID NO 14
<211> LENGTH: 14
<212> TYPE: PRT
<213> ORGANISM: Artificial Sequence
<220> FEATURE:
<223> OTHER INFORMATION: Synthetic peptide

<400> SEQUENCE: 14
```

```
Tyr Gly Arg Lys Lys Arg Arg Gln Arg Arg Gly Tyr Lys
 1               5                   10
```

<210> SEQ ID NO 15
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: 1, 3, 6, 9, 12
<223> OTHER INFORMATION: Xaa=Acp
<220> FEATURE:
<221> NAME/KEY: AMIDATION
<222> LOCATION: 13
<223> OTHER INFORMATION: C-terminal amide

<400> SEQUENCE: 15

```
Xaa Arg Xaa Arg Arg Xaa Arg Arg Xaa Arg Arg Xaa Lys
 1               5                   10
```

<210> SEQ ID NO 16
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: AMIDATION
<222> LOCATION: 13
<223> OTHER INFORMATION: C-terminal amide

<400> SEQUENCE: 16

```
Gly Arg Arg Arg Arg Arg Arg Arg Arg Arg Arg Gly Lys
 1               5                   10
```

<210> SEQ ID NO 17
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: 1
<223> OTHER INFORMATION: Xaa = Acp
<220> FEATURE:
<221> NAME/KEY: AMIDATION
<222> LOCATION: 11
<223> OTHER INFORMATION: C-terminal amide

<400> SEQUENCE: 17

```
Xaa Arg Arg Arg Arg Arg Arg Arg Arg Arg Arg
 1               5                   10
```

<210> SEQ ID NO 18
<211> LENGTH: 10
<212> TYPE: PRT
<213> ORGANISM: Artificial Sequence
<220> FEATURE:
<223> OTHER INFORMATION: Synthetic peptide

<400> SEQUENCE: 18

```
Cys Tyr Pro Tyr Asp Val Pro Asp Tyr Ala
 1               5                   10
```

<210> SEQ ID NO 19
<211> LENGTH: 8

```
<212> TYPE: PRT
<213> ORGANISM: Artificial Sequence
<220> FEATURE:
<223> OTHER INFORMATION: Synthetic peptide

<400> SEQUENCE: 19

Asp Tyr Lys Asp Asp Asp Asp Lys
1               5

<210> SEQ ID NO 20
<211> LENGTH: 11
<212> TYPE: PRT
<213> ORGANISM: Artificial Sequence
<220> FEATURE:
<223> OTHER INFORMATION: Synthetic peptide

<400> SEQUENCE: 20

Cys Glu Gln Lys Leu Ile Ser Glu Glu Asp Leu
1               5                   10

<210> SEQ ID NO 21
<211> LENGTH: 23
<212> TYPE: PRT
<213> ORGANISM: Homo sapiens

<400> SEQUENCE: 21

Ala Glu Pro Arg Gln Glu Phe Glu Val Met Glu Asp His Ala Gly Thr
1               5                   10                  15

Tyr Gly Leu Gly Asp Arg Lys
            20

<210> SEQ ID NO 22
<211> LENGTH: 21
<212> TYPE: PRT
<213> ORGANISM: Homo sapiens

<400> SEQUENCE: 22

Lys Asp Gln Gly Gly Tyr Thr Met His Gln Asp Gln Glu Gly Asp Thr
1               5                   10                  15

Asp Ala Gly Leu Lys
            20

<210> SEQ ID NO 23
<211> LENGTH: 23
<212> TYPE: PRT
<213> ORGANISM: Homo sapiens

<400> SEQUENCE: 23

Glu Ser Pro Leu Gln Thr Pro Thr Glu Asp Gly Ser Glu Glu Pro Gly
1               5                   10                  15

Ser Glu Thr Ser Asp Ala Lys
            20

<210> SEQ ID NO 24
<211> LENGTH: 20
<212> TYPE: PRT
<213> ORGANISM: Homo sapiens

<400> SEQUENCE: 24

Ser Thr Pro Thr Ala Glu Asp Val Thr Ala Pro Leu Val Asp Glu Gly
1               5                   10                  15

Ala Pro Gly Lys
            20
```

<210> SEQ ID NO 25
<211> LENGTH: 12
<212> TYPE: PRT
<213> ORGANISM: Homo sapiens
<220> FEATURE:
<221> NAME/KEY: ACETYLATION
<222> LOCATION: 5, 7

<400> SEQUENCE: 25

Gly Ala Asp Gly Lys Thr Lys Ile Ala Thr Pro Arg
1               5                   10

<210> SEQ ID NO 26
<211> LENGTH: 15
<212> TYPE: PRT
<213> ORGANISM: Homo sapiens
<220> FEATURE:
<221> NAME/KEY: ACETYLATION
<222> LOCATION: 8

<400> SEQUENCE: 26

Gly Ala Ala Pro Pro Gly Gln Lys Gly Gln Ala Asn Ala Thr Arg
1               5                   10                  15

<210> SEQ ID NO 27
<211> LENGTH: 20
<212> TYPE: PRT
<213> ORGANISM: Homo sapiens
<220> FEATURE:
<221> NAME/KEY: ACETYLATION
<222> LOCATION: 4

<400> SEQUENCE: 27

Ile Pro Ala Lys Thr Pro Pro Ala Pro Lys Thr Pro Pro Ser Ser Gly
1               5                   10                  15

Glu Pro Pro Lys
            20

<210> SEQ ID NO 28
<211> LENGTH: 20
<212> TYPE: PRT
<213> ORGANISM: Homo sapiens
<220> FEATURE:
<221> NAME/KEY: ACETYLATION
<222> LOCATION: 6

<400> SEQUENCE: 28

Thr Pro Pro Ala Pro Lys Thr Pro Ser Ser Gly Glu Pro Pro Lys
1               5                   10                  15

Ser Gly Asp Arg
            20

<210> SEQ ID NO 29
<211> LENGTH: 14
<212> TYPE: PRT
<213> ORGANISM: Homo sapiens

<400> SEQUENCE: 29

Thr Pro Pro Ser Ser Gly Glu Pro Pro Lys Ser Gly Asp Arg
1               5                   10

<210> SEQ ID NO 30
<211> LENGTH: 14
<212> TYPE: PRT
<213> ORGANISM: Homo sapiens

```
<400> SEQUENCE: 30

Thr Pro Ser Leu Pro Thr Pro Pro Thr Arg Glu Pro Lys Lys
1               5                   10

<210> SEQ ID NO 31
<211> LENGTH: 17
<212> TYPE: PRT
<213> ORGANISM: Homo sapiens
<220> FEATURE:
<221> NAME/KEY: ACETYLATION
<222> LOCATION: 12, 15

<400> SEQUENCE: 31

Leu Gln Thr Ala Pro Val Pro Met Pro Asp Leu Lys Asn Val Lys Ser
1               5                   10                  15

Lys

<210> SEQ ID NO 32
<211> LENGTH: 13
<212> TYPE: PRT
<213> ORGANISM: Homo sapiens
<220> FEATURE:
<221> NAME/KEY: ACETYLATION
<222> LOCATION: 3, 5

<400> SEQUENCE: 32

Asn Val Lys Ser Lys Ile Gly Ser Thr Glu Asn Leu Lys
1               5                   10

<210> SEQ ID NO 33
<211> LENGTH: 10
<212> TYPE: PRT
<213> ORGANISM: Homo sapiens
<220> FEATURE:
<221> NAME/KEY: ACETYLATION
<222> LOCATION: 10

<400> SEQUENCE: 33

Ser Lys Ile Gly Ser Thr Glu Asn Leu Lys
1               5                   10

<210> SEQ ID NO 34
<211> LENGTH: 21
<212> TYPE: PRT
<213> ORGANISM: Homo sapiens
<220> FEATURE:
<221> NAME/KEY: ACETYLATION
<222> LOCATION: 15, 21

<400> SEQUENCE: 34

Ile Gly Ser Thr Glu Asn Leu Lys His Gln Pro Gly Gly Lys Val
1               5                   10                  15

Gln Ile Ile Asn Lys
            20

<210> SEQ ID NO 35
<211> LENGTH: 13
<212> TYPE: PRT
<213> ORGANISM: Homo sapiens
<220> FEATURE:
<221> NAME/KEY: ACETYLATION
<222> LOCATION: 7

<400> SEQUENCE: 35

His Gln Pro Gly Gly Lys Val Gln Ile Ile Asn Lys
1               5                   10
```

```
<210> SEQ ID NO 36
<211> LENGTH: 16
<212> TYPE: PRT
<213> ORGANISM: Homo sapiens
<220> FEATURE:
<221> NAME/KEY: ACETYLATION
<222> LOCATION: 6, 7

<400> SEQUENCE: 36

Val Gln Ile Ile Asn Lys Lys Leu Asp Leu Ser Asn Val Gln Ser Lys
 1               5                  10                  15

<210> SEQ ID NO 37
<211> LENGTH: 14
<212> TYPE: PRT
<213> ORGANISM: Homo sapiens
<220> FEATURE:
<221> NAME/KEY: ACETYLATION
<222> LOCATION: 10

<400> SEQUENCE: 37

Lys Leu Asp Leu Ser Asn Val Gln Ser Lys Cys Gly Ser Lys
 1               5                  10

<210> SEQ ID NO 38
<211> LENGTH: 13
<212> TYPE: PRT
<213> ORGANISM: Homo sapiens
<220> FEATURE:
<221> NAME/KEY: ACETYLATION
<222> LOCATION: 9

<400> SEQUENCE: 38

Leu Asp Leu Ser Asn Val Gln Ser Lys Cys Gly Ser Lys
 1               5                  10

<210> SEQ ID NO 39
<211> LENGTH: 23
<212> TYPE: PRT
<213> ORGANISM: Homo sapiens
<220> FEATURE:
<221> NAME/KEY: ACETYLATION
<222> LOCATION: 4

<400> SEQUENCE: 39

Asp Asn Ile Lys His Val Pro Gly Gly Gly Ser Val Gln Ile Val Tyr
 1               5                  10                  15

Lys Pro Val Asp Leu Ser Lys
            20

<210> SEQ ID NO 40
<211> LENGTH: 23
<212> TYPE: PRT
<213> ORGANISM: Homo sapiens
<220> FEATURE:
<221> NAME/KEY: ACETYLATION
<222> LOCATION: 19

<400> SEQUENCE: 40

His Val Pro Gly Gly Gly Ser Val Gln Ile Val Tyr Lys Pro Val Asp
 1               5                  10                  15

Leu Ser Lys Val Thr Ser Lys
            20

<210> SEQ ID NO 41
```

```
<211> LENGTH: 14
<212> TYPE: PRT
<213> ORGANISM: Homo sapiens
<220> FEATURE:
<221> NAME/KEY: ACETYLATION
<222> LOCATION: 14

<400> SEQUENCE: 41

Ile Val Tyr Lys Pro Val Asp Leu Ser Lys Val Thr Ser Lys
 1               5                  10

<210> SEQ ID NO 42
<211> LENGTH: 23
<212> TYPE: PRT
<213> ORGANISM: Homo sapiens
<220> FEATURE:
<221> NAME/KEY: ACETYLATION
<222> LOCATION: 4

<400> SEQUENCE: 42

Val Thr Ser Lys Cys Gly Ser Leu Gly Asn Ile His His Lys Pro Gly
 1               5                  10                  15

Gly Gly Gln Val Glu Val Lys
            20

<210> SEQ ID NO 43
<211> LENGTH: 21
<212> TYPE: PRT
<213> ORGANISM: Homo sapiens
<220> FEATURE:
<221> NAME/KEY: ACETYLATION
<222> LOCATION: 4, 20

<400> SEQUENCE: 43

Val Gln Ser Lys Ile Gly Ser Leu Asp Asn Ile Thr His Val Pro Gly
 1               5                  10                  15

Gly Gly Asn Lys Lys
            20

<210> SEQ ID NO 44
<211> LENGTH: 17
<212> TYPE: PRT
<213> ORGANISM: Homo sapiens
<220> FEATURE:
<221> NAME/KEY: ACETYLATION
<222> LOCATION: 16

<400> SEQUENCE: 44

Ile Gly Ser Leu Asp Asn Ile Thr His Val Pro Gly Gly Gly Asn Lys
 1               5                  10                  15

Lys

<210> SEQ ID NO 45
<211> LENGTH: 22
<212> TYPE: PRT
<213> ORGANISM: Homo sapiens
<220> FEATURE:
<221> NAME/KEY: ACETYLATION
<222> LOCATION: 16, 17

<400> SEQUENCE: 45

Ile Gly Ser Leu Asp Asn Ile Thr His Val Pro Gly Gly Gly Asn Lys
 1               5                  10                  15

Lys Ile Glu Thr His Lys
            20
```

```
<210> SEQ ID NO 46
<211> LENGTH: 10
<212> TYPE: PRT
<213> ORGANISM: Homo sapiens
<220> FEATURE:
<221> NAME/KEY: ACETYLATION
<222> LOCATION: 6

<400> SEQUENCE: 46

Lys Ile Glu Thr His Lys Leu Thr Phe Arg
 1               5                  10

<210> SEQ ID NO 47
<211> LENGTH: 16
<212> TYPE: PRT
<213> ORGANISM: Homo sapiens
<220> FEATURE:
<221> NAME/KEY: ACETYLATION
<222> LOCATION: 4, 6

<400> SEQUENCE: 47

Glu Asn Ala Lys Ala Lys Thr Asp His Gly Ala Glu Ile Val Tyr Lys
 1               5                  10                  15

<210> SEQ ID NO 48
<211> LENGTH: 23
<212> TYPE: PRT
<213> ORGANISM: Homo sapiens
<220> FEATURE:
<221> NAME/KEY: ACETYLATION
<222> LOCATION: 2, 12

<400> SEQUENCE: 48

Ala Lys Thr Asp His Gly Ala Glu Ile Val Tyr Lys Ser Pro Val Val
 1               5                  10                  15

Ser Gly Asp Thr Ser Pro Arg
            20

<210> SEQ ID NO 49
<211> LENGTH: 21
<212> TYPE: PRT
<213> ORGANISM: Homo sapiens
<220> FEATURE:
<221> NAME/KEY: ACETYLATION
<222> LOCATION: 10

<400> SEQUENCE: 49

Thr Asp His Gly Ala Glu Ile Val Tyr Lys Ser Pro Val Val Ser Gly
 1               5                  10                  15

Asp Thr Ser Pro Arg
            20

<210> SEQ ID NO 50
<211> LENGTH: 32
<212> TYPE: PRT
<213> ORGANISM: Homo sapiens

<400> SEQUENCE: 50

His Leu Ser Asn Val Ser Ser Thr Gly Ser Ile Asp Met Val Asp Ser
 1               5                  10                  15

Pro Gln Leu Ala Thr Leu Ala Asp Glu Val Ser Ala Ser Leu Ala Lys
            20                  25                  30

<210> SEQ ID NO 51
<211> LENGTH: 20
```

```
<212> TYPE: PRT
<213> ORGANISM: Homo sapiens

<400> SEQUENCE: 51

Met Val Asp Ser Pro Gln Leu Ala Thr Leu Ala Asp Glu Val Ser Ala
 1               5                  10                  15

Ser Leu Ala Lys
            20

<210> SEQ ID NO 52
<211> LENGTH: 24
<212> TYPE: PRT
<213> ORGANISM: Homo sapiens
<220> FEATURE:
<221> NAME/KEY: ACETYLATION
<222> LOCATION: 11, 18

<400> SEQUENCE: 52

Glu Asn Leu Lys His Gln Pro Gly Gly Gly Lys Val Gln Ile Ile Asn
 1               5                  10                  15

Lys Lys Leu Asp Leu Ser Asn Val
            20

<210> SEQ ID NO 53
<211> LENGTH: 2442
<212> TYPE: PRT
<213> ORGANISM: Homo sapiens

<400> SEQUENCE: 53

Met Ala Glu Asn Leu Leu Asp Gly Pro Pro Asn Pro Lys Arg Ala Lys
 1               5                  10                  15

Leu Ser Ser Pro Gly Phe Ser Ala Asn Asp Ser Thr Asp Phe Gly Ser
             20                  25                  30

Leu Phe Asp Leu Glu Asn Asp Leu Pro Asp Glu Leu Ile Pro Asn Gly
         35                  40                  45

Gly Glu Leu Gly Leu Leu Asn Ser Gly Asn Leu Val Pro Asp Ala Ala
     50                  55                  60

Ser Lys His Lys Gln Leu Ser Glu Leu Leu Arg Gly Gly Ser Gly Ser
 65                  70                  75                  80

Ser Ile Asn Pro Gly Ile Gly Asn Val Ser Ala Ser Ser Pro Val Gln
                 85                  90                  95

Gln Gly Leu Gly Gly Gln Ala Gln Gly Gln Pro Asn Ser Ala Asn Met
            100                 105                 110

Ala Ser Leu Ser Ala Met Gly Lys Ser Pro Leu Ser Gln Gly Asp Ser
        115                 120                 125

Ser Ala Pro Ser Leu Pro Lys Gln Ala Ala Ser Thr Ser Gly Pro Thr
    130                 135                 140

Pro Ala Ala Ser Gln Ala Leu Asn Pro Gln Ala Gln Lys Gln Val Gly
145                 150                 155                 160

Leu Ala Thr Ser Ser Pro Ala Thr Ser Gln Thr Gly Pro Gly Ile Cys
                165                 170                 175

Met Asn Ala Asn Phe Asn Gln Thr His Pro Gly Leu Leu Asn Ser Asn
            180                 185                 190

Ser Gly His Ser Leu Ile Asn Gln Ala Ser Gln Gly Gln Ala Gln Val
        195                 200                 205

Met Asn Gly Ser Leu Gly Ala Ala Gly Arg Gly Arg Gly Ala Gly Met
    210                 215                 220

Pro Tyr Pro Thr Pro Ala Met Gln Gly Ala Ser Ser Ser Val Leu Ala
```

```
            225                 230                 235                 240

Glu Thr Leu Thr Gln Val Ser Pro Gln Met Thr Gly His Ala Gly Leu
                245                 250                 255

Asn Thr Ala Gln Ala Gly Gly Met Ala Lys Met Gly Ile Thr Gly Asn
                260                 265                 270

Thr Ser Pro Phe Gly Gln Pro Phe Ser Gln Ala Gly Gly Gln Pro Met
                275                 280                 285

Gly Ala Thr Gly Val Asn Pro Gln Leu Ala Ser Lys Gln Ser Met Val
            290                 295                 300

Asn Ser Leu Pro Thr Phe Pro Thr Asp Ile Lys Asn Thr Ser Val Thr
305                 310                 315                 320

Asn Val Pro Asn Met Ser Gln Met Gln Thr Ser Val Gly Ile Val Pro
                325                 330                 335

Thr Gln Ala Ile Ala Thr Gly Pro Thr Ala Asp Pro Glu Lys Arg Lys
                340                 345                 350

Leu Ile Gln Gln Gln Leu Val Leu Leu Leu His Ala His Lys Cys Gln
                355                 360                 365

Arg Arg Glu Gln Ala Asn Gly Glu Val Arg Ala Cys Ser Leu Pro His
            370                 375                 380

Cys Arg Thr Met Lys Asn Val Leu Asn His Met Thr His Cys Gln Ala
385                 390                 395                 400

Gly Lys Ala Cys Gln Val Ala His Cys Ala Ser Ser Arg Gln Ile Ile
                405                 410                 415

Ser His Trp Lys Asn Cys Thr Arg His Asp Cys Pro Val Cys Leu Pro
                420                 425                 430

Leu Lys Asn Ala Ser Asp Lys Arg Asn Gln Gln Thr Ile Leu Gly Ser
            435                 440                 445

Pro Ala Ser Gly Ile Gln Asn Thr Ile Gly Ser Val Gly Thr Gly Gln
            450                 455                 460

Gln Asn Ala Thr Ser Leu Ser Asn Pro Asn Pro Ile Asp Pro Ser Ser
465                 470                 475                 480

Met Gln Arg Ala Tyr Ala Ala Leu Gly Leu Pro Tyr Met Asn Gln Pro
                485                 490                 495

Gln Thr Gln Leu Gln Pro Gln Val Pro Gly Gln Gln Pro Ala Gln Pro
                500                 505                 510

Gln Thr His Gln Gln Met Arg Thr Leu Asn Pro Leu Gly Asn Asn Pro
            515                 520                 525

Met Asn Ile Pro Ala Gly Gly Ile Thr Thr Asp Gln Gln Pro Pro Asn
530                 535                 540

Leu Ile Ser Glu Ser Ala Leu Pro Thr Ser Leu Gly Ala Thr Asn Pro
545                 550                 555                 560

Leu Met Asn Asp Gly Ser Asn Ser Gly Asn Ile Gly Thr Leu Ser Thr
                565                 570                 575

Ile Pro Thr Ala Ala Pro Pro Ser Ser Thr Gly Val Arg Lys Gly Trp
            580                 585                 590

His Glu His Val Thr Gln Asp Leu Arg Ser His Leu Val His Lys Leu
            595                 600                 605

Val Gln Ala Ile Phe Pro Thr Pro Asp Pro Ala Ala Leu Lys Asp Arg
            610                 615                 620

Arg Met Glu Asn Leu Val Ala Tyr Ala Lys Lys Val Glu Gly Asp Met
625                 630                 635                 640

Tyr Glu Ser Ala Asn Ser Arg Asp Glu Tyr Tyr His Leu Leu Ala Glu
                645                 650                 655
```

-continued

```
Lys Ile Tyr Lys Ile Gln Lys Glu Leu Glu Lys Arg Arg Ser Arg
            660                 665                 670

Leu His Lys Gln Gly Ile Leu Gly Asn Gln Pro Ala Leu Pro Ala Pro
        675                 680                 685

Gly Ala Gln Pro Pro Val Ile Pro Gln Ala Gln Pro Val Arg Pro Pro
    690                 695                 700

Asn Gly Pro Leu Ser Leu Pro Val Asn Arg Met Gln Val Ser Gln Gly
705                 710                 715                 720

Met Asn Ser Phe Asn Pro Met Ser Leu Gly Asn Val Gln Leu Pro Gln
                725                 730                 735

Ala Pro Met Gly Pro Arg Ala Ala Ser Pro Met Asn His Ser Val Gln
            740                 745                 750

Met Asn Ser Met Gly Ser Val Pro Gly Met Ala Ile Ser Pro Ser Arg
        755                 760                 765

Met Pro Gln Pro Pro Asn Met Met Gly Ala His Thr Asn Asn Met Met
    770                 775                 780

Ala Gln Ala Pro Ala Gln Ser Gln Phe Leu Pro Gln Asn Gln Phe Pro
785                 790                 795                 800

Ser Ser Ser Gly Ala Met Ser Val Gly Met Gly Gln Pro Pro Ala Gln
                805                 810                 815

Thr Gly Val Ser Gln Gly Gln Val Pro Gly Ala Ala Leu Pro Asn Pro
            820                 825                 830

Leu Asn Met Leu Gly Pro Gln Ala Ser Gln Leu Pro Cys Pro Pro Val
        835                 840                 845

Thr Gln Ser Pro Leu His Pro Thr Pro Pro Ala Ser Thr Ala Ala
    850                 855                 860

Gly Met Pro Ser Leu Gln His Thr Thr Pro Pro Gly Met Thr Pro Pro
865                 870                 875                 880

Gln Pro Ala Ala Pro Thr Gln Pro Ser Thr Pro Val Ser Ser Ser Gly
                885                 890                 895

Gln Thr Pro Thr Pro Thr Pro Gly Ser Val Pro Ser Ala Thr Gln Thr
            900                 905                 910

Gln Ser Thr Pro Thr Val Gln Ala Ala Ala Gln Ala Gln Val Thr Pro
        915                 920                 925

Gln Pro Gln Thr Pro Val Gln Pro Pro Ser Val Ala Thr Pro Gln Ser
    930                 935                 940

Ser Gln Gln Gln Pro Thr Pro Val His Ala Gln Pro Pro Gly Thr Pro
945                 950                 955                 960

Leu Ser Gln Ala Ala Ala Ser Ile Asp Asn Arg Val Pro Thr Pro Ser
                965                 970                 975

Ser Val Ala Ser Ala Glu Thr Asn Ser Gln Gln Pro Gly Pro Asp Val
            980                 985                 990

Pro Val Leu Glu Met Lys Thr Glu Thr Gln Ala Glu Asp Thr Glu Pro
        995                 1000                1005

Asp Pro Gly Glu Ser Lys Gly Glu Pro Arg Ser Glu Met Met Glu Glu
    1010                1015                1020

Asp Leu Gln Gly Ala Ser Gln Val Lys Glu Glu Thr Asp Ile Ala Glu
1025                1030                1035                1040

Gln Lys Ser Glu Pro Met Glu Val Asp Glu Lys Lys Pro Glu Val Lys
                1045                1050                1055

Val Glu Val Lys Glu Glu Glu Glu Ser Ser Ser Asn Gly Thr Ala Ser
            1060                1065                1070
```

```
Gln Ser Thr Ser Pro Ser Gln Pro Arg Lys Lys Ile Phe Lys Pro Glu
        1075                1080                1085
Glu Leu Arg Gln Ala Leu Met Pro Thr Leu Glu Ala Leu Tyr Arg Gln
        1090                1095                1100
Asp Pro Glu Ser Leu Pro Phe Arg Gln Pro Val Asp Pro Gln Leu Leu
1105                1110                1115                1120
Gly Ile Pro Asp Tyr Phe Asp Ile Val Lys Asn Pro Met Asp Leu Ser
                1125                1130                1135
Thr Ile Lys Arg Lys Leu Asp Thr Gly Gln Tyr Gln Glu Pro Trp Gln
        1140                1145                1150
Tyr Val Asp Asp Val Trp Leu Met Phe Asn Asn Ala Trp Leu Tyr Asn
        1155                1160                1165
Arg Lys Thr Ser Arg Val Tyr Lys Phe Cys Ser Lys Leu Ala Glu Val
        1170                1175                1180
Phe Glu Gln Glu Ile Asp Pro Val Met Gln Ser Leu Gly Tyr Cys Cys
1185                1190                1195                1200
Gly Arg Lys Tyr Glu Phe Ser Pro Gln Thr Leu Cys Cys Tyr Gly Lys
        1205                1210                1215
Gln Leu Cys Thr Ile Pro Arg Asp Ala Ala Tyr Tyr Ser Tyr Gln Asn
        1220                1225                1230
Arg Tyr His Phe Cys Glu Lys Cys Phe Thr Glu Ile Gln Gly Glu Asn
        1235                1240                1245
Val Thr Leu Gly Asp Asp Pro Ser Gln Pro Gln Thr Thr Ile Ser Lys
        1250                1255                1260
Asp Gln Phe Glu Lys Lys Lys Asn Asp Thr Leu Asp Pro Glu Pro Phe
1265                1270                1275                1280
Val Asp Cys Lys Glu Cys Gly Arg Lys Met His Gln Ile Cys Val Leu
        1285                1290                1295
His Tyr Asp Ile Ile Trp Pro Ser Gly Phe Val Cys Asp Asn Cys Leu
        1300                1305                1310
Lys Lys Thr Gly Arg Pro Arg Lys Glu Asn Lys Phe Ser Ala Lys Arg
        1315                1320                1325
Leu Gln Thr Thr Arg Leu Gly Asn His Leu Glu Asp Arg Val Asn Lys
        1330                1335                1340
Phe Leu Arg Arg Gln Asn His Pro Glu Ala Gly Glu Val Phe Val Arg
1345                1350                1355                1360
Val Val Ala Ser Ser Asp Lys Thr Val Glu Val Lys Pro Gly Met Lys
        1365                1370                1375
Ser Arg Phe Val Asp Ser Gly Glu Met Ser Glu Ser Phe Pro Tyr Arg
        1380                1385                1390
Thr Lys Ala Leu Phe Ala Phe Glu Glu Ile Asp Gly Val Asp Val Cys
        1395                1400                1405
Phe Phe Gly Met His Val Gln Glu Tyr Gly Ser Asp Cys Pro Pro Pro
1410                1415                1420
Asn Thr Arg Arg Val Tyr Ile Ser Tyr Leu Asp Ser Ile His Phe Phe
1425                1430                1435                1440
Arg Pro Arg Cys Leu Arg Thr Ala Val Tyr His Glu Ile Leu Ile Gly
                1445                1450                1455
Tyr Leu Glu Tyr Val Lys Lys Leu Gly Tyr Val Thr Gly His Ile Trp
                1460                1465                1470
Ala Cys Pro Pro Ser Glu Gly Asp Asp Tyr Ile Phe His Cys His Pro
        1475                1480                1485
Pro Asp Gln Lys Ile Pro Lys Pro Lys Arg Leu Gln Glu Trp Tyr Lys
```

```
                1490            1495            1500
Lys Met Leu Asp Lys Ala Phe Ala Glu Arg Ile Ile His Asp Tyr Lys
1505            1510            1515            1520

Asp Ile Phe Lys Gln Ala Thr Glu Asp Arg Leu Thr Ser Ala Lys Glu
        1525            1530            1535

Leu Pro Tyr Phe Glu Gly Asp Phe Trp Pro Asn Val Leu Glu Glu Ser
        1540            1545            1550

Ile Lys Glu Leu Glu Gln Glu Glu Glu Arg Lys Lys Glu Glu Ser
        1555            1560            1565

Thr Ala Ala Ser Glu Thr Thr Glu Gly Ser Gln Gly Asp Ser Lys Asn
        1570            1575            1580

Ala Lys Lys Lys Asn Asn Lys Lys Thr Asn Lys Asn Lys Ser Ser Ile
1585            1590            1595            1600

Ser Arg Ala Asn Lys Lys Lys Pro Ser Met Pro Asn Val Ser Asn Asp
        1605            1610            1615

Leu Ser Gln Lys Leu Tyr Ala Thr Met Glu Lys His Lys Glu Val Phe
        1620            1625            1630

Phe Val Ile His Leu His Ala Gly Pro Val Ile Asn Thr Leu Pro Pro
        1635            1640            1645

Ile Val Asp Pro Asp Pro Leu Leu Ser Cys Asp Leu Met Asp Gly Arg
        1650            1655            1660

Asp Ala Phe Leu Thr Leu Ala Arg Asp Lys His Trp Glu Phe Ser Ser
1665            1670            1675            1680

Leu Arg Arg Ser Lys Trp Ser Thr Leu Cys Met Leu Val Glu Leu His
        1685            1690            1695

Thr Gln Gly Gln Asp Arg Phe Val Tyr Thr Cys Asn Glu Cys Lys His
        1700            1705            1710

His Val Glu Thr Arg Trp His Cys Thr Val Cys Glu Asp Tyr Asp Leu
        1715            1720            1725

Cys Ile Asn Cys Tyr Asn Thr Lys Ser His Ala His Lys Met Val Lys
        1730            1735            1740

Trp Gly Leu Gly Leu Asp Asp Glu Gly Ser Ser Gln Gly Glu Pro Gln
1745            1750            1755            1760

Ser Lys Ser Pro Gln Glu Ser Arg Arg Leu Ser Ile Gln Arg Cys Ile
        1765            1770            1775

Gln Ser Leu Val His Ala Cys Gln Cys Arg Asn Ala Asn Cys Ser Leu
        1780            1785            1790

Pro Ser Cys Gln Lys Met Lys Arg Val Val Gln His Thr Lys Gly Cys
        1795            1800            1805

Lys Arg Lys Thr Asn Gly Gly Cys Pro Val Cys Lys Gln Leu Ile Ala
        1810            1815            1820

Leu Cys Cys Tyr His Ala Lys His Cys Gln Glu Asn Lys Cys Pro Val
1825            1830            1835            1840

Pro Phe Cys Leu Asn Ile Lys His Lys Leu Arg Gln Gln Gln Ile Gln
        1845            1850            1855

His Arg Leu Gln Gln Ala Gln Leu Met Arg Arg Arg Met Ala Thr Met
        1860            1865            1870

Asn Thr Arg Asn Val Pro Gln Gln Ser Leu Pro Ser Pro Thr Ser Ala
        1875            1880            1885

Pro Pro Gly Thr Pro Thr Gln Gln Pro Ser Thr Pro Gln Thr Pro Gln
        1890            1895            1900

Pro Pro Ala Gln Pro Gln Pro Ser Pro Val Ser Met Ser Pro Ala Gly
1905            1910            1915            1920
```

-continued

```
Phe Pro Ser Val Ala Arg Thr Gln Pro Thr Thr Val Ser Thr Gly
            1925                1930                1935

Lys Pro Thr Ser Gln Val Pro Ala Pro Pro Pro Ala Gln Pro Pro
            1940                1945                1950

Pro Ala Ala Val Glu Ala Ala Arg Gln Ile Glu Arg Glu Ala Gln Gln
            1955                1960                1965

Gln Gln His Leu Tyr Arg Val Asn Ile Asn Asn Ser Met Pro Pro Gly
            1970                1975                1980

Arg Thr Gly Met Gly Thr Pro Gly Ser Gln Met Ala Pro Val Ser Leu
1985                1990                1995                2000

Asn Val Pro Arg Pro Asn Gln Val Ser Gly Pro Val Met Pro Ser Met
            2005                2010                2015

Pro Pro Gly Gln Trp Gln Gln Ala Pro Leu Pro Gln Gln Pro Met
            2020                2025                2030

Pro Gly Leu Pro Arg Pro Val Ile Ser Met Gln Ala Gln Ala Ala Val
            2035                2040                2045

Ala Gly Pro Arg Met Pro Ser Val Gln Pro Pro Arg Ser Ile Ser Pro
            2050                2055                2060

Ser Ala Leu Gln Asp Leu Leu Arg Thr Leu Lys Ser Pro Ser Ser Pro
2065                2070                2075                2080

Gln Gln Gln Gln Val Leu Asn Ile Leu Lys Ser Asn Pro Gln Leu
            2085                2090                2095

Met Ala Ala Phe Ile Lys Gln Arg Thr Ala Lys Tyr Val Ala Asn Gln
            2100                2105                2110

Pro Gly Met Gln Pro Gln Pro Gly Leu Gln Ser Gln Pro Gly Met Gln
            2115                2120                2125

Pro Gln Pro Gly Met His Gln Gln Pro Ser Leu Gln Asn Leu Asn Ala
            2130                2135                2140

Met Gln Ala Gly Val Pro Arg Pro Gly Val Pro Pro Gln Gln Ala
2145                2150                2155                2160

Met Gly Gly Leu Asn Pro Gln Gly Gln Ala Leu Asn Ile Met Asn Pro
            2165                2170                2175

Gly His Asn Pro Asn Met Ala Ser Met Asn Pro Gln Tyr Arg Glu Met
            2180                2185                2190

Leu Arg Arg Gln Leu Leu Gln Gln Gln Gln Gln Gln Gln Gln Gln
            2195                2200                2205

Gln Gln Gln Gln Gln Gln Gln Gly Ser Ala Gly Met Ala Gly Gly
            2210                2215                2220

Met Ala Gly His Gly Gln Phe Gln Gln Pro Gln Gly Pro Gly Gly Tyr
2225                2230                2235                2240

Pro Pro Ala Met Gln Gln Gln Arg Met Gln Gln His Leu Pro Leu
            2245                2250                2255

Gln Gly Ser Ser Met Gly Gln Met Ala Ala Gln Met Gly Gln Leu Gly
            2260                2265                2270

Gln Met Gly Gln Pro Gly Leu Gly Ala Asp Ser Thr Pro Asn Ile Gln
            2275                2280                2285

Gln Ala Leu Gln Gln Arg Ile Leu Gln Gln Gln Met Lys Gln Gln
            2290                2295                2300

Ile Gly Ser Pro Gly Gln Pro Asn Pro Met Ser Pro Gln Gln His Met
2305                2310                2315                2320

Leu Ser Gly Gln Pro Gln Ala Ser His Leu Pro Gly Gln Gln Ile Ala
            2325                2330                2335
```

-continued

```
Thr Ser Leu Ser Asn Gln Val Arg Ser Pro Ala Pro Val Gln Ser Pro
        2340            2345            2350

Arg Pro Gln Ser Gln Pro Pro His Ser Ser Pro Ser Pro Arg Ile Gln
        2355            2360            2365

Pro Gln Pro Ser Pro His His Val Ser Pro Gln Thr Gly Ser Pro His
        2370            2375            2380

Pro Gly Leu Ala Val Thr Met Ala Ser Ser Ile Asp Gln Gly His Leu
2385            2390            2395            2400

Gly Asn Pro Glu Gln Ser Ala Met Leu Pro Gln Leu Asn Thr Pro Ser
            2405            2410            2415

Arg Ser Ala Leu Ser Ser Glu Leu Ser Leu Val Gly Asp Thr Thr Gly
        2420            2425            2430

Asp Thr Leu Glu Lys Phe Val Glu Gly Leu
        2435            2440
```